(12) United States Patent
Bhatia et al.

(10) Patent No.: US 6,919,187 B2
(45) Date of Patent: Jul. 19, 2005

(54) COMPOUNDS AND METHODS FOR TREATMENT AND DIAGNOSIS OF CHLAMYDIAL INFECTION

(75) Inventors: Ajay Bhatia, Seattle, WA (US); Jeff Guderian, Lynnwood, WA (US); Yasir A. W. Skeiky, Bellevue, WA (US); Jean-Francois L. Maisonneuve, Federal Way, WA (US)

(73) Assignee: Corixa Corporation, Seatle, WA (US)

( * ) Notice: Subject to any disclaimer, the term of this patent is extended or adjusted under 35 U.S.C. 154(b) by 0 days.

(21) Appl. No.: 10/197,220

(22) Filed: Jul. 15, 2002

(65) Prior Publication Data

US 2005/0084499 A1 Apr. 21, 2005

(51) Int. Cl.[7] .................. C12P 21/06; A61K 31/118; A61K 39/02; C07H 21/04
(52) U.S. Cl. .............. 435/69.1; 424/263.1; 424/200.1; 424/190.1; 536/23.1; 536/23.7; 514/44
(58) Field of Search .......................... 424/263.1, 200.1, 424/190.1; 435/69.1; 536/23.1, 23.7; 514/44

(56) References Cited

U.S. PATENT DOCUMENTS

| | | | |
|---|---|---|---|
| 4,118,469 A | 10/1978 | Caldwell et al. | 424/1 |
| 4,497,899 A | 2/1985 | Armstrong et al. | 436/510 |
| 5,166,053 A | 11/1992 | Huguenel et al. | 435/7.36 |
| 5,318,892 A | 6/1994 | Watanabe et al. | 435/7.36 |
| 5,725,863 A | 3/1998 | Daniels et al. | 424/263.1 |
| 5,869,608 A | 2/1999 | Caldwell et al. | 530/350 |
| 6,166,177 A | 12/2000 | Probst et al. | 530/300 |
| 6,432,916 B1 * | 8/2002 | Probst et al. | 514/2 |
| 6,448,234 B1 * | 9/2002 | Fling | 514/44 |
| 6,565,856 B1 * | 5/2003 | Skeiky et al. | 424/263.1 |

FOREIGN PATENT DOCUMENTS

| | | |
|---|---|---|
| EP | 348725 A2 | 1/1990 |
| EP | 784059 A1 | 7/1997 |
| WO | WO 94/06827 | 3/1994 |
| WO | WO 97/06263 | 2/1997 |
| WO | WO 98/02546 | 1/1998 |
| WO | WO 98/10789 | 3/1998 |
| WO | WO 99/17741 | 4/1999 |
| WO | WO 99/27105 | 6/1999 |
| WO | WO 99/28475 | 6/1999 |
| WO | WO 99/51748 | 10/1999 |
| WO | WO 00/34483 | 6/2000 |
| WO | WO 01/40474 | 6/2001 |

OTHER PUBLICATIONS

Stephenes et al 1998 (Accession No. H71468 and AE001353).*
Unanue. ER 1999 (see attached review article, American Journal of Pathology, 154; 651–664).*
Burgess et al., The Journal of Cell Biology, 111:2129–2138, 1990.*
Jobling et al. (Mol. Microbiol., 1991, 5(7):1755–67.*

Allen and Stephens, "An intermolecular mechanism of T cell help for the production of antibodies to the bacterial pathogen, *Chlamydia trachomatis*," *European Journal of Immunology* 23: 1169–1172, 1993.
Baehr et al., "Mapping antigenic domains expressed by *chlamydia trachomatis* major outer membrane protein genes," *Proc Natl Acad Sci* 85(1):4000–4004, Jun. 1, 1988.
Brunham et al., "*Chlamydia trachomatis* antigens: role in immunity and pathogenesis," *Infectious Agents and Disease* 3(5):218–233, Oct. 1994.
Chakrabarti et al., "Vaccinia virus expression vector: coexpression of β–galactosidase provides visual screening of recombinant virus plaques," *Molecular and Cellular Biology* 5(12):3403–3409, Dec. 1985.
Conlan, J.W. et al., "Isolation of recombinant fragments of the major outer–membrane protein of *Chlamydia trachomatis*: their potential as subunit vaccines," *Journal of General Microbiology* 136: 2013–2020, 1990.
Earl et al., "Biological and immunological properties of human immunodeficiency virus type 1 envelope glycoprotein: analysis of proteins and truncations and deletions expressed by recombinant vaccinia viruses," *Journal of Virology* 65(1):31–41, Jan. 1991.
GenBank Accession No. AE001273, "Genome sequence of an obligate intracellular pathogen of humans: *Chlamydia trachomatis*," Jun. 2, 2004.
Genbank Database, Accession No. AE001316, Jun. 1, 2004.
Genbank Database, Accession No. AE001320, Jun. 1, 2004.
GenBank Database, Accession No. AE001323, "Genome sequence of an obligate intracellular pathogen of humans: *Chlamydia trachomatis*," Jun. 1, 2004.
GenBank Database, Accession No. AE001324, "Genome sequence of an obligate intracellular pathogen of humans: *Chlamydia trachomatis*," Jun. 1, 2004.
Genbank Database, Accession No. AE001326, Jun. 1, 2004.
Genbank Database, Accession No. AE001335, "Genome sequence of an obligate intracellular pathogen of humans: *Chlamydia trachomatis*," Jun. 1, 2004.
Genbank Database, Accession No. AE001361, Jun. 1, 2004.
GenBank Database, Accession No. E71500, "Genome sequence of an obligate intracellular pathogen of humans: *Chlamydia trachomatis*," Nov. 3, 2000.

(Continued)

*Primary Examiner*—Mark Navarro
*Assistant Examiner*—Padma Baskar
(74) *Attorney, Agent, or Firm*—Seed IP Law Group PLLC

(57) ABSTRACT

Compounds and methods for the diagnosis and treatment of Chlamydial infection are disclosed. The compounds provided include polypeptides that contain at least one antigenic portion of a *Chlamydia* antigen and DNA sequences encoding such polypeptides. Pharmaceutical compositions and vaccines comprising such polypeptides or DNA sequences are also provided, together with antibodies directed against such polypeptides. Diagnostic kits containing such polypeptides or DNA sequences and a suitable detection reagent may be used for the detection of Chlamydial infection in patients and in biological samples.

3 Claims, No Drawings

OTHER PUBLICATIONS

GenBank Database, Accession No. H71501, "Genome sequence of an obligate intracellular pathogen of humans: *Chlamydia trachomatis*," Jul. 28, 2000.

GenBank Database, Accession No. H71510, "Genome sequence of an obligate intracellular pathogen of humans: *Chlamydia trachomatis*," Oct. 8, 1999.

GenBank Database, Accession No. AAC68408, Jun. 1, 2004.

GenBank Database, Accession No. AAF39070, Mar. 26, 2003.

GenBank Database, Accession No. AE001333, Jun. 1, 2004.

GenBank Database, Accession No. AE002286, Mar. 26, 2003.

GenBank Database, Accession No. AE002343, Mar. 26, 2003.

EMBL Database, Accession No. O84466, Jun. 1, 2003.

GenBank Database, Accession No. NC_000117, Sep. 14, 2004.

Grimwood, J. et al., "Expression of *Chlamydia pneumoniae* Polymorphic Membrane Protein Family Genes," *Infection and Immunity* 69(4):2383–2389, Apr. 2001.

Gu et al., "*Chlamydia trachomatis* RNA polymerase α subunit: sequence and structural analysis," *J. Bacteriology* 177:2594–2601, May 1995.

Hayes, L.J. et al., "*Chlamydia trachomatis* major outer membrane protein epitopes expressed as fusions with LamB in an attenuated aroA strain of *Salmonella typhimurium*; their application as potential immunogens," *Journal of General Microbiology* 137: 1557–1564, 1991.

Hayes, L.J. et al., "The major outer–membrane proteins of *Chlamydia trachomatis* serovars A and B: intra–serovar amino acid changes do not alter specificities of serovar– and C subspecies–reactive antibody–binding domains," *Journal of General Microbiology* 136: 1559–1566, 1990.

Janeway et al. (eds.), *Immunobiology: The Immune System in Health and Disease,* Garland Pub., New York, NY, 1997, pp. 7:6–7:10.

Jensen et al., "Infection of human and simian tissue cultures with rous sarcoma virus," *Proc. Natl. Acad. Sci. USA* 52:53–59, Jul. 1964.

Kalman, S. et al., "Comparative genomes of *Chlamydia pneumoniae* and *C. trachomatis,*" *Nature Genetics* 21:385–389, Apr. 1999.

Kim, S.–K. et al., "Induction of HLA Class I–Restricted CD8$^+$ CTLs Specific for the Major Outer Membrane Protein of *Chlamydia trachomatis* in Human Genital Tract Infections," *The Journal of Immunology* 162: 6855–6866, 1999.

Knudsen, K. et al., "Identification of Two Novel Genes Encoding 97– to 99– Kilodalton Outer Membrane Proteins of *Chlamydia pneumoniae,*" *Infection and Immunity* 67(1): 375–383, Jan. 1999.

Kuon, W. et al., "Recognition of Chlamydial Antigen By HLA–B27–Restricted Cytotoxic T Cells in HLA–B*2705 Transgenic CBA(H–2$^k$) Mice," *Arthritis & Rheumatism* 40(5): 945–954, May 1997.

Lalvani et al., "Rapid effector function in CD8$^+$ memory T cells," *J. Exp. Med.* 186(6):859–865, Sep. 15, 1997.

Lazar, E. et al., "Transforming Growth Factor α: Mutation of Aspartic Acid 47 and Leucine 48 Results in Different Biological Activities," *Molecular and Cellular Biology* 8(3): 1247–1252, Mar. 1988.

Levinson and Jawetz, *Medical Microbiology & Immunology,* 3d ed., Appleton & Lange, 1994, pp. 292–293.

Lu and Zhong, "Interleukin–12 Production IS Required for Chlamydial Antigen–Pulsed Dendritic Cells To Induce Protection against Live *Chlamydia trachomatis* Infection," *Infection and Immunity* 67(4): 1763–1769, Apr. 1999.

Maclean, J.W. et al., "Characterization of *Chlamydia trachomatis* antigens with monoclonal and polyclonal antibodies," *Can. J. Microbiol.* 34: 141–147, 1988.

Murdin, A.D. et al., "A Poliovirus Hybrid Expressing a Neutralization Epitope from the Major Outer Membrane Protein of *Chlamydia trachomatis* Is Highly Immunogenic," *Infection and Immunity* 61(10): 4406–4414, Oct. 1993.

Mygind, P.H. et al., "Membrane proteins PmpG and PmpH are major constituents of *Chlamydia trachomatis* L2 outer membrane complex," *FEMS Microbiol. Lett.* 186(2): 163–169, May 15, 2000.

Pal, S. et al., "Immunization with an Acellular Vaccine Consisting of the Outer Membrane Complex of *Chlamydia trachomatis* Induces Protection against a Genital Challenge," *Infection and Immunity* 65(8): 3361–3369, Aug. 1997.

Pawlikowska and Deptula, "Adherence and ingesting capacity of peripheral blood granulocytes in rabbits immunized with various antigens of *Chlamydia sp.,* " *Central European Journal of Immunology* 24: 293–298, 1999.

Peterson, E.M. et al., "The Effect of Orientation Within a Chimeric Peptide on the Immunogenicity of *Chlamydia trachomatis* Epitopes," *Molecular Immunology* 33(4/5): 335–339, 1996.

Rank et al., "Immunization against Chlamydial Genital Infection in Guinea Pigs with UV–Inactivated and Viable Chlamydiae Administered by Different Routes," *Infection and Immunity,* 58(8):2599–2605, Aug. 1990.

Read et al., "Genome sequences of *Chlamydia trachomatis* MoPn and *Chlamydia pneumoniae* AR39," *Nucleic Acids Research* 28(6):1397–1406, 2000.

Rudinger, J., "Characteristics of the amino acids as components of a peptide hormone sequence," in *Peptide Hormones,* Parsons, J.A. (ed.), University Park Press, Baltimore, MD, Jun. 1976, pp. 1–5.

Sanderson et al., "Identification of a CD4$^+$ T Cell–stimulating Antigen of Pathogenic Bacteria by Expression Cloning," *J. Exp. Med.* 182(6):1751–1757, 1995.

Scudiero et al., "Evaluation of a soluble tetrazolium/formazan assay for cell growth and drug sensitivity in culture using human and other tumor cell lines," *Cancer Research* 48:4827–4833, Sep. 1, 1988.

Shirai, M. et al., "Comparison of whole genome sequences of *Chlamydia pneumoniae* J138 from Japan and CWL029 from USA," *Nucleic Acid Research* 28(12): 2311–2314, 2000.

Stagg, A.J. et al., "Vaccines against *Chlamydia:* approaches and progress," *Molecular Medicine Today* 4(4): 166–173, Apr. 1998.

Starnbach et al., "Protective cytotoxic T lymphocytes are induced during murine infection with *Chlamydia trachomatis,*" *The Journal of Immunology* 153(11):5183–5189, Dec. 1, 1994.

Stephens et al., "Genome Sequence of an Obligate Intracellular Pathogen of Humans: *Chlamydia trachomatis,*" *Science* 282:754–759, 1998.

Su and Caldwell, "Immunogenicity of a synthetic oligopeptide corresponding to antigenically common T–helper and B–cell neutralizing epitopes of the major outer membrane protein of *Chlamydia trachomatis*," *Vaccine* *11*(11): 1159–1166, 1993.

Su, H. et al., "Protective efficacy of a parenterally administered MOMP–derived synthetic oligopeptide vaccine in a murine model of *Chlamydia trachomatis* genital tract infection: serum neutralizing IgG antibodies do not protect against chlamydial genital tract infection," *Vaccine 13*(11): 1023–1032, 1995.

Webb et al., "Molecular cloning of a novel protein antigen of Leishmania major that elicits a potent immune response in experimental murine leishmaniasis," *The Journal of Immunology 157*:5034–5041, 1996.

Yasuda, K. et al., "Serine 6 of Lck Tyrosine Kinase: A Critical Site for Lck Myristoylation, Membrane Localization, and Function in T Lymphocytes," *The Journal of Immunology 165*: 3226–3231, 2000.

Zhang, D. et al., "DNA vaccination with the major outer–membrane protein gene induces acquired immunity to *Chlamydia trachomatis* (mouse pneumonitis) infection," *J. Infect. Dis. 176*(4): 1035–1040, Oct. 1997.

Zhong, G. et al., "Immunogenicity Evaluation of a Lipidic Amino Acid–Based Synthetic Peptide Vaccine for *Chlamydia trachomatis*," *The Journal of Immunology 151*(7): 3728–3736, Oct. 1, 1993.

Zhong, G. et al., "Mapping epitopes of neutralizing monoclonal antibodies using phage random peptide libraries," *Journal of Industrial Microbiology & Biotechnology 19*: 71–76, 1997.

Zhong, G., "Conformational Mimicry of a Chlamydial Neutralization Epitope on Filamentous Phage," *Journal of Biological Chemistry 269*(39): 24183–24188, Sep. 30, 1994.

\* cited by examiner

COMPOUNDS AND METHODS FOR TREATMENT AND DIAGNOSIS OF CHLAMYDIAL INFECTION

BACKGROUND OF THE INVENTION

1. Field of the Invention

The present invention relates generally to the detection and treatment of Chlamydial infection. In particular, the invention is related to polypeptides comprising a *Chlamydia* antigen and the use of such polypeptides for the serodiagnosis and treatment of Chlamydial infection.

2. Description of Related Art

Chlamydiae are intracellular bacterial pathogens that are responsible for a wide variety of important human and animal infections. *Chlamydia trachomatis* is one of the most common causes of sexually transmitted diseases and can lead to pelvic inflammatory disease (PID), resulting in tubal obstruction and infertility. *Chlamydia trachomatis* may also play a role in male infertility. In 1990, the cost of treating PID in the US was estimated to be $4 billion. Trachoma, due to ocular infection with *Chlamydia trachomatis*, is the leading cause of preventable blindness worldwide. *Chlamydia pneumonia* is a major cause of acute respiratory tract infections in humans and is also believed to play a role in the pathogenesis of atherosclerosis and, in particular, coronary heart disease. Individuals with a high titer of antibodies to *Chlamydia pneumonia* have been shown to be at least twice as likely to suffer from coronary heart disease as seronegative individuals. Chlamydial infections thus constitute a significant health problem both in the US and worldwide.

Chlamydial infection is often asymptomatic. For example, by the time a woman seeks medical attention for PID, irreversible damage may have already occurred resulting in infertility. There thus remains a need in the art for improved vaccines and pharmaceutical compositions for the prevention and treatment of *Chlamydia* infections. The present invention fulfills this need and further provides other related advantages.

BRIEF SUMMARY OF THE INVENTION

The present invention provides compositions and methods for the diagnosis and therapy of *Chlamydia* infection. In one aspect, the present invention provides polypeptides comprising an immunogenic portion of a *Chlamydia* antigen, or a variant of such an antigen. Certain portions and other variants are immunogenic, such that the ability of the variant to react with antigen-specific antisera is not substantially diminished. Within certain embodiments, the polypeptide comprises an amino acid sequence encoded by a polynucleotide sequence selected from the group consisting of (a) a sequence of SEQ ID NO: 1–48, 114–121, 125–138, 141–175; (b) the complements of said sequences; and (c) sequences that hybridize to a sequence of (a) or (b) under moderately stringent conditions. In specific embodiments, the polypeptides of the present invention comprise at least a portion of a Chlamydial protein that includes an amino acid sequence selected from the group consisting of sequences recited in SEQ ID NO:122–124 and 139–140 and 167–175 and variants thereof.

The present invention further provides polynucleotides that encode a polypeptide as described above, or a portion thereof (such as a portion encoding at least 15 amino acid residues of a Chlamydial protein), expression vectors comprising such polynucleotides and host cells transformed or transfected with such expression vectors.

In a related aspect, polynucleotide sequences encoding the above polypeptides, recombinant expression vectors comprising one or more of these polynucleotide sequences and host cells transformed or transfected with such expression vectors are also provided.

In another aspect, the present invention provides fusion proteins comprising an inventive polypeptide, or, alternatively, an inventive polypeptide and a known *Chlamydia* antigen, as well as polynucleotides encoding such fusion proteins, in combination with a physiologically acceptable carrier or immunostimulant for use as pharmaceutical compositions and vaccines thereof.

The present invention further provides pharmaceutical compositions that comprise: (a) an antibody, both polyclonal and monoclonal, or antigen-binding fragment thereof that specifically binds to a Chlamydial protein; and (b) a physiologically acceptable carrier. Within other aspects, the present invention provides pharmaceutical compositions that comprise one or more *Chlamydia* polypeptides disclosed herein, for example, a polypeptide of SEQ ID NO: 95–109, 122–124 and 139–140 and 167–175, or a polynucleotide molecule encoding such a polypeptide, such as a polynucleotide sequence of SEQ ID NO: 1–48, 80–94, 114–121 125–138, and 141–166, and a physiologically acceptable carrier. The invention also provides compositions for prophylactic and therapeutic purposes comprising one or more of the disclosed polynucleotides and/or polypeptides and an immunostimulant, e.g., an adjuvant.

In yet another aspect, methods are provided for stimulating an immune response in a patient, e.g., for inducing protective immunity in a patient, comprising administering to a patient an effective amount of one or more of the above pharmaceutical compositions or vaccines.

In yet a further aspect, methods for the treatment of *Chlamydia* infection in a patient are provided, the methods comprising obtaining peripheral blood mononuclear cells (PBMC) from the patient, incubating the PBMC with a polypeptide of the present invention (or a polynucleotide that encodes such a polypeptide) to provide incubated T cells and administering the incubated T cells to the patient. The present invention additionally provides methods for the treatment of *Chlamydia* infection that comprise incubating antigen presenting cells with a polypeptide of the present invention (or a polynucleotide that encodes such a polypeptide) to provide incubated antigen presenting cells and administering the incubated antigen presenting cells to the patient. Proliferated cells may, but need not, be cloned prior to administration to the patient. In certain embodiments, the antigen presenting cells are selected from the group consisting of dendritic cells, macrophages, monocytes, B-cells, and fibroblasts. Compositions for the treatment of *Chlamydia* infection comprising T cells or antigen presenting cells that have been incubated with a polypeptide or polynucleotide of the present invention are also provided. Within related aspects, vaccines are provided that comprise: (a) an antigen presenting cell that expresses a polypeptide as described above and (b) an immunostimulant.

The present invention further provides, within other aspects, methods for removing Chlamydial-infected cells from a biological sample, comprising contacting a biological sample with T cells that specifically react with a Chlamydial protein, wherein the step of contacting is performed under conditions and for a time sufficient to permit the removal of cells expressing the protein from the sample.

Within related aspects, methods are provided for inhibiting the development of Chlamydial infection in a patient, comprising administering to a patient a biological sample treated as described above. In further aspects of the subject invention, methods and diagnostic kits are provided for detecting *Chlamydia* infection in a patient. In one embodiment, the method comprises: (a) contacting a biological sample with at least one of the polypeptides or fusion proteins disclosed herein; and (b) detecting in the sample the presence of binding agents that bind to the polypeptide or fusion protein, thereby detecting *Chlamydia* infection in the biological sample. Suitable biological samples include whole blood, sputum, serum, plasma, saliva, cerebrospinal fluid and urine. In one embodiment, the diagnostic kits comprise one or more of the polypeptides or fusion proteins disclosed herein in combination with a detection reagent. In yet another embodiment, the diagnostic kits comprise either a monoclonal antibody or a polyclonal antibody that binds with a polypeptide of the present invention.

The present invention also provides methods for detecting *Chlamydia* infection comprising: (a) obtaining a biological sample from a patient; (b) contacting the sample with at least two oligonucleotide primers in a polymerase chain reaction, at least one of the oligonucleotide primers being specific for a polynucleotide sequence disclosed herein; and (c) detecting in the sample a polynucleotide sequence that amplifies in the presence of the oligonucleotide primers. In one embodiment, the oligonucleotide primer comprises at least about 10 contiguous nucleotides of a polynucleotide sequence peptide disclosed herein, or of a sequence that hybridizes thereto.

In a further aspect, the present invention provides a method for detecting *Chlamydia* infection in a patient comprising: (a) obtaining a biological sample from the patient; (b) contacting the sample with an oligonucleotide probe specific for a polynucleotide sequence disclosed herein; and (c) detecting in the sample a polynucleotide sequence that hybridizes to the oligonucleotide probe. In one embodiment, the oligonucleotide probe comprises at least about 15 contiguous nucleotides of a polynucleotide sequence disclosed herein, or a sequence that hybridizes thereto.

These and other aspects of the present invention will become apparent upon reference to the following detailed description. All references disclosed herein are hereby incorporated by reference in their entirety as if each was incorporated individually.

Sequence Identifiers

SEQ ID NO:1 sets forth a DNA sequence identified for clone E4-A2-39 (CT10 positive) that is 1311 bp and contains the entire ORF for CT460 (SWIB) and a partial ORF for CT461 (yael).

SEQ ID NO:2 sets forth a DNA sequence for clone E2-B10-52 (CT10 positive) that has a 1516 bp insert that contains partial ORFs for genes CT827 (nrdA-ribonucleoside reductase large chain) and CT828 (ndrB-ribonucleoside reductase small chain). These genes were not identified in a Ct L2 library screening.

SEQ ID NO:3 sets forth a DNA sequence for clone E1-B1-80 (CT10 positive) (2397 bp) that contains partial ORFs for several genes, CT812 (pmpD), CT015 (phoH ATPase), CT016 (hypothetical protein) and pGp1-D (*C. trachomatis* plasmid gene).

SEQ ID NO:4 sets forth a DNA sequence for clone E4-F9-4 (CT10, CL8, CT1, CT5, CT13, and CHH037 positive) that contains a 1094 bp insert that has a partial ORF for the gene CT316 (L7/L12 ribosomal protein) as well as a partial ORF for gene CT315 (RNA polymerase beta).

SEQ ID NO:5 sets forth a DNA sequence for clone E2-H6-40 (CT3 positive) that has a 2129 bp insert that contains the entire ORF for the gene CT288 and very small fragments of genes CT287 and CT289. Genes in this clone have not been identified in screening with a Ct L2 library.

SEQ ID NO:6 sets forth a DNA sequence for clone E5-D4-2 (CT3, CT10, CT1, CT5, CT12, and CHH037 positive) that has a 1828 bp insert that contains a partial ORF for gene CT378 (pgi), complete ORF for gene CT377 (ItuA) and a complete ORF for the gene CT376 (malate dehydrogenase). In addition, the patient lines CT10, CT1, CT5, CT12, and CHH037 also identified this clone.

SEQ ID NO:7 sets forth a DNA sequence for clone E6-C1-31 (CT3 positive) that has a 861 bp insert that contains a partial ORF for gene CT858.

SEQ ID NO:8 sets forth a DNA sequence for clone E9-E11-76 (CT3 positive) that contains a 763 bp insert that is an amino terminal region of the gene for CT798 (Glycogen synthase). This gene was not identified in a previous screening with a Ct L2 library.

SEQ ID NO:9 sets forth a DNA sequence for clone E2-A9-26 (CT1-positive) that contains part of the gene for ORF-3 which is found on the plasmid in *Chlamydia trachomatis*.

SEQ ID NO:10 sets forth a DNA sequence for clone E2-G8-94 (CT1-positive) that has the carboxy terminal end of Lpda gene as well as a partial ORF for CT556.

SEQ ID NO: 11 sets forth a DNA sequence for clone E1-H1-14 (CT1 positive) that has a 1474 bp insert that contains the amino terminal part of an Lpda ORF on the complementary strand.

SEQ ID NO: 12 sets forth a DNA sequence for clone E1-A5-53 (CT1 positive) that contains a 2017 bp insert that has an amino terminal portion of the ORF for dnak gene on the complementary strand, a partial ORF for the grpE gene (CT395) and a partial ORF for CT166.

SEQ ID NO: 13 sets forth a DNA sequence for clone E3-A1-50 (positive on CT1 line) that is 1199 bp and contains a carboxy terminal portion of the ORF for CT622.

SEQ ID NO: 14 sets forth a DNA sequence for clone E3-E2-22 that has 877 bp, containing a complete ORF for CT610 on the complementary strand, and was positive on both CT3 and CT10 lines.

SEQ ID NO: 15 sets forth the DNA sequence for clone E5-E2-10 (CT10 positive) which is 427 bp and contains a partial ORF for the major outer membrane protein omp1.

SEQ ID NO: 16 sets forth the DNA sequence for clone E2-D5-89 (516 bp) which is a CT10 positive clone that contains a partial ORF for pmpD gene (CT812).

SEQ ID NO: 17 sets forth the DNA sequence for clone E4-G9-75 (CT10 positive) which is 723 bp and contains a partial ORF for the amino terminal region of the pmpH gene (CT872).

SEQ ID NO: 18 sets forth the DNA sequence for clone E3-F2-37 (CT10, CT3, CT11, and CT13 positive-1377 bp insert) which contains a partial ORF for the tRNA-Trp (CT322) gene and a complete ORF for the gene secE (CT321).

SEQ ID NO: 19 sets forth a DNA sequence for clone E5-A11-8 (CT10 positive-1736 bp) which contains the complete ORF for groES (CT111) and a majority of the ORF for groEL (CT110).

SEQ ID NO: 20 sets forth the DNA sequence for clone E7-H11-61 (CT3 positive-1135 bp) which has partial inserts for fliA (CT061), tyrS (CT062), TSA (CT603) and a hypothetical protein (CT602).

SEQ ID NO: 21 sets forth a DNA sequence for clone E6-C8-95 which contains a 731 bp insert that was identified using the donor lines CT3, CT1, and CT12 line. This insert has a carboxy terminal half for the gene for the 60 kDa ORF.

SEQ ID NO: 22 sets forth the DNA sequence for clone E4-D2-79 (CT3 positive) which contains a 1181 bp insert that is a partial ORF for nrdA gene. The ORF for this gene was also identified from clone E2-B10-52 (CT10 positive).

SEQ ID NO: 23 sets forth the DNA sequence for clone E1-F9-79 (167 bp; CT11 positive) which contains a partial ORF for the gene CT133 on the complementary strand. CT133 is a predicted rRNA methylase.

SEQ ID NO: 24 sets forth the DNA sequence for clone E2-G12-52 (1265 bp; CT11 positive) which contains a partial ORF for clpB, a protease ATPase.

SEQ ID NO: 25 sets forth the DNA sequence for clone E4-H3-56 (463 bp insert; CT1 positive) which contains a partial ORF for the TSA gene (CT603) on the complementary strand.

SEQ ID NO: 26 sets forth the DNA sequence for clone E5-E9-3 (CT1 positive) that contains a 636 bp insert partially encoding the ORF for dnaK like gene. Part of this sequence was also identified in clone E1-A5-53.

SEQ ID NO:27 sets forth the full-length serovar E DNA sequence of CT875.

SEQ ID NO:28 sets for the full-length serovar E DNA sequence of CT622.

SEQ ID NO:29 sets forth the DNA sequence for clone E3-B4-18 (CT1 positive) that contains a 1224 bp insert containing 4 ORFs. The complete ORF for CT772, and the partial ORFs of CT771, CT191, and CT190.

SEQ ID NO:30 sets forth the DNA sequence for the clone E9-E10-51 (CT10 positive) that contains an 883 bp insert containing two partial ORF, CT680 and CT679.

SEQ ID NO:31 sets forth the DNA sequence of the clone E9-D5-8 (CT10, CTCT1, CT4, and CT11 positive) that contains a393 bp insert containing the partial ORF for CT680.

SEQ ID NO:32 sets forth the DNA sequence of the clone E7-B1-16 (CT10, CT3, CT5, CT11, CT13, and CHH037 positive) that contains a 2577 bp insert containing three ORFs, two full length ORFs for CT694 and CT695 and the third containing the N-terminal portion of CT969.

SEQ ID NO:33 sets forth the DNA sequence of the clone E9-G2-93 (CT10 positive) that contains a 554 bp insert containing a partial ORF for CT178.

SEQ ID NO:34 sets forth the DNA sequence of the clone E5-A8-85 (CT1 positive) that contains a 1433 bp insert containing two partial ORFs for CT875 and CT001.

SEQ ID NO:35 sets forth the DNA sequence of the clone E10-C6-45 (CT3 positive) that contains a 196 bp insert containing a partial ORF for CT827.

SEQ ID NO:36 sets forth the DNA sequence of the clone E7-H11-10 (CT3 positive) that contains a 1990 bp insert containing the partial ORFs of CT610 and CT613 and the complete ORFs of CT611 and CT612.

SEQ ID NO:37 sets forth the DNA sequence of the clone E2-F7-11 (CT3 and CT10 positive) that contains a 2093 bp insert. It contains a large region of CT609, a complete ORF for CT610 and a partial ORF for CT611.

SEQ ID NO:38 sets forth the DNA sequence of the cloneE3-A3-31 (CT1 positive) that contains an 1834 bp insert containing a large region of CT622.

SEQ ID NO:39 sets forth the DNA sequence of the clone E1-G9-23 (CT3 positive) that contains an 1180 bp insert containing almost the entire ORF for CT798.

SEQ ID NO:40 sets forth the DNA sequence of the clone E4-D6-21 (CT3 positive) that contains a 1297 bp insert containing the partial ORFs of CT329 and CT327 and the complete ORF of CT328.

SEQ ID NO:41 sets forth the DNA sequence of the clone E3-F3-18 (CT1 positive) that contains an 1141 bp insert containing the partial ORF of CT871.

SEQ ID NO:42 sets forth the DNA sequence of the clone E10-B2-57 (CT10 positive) that contains an 822 bp insert containing the complete ORF of CT066.

SEQ ID NO:43 sets forth the DNA sequence of the clone E3-F3-7 (CT1 positive) that contains a 1643 bp insert containing the partial ORFs of CT869 and CT870.

SEQ ID NO:44 sets forth the DNA sequence of the clone E10-H8-1 (CT3 and CT10 positive) that contains an 1862 bp insert containing the partial ORFs of CT871 and CT872.

SEQ ID NO:45 sets forth the DNA sequence of the clone E3-D10-46 (CT1, CT3, CT4, CT11, and CT12 positive) that contains a 1666 bp insert containing the partial ORFs for CT770 and CT773 and the complete ORFs for CT771 and CT722.

SEQ ID NO:46 sets forth the DNA sequence of the clone E2-D8-19 (CT1 positive) that contains a 2010 bp insert containing partial ORFs, ORF3 and ORF6, and complete ORFs, ORF4 and ORF5.

SEQ ID NO:47 sets forth the DNA sequence of the clone E4-C3-40 (CT10 positive) that contains a 2044 bp insert containing the partial ORF for CT827 and a complete ORF for CT828.

SEQ ID NO:48 sets forth the DNA sequence of the clone E3-H6-10 (CT12 positive) that contains a 3743 bp insert containing the partial ORFs for CT223 and CT229 and the complete ORFs for CT224 and CT224, CT225, CT226, CT227, and CT228.

SEQ ID NO:49 sets forth the DNA sequence for the *Chlamydia pneumoniae* homologue, CPn0454 of the *Chlamydia trachomatis* gene CT872.

SEQ ID NO:50 sets forth the DNA sequence for the *Chlamydia pneumoniae* homologue, CPn0187, of the *Chlamydia trachomatis* gene CT133.

SEQ ID NO:51 sets forth the DNA sequence for the *Chlamydia pneumoniae* homologue, CPn0075, of the *Chlamydia trachomatis* gene CT321.

SEQ ID NO:52 sets forth the DNA sequence for the *Chlamydia pneumoniae* homologue, CPn0074, of the *Chlamydia trachomatis* gene CT322.

SEQ ID NO:53 sets forth the DNA sequence for the *Chlamydia pneumoniae* homologue, CPn0948, of the *Chlamydia trachomatis* gene CT798.

SEQ ID NO:54 sets forth the DNA sequence for the *Chlamydia pneumoniae* homologue, CPn0985, of the *Chlamydia trachomatis* gene CT828.

SEQ ID NO:55 sets forth the DNA sequence for the *Chlamydia pneumoniae* homologue, CPn0984, of the *Chlamydia trachomatis* gene CT827.

SEQ ID NO:56 sets forth the DNA sequence for the *Chlamydia pneumoniae* homologue, CPn0062, of the *Chlamydia trachomatis* gene CT289.

SEQ ID NO:57 sets forth the DNA sequence for the *Chlamydia pneumoniae* homologue, CPn00065, of the *Chlamydia trachomatis* gene CT288.

SEQ ID NO:58 sets forth the DNA sequence for the *Chlamydia pneumoniae* homologue, CPn0438, of the *Chlamydia trachomatis* gene CT287.

SEQ ID NO:59 sets forth the DNA sequence for the *Chlamydia pneumoniae* homologue, CPn0963, of the *Chlamydia trachomatis* gene CT812.

SEQ ID NO:60 sets forth the DNA sequence for the *Chlamydia pneumoniae* homologue, CPn0778, of the *Chlamydia trachomatis* gene CT603.

SEQ ID NO:61 sets forth the DNA sequence for the *Chlamydia pneumoniae* homologue, CPn0503, of the *Chlamydia trachomatis* gene CT396.

SEQ ID NO:62 sets forth the DNA sequence for the *Chlamydia pneumoniae* homologue, CPn1016, of the *Chlamydia trachomatis* gene CT858.

SEQ ID NO:63 sets forth the DNA sequence for the *Chlamydia pneumoniae* homologue, CPn0728, of the *Chlamydia trachomatis* gene CT622.

SEQ ID NO:64 sets forth the DNA sequence for the *Chlamydia pneumoniae* homologue, CPn0557, of the *Chlamydia trachomatis* gene CT460.

SEQ ID NO:65 sets forth the amino acid sequence for the *Chlamydia pneumoniae* homologue, CPn0454, of the *Chlamydia trachomatis* gene CT872.

SEQ ID NO:66 sets forth the amino acid sequence for the *Chlamydia pneumoniae* homologue, CPn0187, of the *Chlamydia trachomatis* gene CT133.

SEQ ID NO:67 sets forth the amino acid sequence for the *Chlamydia pneumoniae* homologue, CPn0075, of the *Chlamydia trachomatis* gene CT321.

SEQ ID NO:68 sets forth the amino acid sequence for the *Chlamydia pneumoniae* homologue, CPn0074, of the *Chlamydia trachomatis* gene CT322.

SEQ ID NO:69 sets forth the amino acid sequence for the *Chlamydia pneumoniae* homologue, CPn0948, of the *Chlamydia trachomatis* gene CT798.

SEQ ID NO:70 sets forth the amino acid sequence for the *Chlamydia pneumoniae* homologue, CPn0985, of the *Chlamydia trachomatis* gene CT828.

SEQ ID NO:71 sets forth the amino acid sequence for the *Chlamydia pneumoniae* homologue, CPn0984, of the *Chlamydia trachomatis* gene CT827.

SEQ ID NO:72 sets forth the amino acid sequence for the *Chlamydia pneumoniae* homologue, CPn0062, of the *Chlamydia trachomatis* gene CT289.

SEQ ID NO:73 sets forth the amino acid sequence for the *Chlamydia pneumoniae* homologue, CPn0065, of the *Chlamydia trachomatis* gene CT288.

SEQ ID NO:74 sets forth the amino acid sequence for the *Chlamydia pneumoniae* homologue, CPn0438, of the *Chlamydia trachomatis* gene CT287.

SEQ ID NO:75 sets forth the amino acid sequence for the *Chlamydia pneumoniae* homologue, CPn0963, of the *Chlamydia trachomatis* gene CT812.

SEQ ID NO:76 sets forth the amino acid sequence for the *Chlamydia pneumoniae* homologue, CPn0778, of the *Chlamydia trachomatis* gene CT603.

SEQ ID NO:77 sets forth the amino acid sequence for the *Chlamydia pneumoniae* homologue, CPn1016, of the *Chlamydia trachomatis* gene CT858.

SEQ ID NO:78 sets forth the amino acid sequence for the *Chlamydia pneumoniae* homologue, CPn0728, of the *Chlamydia trachomatis* gene CT622.

SEQ ID NO:79 sets forth the amino acid sequence for the *Chlamydia pneumoniae* homologue, CPn0557, of the *Chlamydia trachomatis* gene CT460.

SEQ ID NO:80 sets forth the full-length serovar D DNA sequence of the *Chlamydia trachomatis* gene CT872.

SEQ ID NO:81 sets forth the full-length serovar D DNA sequence of the *Chlamydia trachomatis* gene CT828.

SEQ ID NO:82 sets forth the full-length serovar D DNA sequence of the *Chlamydia trachomatis* gene CT827.

SEQ ID NO:83 sets forth the full-length serovar D DNA sequence of the *Chlamydia trachomatis* gene CT812.

SEQ ID NO:84 sets forth the full-length serovar D DNA sequence of the *Chlamydia trachomatis* gene CT798.

SEQ ID NO:85 sets forth the full-length serovar D DNA sequence of the *Chlamydia trachomatis* gene CT681 (MompF).

SEQ ID NO:86 sets forth the full-length serovar D DNA sequence of the *Chlamydia trachomatis* gene CT603.

SEQ ID NO:87 sets forth the full-length serovar D DNA sequence of the *Chlamydia trachomatis* gene CT460.

SEQ ID NO:88 sets forth the full-length serovar D DNA sequence of the *Chlamydia trachomatis* gene CT322.

SEQ ID NO:89 sets forth the full-length serovar D DNA sequence of the *Chlamydia trachomatis* gene CT321.

SEQ ID NO:90 sets forth the full-length serovar D DNA sequence of the *Chlamydia trachomatis* gene CT289.

SEQ ID NO:91 sets forth the full-length serovar D DNA sequence of the *Chlamydia trachomatis* gene CT288.

SEQ ID NO:92 sets forth the full-length serovar D DNA sequence of the *Chlamydia trachomatis* gene CT287.

SEQ ID NO:93 sets forth the full-length serovar D DNA sequence of the *Chlamydia trachomatis* gene CT133.

SEQ ID NO:94 sets forth the full-length serovar D DNA sequence of the *Chlamydia trachomatis* gene CT113.

SEQ ID NO:95 sets forth the full-length serovar D amino acid sequence of the *Chlamydia trachomatis* gene CT872.

SEQ ID NO:96 sets forth the full-length serovar D amino acid sequence of the *Chlamydia trachomatis* gene CT828.

SEQ ID NO:97 sets forth the full-length serovar D amino acid sequence of the *Chlamydia trachomatis* gene CT827.

SEQ ID NO:98 sets forth the full-length serovar D amino acid sequence of the *Chlamydia trachomatis* gene CT812.

SEQ ID NO:99 sets forth the full-length serovar D amino acid sequence of the *Chlamydia trachomatis* gene CT798.

SEQ ID NO:100 sets forth the full-length serovar D amino acid sequence of the *Chlamydia trachomatis* gene CT681.

SEQ ID NO:101 sets forth the full-length serovar D amino acid sequence of the *Chlamydia trachomatis* gene CT603.

SEQ ID NO:102 sets forth the full-length serovar D amino acid sequence of the *Chlamydia trachomatis* gene CT460.

SEQ ID NO:103 sets forth the full-length serovar D amino acid sequence of the *Chlamydia trachomatis* gene CT322.

SEQ ID NO:104 sets forth the full-length serovar D amino acid sequence of the *Chlamydia trachomatis* gene CT321.

SEQ ID NO:105 sets forth the full-length serovar D amino acid sequence of the *Chlamydia trachomatis* gene CT289.

SEQ ID NO:106 sets forth the full-length serovar D amino acid sequence of the *Chlamydia trachomatis* gene CT288.

SEQ ID NO:107 sets forth the full-length serovar D amino acid sequence of the *Chlamydia trachomatis* gene CT287.

SEQ ID NO:108 sets forth the full-length serovar D amino acid sequence of the *Chlamydia trachomatis* gene CT133.

SEQ ID NO:109 sets forth the full-length serovar D amino acid sequence of the *Chlamydia trachomatis* gene CT113.

SEQ ID NO:110 sets forth the DNA sequence for the *Chlamydia pneumoniae* homologue, CPn0695, of the *Chlamydia trachomatis* gene CT681.

SEQ ID NO:111 sets forth the DNA sequence for the *Chlamydia pneumoniae* homologue, CPn0144, of the *Chlamydia trachomatis* gene CT113.

SEQ ID NO:112 sets forth the amino acid sequence for the *Chlamydia pneumoniae* homologue, CPn0695, of the *Chlamydia trachomatis* gene CT681.

SEQ ID NO:113 sets forth the amino acid sequence for the *Chlamydia pneumoniae* homologue, CPn0144, of the *Chlamydia trachomatis* gene CT113.

SEQ ID NO:114 sets forth the DNA sequence of the clone E7-B12-65 (CHH037 positive) that contains a 1179 bp insert containing complete ORF for 376.

SEQ ID NO:115 sets forth the DNA sequence of the clone E4-H9-83 (CHH037 positive) that contains the partial ORF for the heat shock protein GroEL (CT110).

SEQ ID NO:116 sets forth the DNA sequence of the clone E9-B10-52 (CHH037 positive) that contains the partial ORF for the the gene yscC (CT674).

SEQ ID NO:117 sets forth the DNA sequence of the clone E7-A7-79 (CHH037 positive) that contains the complete ORF for the histone like development gene hctA (CT743) and a partial ORF for the rRNA methyltransferase gene ygcA (CT742).

SEQ ID NO:118 sets forth the DNA sequence of the clone E2-D11-18 (CHH037 positive) that contains the partial ORF for hcta (CT743).

SEQ ID NO:119 sets forth the DNA sequence for the *Chlamydia trachomatis* serovar E hypothetical protein CT694.

SEQ ID NO:120 sets forth the DNA sequence for the *Chlamydia trachomatis* serovar E hypothetical protein CT695.

SEQ ID NO:121 sets forth the DNA sequence for the *Chlamydia trachomatis* serovar E L1 ribosomal protein.

SEQ ID NO:122 sets forth the amino acid sequence for the *Chlamydia trachomatis* serovar E hypothetical protein CT694.

SEQ ID NO:123 sets forth the amino acid sequence for the *Chlamydia trachomatis* serovar E hypothetical protein CT695.

SEQ ID NO:124 sets forth the amino acid sequence for the *Chlamydia trachomatis* serovar E L1 ribosomal protein.

SEQ ID NO:125 sets forth the DNA sequence of the clone E9-H6-15 (CT3 positive) that contains the partial ORF for the pmpB gene (CT413).

SEQ ID NO:126 sets forth the DNA sequence of the clone E3-D10-87 (CT1 positive) that contains the partial ORFs for the hypothetical genes CT388 and CT389.

SEQ ID NO:127 sets forth the DNA sequence of the clone E9-D6-43 (CT3 positive) that contains the partial ORF for the CT858.

SEQ ID NO:128 sets forth the DNA sequence of the clone E3-D10-4 (CT1 positive) that contains the partial ORF for pGP3-D, an ORF encoded on the plasmid pCHL1.

SEQ ID NO:129 sets forth the DNA sequence of the clone E3-G8-7 (CT1 positive) that contains the partial ORFs for the CT557 (LpdA) and CT558 (LipA).

SEQ ID NO:130 sets forth the DNA sequence of the clone E3-F11-32 (CT1 positive) that contains the partial ORF for pmpD (CT812).

SEQ ID NO:131 sets forth the DNA sequence of the clone E2-F8-5 (CT12 positive) that contains the complete ORF for the 15 kDa ORF (CT442) and a partial ORF for the 60 kDa ORF (CT443).

SEQ ID NO:132 sets forth the DNA sequence of the clone E2-G4-39 (CT12 positive) that contains the partial ORF for the 60 kDa ORF (CT443).

SEQ ID NO:133 sets forth the DNA sequence of the clone E9-D1-16 (CT10 positive) that contains the partial ORF for pmpH (CT872).

SEQ ID NO:134 sets forth the DNA sequence of the clone E3-F3-6 (CT1 positive) that contains the partial ORFs for the genes accB (CT123), L1 ribosomal (CT125) and S9 ribosomal (CT126).

SEQ ID NO:135 sets forth the DNA sequence of the clone E2-D4-70 (CT12 positive) that contains the partial ORF for the pmpC gene (CT414).

SEQ ID NO:136 sets forth the DNA sequence of the clone E5-A1-79 (CT1 positive) that contains the partial ORF for ydhO (CT127), a complete ORF for S9 ribosomal gene (CT126), a complete ORF for the L1 ribosomal gene (CT125) and a partial ORF for accC (CT124).

SEQ ID NO:137 sets forth the DNA sequence of the clone E1-F7-16 (CT12, CT3, and CT11 positive) that contains the partial ORF for the ftsH gene (CT841) and the entire ORF for the pnp gene (CT842).

SEQ ID NO:138 sets forth the DNA sequence of the clone E1-D8-62 (CT12 positive) that contains the partial ORFs for the ftsH gene (CT841) and for the pnp gene (CT842).

SEQ ID NO:139 sets forth the amino acid sequence for the serovar E protein CT875.

SEQ ID NO:140 sets forth the amino acid sequence for the serovar E protein CT622.

SEQ ID NO:141 sets forth the DNA sequence for the clone E8-C12-38, identified using the line CHH042 that contains the partial ORFs for sfhB (CT658) and CT659.

SEQ ID NO:142 sets forth the DNA sequence for the clone E1-D12-36, identified using the line CHH042 that contains the partial ORFs for mreB (CT709) (CT658) and pckA (CT710).

SEQ ID NO:143 sets forth the DNA sequence for the clone E8-D1-46, identified using the line CHH037 that contains the almost complete ORF for the pepA gene (CT045).

SEQ ID NO:144 sets forth the DNA sequence for the clone E10-A11-10, identified using the line CHH007 that contains the partial ORFs for yscU (CT091) and truB gene (CT094) as well as complete ORFs for ychF (CT092) and ribF (CT093).

SEQ ID NO:145 sets forth the DNA sequence for the clone E8-B12-80, identified using the line CHH037 that contains a partial ORF for the dag_2 gene (CT735), a short fragment of the SET domain protein (CT737), as well as a complete ORF for ybcL (CT736).

SEQ ID NO:146 sets forth the DNA sequence for the clone E2-A8-70, identified using the line CHH037 that contains partial ORFs for the mutS gene (CT792) and the dag_2 gene (CT735) as well as a complete ORF for the ybcL gene (CT736).

SEQ ID NO:147 sets forth the DNA sequence for the clone E10-C1-47, identified using the line CHH037 that contains the partial ORFs for the yael gene (CT461) and the prfB gene (CT459) as well as a complete ORF for the SWIB gene (CT460).

SEQ ID NO:148 sets forth the DNA sequence for the clone E8-G7-86, identified using the line CHH037 that contains partial ORFs for the mesJ gene (CT840) and the ftsH gene (CT841).

SEQ ID NO:149 sets forth the DNA sequence for the clone E3-E6-84, identified using the line CHH037 that contains partial ORFs for the pmpC gene (CT414) and the hypothetical protein CT611.

SEQ ID NO:150 sets for the DNA sequence for the clone E2-A11-49, identified using the patient line CHH042, that contains partial ORFs for the HAD superfamily (CT103) and the hypothetical protein CT105, as well as a complete ORF for fabl (CT104).

SEQ ID NO:151 sets for the DNA sequence for the clone E9-E6-4, identified using the patient line CHH042, it contains a complete ORF for the hypothetical protein CT659 and a partial ORF for gyrA-2 (CT660).

SEQ ID NO:152 sets for the DNA sequence for the clone E4-G8-49, identified using the patient line CHH042, it contains partial ORFs for the genes pckA (CT710) and mreB (CT709), as well as a partial ORF for the pGP2-D sequence derived from the plasmid.

SEQ ID NO:153 sets for the DNA sequence for the clone E10-A8-16, identified using the patient line CHH042, it contains partial ORFs for the genes rS3 (CT522) and rL3 (CT528), as well as complete ORFs for the genes rL22 (CT523), rS19 (CT524), rL2 (CT525), rL23 (CT526) and rL4 (CT527).

SEQ ID NO:154 sets for the DNA sequence for the clone E10-F12-58, identified using the patient line CHH042, that contains partial ORFs for the genes mhpA (CT148), rL16 (CT521), and rL22 (CT523) as well as complete ORFs for the genes rS3 (CT522), rL22 (CT523) and rS19 (CT524).

SEQ ID NO:155 sets for the DNA sequence for the clone E10-F12-42, identified using the patient line CHH042, that contains partial ORFs for the genes rS3 (CT522) and rL23 (CT526), as well as complete ORFs for the genes rL22 (CT523), rS19 (CT524) and rL2 (CT525).

SEQ ID NO:156 sets for the DNA sequence for the clone E2-C3-27, identified using the patient line CHH042, that contains partial ORFs for the genes rL16 (CT521) and rS19 (CT524), as well as complete ORFs for the genes rS3 (CT522) and rL22 (CT523).

SEQ ID NO:157 sets forth the DNA sequence for the clone E2-A11-49, identified using the patient CHH037, that contains partial ORFs for the ftsH gene (CT841), pGP7-D and pGP5-D, as well as a complete ORF for pGP6-D.

SEQ ID NO:158 sets forth a DNA sequence corresponding to the passenger domain of pmpI.

SEQ ID NO:159 sets forth a DNA sequence corresponding to the passenger domain of pmpH.

SEQ ID NO:160 sets forth a DNA sequence corresponding to the passenger domain of pmpG.

SEQ ID NO:161 sets forth a DNA sequence corresponding to the passenger domain of pmpF.

SEQ ID NO:162 sets forth a DNA sequence corresponding to the passenger domain of pmpE.

SEQ ID NO:163 sets forth a DNA sequence corresponding to the passenger domain of pmpD.

SEQ ID NO:164 sets forth a DNA sequence corresponding to the passenger domain of pmpC.

SEQ ID NO:165 sets forth a DNA sequence corresponding to the passenger domain of pmpB.

SEQ ID NO:166 sets forth a DNA sequence corresponding to the passenger domain of pmpA.

SEQ ID NO:167 sets forth an amino acid sequence corresponding to the passenger domain of pmpI.

SEQ ID NO:168 sets forth an amino acid sequence corresponding to the passenger domain of pmpH.

SEQ ID NO:169 sets forth an amino acid sequence corresponding to the passenger domain of pmpG.

SEQ ID NO:170 sets forth an amino acid sequence corresponding to the passenger domain of pmpF.

SEQ ID NO:171 sets forth an amino acid sequence corresponding to the passenger domain of pmpE.

SEQ ID NO:172 sets forth an amino acid sequence corresponding to the passenger domain of pmpD.

SEQ ID NO:173 sets forth an amino acid sequence corresponding to the passenger domain of pmpC.

SEQ ID NO:174 sets forth an amino acid sequence corresponding to the passenger domain of pmpB.

SEQ ID NO:175 sets forth an amino acid sequence corresponding to the passenger domain of pmpA.

DESCRIPTION OF ILLUSTRATIVE EMBODIMENTS

As noted above, the present invention is generally directed to compositions and methods for the diagnosis and treatment of Chlamydial infection. In one aspect, the compositions of the subject invention include polypeptides that comprise at least one immunogenic portion of a *Chlamydia* antigen, or a variant thereof.

In specific embodiments, the subject invention discloses polypeptides comprising an immunogenic portion of a *Chlamydia* antigen, wherein the *Chlamydia* antigen comprises an amino acid sequence encoded by a polynucleotide molecule including a sequence selected from the group consisting of (a) nucleotide sequences recited in SEQ ID NO:1–48, 114–121, 125–138, and 141–166 (b) the complements of said nucleotide sequences, and (c) variants of such sequences.

Polynucleotide Compositions

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

"Isolated," as used herein, means that a polynucleotide is substantially away from other coding sequences, and that the DNA segment does not contain large portions of unrelated coding DNA, such as large chromosomal fragments or other functional genes or polypeptide coding regions. Of course, this refers to the DNA segment as originally isolated, and does not exclude genes or coding regions later added to the segment by the hand of man.

As will be recognized by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native *Chlamydia* sequence or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native *Chlamydia* protein. The effect on the immunogenicity of the encoded polypeptide may generally be assessed as described herein. The term "Variants" also encompasses homologous genes of xenogenic origin.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numetical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, the present invention encompasses polynucleotide and polypeptide sequences having substantial identity to the sequences disclosed herein, for example those comprising at least 50% sequence identity, preferably at least 55%, 60%, 65%, 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Probes and Primers

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10–14, 15–20, 30, 50, or even of 100–200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15–25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequence set forth in SEQ ID NO:1–48, 114–121, 125–138, and 141–166, or to any continuous portion of the sequence, from about 15–25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

Polynucleotide Identification and Characterization

Polynucleotides may be identified, prepared and/or manipulated using any of a variety of well established techniques. For example, a polynucleotide may be identified, by screening a microarray of cDNAs for *Chlamydia* expression. Such screens may be performed, for example, using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polynucleotides may be amplified from cDNA prepared from cells expressing the proteins described herein. Such polynucleotides may be amplified via polymerase chain reaction (PCR). For this approach, sequence specific primers may be designed based on the sequences provided herein, and may be purchased or synthesized.

An amplified portion of a polynucleotide of the present invention may be used to isolate a full length gene from a suitable library (e.g., *Chlamydia* cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, after glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980)

Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202–204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503–5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516–544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307–311. Alternatively, plant promoters such as the small subunit of RUBISCO or heat shock promoters may be used (Coruzzi, G. et al. (1984) *EMBO J.* 3:1671–1680; Broglie, R. et al. (1984) *Science* 224:838–843; and Winter, J. et al. (1991) *Results Probl. Cell Differ.* 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard, E. K. et al. (1994) *Proc. Natl. Acad. Sci.* 91:3224–3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223–32) and adenine phosphoribosyltransferase (Lowy, I. et al. (1990) *Cell* 22:817–23) genes which can be employed in tk.sup.- or aprt.sup.- cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides, neomycin and G-418 (Colbere-Garapin, F. et al (1981) *J. Mol. Biol.* 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047–51). Recently, the use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, endlabeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263–281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441–453).

In addition to recombinant production methods, polypeptides of the invention, and fragments thereof, may be produced by direct peptide synthesis using solid-phase techniques (Merrifield J. (1963) *J. Am. Chem. Soc.* 85:2149–2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Site-Specific Mutagenesis

Site-specific mutagenesis is a technique useful in the preparation of individual peptides, or biologically functional equivalent polypeptides, through specific mutagenesis of the underlying polynucleotides that encode them. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to after one or more properties of the encoded polypeptide, such as the antigenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptideencoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

Polynucleotide Amplification Techniques

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308 (specifically incorporated herein by reference in its entirety). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Intl. Pat. Appl. Publ. No. PCT/US87/00880, incorporated herein by reference in its entirety, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Sequences can also be detected using a cyclic probe reaction (CPR). In CPR, a probe having a 3' and 5' sequences of non-target DNA and an internal or "middle" sequence of the target protein specific RNA is hybridized to DNA which is present in a sample. Upon hybridization, the reaction is treated with RNaseH, and the products of the probe are identified as distinctive products by generating a signal that is released after digestion. The original template is annealed to another cycling probe and the reaction is repeated. Thus, CPR involves amplifying a signal generated by hybridization of a probe to a target gene specific expressed nucleic acid.

Still other amplification methods described in Great Britain Pat. Appl. No. 2 202 328, and in PCT Intl. Pat. Appl. Publ. No. PCT/US89/01025, each of which is incorporated herein by reference in its entirety, may be used in accordance with the present invention. In the former application, "modified" primers are used in a PCR-like, template and enzyme dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; PCT Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer that has sequences specific to the target sequence. Following polymerization, DNA/RNA hybrids are digested with RNase H while double stranded DNA molecules are heat-denatured again. In either case the single stranded DNA is made fully double stranded by addition of second target-specific primer, followed by polymerization. The double stranded DNA molecules are then multiply transcribed by a polymerase such as T7 or SP6. In an isothermal cyclic reaction, the RNAs are reverse transcribed into DNA, and transcribed once again with a polymerase such as T7 or SP6. The resulting products, whether truncated or complete, indicate target-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "TRACE" (Frohman, 1990), and "one-sided PCR" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

Biological Functional Equivalents

Modification and changes may be made in the structure of the polynucleotides and polypeptides of the present invention and still obtain a functional molecule that encodes a polypeptide with desirable characteristics. As mentioned above, it is often desirable to introduce one or more mutations into a specific polynucleotide sequence. In certain circumstances, the resulting encoded polypeptide sequence is altered by this mutation, or in other cases, the sequence of the polypeptide is unchanged by one or more mutations in the encoding polynucleotide.

When it is desirable to alter the amino acid sequence of a polypeptide to create an equivalent, or even an improved, second-generation molecule, the amino acid changes may be achieved by changing one or more of the codons of the encoding DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE I

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |

TABLE I-continued

| Amino Acids | | | Codons | | | | | |
|---|---|---|---|---|---|---|---|---|
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

In Vivo Polynucleotide Delivery Techniques

In additional embodiments, genetic constructs comprising one or more of the polynucleotides of the invention are introduced into cells in vivo. This may be achieved using any of a variety or well known approaches, several of which are outlined below for the purpose of illustration.

1. Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) express a polynucleotide that has been cloned therein in a sense or antisense orientation. Of course, in the context of an antisense construct, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et at., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1 deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Strafford-Perricaudet and Perricaudet, 1991; Stratford-Perricaudet et al, 1990; Rich et al., 1993). Studies in administering recombinant adenovirus to different tissues include trachea instillation (Rosenfeld et at., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

2. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

3. Adeno-Associated Viruses

AAV (Ridgeway, 1988; Hermonat and Muzycska, 1984) is a parovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka and McLaughlin, 1988).

The AAV DNA is approximately 4.7 kilobases long. It contains two open reading frames and is flanked by two ITRs (FIG. 2). There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat and Muzyczka, 1984).

There are several factors that prompted researchers to study the possibility of using rAAV as an expression vector. One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response.

4. Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, 1988; Coupar et al., 1988), lentiviruses, polio viruses and herpes viruses may be employed. They offer several attractive features for various mammalian cells (Friedmann, 1989; Ridgeway, 1988; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liverdirected gene transfer. Chang et al. (1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

5. Non-Viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

Antisense Oligonucleotides

The end result of the flow of genetic information is the synthesis of protein. DNA is transcribed by polymerases into messenger RNA and translated on the ribosome to yield a folded, functional protein. Thus there are several steps along the route where protein synthesis can be inhibited. The native DNA segment coding for a polypeptide described herein, as all such mammalian DNA strands, has two strands: a sense strand and an antisense strand held together by hydrogen bonding. The messenger RNA coding for polypeptide has the same nucleotide sequence as the sense DNA strand except that the DNA thymidine is replaced by uridine. Thus, synthetic antisense nucleotide sequences will bind to a mRNA and inhibit expression of the protein encoded by that mRNA.

The targeting of antisense oligonucleotides to mRNA is thus one mechanism to shut down protein synthesis, and, consequently, represents a powerful and targeted therapeutic approach. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829, each specifically incorporated herein by reference in its entirety). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., 1988; Vasanthakumar and Ahmed, 1989; Peris et al., 1998; U.S. Pat. No. 5,801,154; U.S. Pat. No. 5,789,573; U.S. Pat. No. 5,718,709 and U.S. Pat. No. 5,610,288, each specifically incorporated herein by reference in its entirety). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683, each specifically incorporated herein by reference in its entirety).

Therefore, in exemplary embodiments, the invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein.

Selection of antisense compositions specific for a given gene sequence is based upon analysis of the chosen target sequence (i.e. in these illustrative examples the rat and human sequences) and determination of secondary structure, $T_m$, binding energy, relative stability, and antisense compositions were selected based upon their relative inability to form dimers, hairpins, or other secondary structures that would reduce or prohibit specific binding to the target mRNA in a host cell.

Highly preferred target regions of the mRNA, are those which are at or near the AUG translation initiation codon, and those sequences which were substantially complementary to 5' regions of the mRNA. These secondary structure analyses and target site selection considerations were performed using v.4 of the OLIGO primer analysis software (Rychlik, 1997) and the BLASTN 2.0.5 algorithm software (Altschul et al., 1997).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., 1997). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane (Morris et al., 1997).

Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis $\delta$ virus, group I intron or RNaseP RNA (in association with an RNA guide sequence) or Neurospora VS RNA motif. Examples of hammerhead motifs are described by Rossi et al. (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis $\delta$ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described in (U.S. Pat. No. 4,987,071, specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents which exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see e.g., Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al., 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes may be used as diagnostic tools to examine genetic drift and mutations within diseased cells. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These studies will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes are well known in the art, and include detection of the presence of mRNA associated with an IL-5 related condition. Such RNA is detected by determining the presence of a cleavage product after treatment with a ribozyme using standard methodology.

Peptide Nucleic Acids

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (1997) and is incorporated herein by reference. As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethylglycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass.). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography (Norton et al., 1995) providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Ulmann et al., 1996; Koch et al., 1995; Orum et a., 1995; Footer et al., 1996; Griffith et al., 1995; Kremsky et al., 1996; Pardridge et al., 1995; Boffa et al., 1995; Landsdorp et al., 1996; Gambacorti-Passerini et al., 1996; Armitage et al., 1997; Seeger et al., 1997; Ruskowski et al., 1997). U.S. Pat. No. 5,700,922 discusses PNA-DNA-PNA chimeric molecules and their uses in diagnostics, modulating protein in organisms, and treatment of conditions susceptible to therapeutics.

In contrast to DNA and RNA, which contain negatively charged linkages, the PNA backbone is neutral. In spite of this dramatic alteration, PNAs recognize complementary DNA and RNA by Watson-Crick pairing (Egholm et al., 1993), validating the initial modeling by Nielsen et al. (1991). PNAs lack 3' to 5' polarity and can bind in either parallel or antiparallel fashion, with the antiparallel mode being preferred (Egholm et al., 1993).

Hybridization of DNA oligonucleotides to DNA and RNA is destabilized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono- or divalent cations (Nielsen et al., 1991). The enhanced rate and affinity of hybridization are significant because they are responsible for the surprising ability of PNAs to perform strand invasion of complementary sequences within relaxed doublestranded DNA. In addition, the efficient hybridization at inverted repeats suggests that PNAs can recognize secondary structure effectively within double-stranded DNA. Enhanced recognition also occurs with PNAs immobilized on surfaces, and Wang et al. have shown that support-bound PNAs can be used to detect hybridization events (Wang et al., 1996).

One might expect that tight binding of PNAs to complementary sequences would also increase binding to similar (but not identical) sequences, reducing the sequence specificity of PNA recognition. As with DNA hybridization, however, selective recognition can be achieved by balancing oligomer length and incubation temperature. Moreover, selective hybridization of PNAs is encouraged by PNA-DNA hybridization being less tolerant of base mismatches than DNA-DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1996; Carlsson et al., 1996; Thiede et al., 1996; Webb and Hurskainen, 1996; Perry-O'Keefe et al., 1996).

High-affinity binding provides clear advantages for molecular recognition and the development of new applications for PNAs. For example, 11–13 nucleotide PNAs inhibit the activity of telomerase, a ribonucleo-protein that extends telomere ends using an essential RNA template, while the analogous DNA oligomers do not (Norton et al., 1996).

Neutral PNAs are more hydrophobic than analogous DNA oligomers, and this can lead to difficulty solubilizing them at neutral pH, especially if the PNAs have a high purine content or if they have the potential to form secondary structures. Their solubility can be enhanced by attaching one or more positive charges to the PNA termini (Nielsen et al., 1991).

Findings by Allfrey and colleagues suggest that strand invasion will occur spontaneously at sequences within chromosomal DNA (Boffa et al., 1995; Boffa et al., 1996). These studies targeted PNAs to triplet repeats of the nucleotides CAG and used this recognition to purify transcriptionally active DNA (Boffa et al., 1995) and to inhibit transcription (Boffa et al., 1996). This result suggests that if PNAs can be delivered within cells then they will have the potential to be general sequence-specific regulators of gene expression. Studies and reviews concerning the use of PNAs as antisense and anti-gene agents include Nielsen et al. (1993b), Hanvey et al. (1992), and Good and Nielsen (1997). Koppelhus et al. (1997) have used PNAs to inhibit HIV-1 inverse transcription, showing that PNAs may be used for antiviral therapies.

Methods of characterizing the antisense binding properties of PNAs are discussed in Rose (1993) and Jensen et al. (1997). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et a., 1995), isolation of transcriptionally active genes (Boffa et al., 1995), blocking of transcription factor binding (Vickers et al., 1995), genome cleavage (Veselkov et al., 1996), biosensors (Wang et al., 1996), in situ hybridization (Thisted et al., 1996), and in a alternative to Southern blotting (Perry-O'Keefe, 1996).

Polyypetide Compositions and Uses

The present invention, in other aspects, provides polypeptide compositions. Generally, a polypeptide of the invention will be an isolated polypeptide (or an epitope, variant, or active fragment thereof) derived from a mammalian species. Preferably, the polypeptide is encoded by a polynucleotide sequence disclosed herein or a sequence which hybridizes under moderately stringent conditions to a polynucleotide sequence disclosed herein. Alternatively, the polypeptide may be defined as a polypeptide which comprises a contiguous amino acid sequence from an amino acid sequence disclosed herein, or which polypeptide comprises an entire amino acid sequence disclosed herein.

Likewise, a polypeptide composition of the present invention is understood to comprise one or more polypeptides that are capable of eliciting antibodies that are immunologically reactive with one or more polypeptides encoded by one or more contiguous nucleic acid sequences contained in SEQ ID NO:148, 114–121, 125–138 and 141–166, or to active fragments, or to variants thereof, or to one or more nucleic acid sequences which hybridize to one or more of these sequences under conditions of moderate to high stringency.

As used herein, an active fragment of a polypeptide includes a whole or a portion of a polypeptide which is modified by conventional techniques, e.g., mutagenesis, or by addition, deletion, or substitution, but which active fragment exhibits substantially the same structure function, antigenicity, etc., as a polypeptide as described herein.

In certain illustrative embodiments, the polypeptides of the invention will comprise at least an immunogenic portion of a Chlamydia protein or a variant thereof, as described herein. Proteins that are Chlamydia proteins generally also react detectably within an immunoassay (such as an ELISA) with antisera from a patient with a Chlamydial infection. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a Chlamydia protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, Fundamental Immunology, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native Chlamydia protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, Antibodies: A Laboratory Manual, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native Chlamydia protein. A polypeptide "variant," as used herein, is a polypeptide that differs from a native Chlamydia protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants encompassed by the present invention include those exhibiting at least about 70%, 75%, 80%, 85%, 90%, 91%, 92%, 93%, 94%, 95%, 96%, 97%, 98%, or 99% or more identity (determined as described above) to the polypeptides disclosed herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or posttranslationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. Coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known *Chlamydia* protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided. Such proteins comprise a polypeptide as described herein together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the nonstructural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Illustrative Therapeutic Compositions and Uses

In another aspect, the present invention provides methods for using one or more of the above polypeptides or fusion proteins (or polynucleotides encoding such polypeptides or fusion proteins) to induce protective immunity against Chlamydial infection in a patient. As used herein, a "patient" refers to any warm-blooded animal, preferably a human. A patient may be afflicted with a disease, or may be free of detectable disease and/or infection. In other words, protective immunity may be induced to prevent or treat Chlamydial infection.

In this aspect, the polypeptide, fusion protein or polynucleotide molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and an immunostimulant, such as an adjuvant or a liposome (into which the polypeptide is incorporated). Such pharmaceutical compositions and vaccines may also contain other *Chlamydia* antigens, either incorporated into a combination polypeptide or present within a separate polypeptide.

Alternatively, a vaccine may contain polynucleotides encoding one or more polypeptides or fusion proteins as described above, such that the polypeptide is generated in situ. In such vaccines, the polynucleotides may be present within any of a variety of delivery systems known to those of ordinary skill in the art, including nucleic acid expression systems, bacterial and viral expression systems. Appropriate nucleic acid expression systems contain the necessary polynucleotide sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface. In a preferred embodiment, the polynucleotides may be introduced using a viral expression system (e.g., vaccinia or other pox virus, retrovirus, or adenovirus), which may involve the use of a non-pathogenic (defective) virus. Techniques for incorporating polynucleotides into such expression systems are well known to those of ordinary skill in the art. The polynucleotides may also be administered as "naked" plasmid vectors as described, for example, in Ulmer et al., *Science* 259:1745–1749, 1993 and reviewed by Cohen, *Science* 259:1691–1692, 1993. Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The uptake of naked polynucleotides may be increased by incorporating the polynucleotides into and/or onto biodegradable beads, which are efficiently transported into the cells. The preparation and use of such systems is well known in the art.

In a related aspect, a polynucleotide vaccine as described above may be administered simultaneously with or sequentially to either a polypeptide of the present invention or a known *Chlamydia* antigen. For example, administration of polynucleotides encoding a polypeptide of the present invention, either "naked" or in a delivery system as described above, may be followed by administration of an antigen in order to enhance the protective immune effect of the vaccine.

Polypeptides and polynucleotides disclosed herein may also be employed in adoptive immunotherapy for the treatment of Chlamydial infection. Adoptive immunotherapy may be broadly classified into either active or passive immunotherapy. In active immunotherapy, treatment relies on the in vivo stimulation of the endogenous host immune system with the administration of immune response-modifying agents (for example, vaccines, bacterial adjuvants, and/or cytokines).

In passive immunotherapy, treatment involves the delivery of biologic reagents with established immune reactivity (such as effector cells or antibodies) that can directly or indirectly mediate anti-*Chlamydia* effects and does not necessarily depend on an intact host immune system. Examples of effector cells include T lymphocytes (for example, CD8+ cytotoxic T-lymphocyte, CD4+ T-helper), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage, monocyte, fibroblast, or B-cells, may be pulsed with immunoreactive polypeptides, or polynucleotide sequence(s) may be introduced into antigen presenting cells, using a variety of standard techniques well known in the art. For example, antigen presenting cells may be transfected or transduced with a polynucleotide sequence, wherein said sequence contains a promoter region appropriate for increasing expression, and can be expressed as part of a recombinant virus or other expression system. Several viral vectors may be used to transduce an antigen presenting cell, including pox virus, vaccinia virus, and adenovirus; also, antigen presenting cells may be transfected with polynucleotide sequences disclosed herein by a variety of means, including gene-gun technology, lipid-mediated delivery, electroporation, osmotic shock, and particlate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al., "Therapy With Cultured T Cells: Principles Revisited," *Immunological Reviews*, 157:177, 1997).

The polypeptides disclosed herein may also be employed to generate and/or isolate chlamydial-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ or CD4+ T-cell clones may be isolated from the patient, expanded using standard tissue culture techniques, and returned to the patient.

Alternatively, peptides corresponding to immunogenic portions of the polypeptides may be employed to generate *Chlamydia* reactive T cell subsets by selective in vitro stimulation and expansion of autologous T cells to provide antigen-specific T cells which may be subsequently transferred to the patient as described, for example, by Chang et al., (*Crit. Rev. Oncol. Hematol.*, 22(3), 213, 1996). Cells of the immune system, such as T cells, may be isolated from the peripheral blood of a patient, using a commercially available cell separation system, such as Isolex™ System, available from Nexell Therapeutics, Inc. Irvine, Calif. The separated cells are stimulated with one or more of the immunoreactive polypeptides contained within a delivery vehicle, such as a microsphere, to provide antigen-specific T cells. The population of antigen-specific T cells is then expanded using standard techniques and the cells are administered back to the patient.

In other embodiments, T-cell and/or antibody receptors specific for the polypeptides disclosed herein can be cloned, expanded, and transferred into other vectors or effector cells for use in adoptive immunotherapy. In particular, T cells may be transfected with the appropriate genes to express the variable domains from chlamydia specific monoclonal antibodies as the extracellular recognition elements and joined to the T cell receptor signaling chains, resulting in T cell activation, specific lysis, and cytokine release. This enables the T cell to redirect its specificity in an MHC-independent manner. See for example, Eshhar, Z., *Cancer Immunol Immunother*, 45(3–4):131–6, 1997 and Hwu, P., et al, *Cancer Res*, 55(15):3369–73, 1995. Another embodiment may include the transfection of *chlamydia* antigen specific alpha and beta T cell receptor chains into alternate T cells, as in Cole, D J, et al, *Cancer Res*, 55(4):748–52, 1995.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate disease in a murine model has been demonstrated by Cheever et al., *Immunological Reviews*, 157:177, 1997). Additionally, vectors expressing the disclosed polynucleotides may be introduced into stem cells taken from the patient and clonally propagated in vitro for autologous transplant back into the same patient.

Within certain aspects, polypeptides, polynucleotides, T cells and/or binding agents disclosed herein may be incorporated into pharmaceutical compositions or immunogenic compositions (i.e., vaccines). Alternatively, a pharmaceutical composition may comprise an antigen-presenting cell (e.g. a dendritic cell) transfected with a Chlamydial polynucleotide such that the antigen presenting cell expresses a Chlamydial polypeptide. Pharmaceutical compositions comprise one or more such compounds and a physiologically acceptable carrier. Vaccines may comprise one or more such compounds and an immunostimulant. An immunostimulant may be any substance that enhances or potentiates an immune response to an exogenous antigen. Examples of immunostimulants include adjuvants, biodegradable microspheres (e.g., polylactic galactide) and liposomes (into which the compound is incorporated; see e,g., Fullerton, U.S. Pat. No. 4,235,877). Vaccine preparation is generally described in, for example, M. F. Powell and M. J. Newman, eds., "Vaccine Design (the subunit and adjuvant approach),"

Plenum Press (NY, 1995). Pharmaceutical compositions and vaccines within the scope of the present invention may also contain other compounds, which may be biologically active or inactive. For example, one or more immunogenic portions of other Chlamydial antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface or secretes such an epitope.

In a preferred embodiment, the DNA may be introduced using a viral expression system (e.g., vaccinia or other pox virus, retrovirus, adenovirus, baculovirus, togavirus, bacteriophage, and the like), which often involves the use of a non-pathogenic (defective), replication competent virus.

For example, many viral expression vectors are derived from viruses of the retroviridae family. This family includes the murine leukemia viruses, the mouse mammary tumor viruses, the human foamy viruses, Rous sarcoma virus, and the immunodeficiency viruses, including human, simian, and feline. Considerations when designing retroviral expression vectors are discussed in Comstock et al. (1997).

Excellent murine leukemia virus (MLV)-based viral expression vectors have been developed by Kim et al. (1998). In creating the MLV vectors, Kim et al. found that the entire gag sequence, together with the immediate upstream region, could be deleted without significantly affecting viral packaging or gene expression. Further, it was found that nearly the entire U3 region could be replaced with the immediately-early promoter of human cytomegalovirus without deleterious effects. Additionally, MCR and internal ribosome entry sites (IRES) could be added without adverse effects. Based on their observations, Kim et al. have designed a series of MLV-based expression vectors comprising one or more of the features described above.

As more has been learned about human foamy virus (HFV), characteristics of HFV that are favorable for its use as an expression vector have been discovered. These characteristics include the expression of pol by splicing and start of translation at a defined initiation codon. Other aspects of HFV viral expression vectors are reviewed in Bodem et al. (1997).

Murakami et al. (1997) describe a Rous sarcoma virus (RSV)-based replication-competent avian retrovirus vectors, IR1 and IR2 to express a heterologous gene at a high level. In these vectors, the IRES derived from encephalomyocarditis virus (EMCV) was inserted between the env gene and the heterologous gene. The IR1 vector retains the splice-acceptor site that is present downstream of the env gene while the IR2 vector lacks it. Murakami et al. have shown high level expression of several different heterologous genes by these vectors.

Recently, a number of lentivirus-based retroviral expression vectors have been developed. Kafri et al. (1997) have shown sustained expression of genes delivered directly into liver and muscle by a human immunodeficiency virus (HIV)-based expression vector. One benefit of the system is the inherent ability of HIV to transduce non-dividing cells. Because the viruses of Kafri et al. are pseudotyped with vesicular stomatitis virus G glycoprotein (VSVG), they can transduce a broad range of tissues and cell types.

A large number of adenovirus-based expression vectors have been developed, primarily due to the advantages offered by these vectors in gene therapy applications. Adenovirus expression vectors and methods of using such vectors are the subject of a number of United States patents, including U.S. Pat. No. 5,698,202, U.S. Pat. No. 5,616,326, U.S. Pat. No. 5,585,362, and U.S. Pat. No. 5,518,913, all incorporated herein by reference.

Additional adenoviral constructs are described in Khatri et al. (1997) and Tomanin et al. (1997). Khatri et at. describe novel ovine adenovirus expression vectors and their ability to infect bovine nasal turbinate and rabbit kidney cells as well as a range of human cell type, including lung and foreskin fibroblasts as well as liver, prostate, breast, colon and retinal lines. Tomanin et al. describe adenoviral expression vectors containing the T7 RNA polymerase gene. When introduced into cells containing a heterologous gene operably linked to a T7 promoter, the vectors were able to drive gene expression from the T7 promoter. The authors suggest that this system may be useful for the cloning and expression of genes encoding cytotoxic proteins.

Poxviruses are widely used for the expression of heterologous genes in mammalian cells. Over the years, the vectors have been improved to allow high expression of the heterologous gene and simplify the integration of multiple heterologous genes into a single molecule. In an effort to diminish cytopathic effects and to increase safety, vaccinia virus mutant and other poxviruses that undergo abortive infection in mammalian cells are receiving special attention (Oertli et al., 1997). The use of poxviruses as expression vectors is reviewed in Carroll and Moss (1997).

Togaviral expression vectors, which includes alphaviral expression vectors have been used to study the structure and function of proteins and for protein production purposes. Attractive features of togaviral expression vectors are rapid and efficient gene expression, wide host range, and RNA genomes (Huang, 1996). Also, recombinant vaccines based on alphaviral expression vectors have been shown to induce a strong humoral and cellular immune response with good immunological memory and protective effects (Tubulekas et al., 1997). Alphaviral expression vectors and their use are discussed, for example, in Lundstrom (1997).

In one study, Li and Garoff (1996) used Semliki Forest virus (SFV) expression vectors to express retroviral genes and to produce retroviral particles in BHK-21 cells. The particles produced by this method had protease and reverse transcriptase activity and were infectious. Furthermore, no helper virus could be detected in the virus stocks. Therefore, this system has features that are attractive for its use in gene therapy protocols.

Baculoviral expression vectors have traditionally been used to express heterologous proteins in insect cells. Examples of proteins include mammalian chemokine receptors (Wang et al., 1997), reporter proteins such as green fluorescent protein (Wu et al., 1997), and FLAG fusion proteins (Wu et al., 1997; Koh et al., 1997). Recent advances in baculoviral expression vector technology, including their use in virion display vectors and expression in mammalian cells is reviewed by Possee (1997). Other reviews on baculoviral expression vectors include Jones and Morikawa (1996) and O'Reilly (1997).

Other suitable viral expression systems are disclosed, for example, in Fisher-Hoch et al., *Proc. Natl. Acad. Sci. USA* 86:317–321,1989; Flexner et al., *Ann. N.Y. Acad. Sci.* 569:86–103,1989; Flexner et al., *Vaccine* 8:17–21,1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 8:2838–2848, 1993; and Guzman et al., *Cir. Res.* 73:1202–1207, 1993. Techniques for incorporating DNA into such expression systems are well known to those of ordinary skill in the art. In other systems, the DNA may be introduced as "naked" DNA, as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

It will be apparent that a vaccine may comprise a polynucleotide and/or a polypeptide component, as desired. It will also be apparent that a vaccine may contain pharmaceutically acceptable salts of the polynucleotides and/or polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts). While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobactedum tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, under select circumstances, the adjuvant composition may be designed to induce an immune response predominantly of the Th1 type or Th2 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555 and WO 99/33488. Immunostimulatory DNA sequences are also described, for example, by Sato et al., *Science* 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Corixa Corporation; Seattle, Wash.), RC-529 (Corixa Corporation; Seattle, Wash.) and other aminoalkyl glucosaminide 4-phosphates (AGPs), such as those described in pending U.S. patent application Ser. Nos. 08/853,826 and 09/074,720, the disclosures of which are incorporated herein by reference in their entireties.

Any vaccine provided herein may be prepared using well known methods that result in a combination of antigen, immunostimulant and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429–1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-coglycolide), as well as polyacrylate, latex, starch, cellulose and dextran. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets *Chlamydia*-infected cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-*Chlamydia* effects per se and/or to be immunologically compatible with the receiver (i.e., matched HLA haplotype). APCs may generally be isolated from any of a variety of biological fluids and organs, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency, and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-–loaded dendritic cells (called exosomes) may be used within a vaccine (see Zitvogel et al., *Nature Med.* 4:594–600, 1998).

Dendritic cells and progenitors may be obtained from peripheral blood, bone marrow, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFcA to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a Chlamydial protein (or portion or other variant thereof) such that the Chlamydial polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the Chlamydial polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Routes and frequency of administration of pharmaceutical compositions and vaccines, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from Chlamydial infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 μg. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

In general, an appropriate dosage and treatment regimen provides the active compound(s) in an amount sufficient to provide therapeutic and/or prophylactic benefit. Such a response can be monitored by establishing an improved clinical outcome in treated patients as compared to non-treated patients.

Increases in preexisting immune responses to a Chlamydial protein generally correlate with an improved clinical outcome. Such immune responses may generally be evaluated using standard proliferation, cytotoxicity or cytokine assays, which may be performed using samples obtained from a patient before and after treatment.

Detection and Diagnosis

In another aspect, the present invention provides methods for using the polypeptides described above to diagnose Chlamydial infection. In this aspect, methods are provided for detecting Chlamydial infection in a biological sample, using one or more of the above polypeptides, either alone or in combination. For clarity, the term "polypeptide" will be used when describing specific embodiments of the inventive diagnostic methods. However, it will be clear to one of skill in the art that the fusion proteins of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to *Chlamydia* antigens which may be indicative of *Chlamydia*-infection.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with *Chlamydia*. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, Antibodies: *A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate, or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 μg. and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody is allowed to bind to the antigen. The sample may be diluted with a suitable dilutent, such as phosphate-buffered saline (PBS) prior to incubation. In general, an appropriate contact time (ie., incubation time) is that period of time that is sufficient to detect the presence of antibody within an HGE-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-*Chlamydia* antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for *Chlamydia*-infection. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for Chlamydial infection.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*Chlamydia* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 µg, and more preferably from about 50 ng to about 500 ng. Such tests can typically be performed with a very small amount (e.g., one drop) of patient serum or blood.

Of course, numerous other assay protocols exist that are suitable for use with the polypeptides of the present invention. The above descriptions are intended to be exemplary only. One example of an alternative assay protocol which may be usefully employed in such methods is a Western blot, wherein the proteins present in a biological sample are separated on a gel, prior to exposure to a binding agent. Such techniques are well known to those of skill in the art.

Binding Agents and their Uses

The present invention further provides agents, such as antibodies and antigen-binding fragments thereof, that specifically bind to a Chlamydial protein. As used herein, an antibody, or antigen-binding fragment thereof, is said to "specifically bind" to a Chlamydial protein if it reacts at a detectable level (within, for example, an ELISA) with a Chlamydial protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a Chlamydial infection using the representative assays provided herein. In other words, antibodies or other binding agents that bind to a Chlamydial protein will generate a signal indicating the presence of a Chlamydial infection in at least about 20% of patients with the disease, and will generate a negative signal indicating the absence of the disease in at least about 90% of individuals without infection. To determine whether a binding agent satisfies this requirement, biological samples (e.g., blood, sera, sputum urine and/or tissue biopsies ) from patients with and without Chlamydial infection (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in site-specific regions by appropriate methods. It will be evident that the precise dose of the antibody/ immunoconjugate will vary depending upon the antibody used, the antigen density, and the rate of clearance of the antibody.

Antibodies may be used in diagnostic tests to detect the presence of *Chlamydia* antigens using assays similar to those detailed above and other techniques well known to those of skill in the art, thereby providing a method for detecting Chlamydial infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify *Chlamydia*-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

The following Examples are offered by way of illustration and not by way of limitation.

EXAMPLES

Example 1

CD4 T CELL EXPRESSION CLINGING FOR THE IDENTIFICATION OF T CELL STIMULATING ANTIGENS FROM *CHLAMYDIA TRACHOMATIS* SEROVAR E

In this example, a CD4+ T cell expression cloning strategy was used to identify *Chlamydia trachomatis* antigens recognized by patients enrolled in Corixa Corporation's blood donor program. A genomic library of *Chlamydia trachomatis* serovar E was constructed and screened with *Chlamydia* specific T cell lines generated by stimulating PBMCs from these donors. Donor CT1 is a 27 yr. old male whose clinical manifestation was non-gonococcal urethritis and his urine was tested positive for *Chlamydia* by ligase chain reaction. Donor CT3 is a 43 yr. old male who is asymptomatic and infected with serovar J. Donor CT10 is a 24 yr. old female who is asymptomatic and was exposed to *Chlamydia* through her partner but did not develop the disease. Donor CT11 is a 24 yr. old female with multiple infections (serovar J, F and E).

*Chlamydia* specific T-cell lines were generated from donors with *Chlamydia* genital tract infection or donors exposed to chlamydia who did not develop the disease. T cell lines from donor CT-1, CT-3 and CT-10 were generated by stimulating PBMCs with reticulate bodies of *C. trachomatis* serovar E. T-cell lines from donor CT-11 were generated by stimulating PBMCs with either reticulate bodies or elementary bodies of *C. trachomatis* serovar E. A randomly sheared genomic library of *C. trachomatis* serovar E was constructed in lambda Zap II vector and an amplified library plated out in 96 well microtiter plates at a density of 25 clones/well. Bacteria were induced to express the recombinant protein in the presence of 2 mM IPTG for 2 hr, then pelleted and resuspended in 200 ul RPMI/10% FBS. 10 ul of the induced bacterial suspension was transferred to 96 well plates containing autologous monocyte-derived dendritic cells. After a 2 hour incubation, dendritic cells were washed to remove *E. coli* and the T cells were added. Positive *E. coli* pools were identified by determining IFN gamma production and proliferation of T cells in the pools. The number of pools identified by each T-cell line is as follows: CT1 line : 30/480 pools; CT3 line : 91/960 pools; CT10 line: 40/480 pools; CT11 line: 51/480 pools. The clones identified using this approach are set forth in SEQ ID NO:1–14.

In another example using substantially the same approach described above, we identified 12 additional T-cell reactive clones from *Chlamydia trachomatis* serovar E expression screening. Clone E5-E9-3 (CT1 positive) contains a 636 bp insert that encodes partially the ORF for dnaK like gene. Part of this sequence was also identified in clone E1-A5-53. Clone E4-H3-56 (CT1 positive, 463 bp insert) contains a partial ORF for the TSA gene, (CT603) on the complementary strand. The insert for clone E2-G12-52 (1265 bp) was identified with the CT11 line. It contains a partial ORF for clpB, a protease ATPase. Another clone identified with the CT11 line, E1-F9-79 (167 bp), contains a partial ORF for the gene CT133 on the complementary strand. CT133 is a predicted rRNA methylase. Clone E4-D2-79 (CT3 positive) contains a 1181 bp insert that is a partial ORF for nrdA gene. The ORF for this gene was also identified in clone E2-B10-52 (CT10 positive). Clone E6-C8-95 contains a 731 bp insert that was identified using the donor lines CT3, CT1, and CT12. This insert has a carboxy terminal half for the gene for the 60 kDa ORF. Clone E7-H11-61 (CT3 positive-1135 bp) has partial inserts for fliA (CT061), tyrS (CT062), TSA (CT603) and a hypothetical protein (CT602). The insert for clone E5-A11-8 (CT10 positive-1736 bp) contains the complete ORF for groES (CT111) and a majority of the ORF for groEL (CT110). Clone E3-F2-37 (CT10, CT3, CT11, and CT12 positive-1377 bp insert) contains a partial ORF for gene tRNA-Trp (CT322) and a complete ORF for the gene secE (CT321). E4-G9-75 is another CT10 clone that contains a partial ORF (723 bp insert) for the amino terminal region of the pmpH gene (CT872). Clone E2-D5-89 (516bp) is also a CT10 positive clone that contains a partial ORF for pmpD gene (12). The insert for clone E5-E2-10 (CT10 positive) is 427 bp and contains a partial ORF for the major outer membrane protein omp1.

Example 2

ADDITIONAL CD4 T CELL EXPRESSION CLONING FOR THE IDENTIFICATION OF T CELL STIMULATING ANTIGENS FROM *CHLAMYDIA TRACHOMATIS* SEROVAR E

Twenty sequences were isolated from single clones using a *Chlamydia trachomatis* serovar E (Ct E) library expression screening method. Descriptions of how the clones and lines were generated are provided in Example 1.

Clone E5-A8-85 (identified using the CT1 patient line) was found to contain a 1433 bp insert. This insert contains a large region of the C-terminal half of the CT875, a *Chlamydia trachomatis* hypothetical specific gene that is disclosed in SEQ ID NO:34. Also present in the clone is a partial open reading frame (ORF) of a hypothetical protein CT001 which is on the complementary strand.

The clone E9-G2-93 (identified using the C10 patient line) was shown to contain a 554 bp insert, the sequence of which is disclosed in SEQ ID NO:33. This sequence encodes a partial ORF for CT178, a hypothetical CT protein.

Clone E7-B1-16 (identified using the patient lines CT10, CT3, CT5, CT11, CT13, and CHH037) has a 2577 bp insert, the sequence of which is disclosed in SEQ ID NO:32. This clone was found to contain three ORFs. The first ORF contains almost the entire ORF for CT694, a *Chlamydia trachomatis* (CT) specific hypothetical protein. The second ORF is a full length ORF for CT695, another hypothetical CT protein. The third ORF is the N-terminal portion of CT696.

Clone E9-D5-8 (identified using the patient lines CT10, CT1, CT4, and CT11) contains a 393 bp insert, which is disclosed in SEQ ID NO:31. It was found to encode a partial ORF for CT680, the S2 ribosomal protein.

Clone E9-E10-51 (identified using the patient line CT10) contains an 883 bp insert, the sequence of which is disclosed in SEQ ID NO:30. This clone contains two partial ORF. The first of these is for the C-terminal half of CT680, which may show some overlap with the insert present in clone E9-D5-8. The second ORF is the N-terminal partial ORF for CT679, which is the elongation factor TS.

Clone E3-B4-18 (identified using the CT1 patient line) contains a 1224 bp insert, the sequence of which is disclosed in SEQ ID NO:29. This clone contains 4 ORFs. At the N-terminal end of the clone is the complete ORF for CT772, coding for inorganic pyrophosphatase. The second ORF is a small portion of the C-terminal end of CT771, on the complementary frame. The third is a partial ORF of the hypothetical protein, CT191 and the fourth is a partial ORF for CT190, DNA gyrase-B.

Clone E10-B2-57 (identified using the CT10 patient line) contains an 822 bp insert, the sequence of which is disclosed in SEQ ID NO:42. This clone contains the complete ORF for CT066, a hypothetical protein, on the complementary strand.

Clone E3-F3-18 (identified using the CT1 patient line) contains an 1141 bp insert, the sequence of which is disclosed in SEQ ID NO:41. It contains a partial ORF for pmpG (CT871) in frame with the β-gal gene.

Clone E4-D6-21 (identified using the CT3 patient line) contains a 1297 bp insert, the sequence of which is disclosed in SEQ ID NO:40. This clone contains a very small portion of xseA (CT329), the entire ORF for tpiS (CT328) on the complementary strand, and a partial amino terminal ORF for trpC (CT327) on the top frame.

Clone E1-G9-23 (identified using the CT3 patient line) contains an 1180 bp insert, the sequence of which is disclosed in SEQ ID NO:39. This clone contains almost the entire ORF for glycogen synthase (CT798).

Clone E3-A3-31 (identified using the CT1 patient line) contains an 1834 bp insert, the sequence of which is disclosed in SEQ ID NO:38. This clone contains a large region of the hypothetical gene CT622.

Clone E2-F7-11 (identified using both the CT3 and CT10 patient lines) contains a 2093 bp insert, the sequence of which is disclosed in SEQ ID NO:37. This clone contains a large region of the rpoN gene (CT609) in frame with β-gal and the complete ORF for the hypothetical gene CT610 on the complementary strand. In addition, it also contains the carboxy-terminal end of CT611, another hypothetical gene.

Clone E7-H11-10 (identified using the CT3 patient line) contains a 1990 bp insert, the sequence of which is disclosed in SEQ ID NO:36. This clone contains the amino terminal partial ORF for CT610, a complete ORF for CT611, another complete ORF for CT612, and a carboxy-terminal portion of CT613. All of these genes are hypothetical and all are present on the complementary strand.

Clone E10-C6-45 (identified using the CT3 patient line) contains a 196 bp insert, the sequence of which is disclosed in SEQ ID NO:35. This clone contains a partial ORF for nrdA (CT827) in frame with β-gal. This clone contains a relatively small insert and has particular utility in determining the epitope of this gene that contributes to the immunogenicity of Serovar E.

Clone E3-H6-10 (identified using the CT12 patient line) contains a 3734 bp insert, the sequence of which is disclosed in SEQ ID NO:48. This clone contains ORFs for a series of hypothetical proteins. It contains the partial ORFs for CT223 and CT229 and the complete ORFs for CT224, CT225, CT226, CT227, and CT228.

Clone E4-C3-40 (identified using the CT10 patient line) contains a 2044 bp insert, the sequence of which is disclosed in SEQ ID NO:47. This clone contains a partial ORF for nrdA (CT827) and the complete ORF for nrdB (CT828).

Clone E2-D8-19 (identified using the CT1 patient line) contains a 2010 bp insert, the sequence of which is disclosed in SEQ ID NO:46. This clone contains ORF from the *Chlamydia trachomatis* plasmid as well as containing partial ORFs for ORF3 and ORF6, and complete ORFs for ORF4 and ORF5.

Clone E3-D10-46 (identified using the patient lines CT1, CT3, CT4, CT11, and CT12) contains a 1666 bp insert, the sequence of which is identified in SEQ ID NO:45. This clone contains a partial ORF for CT770 (fab F), a complete ORF for CT771 (hydrolase/phosphatase homologue), a complete ORF for CT772 (ppa, inorganic phosphatase), and a partial ORF for CT773 (ldh, Leucine dehydrogenase).

Clone E10-H8-1 (identified using both the CT3 and CT10 patient lines) contains an 1862 bp insert, the sequence of which is disclosed in SEQ ID NO:44. It contains the partial ORFs for CT871 (pmpG) as well as CT872 (pmpH).

Clone E3-F3-7 (identified using the CT1 patient line) contains a 1643 bp insert, the sequence of which is identified in SEQ ID NO:43. It contains the partial ORFs for both CT869 (pmpE) and CT870 (pmpF).

Example 3

ADDITIONAL CD4 T CELL EXPRESSION CLONING FOR THE IDENTIFICATION OF T CELL STIMULATING ANTIGENS FROM *CHLAMYDIA TRACHOMATIS* SEROVAR E

The T cell line CHH037 was generated from a 22 year-old healthy female sero-negative for *Chlamydia*. This line was used to screen the *Chlamydia trachomatis* serovar E library. Nineteen clones were identified from this screen, as described below.

Clone E7-B12-65, contains an 1179 bp insert, the sequence of which is disclosed in SEQ ID NO:114. It contains the complete ORF of the gene for Malate dehydrogenase (CT376) on the complementary strand.

Clone E4-H9-83 contains a 772 bp insert, the sequence of which is identified in SEQ ID NO:115. It contains the partial ORF for the heat shock protein GroEL (CT110).

Clone E9-B10-52 contains a 487 bp insert, the sequence of which is identified in SEQ ID NO:116. It contains a partial ORF for the gene yscC (CT674), a general secretion pathway protein.

Clone E7-A7-79 contains a 1014 bp insert, the sequence of which is disclosed in SEQ ID NO:117. It contains the complete ORF for the histone like development gene, hctA (CT743) and a partial ORF for the rRNA methyltransferase gene ygcA (CT742).

Clone E2-D11-18 contains a 287 bp insert, the sequence of which is disclosed in SEQ ID NO:118. It contains the partial ORF for hctA (CT743).

Clone E9-H6-15, identified using the CT3 line, contains a 713 bp insert the sequence of which is disclosed in SEQ ID NO:125. It contains the partial ORF of the pmpB gene (CT413).

Clone E3-D10-87, identified using the CT1 line, contains a 780 bp insert, the sequence of which is disclosed in SEQ ID NO:126. It contains the partial ORF for CT388, a hypothetical gene, on the complementary strand, and a partial ORF for CT389, another hypothetical protein.

Clone E9-D6-43, identified using the CT3 line, contains a 433 bp insert, the sequence of which is disclosed in SEQ ID NO:127. It contains a partial ORF for CT858.

Clone E3-D10-4, identified using the CT1 line, contains an 803 bp insert, the sequence of which is disclosed in SEQ ID NO:128. It contains a partial ORF for pGP3-D, an ORF encoded on the plasmid pCHL1.

Clone E3-G8-7, identified using the CT1 line, contains an 842 bp insert, the sequence of which is disclosed in SEQ ID NO:129. Itcontains partial ORFs for CT557 (Lpda) and CT558 (LipA).

Clone E3-F11-32, identified using the CT1 line, contains an 813 bp insert, the sequence of which is disclosed in SEQ ID NO:130. It contains a partial ORF for pmpD (CT812).

Clone E2-F8-5, identified using the CT12 line, contains a 1947 bp insert, the sequence of which is disclosed in SEQ ID NO:131. It contains a complete ORF for the 15 kDa ORF (CT442) and a partial ORF for the 60 kDa ORF (CT443).

Clone E2-G4-39, identified using the CT12 line, contains a 1278 bp insert, the sequence of which is disclosed in SEQ ID NO:132. It contains the partial ORF of the 60 kDa ORF (CT443).

Clone E9-D1-16, identified using the CT10 line, contains a 916 bp insert, the sequence of which is disclosed in SEQ ID NO:133. It contains the partial ORF for the pmpH (CT872).

Clone E3-F3-6, identified using the CT1 line, contains a 751 bp insert, the sequence of which is disclosed in SEQ ID NO:134. It contains the partial ORFs, all on he complementary strand, for genes accB (CT123), L13 ribosomal (CT125), and S9 ribosomal (CT126).

Clone E2-D4-70, identified using the CT12 line, contains a 410 bp insert, the sequence of which is disclosed in SEQ ID NO:135. It contains the partial ORF for the pmpC gene (CT414).

Clone E5-A1-79, identified using the CT1 line, contains a 2719 bp insert, the sequence of which is disclosed in SEQ ID NO:136. It contains a partial ORF for ydhO (CT127), a complete ORF for S9 ribosomal gene (CT126 on the complementary strand), a complete ORF for the L13 ribosomal gene (CT125 on the complementary strand) and a partial ORF for accC (CT124 on the complementary strand).

Clone E1-F7-16, identified using the lines CT12, CT3, and CT11, contains a 2354 bp insert, the sequence of which is disclosed in SEQ ID NO:137. It contains a partial ORF of the ftsH gene (CT841) and the entire ORF for the pnp gene (CT842) on the complementary strand.

Clone E1-D8-62, identified using the CT12 line, contains an 898 bp insert, the sequence of which is disclosed in SEQ ID NO:138. It contains partial ORFs for the ftsH gene (CT841) and for the pnp gene (CT842).

Example 4

EXPRESSION OF *CHLAMYDIA TRACHOMATIS* RECOMBINANT PROTEINS

Several *Chlamydia trachomatis* serovar E specific genes were cloned into pET17b. This plasmid incorporates a 6× histidine tag at the N-terminal to allow for expression and purification of recombinant protein.

Two full-length recombinant proteins, CT622 and CT875, were expressed in *E. coli*. Both of these genes were identified using CtLGVII expression screening, but the serovar E homologues were expressed. The primers used to amplify these genes were based on serovar D sequences. The genes were amplified using serovar E genomic DNA as the template. Once amplified, the fragments were cloned in pET-17b with a N-terminal 6x-His Tag. After transforming the recombinant plasmid in XL-I blue cells, the DNA was prepared and the clones fully sequenced. The DNA was then transformed into the expression host BL21-pLysS cells (Novagen) for production of the recombinant proteins. The proteins were induced with IPTG and purified on Ni-NTA agarose using standard methods. The DNA sequences for CTE622 and CTE875 are disclosed in SEQ ID NO:28 and 27 respectively, and their amino acid sequences are disclosed in SEQ ID NO: 140 and 139, respectively Five additional *Chlamydia trachomatis* genes were cloned. The *Chlamydia trachomatis* specific protein CT694, the protein CT695, and the L1 ribosomal protein, the DNA sequences of which are disclosed in SEQ ID NO:119, 120 and 121 respectively. The protein sequences of these 6×-histidine recombinant proteins are disclosed in SEQ ID NO: 122 (CT694), 123 (CT695), and 124 (L1 ribosomal protein). The genes CT875 and CT622, from serovar E were also cloned using pET17b as 6×-His fusion proteins. These recombinant proteins were expressed and purified and their amino acid sequences disclosed in SEQ ID NO:139 and 140, respectively.

Example 5

Recombinant Chlamydial Antigens Recognized By T Cell Lines

Patient T cell lines were generated from the following donors: CT1, CT2, CT3, CT4, CT5, CT6, CT7, CT8, CT9, CT10, CT11, CT12, CT13, CT14, CT15, and CT16. A summary of their details is included in Table II.

TABLE II

C. trachomatis patients

| Patients | Gender | Age | Clinical Manifestation | Serovar | IgG titer | Multiple Infections |
|---|---|---|---|---|---|---|
| CT1 | M | 27 | NGU | LCR | Negative | No |
| CT2 | M | 24 | NGU | D | Negative | E |
| CT3 | M | 43 | Asymptomatic<br>Shed Eb<br>Dx was HPV | J | Ct 1:512<br>Cp 1:1024<br>Cps 1:256 | No |
| CT4 | F | 25 | Asymptomatic<br>Shed Eb | J | Ct 1:1024 | Y |
| CT5 | F | 27 | BV | LCR | Ct 1:256<br>Cp 1:256 | F/F |
| CT6 | M | 26 | Perinial rash<br>Discharge,<br>dysuria | G | Cp 1:1024 | N |
| CT7 | F | 29 | BV<br>Genital ulcer | E | Ct 1:512<br>Cp 1:1024 | N |
| CT8 | F | 24 | Not Known | LCR | Not tested | NA |
| CT9 | M | 24 | asymptomatic | LCR | Ct 1:128<br>Cp 1:128 | N |
| CT10 | F | 20 | Mild itch vulvar | negative | negative | Dec. 1, 1998 |
| CT11 | F | 21 | BV<br>Abnormal pap<br>smear | J | Ct 1:512 | F/F/J/E/E<br>PID June 1996 |
| CT12 | M | 20 | asymptomatic | LCR | Cp 1:512 | N |
| CT13 | F | 18 | BV, gonorrhea,<br>Ct vaginal<br>discharge,<br>dysuria | G | Ct 1:1024 | N |
| CT14 | M | 24 | NGU | LCR | Ct 1:256<br>Cp 1:256 | N |
| CT15 | F | 21 | Muco-purulint<br>cervicitis<br>Vaginal<br>discharge | culture | Ct 1:256<br>Ct IgM 1:320<br>Cp 1:64 | N |
| CT16 | M | 26 | Asymptomatic/<br>contact | LCR | NA | N |
| CL8 | M | 38 | No clinical<br>history of<br>disease | negative | negative | No |

NGU = Non-Gonococcal Urethritis;
BV = Bacterial Vaginosis;
CT = Chlamydia trachomatis;
Cp = Chlamydia pneumoniae;
Eb = Chlamydia elementary bodies;
HPV = human papiloma virus;
Dx = diagnosis;
PID = pelvic inflammatory disease;
LCR = Ligase change reaction.

PBMC were collected from a second series of donors and T cell lines have been generated from a sub-set of these. A summary of the details for three such T cell lines is listed in the table below.

TABLE III

| | | Normal Donors | | |
|---|---|---|---|---|
| Donor | Gender | Age | CT IgG Titer | CP IgG Titer |
| CHH011 | F | 49 | 1:64 | 1:16 |
| CHH037 | F | 22 | 0 | 0 |
| CHH042 | F | 25 | 0 | 1:16 |

Donor CHH011 is a healthy 49 year old female donor sero-negative for *C. trachomatis*. PBMC produced higher quantities of IFN-gamma in response to *C. trachomatis* elementary bodies as compared to *C. pneumoniae* elementary bodies, indicating a *C. trachomatis*-specific response. Donor CHH037 is a 22 year old healthy female donor sero-negative for *C. trachomatis*. PBMC produced higher quantities of IFN-gamma in response to *C. trachomatis* elementary bodies as compared to *C. pneumoniae* elementary bodies, indicating a *C. trachomatis*-specific response. CHH042 is a 25 year old healthy female donor with an IgG titer of 1:16 to *C. pneumoniae*. PBMC produced higher quantities of IFN-gamma in response to *C. trachomatis* elementary bodies as compared to *C. pneumoniae* elementary bodies, indicating a *C. trachomatis*-specific response.

Recombinant proteins for several *Chlamydia trachomatis* genes were generated as described above. Sequences for MOMP were derived from serovar F. The genes CT875, CT622, pmp-B-2, pmpA, and CT529 were derived from serovar E and sequences for the genes gro-EL, Swib, pmpD, pmpG, TSA, CT610, pmpC, pmpE, S13, IpdA, pmpI, and pmpH-C were derived from LII.

Several of the patient and donor lines described above were tested against the recombinant *Chlamydia* proteins. Table IV summarizes the results of the T cell responses to the recombinant *Chlamydia* proteins.

Example 6
CD4 T Cell Expression Cloning for Identification of T Cell Stimulating Antigens from *CHLAMYDIA TRACHOMATIS* Serovar E The T cell line CHH037 was generated from a 22 year-old healthy female sero-negative for *Chlamydia*. This line was used to screen the *Chlamydia trachomatis* serovar E library (essentially as described in Example 1). Using this T cell line, we describe the identification of 7 clones.

Clone E8-D1-46 contains a 1754 bp insert, the sequence of which is disclosed in SEQ ID NO:143. It contains an almost complete ORF for the pepA gene (CT045) on the complememntary strand, lacking a few amino acids towards the carboxy terminal end.

Clone E10-A1-10 contains a 3035 bp insert, the sequence of which is disclosed in SEQ ID NO:144. It contains partial ORFs for the yscU gene (CT091) and the truB gene (CT094) on the complementary strand and complete ORFs for the ychF gene (CT092) on the complementary strand and for the ribF gene (CT093) on the complementary strand.

Clone E8-B12-80 contains a 1353 bp insert, the sequence of which is disclosed in SEQ ID NO:145. It contains a short fragment of the SET domain protein gene (CT737) in frame with β-gal, a complete ORF in the complementary strand for the ybcL gene (CT736) as well as a partial ORF for the dag_2 gene (CT735) on the complementary strand.

Clone E2-A8-70 contains a 1627 bp insert, the sequence of which is disclosed in SEQ ID NO:146. It contains a partial ORF for the mutS gene (CT792), a complete ORF for the ybcL gene (CT736) on the complementary strand, in addition to a partial ORF for the dag_2 gene (CT735).

Clone E10-C1-47 contains a 1262 bp insert, the sequence of which is disclosed in SEQ ID NO:147. It contains a partial ORF for yael (CT461) on the complementary strand, a complete ORF for SWIB (CT460) on the complementary strand and a partial ORF for prfB (CT459) on the top strand.

Clone E8-G7-86 contains a 1596 bp insert, the sequence of which is disclosed in SEQ ID NO:148. It contains a partial ORF for the mesJ (CT840) that is in frame with β-gal and a second partial ORF for the ftsH gene (CT841).

Clone E3-E6-84 contains a 2624 bp insert, the sequence of which is disclosed in SEQ ID NO:149. It contains a partial

TABLE IV

Recombinant Chlamydia Antigens Recognized By T Cell Lines

| Antigen | Sero-var | #of hits | CL8 L2 | CT10 E | CT1 E | CT3 E | CT4 L2 | CT5 E | CT11 E | CT12 E | CT13 E | CHH-011 E | CHH-037 E |
|---|---|---|---|---|---|---|---|---|---|---|---|---|---|
| gro-EL (CT110) | L2 | 10 | − | + | + | + | + | + | + | + | + | + | + |
| MompF (CT681) | F | 10 | − | + | + | + | + | + | + | + | + | + | + |
| CT875 | E | 8 | − | + | + | − | + | + | + | + | + | − | + |
| SWIB (CT460) | L2 | 8 | + | + | − | + | − | + | − | + | + | + | + |
| pmpD (CT812) | L2 | 5 | − | + | + | + | + | − | − | + | + | − | − |
| pmpG (CT871) | L2 | 6 | − | + | + | − | + | + | nt | − | + | + | − |
| TSA (CT603) | L2 | 6 | − | − | + | + | + | + | − | − | + | − | + |
| CT622 | E | 3 | − | − | + | − | + | − | − | − | + | − | − |
| CT610 | L2 | 3 | − | + | − | + | − | − | − | + | − | − | − |
| pmpB-2 (CT413) | E | 3 | − | − | + | + | + | − | − | − | − | − | − |
| pmpC (CT414) | L2 | 4 | − | − | − | + | − | + | − | + | − | − | + |
| pmpE (CT869) | L2 | 3 | − | + | + | − | − | − | − | − | + | − | − |
| S13 (CT509) | L2 | 2 | + | − | − | − | + | − | − | − | − | − | − |
| IpdA (CT557) | L2 | 3 | − | − | + | + | − | − | − | − | − | + | − |
| pmpI (CT874) | L2 | 2 | − | − | + | − | − | − | − | − | − | + | − |
| pmpH-C (CT872) | L2 | 1 | − | − | − | − | − | − | − | + | − | − | − |
| pmpA (CT412) | E | 0 | − | − | − | − | − | − | − | − | − | − | − |
| CT529 | E | 0 | − | − | − | − | − | − | − | − | − | − | − |

ORF for the pmpC gene (CT414) as well as a partial ORF on the complementary strand for the hypothetic gene CT611.

A second line, CHH042, which was generated from a healthy 25 year old female donor, seronegative for *Chlamydia*, was also screened against the *Chlamydia trachomatis* serovar E library. This screen led to the identification of 2 clones, E8-C12-38 and E1-D12-36.

Clone E8-C12-38 contains a 788 bp insert, the sequence of which is disclosed in SEQ ID NO:141. It contains partial ORFs for sfhB (CT658) and for the hypothetical gene, CT659.

Clone E1-D12-36 contains a 976 bp insert, the sequence of which is disclosed in SEQ ID NO:142. It contains a partial ORF for merB (CT709) in frame with β-gal, as well as a second partial ORF for the pckA gene (CT710).

Example 7

CD4 T CELL EXPRESSION CLONING FOR IDENTIFICATION OF T CELL STIMULATING ANTIGENS FROM *CHLAMYDIA TRACHOMATIS* SEROVAR E

The T cell line CHH037 was generated from a 22 year-old healthy female sero-negative for Chlamydia. This line was used to screen the *Chlamydia trachomatis* serovar E library (essentially as described in Example 1). Using this T cell line, we describe the identification of clone E8-G7-54. This clone was found to contain a 3957 bp, the sequence of which is disclosed in SEQ ID NO:157. It contains a partial ORF for the ftsH gene (CT841), which is in frame with β-gal. Clone E8-G7-54 also contains 2 partial ORFs on the complementary strand, for pGP7-D and pGP5-D, as well as a complete ORF for pGP6-D, all three of which were from plasmid sequence.

A second T cell line, CHH042, which was generated from a healthy 25 year old female donor, seronegative for *Chlamydia*, was also screened against the *Chlamydia trachornatis* serovar E library. Using this T cell line, we describe the identification of 7 clones.

Clone E2-C3-27 contains a 1157 bp insert, the sequence of which is disclosed in SEQ ID NO:156. This clone contains complete ORFs for the genes rS3 (CT522) and rL22 (CT523) as well as partial oRFs for the genes rL16 (CT521) and rS19 (CT524).

Clone E10-F12-42 contains a 1909 bp insert, the sequence of which is disclosed in SEQ ID NO:155. It contains partial ORFs for the genes rS3 (CT522) and rL23 (CT526) as well as complete ORFs for the genes rL122 (CT523) rS19 (CT524) and rL2 (CT525).

Clone E10-F12-58 contains a 2275 bp insert, the sequence of which is disclosed in SEQ ID NO:154. It contains partial ORFs for the genes mhpA (CT148), rL16 (CT521), and rL2 (CT525) as well as complete ORFs for the genes rS3 (CT522), rL22 (CT523), and rS19 (CT524).

Clone E10-A8-16 contains a 3141 bp insert, the sequence of which is disclosed in SEQ ID NO:153. It contains partial ORFs for the genes rS3 (CT522) and rL3 (CT528) as well as complete ORFs for the genes rL22 (CT523), rS19 (CT524), rL2 (CT525), rL23 (CT526), and rL4 (CT527).

Clone E4-G8-49 contains a 1326 bp insert, the sequence of which is disclosed in SEQ ID NO:152. It contains partial ORFs for the genes pckA (CT710) and mreB (CT709), as well as a partial ORF for the pGP2-D from the plasmid.

Clone E9-E64 contains a 725 bp insert, the sequence of which is disclosed in SEQ ID NO:151. It contains a complete ORF for the hypothetical protein CT659 and a partial ORF for gyrA-2 (CT660).

Clone E2-A11-49 contains a 2052 bp insert, the sequence of which is disclosed in SEQ ID NO:150. It contains partial ORFs for the HAD superfamily (CT103) and the hypothetical protein, CT105, as well as a complete ORF for fabI (CT104).

Example 8

IMMUNIZATION AGAINST *CHLAMYDIA* GENITAL TRACT INFECTION USING THE MAJOR OUTER MEMBRANE PROTEIN (MOMP) FROM SEROVAR F, OR THE POLYMORPHIC MEMBRANE PROTEINS G OR C FROM SEROVAR L2

A murine model of genital tract infection with human serovar K strain of *Chlamydia trachomatis* (Ct) was developed that closely resembles the pathology of infection in humans. This model was used to evaluate the effectiveness of immunizing mice with a variety of Ct-specific antigens from different serovars. Specifically, Balb/c mice were vaccinated with a formulation comprising SBAS1 and 10 μg of a recombinant form of either: (1) MOMP from serovar F, (2) pmpC from serovar L2, or (3) pmpG from serovar L2. Control animals consisted of: (1) 2 uninfected animals, (2) 2 AS1-sham vaccinated/infected animals, and (3) 2 animals immunized with AS1-adjuvant and UV-irradiated EB.

Four weeks following the final vaccination, the animals were treated with 1.25 mg of progesterone prior to being infected with $1\times10^7$ IFU of purified serovar K. Bacterial shedding was then followed over a two-week period, at which time the animals were sacrificed.

Mice vaccinated with MOMP, pmpG, and to a lesser extent, pmpC demonstrated reduced viral shedding 4 days post-infection when compared to controls. These data demonstrate that heteroptypic protection against Ct genital infection with subunit systemic vaccines containing either MOMP, pmpG, or pmpC is possible.

Example 9

VACCINATION AGAINST *CHLAMYDIA* GENITAL INFECTION USING SINGLE CHLAMYDIAL ANTIGENS FROM SEROVAR E OR L2 ADJUVANTED WITH AS1

Using essentially the same protocol as outlined in Examples 8, several additional *Chlamydia* antigens were tested for their ability to protect against challenge when used at 10 ug per dose, in combination with AS1, in Balb/c mice. Each experiment contained a negative control group (AS1-sham-vaccinated infected animals) and a positive control group that comprised animals immunized with 10 ug AS1-adjuvanted UV-irradiated elementary bodies (EBs). All the vaccine preparations were administered in the base of the tail, twice, at 3 weeks interval. Mice were challenged 4 weeks post last immunization.

All mice were treated with 1.25 mg of progesterone and subsequently infected with $1\times10^6$ or $1\times10^7$ purified EBs from serovar K. Bacterial shedding was followed over a 2 week period, at which point the animals were sacrificed. Four antigens including rpoB (fragments N+C used at 5 ug each), pmpDpd, pmpHpd and CT322 showed clear protection against chlamydial shedding (as defined by reaching at least 1 Log10), 6 others showed marginal but nonetheless quite consistent protection against shedding (CT089, Lpda, CT858, CT622, porB and orf3).

TABLE V

Summary of Vaccination Experiments

| Candidate | Infection 10x ifu | Protection (xLog$_{10}$/AS1) | | |
|---|---|---|---|---|
| | | D4 | D7 | D4/7 |
| PmpDpd | 6 | 0.67 | 1.5 | 0.67 |
| RpoB (CT315) | 6 | 0.67 | 1.33 | 0.8 |
| Indeed rpobN + rpobC | | | | |
| PmpHpd (CT872) | 7 | 0.83 | 1.42 | 0.8 |
| CT322 | 6 | 0.8 | 1.66 | 1 |
| Lpda (CT557) | 6 | 0 | 0.67 | 0.33 |
| CT089 | 6 | 0.66 | 0.33 | 0.6 |
| 858 | 7 | 0.42 | 0.92 | 0.4 |
| 622 | 6 | 0.33 | 0.33 | 0.33 |
| PorB (CT713) | 6 | 0 | 0.5 | 0.33 |
| Orf3 (pgp3, plasmidic) | 6 | 0 | 0.5 | 0.4 |

Summary of the protection data obtained in the murine model utilizing *Chlamydia* antigens derived from serovar K. The dose of infection is given. Protection is calculated by comparing medians, and is expressed as a Log 10 reduction factor by comparison of the candidate with the negative control (AS1). D4 and D7 are calculated using individual shedding data taken at day 4 and 7 post infection. D4/7 is a more global protection value calculated using a "mean over 1$^{st}$ week" obtained by averaging day 4 and 7 value for each individual. Protection ration <0.33 is assimilated to 0.

Example 10

VACCINATION AGAINST *CHLAMYDIA* GENITAL INFECTION USING THE MAJOR OUTER MEMBRANE PROTEIN (MOMP) FROM SEROVAR F ALONE, OR *COMBINED WITH OTHER CHLAMYDIAL ANTIGENS*

Using a similar method as described in Example 8, Balb/c mice were vaccinated with a formulation comprising SBAS1 and 10 g of recombinant forms of the MOMP from serovar F. A negative control group included AS1-sham-vaccinated infected animals. The positive control group comprised animals immunized with 10 ug AS1-adjuvanted UV-irradiated elementary bodies (EBs). All the vaccine preparations were administered base of the tail, twice, at 3 weeks interval; mice are challenged 4 weeks post last immunization.

All the mice were treated with 1.25 mg of progesterone twice (10 and 3 days before infection) and subsequently infected with 1×10$^5$ purified EBs from serovar K. Bacterial shedding was followed over a 1-week period (day 4 and 7), and 2 weeks post challenge, the animals were sacrificed.

The animals, which had been vaccinated with MOMP, showed drastically reduced levels of bacterial shedding 4–7 days post-infection, when compared to the negative control groups. By day 7 post-infection, a level of bacterial shedding in the MOMP vaccinated animals was comparable with that of the positive control groups.

The protective qualities of MOMP demonstrates that this antigen is suitable to be used as a base for combination with one or more other chlamydial antigens, formulated in AS1. To illustrate this proposal, Momp was combined with the following CT875 antigens: (5 ug of each antigen used to vaccinate), CT875 and rpob (10 ug of Momp and of CT875, 5 ug of rpobN and 5 ug of rpobC), pmpGpd (5 ug of Momp and 5 ug of pmpGpd), pmpDpd (5 ug of Momp and 5 ug of pmpDpd), and rpoB (5 ug of Momp, 5 ug of rpobN and 5 ug of rpobC).

The experiments were conducted using essentially the same protocol as above, except that we increased the challenging dose to 1×10$^6$ purified EBs from serovar K. The results of these experiments are disclosed in Table VI. All combinations gave moderate to good protection, with protection levels better than Momp alone (10 ug per doses). In particular, very good protection was obtained when combining Momp, rpoB, and CT875 together.

TABLE VI

Summary of Vaccination Experiments

| Candidate | Experiment 10$^x$ifu | Protection (xLog$_{10}$/AS1) | | |
|---|---|---|---|---|
| | | D4 | D7 | D4/7 |
| Momp (CT681) | 5 | 3 | 3 | 3 |
| Momp | 6 | 1.08 | 0.75 | 0.66 |
| Momp/CT875 | 6 | 0.6 | 3 | 0.8 |
| Momp/CT875/rpoB(CT315) | 6 | 1.2 | 3.6 | 1.66 |
| Momp | 6 | 0 | 0.75 | 0.4 |
| Momp/pmpGpd (CT871) | 6 | 1.6 | 3 | 2 |
| Momp | 6 | 0 | 0.4 | 0 |
| Momp/pmpDpd (CT812) | 6 | 0.33 | 0.6 | 0.6 |
| Momp | 6 | 0 | 0.4 | 0 |
| Momp/rpoB (n + c) (CT315) | 6 | 0 | 1 | 0.33 |

Summary of the protection data obtained so far in the K model for each individual antigen formulation: Immune responses are expressed qualitatively. Infection dose for each experiment are given. Protection is calculated by comparing medians, and is expressed as a Log 10 reduction factor by comparison of the candidate with the negative control (AS1). D4 and D7 are calculated using individual shedding data taken at day 4 and 7 post infection. D4/7 is a more global protection value calculated using a "mean over 1$^{st}$ week" obtained by averaging day 4 and 7 value for each individual.

Example 11

VACCINATIONS WITH UV-IRRADIATED ELEMENTARY BODIES (EB) AND THE MAJOR OUTER MEMBRANE PROTEINS: MECHANISMS OF PROTECTION

The above examples have described a murine model of genital infection with human serovar K of *Chlamydia trachomatis*, which closely resembles the pathology of *Chlamydia* infection in humans. We have previously described that vaccination of animals with either UV-inactivated EBs from serovar K or the MOMP from serovar F prior to infection with serovar K markedly reduces the amount of bacterial shedding detected.

To determine the immune mechanisms responsible for protection, the mice were deplete of their CD4$^+$ T cells post-immunization, but prior to and during the course of infection. The level of protection obtained from the animals vaccinated with UV-irradiated EBs was significantly reduced (i.e. a two log increase in the level of bacterial shedding) in the depleted animals compared to the non-completed control group.

To determine if the T cells from the vaccinated group could be adoptively transferred and confer protection against *Chlamydia*-infection, T cells were isolated from both groups of vaccinated animals and transferred to naive RAG1 mice that contained no mature T or B cells. To perform these experiments, mice were immunized essentially as described above. Thirty days following the final immunization, the mice were sacrificed and their spleens removed, the erythrocytes lyzed and the white blood cells enriched for T cells using negative selection. Approximately 1×10$^6$ T cells from either the MOMP or EB-vaccinated animals were then transferred intravenously to the progesteronized RAG1 mice. Twenty-four hours following the adoptive transfer of the T cells, the RAG1 mice were infected cervico-vaginally with 1×10[7] IFU of serovar K. Bacterial shedding was reduced in RAG1 animals that had received enriched T cells from either EB- or MOMP-vaccinated animals, when compared to controls.

These findings suggest that vaccination with either EBs or MOMP adjuvated with AS1 results in the stimulation and expansion of chlamydia-specific T cells which play a major, active role in protection against chlamydial infection. Additionally, it demonstrates that a strong T cell component is essential to a successful vaccine against chlamydia infection, and that the model developed here provides this protection.

Example 12

IDENTIFICATION OF *CHLAMYDIA TRACHOMATIS* PMP-PASSENGER DOMAINS

Amino acid sequences of all the polymorphic membrane proteins (pmps) of *Chlamydia trachomatis* were analyzed for the presence of different domains. This analysis suggests that the pmps belong to a class of proteins called autotransporter proteins. Autotransporters are a family of secreted proteins from Gram-negative bacteria, possess an overall unifying structure comprising three functional domains: the amino-terminal leader sequence, the secreted mature protein or passenger domain, and a carboxy-terminal (beta-) domain that forms a beta-barrel pore to allow secretion of the passenger protein. Members of this family are important or putative virulence factors in a gram-negative bacteria (Henderson et al. (1998) *Trends Microbiol* 6(9):370–8).

Using domain homology searches and sequence alignments, regions of the pmps that are surface exposed were identified and these regions are refered to as passenger domains (PD). The passenger domains were identified as being contained within the following regions:

PmpA amino acids 52-661, with the corresponding DNA and amino acid sequences disclosed in SEQ ID NOs:166 and 175, respectively;

PmpB amino acids 24-1420, with the corresponding DNA and amino acid sequences disclosed in SEQ ID NOs:165 and 174, respectively;

PmpC amino acids 21-1439, with the corresponding DNA and amino acid sequences disclosed in SEQ ID NOs:164 and 173, respectively;

PmpD amino acids 31-1203, with the corresponding DNA and amino acid sequences disclosed in SEQ ID NOs:163 and 172, respectively;

PmpE amino acids 19-650, with the corresponding DNA and amino acid sequences disclosed in SEQ ID NOs:162 and 171, respectively;

PmpF amino acids 26-727, with the corresponding DNA and amino acid sequences disclosed in SEQ ID NOs:161 and 170, respectively;

PmpG amino acids 28-697, with the corresponding DNA and amino acid sequences disclosed in SEQ ID NOs:160 and 169, respectively;

PmpH amino acids 25-688, with the corresponding DNA and amino acid sequences disclosed in SEQ ID NOs:159 and 168, respectively; and PmpI amino acids 25-566, with the corresponding DNA and amino acid sequences disclosed in SEQ ID NOs:158 and 167, respectively.

U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing, although the present invention has been described in some detail by way of illustration and example for purposes of clarity of understanding, changes and modifications can be carried out without departing from the scope of the invention which is intended to be limited only by the scope of the appended claims.

What is claimed is:

1. An isolated polypeptide consisting of SEQ ID NO: 172 or an immunogenic fragment of SEQ ID NO: 172 effective for inducing immunity against *Chlamydia* infection.

2. A fusion protein comprising a polypeptide according to claim 1 and a fusion partner.

3. A composition comprising a first component selected from the group consisting of physiologically acceptable carriers and immunostmulants, and a second component selected from the group consisting of a polypeptide according to claim 1, a polypeptide according to claim 1 in combination with at least one or more other *Chlamydia trachomatis* polypeptides, a fusion protein according to claim 2, and an antigen presenting cell that expresses a polypeptide according to claim 1.

* * * * *

SEQUENCE LISTING

```
<160> NUMBER OF SEQ ID NOS: 175

<210> SEQ ID NO 1
<211> LENGTH: 1311
<212> TYPE: DNA
<213> ORGANISM: Chlamydia trachomatis

<400> SEQUENCE: 1
taattcgctt ttacctctct tcttgctgaa gacttggcta tgtttttat tttgacgata      60 aacctagtta aggcataaaa gagttgcgaa ggaagagccc taaacttttc ttatcatctt     120
ctttaactag gagtcatcca tgagtcaaaa taagaactct gctttcatgc agcctgtgaa    180
cgtatccgct gatttagctg ccatcgttgg tgcaggacct atgcctcgca cagagatcat    240
taagaaaatg tgggattaca ttaagaagaa tagccttcaa gatcctacaa acaaacgtaa    300
tatcaatccc gatgataaat tggctaaagt ttttggaact gaaaaaccta tcgatatgtt    360
ccaaatgaca aaaatggttt ctcaacacat cattaaataa aatagaaatt gactcacgtg    420
ttcctcgtct ttaagatgag gaactagttc attcttttg ttcgtttctg tgggtattac     480
tgtatcttta acaactatct tagcagcacc tgttttgaca tgggtttggg ccaatcactt    540
```

-continued

```
agagcctaac ctattgagag taacgcgttt aaattggaat ctgcctaaaa aatttgctca      600
tcttcatggg cttcgcatta tacagatttc ggatttacac ctaaaccact cgacgcctga      660
tgcctttcta aaaaagtat ctcgtaagat ctcttctctt tctccagata ttcttgtatt       720
tacaggagac tttgtctgtc gcgctaaagt agaaactcct gaaagattaa acatttcct      780 atgttctctg catgcgccct taggctgttt tgcttgccta ggaaatcatg attacgccac      840
ctacgtatcc cgtgatattc acgggaaaat taataccatc tcagcaatga atagccgtcc      900
tttaaaaaga gcttttacct ctgtttatca aagtctattc gcctcttctc gcaatgaatt      960
tgcagatact ctgaatccac aaattcctaa tccacaccta gtcagtatat tacgcaatac     1020
tccatttcaa ttattgcata atcaaagcgc gacactttcc gatacaatca acatcgtggg     1080
attaggcgat ttttttgcca aacaattcga tcccaaaaaa gcttttactg actataatcc     1140
cacgttacct ggtattatcc tttctcataa tcccgatacg attccaccatc tccaagatta    1200 cccaggtgat gttgtttttt ccgggcactc gcatggccct caaatctctc ttccctggcc     1260
taagtttgcc aatacgataa ccaataaact ttcagggtta gaaaacccag a              1311
```

<210> SEQ ID NO 2
<211> LENGTH: 1516
<212> TYPE: DNA
<213> ORGANISM: Chlamydia trachomatis

<400> SEQUENCE: 2

```
tttgagctcg tgccgctcgt gccggtgcgt gtgaaccgct tcttcaaaag cttgtcttaa       60
aagatattgt ctcgcttccg gattagttac atgtttaaaa attgctagaa caatattatt      120
cccaaccaag ctctctgcgg tgctgaaaaa acctaaattc aaaagaatga ctcgccgctc      180
atcttcagaa agacgatccg acttccataa ttcgatgtct ttccccatgg ggatctctgt      240
agggagccag ttatttgcgc agccattcaa ataatgttcc caagcccatt tgtacttaat      300
aggaacaagt tggttgacat cgacctggtt gcagttcact agacgcttgc tatttagatt      360
aacgcgtttc tgttttccat ctaaaatatc tgccttgcata agaaccgtta attttattgt     420
taatttatat gattaattac tgacatgctt cacacccttc ttccaaagaa cagacaggtg     480
ctttcttcgc ctctttcaaca ataattcctg ccgaagcaga cttattcttc atccaacgag     540
gctgaattcc tctcttatta atatctacaa agattttttc aacggtcgtt gctgatgaag     600
atctcagata tacgtagtt ttcaaaccttt ttttccaagc cgttaaatac atattcgaca     660
gttttttccc gtctggctgg gcaagataaa ggttgaggga ttgccccata tcaatccatt     720
tttgtcttcg agacgcgcat tcgataatcc attctggttc aatctcaaaa gctgtcaaga     780
aaatatgttt taagtgatct ggtatacgct cgatttccaa taaagaccca tcaaaatatt     840
tcaggtcatc taacatatca gcatcccaga tacctaattt cttcaacttc tcaattaaat    900
acacatttgg aatcgtgaat tctccggaca aattagactt cacaaacaaa tgtttgtacg     960
ttggctcaat agattgagtt actcctataa tgttggagat cgtcgctgtc ggagctatag    1020
ccataagctg acaatgtcgc ataccatgct ctttaaccaa actacggata ggttcccaat    1080
cttttcttga tgacgtatcc atctggagat ttgcttctcc tcgatagttc gctaacaact    1140
gaatcgtatc aatagggagc aaacctctat cccatttcga tcctttataa gagctgtaag    1200
tgcctcgttc tttagcgagc agacaagaag cttgaatcgc atagtaagaa atcaactctg    1260
aactgtagtc agcaaattct acagcttctt gcgaagcata gcttatatct agcttataca    1320
```

```
aggcatcttg gaatcccatc acccctaatc caatagcgcg gtgagcaaag ttcgcctctt    1380
tagcttcctt tgttggataa aagttaatat caatcacgtt atccaacata cggactgcta    1440
tagagatcgt ctcagagagt ttttcctcat caaacccatc ccctacgata tgttgaacta    1500
agttaatcga tcctaa                                                    1516

<210> SEQ ID NO 3
<211> LENGTH: 2397
<212> TYPE: DNA
<213> ORGANISM: Chlamydia trachomatis

<400> SEQUENCE: 3
agagtgtgct ggaggagcta tttttgcaaa acgggttcgt attgtagata accaagaggc      60
cgttgtattc tcgaacaact tctctgatat ttatggcggc gccatttta caggttctct     120 tcgagaagag gataagttag atgggcaaat ccctgaagtc ttgatctcag gcaatgcagg     180
ggatgttgtt ttttccggaa attcctcgaa gcgtgatgag catcttcctc atacaggtgg     240
gggagccatt tgtactcaaa atttgacgat ttctcagaat acaggaatg ttctgtttta     300 taacaacgtg gcctgttcgg gaggagctgt tcgtatagag gatcatggta atgttctttt     360
agaagctttt ggaggagata ttgtttttaa aggaaattct tctttcagag cacaaggatc     420
cgatgccatc tattttgcag gtaaagaatc gcatattaca gccctgaatg ctacggaagg     480
acatgctatt gttttccacg acgcattagt ttttgaaaat ctagaagaaa ggaaatctgc     540
tgaagtattg ttaatcaata gtcgagaaaa tccaggttca aaatttctca gtttgatgc     600 aattgtgcta ttcgctacct ttagttttct atgtccacgg taagggatc ggaaagatac     660 gcatttattt tcatagtctt tagcttcgat ccctagtgct tccgcatgga ctcgtctgcc     720
aagacttttg gttacgaaaa caacaggctc tcgttgagaa atgatttgga gtagctctag     780
cgtgaggtgt tttttctgtt tctcgtggtt tgaaagattg actagaggag agacttcaat     840
acataactcg ctgccgtttt taataaaat ttgaccagag gagggtcttt ccgactgctc     900
tagtaataga cgaatattgc ccaatgctct ggaagcattt ttccctgatt catctcgaaa     960 cttttgcgcag gattccaatt cttcgattac tgtaaaaggg ataatgatgc gagtgttaga    1020
aaaagaggaa agggccttag gatcgtaaat caaaacgctg gtatcaataa cagaggtttt    1080
tttcattaca aattcctaaa tgactcaagt gtaaggggga gatagtactt tgattgtgta    1140
tcatatccag aaaaattaaa acatgtcttt gttagagaga agtcgggaga gagggttttt    1200
agcaatcaac ctccgcgtgt gctaatctgt ttgtcaaaaa tgtaccccctt aactacaatg    1260 ccgaggaaag cgagtccttc tgttggaggt tgttatgaaa gtcaaaatta atgatcagtt    1320
catttgtatt tccccataca tttctgctcg atggaatcag atagctttca tagagtcttg    1380
tgatggaggg acggaagggg gtattacttt gaaactccat ttaattgatg gagagacagt    1440
ctctataccc aatctaggac aagcgattgt tgatgaggtg ttccaagagc acttgctata    1500
tttagagtcc acagctcctc agaaaaacaa ggaagaggaa aaattagct ctttgttagg    1560 agctgttcaa caaatggcta aaggatgcga agtacaggtt ttttctcaaa agggcttggt    1620
ttctatgtta ctaggaggag ctggttcgat taatatgttg ttgcaacatt ctccagaaca    1680
taaggatcat cctgatcttc ctaccgattt actggagagg atagcgcaaa tgatgcgttc    1740
attatctata ggaccaactt ctatttagc taagccagag cctcattgca actgtttgca    1800
ttgtcaaatt ggacgagcta cagtggaaga agaggatgcc ggagtatcgg atgaggatct    1860
cacttttcgt tcatgggata tctctcaaag tggagaaaag atgtacactg ttacagatcc    1920
```

```
tttgaatcca gaagtatacc ttttgttttt tttatacgag ccagcactcc aatttctgac    1980
tgtgagaata tatcataaat agaccggcct ctagcgctgc gaatagaaaa agtctttgct    2040
atagcactat caagccttcc ctttatacgc tcaagcaata gaaacggaga tctacgcaat    2100
ggattttcat tgtactcatt aaacgagcgg aaaatgaaat tactcaaatt ttcttcagcg    2160
ctacacacgc tcaaatcatc gaggaaaacc gtatgagaaa cggatctact cgtgccgaat    2220
tcggcacgag gtctctaatc ttgcagaagg agcacaaatt tttgctgtcc aagggttaaa    2280
tactgctgga gaaataggat actgccctcc ttgccctcca gatgcgaagc atcgctatta    2340
cttttatgct tatgcgctcg atgttgtgct ttccgatgaa gaaggagtga ccaaaga      2397
```

<210> SEQ ID NO 4
<211> LENGTH: 1094
<212> TYPE: DNA
<213> ORGANISM: Chlamydia trachomatis

<400> SEQUENCE: 4

```
tgatgcagaa gacactgtta agaagttaca agaagccggt gctaaggctg ttgctaaagg      60
gctgtaattg ttatgggaaa gagaatgctt tggggggttgc ttgcaagctt ctcttttcgt    120
ttagctgcac agtagctggg cacagagggg ttcccggtac gtcttaacag atttgtctgg    180
acttaacttt tagtgtttgg catcgcaaac agaatatttc tgttgcaatg gttttttctt    240
aatggaatca aggtgatagt atttgtcgga tggacaagtg tatagagagt atccagtgtc    300
tctgtattgg atagactctg ttttgtccta gctggaaagc atctgtcgta ttcctgttta    360
gagatcacag agggactaaa tagggaaatg gtatcgccaa agtcttaaa gtcttaggag     420 agctcgcatg ttcaagtgcc cggagcgggt cagcgtcaaa agaaagaag atattttaga    480 tcttcctaat cttgtcgaag ttcaaatcaa gtcgtataag cagtttcttc aaatcgggaa    540
gcttgctgaa gagcgagaaa acattggttt agaagaagtc ttcagagaaa ttttccctat    600
caagtcttat aatgaagcta cgattttaga gtacctctct tataacttag gagtgcccaa    660
atactcccca gaagagtgta ttcgtcgggg aatcacctat agtgttactt taaaggttcg    720
tttccgttta actgatgaaa cggggattaa agaagaagaa gtctatatgg gaaccatccc    780
catcatgact cataagggaa ccttttattat taatggggca gagagagtcg ttgtttctca    840
agtccaccgt tctccaggaa tcaattttga acaagaaaaa cattctaaag ggaatgtttt    900
attttctttt agaattattc cttatcgagg aagttggtta gaagctgtct tcgacattaa    960
tgaccttatc tatatccata ttgataggaa aaaacgtcgc agaaagattt tagctattga   1020
cgtttatccg agctttagga tattcaacag atgcagatat tattgaagag ttctttttctg   1080 tagaggagcg ttcc                                                      1094
```

<210> SEQ ID NO 5
<211> LENGTH: 2129
<212> TYPE: DNA
<213> ORGANISM: Chlamydia trachomatis

<400> SEQUENCE: 5

```
gcttctttaa gagataagca acaaccgagg aatccactcc tccagacata gcaacaatga     60
tagttttacg cacaatgagc ccagaaaacg ctttcgttta ttgaagtttg cacattacaa    120
agggccatca tgttagcaaa aaacaggat caaaaaaacc tatttctcaa gccgcctctt    180
ttaaatctta attacaaaaa taaaaatcaa ttcaactttt caaaaaaaga atttaaacat    240
```

-continued

```
taattgttat aaaaacaata tttattataa aataataacc atagttgcgg ggaaatctct    300
ttcatggttt attttagagc tcatcaacct aggcatacgc ctaaaacatt tcctttggaa    360
gttcaccatt cgttctccga taagcatcct caaattgcta aagctatgcg gattacgggg    420
ataaccctcg cagctctatc tctgctcgct gtagtcgcct gcgttattgc cgtctctgcg    480
ggaggagctg ccattcctct tgctgtcatt ggtggaattg ctgcaatgtc tggcctctta    540
tccgctgcca ccattatctg ttctgcaaaa aaggctctgg ctcaacgaaa acaaaaacaa    600
ctagaagagt tgcttccgtt agataatgcg accgagcatg tgaattacct gacctcagac    660
acctcttatt ttaatcaatg gaatccttta gatgctctaa ataagcagtt gtctcagatt    720
gacttaacta ttcaagctcc cgaaaaaaaa ctattaaaag aagttcttgg ttccagatac    780
gattccatta atcactccat cgaagagatc tccgatcgct ttacgaaaat gctctctctt    840
cttcgattaa gagaacattt tgtcgagga gaagagcgtt atgccccta tttaagccct    900
cctctactta caagaatcg tttgctgacc caaatcacat ccaatatgat taggatgcta    960
ccaaaatccg gtggtgtttt tcccctcaaa gccaatacac taagtcatgc cagccgcaca    1020
ctatatacag tattgaaagt cgctttatcc ttaggagttc tcgctggagt cgctgctctt    1080
atcatctttc ttcccctag cctgcctttt atcgctgtta taggagtatc ttccttagca    1140
ttggggatgg catctttcct tatgattcgg ggcattaagt atttgctcga acattctcct    1200
ctgaatagaa agcaattagc taaagatatt caaaaaacca ttatcccaga tgtcttggcc    1260
tctatggttc attaccagca tcaattacta tcacatctac atgaaactct attagatgaa    1320
gccatcacag ctagatggag cgagccttc tttattgaac acgctaatct taaggcaaaa    1380
attgaagatt tgacaaaaca atatgatata ttgaacgcag cctttaataa atctttacaa    1440
caagatgagg cgctccgttc tcaattagag aaacgagctt acttattccc aattcctaat    1500
aacgacgaaa atgctaaaac taagaatcg cagcttctag actcagaaaa tgattcaaat    1560
tctgaatttc aggagattat aaataaagga ctagaagctg ccaataaacg acgagctgac    1620
gctaagtcaa aattctatac ggaagacgaa acctctgaca aaagattctc tatatggaaa    1680
cccacaaaga acttggcatt agaagatttg tggagagtgc atgaagcttg caatgaagag    1740
caacaagctc tcctcttaga agattatatg agttataaaa cctcagaatg tcaagctgca    1800
ctccaaaag tgagtcaaga actgaaggcg gcacaaaaat cattcgcagt cctagaaaag    1860
catgctctag acagatctta tgaatccagt gtagccatga tggatttagc tagagcgaat    1920
caagaaacac accggcttct gaacatcctc tctgaattac aacaactagc acaatacctg    1980
ttagataatc actaacggtt cttcataaat gacaaaaaga aaaggagag ctgttgctgt    2040
gctctccttt ttctctaaat attcctgaaa gactaacctt tttatggttg cgttgagcct    2100
cctcctcctg ttcccgagga gcccgcaac    2129
```

<210> SEQ ID NO 6
<211> LENGTH: 1828
<212> TYPE: DNA
<213> ORGANISM: Chlamydia trachomatis

<400> SEQUENCE: 6

```
gagggagcag cctaactctc ccctctcttc ttaaaaaga ggggagcctt ttttccttac     60
aaagatacgc tagctttttc ctgaagaatc tcatcaagag atatttgcat tttcccacgg    120
ataaaggcat cccaaggaag ccctggaatc acttcatatt ctcccgttgc tagcattcga    180
caagggaaac caaagattaa atcttccggt aatccatagg gattgtggtc cgaacacact    240
```

```
ccggaagaaa accattctcc ttcttttggc tgatatattg atcgagcagc ctctgctaaa      300
gctcgtgctg cagaagctgc cgaagacttc cctcgtgctt cgattactgc actaccacga      360
ctctgtacag aaggcaccat aatattctct aaccaatcac gatccgctat cgtctctgcg      420
ataggacggt cattaatcag agcttgcgta aaatcaggca cttgtttggc ggagtgattt      480
ccccaaacca caacttgtga tacagccgat aaaggtactt ctgctctatg cgataacatg      540
ctatgcatac gattctggtc aatcgtagc atcgcatgaa agttctttct caataatctg       600
ggagcatgat tcattgctat ccagcaattg gtattcacag gttcccaac aacaaaaatc       660 tttgcatccc gcttggctgt tgtgttcaaa gcttttcctt gcgtagcaaa atctcccca       720 tttttcttta aagatccct ctctccatt cctgggcctc taggaactga ccctataagg        780
aatgccgcat caatgccatc aaaagcatca tgcaatgatg tcgttacctg cacacgctgt      840
aataagggga agcaccatc atctagctcc atgcgcacac cagataaagc cctttctgtt       900
ccaggaatat cgtagatacg cagatcgatg ccacaatcaa ggccaaaaac atctccatga      960
gccagagaaa atagaaagct ataggctatt gccctgttc ctcctgttac tgctacactc       1020
actgtttgag aaaccataag ccaccctctc tttacttta caaaacgcac atactctcaa       1080
cactacgttt gcaactaact aattttggtc ccaacatacg tttggatgat aaaagaatca      1140
agtacctaga ttccttagta aaagcttttg gcaaaaaaaa gctcatctat ttttcaatag      1200
atgagccgac tttaactgaa taagaactta gaaaacttta taaaaaatag gcccgtgtga      1260
tcctacccat atacttgatc ccgaccgcat aacttgttgt ccctttttag cagccaaata      1320
accgtggaca tctaaaaaac caataaaccg tgcgcgaata agaacataa agcccctaaa       1380 aaaacgattt taagagagaa gtaatagaca gattgtaaca tatttaaaat aaaaactctg      1440
caaacaaaaa aactttgcct ggccgtctcc gtagaaagca ctttatgtta aacgttaaa       1500 aagtcttaac atacctcgag cttcgggaaa ctctacagga gcattcccg acatgatgcc       1560 tataatttgc gttgccaatt ctttcccta tgaaacccct tcttgatcaa agaattgat        1620 tccccagcaa aacccttgaa atgcaaattt atgctcataa aaagccaata aactaccagc     1680
aatacgagga gaaagctgtt gcgctaccaa tatcgaagaa ggtctgttcc ctttaaacct     1740
cttattcggg ttcgcattat ctctaccctg agctaaagct aaagattgag caacaaggtt     1800
tgcaaagagc ttttgagatc tcgtgccg                                        1828

<210> SEQ ID NO 7
<211> LENGTH: 861
<212> TYPE: DNA
<213> ORGANISM: Chlamydia trachomatis

<400> SEQUENCE: 7
gggcgcacta ctttaaagat tcgtcgtcct tttggtacta cgagagaagt tcgtgtgaaa     60
tggcgttatg ttcctgaagg tgtaggagat ttggctacca tagctccttc tatcagggct    120
ccacagttac agaaatcgat gagaagcttt tccctaaga aagatgatgc gtttcatcgg     180
tctagttcgc tattctactc tccaatggtt ccgcattttt gggcagagct tcgcaatcat    240
tatgcaacga gtggtttgaa aagcgggtac aatattggga gtaccgatgg gtttctccct    300
gtcattgggc ctgttatatg ggagtcggag ggtctttttcc gcgcttatat ttcttcggtg    360
actgatgggg atggtaagag ccataaagta ggatttctaa gaattcctac atatagttgg    420
caggacatgg aagattttga tccttcagga ccgcctcctt gggaagaatt tgctaagatt    480
```

-continued

```
attcaagtat tttcttctaa tacagaagct ttgattatcg accaaacgaa caacccaggt    540
ggtagtgtcc tttatcttta tgcactgctt tccatgttga cagaccgtcc tttagaactt    600
cctaaacata gaatgattct gactcaggat gaagtggttg atgctttaga ttggttaacc    660
ctgttggaaa acgtagacac aaacgtggag tctcgccttg ctctgggaga caacatggaa    720
ggatatactg tggatctaca ggttgccgag tatttaaaaa gctttggacg tcaagtattg    780
aattgttgga gtaaggggga tatcgagtta tcaacgccta ttcctctttt tggttttgag    840
aagattcatc cacatcctcg a                                              861
```

<210> SEQ ID NO 8
<211> LENGTH: 763
<212> TYPE: DNA
<213> ORGANISM: Chlamydia trachomatis

<400> SEQUENCE: 8

```
ataacaaaaa catcttgatt attttttgtta aagaaatac ttaatgagtt ttatttaatt     60
aacgaaacga aaagcttgct aatgaaaatt attcacacag ctatcgaatt tgctccggta    120
atcaaagccg gaggcctggg agacgcgcta tacggactag caaaagcttt agccgctaat    180
cacacaacgg aagtggtaat cccttttatac cctaaattat ttactttgcc caaagaacaa    240
gatctttgct cgatccaaaa attatcttat ttttttgctg gagagcaaga agcaactgct    300
ttctcctact tttatgaagg aattaaagta actctattca aactcgacac acagccagag    360
ttattcgaga atgcggaaac aatctacaca agcgatgatg ccttccgttt ttgcgctttt    420
tctgctgctg cggcctccta catccaaaaa gaaggagcca atatcgttca tttacacgat    480
tggcatacag gattagttgc tggactactc aaacaacagc cctgctctca attacaaaag    540
attgttctta ccctacataa ttttggttat cgaggctata caacacgaga atattagaa    600 gcctcctctt tgaatgaatt ttatatcagc cagtaccaac tatttcgcga tccacaaact    660
tgtgtgttgc taaaaggagc tttatactgt tcagatttcg tgactacggt ttctcctaca    720
tacgccaaag aaattcttga agattattcc gattacgaaa ttc                      763
```

<210> SEQ ID NO 9
<211> LENGTH: 665
<212> TYPE: DNA
<213> ORGANISM: Chlamydia trachomatis

<400> SEQUENCE: 9

```
ttgaaactaa aaacctaatt tatttaaagc tcaaaataaa aaagagtttt aaaatgggaa     60
attctggttt ttatttgtat aacactgaaa actgcgtctt tgctgataat atcaaagttg    120
ggcaaatgac agagccgctc aaggaccagc aaataatcct tgggacaaca tcaacacctg    180
tcgcagccaa aatgacagct tctgatggaa tatctttaac agtctccaat aattcatcaa    240
ccaatgcttc tattacaatt ggtttggatg cggaaaaagc ttaccagctt attctagaaa    300
agttgggaga tcaaattctt gatggaattg ctgatactat tgttgatagt acagtccaag    360
atattttaga caaaatcaaa acagacccct ctctaggttt gttgaaagct tttaacaact    420
ttccaatcac taataaaatt caatgcaacg ggttattcac tcccagtaac attgaaactt    480
tattaggagg aactgaaata ggaaaattca cagtcacacc caaagctctg ggagcatgt     540 tcttagtctc agcagatatt attgcatcaa gaatggaagg cggcgttgtt ctagctttgg    600
tacgagaagg tgattctaag ccctgcgcga ttagttatgg atactcatca ggcattccta    660
attta                                                                665
```

<210> SEQ ID NO 10
<211> LENGTH: 843
<212> TYPE: DNA
<213> ORGANISM: Chlamydia trachomatis

<400> SEQUENCE: 10

| | | | | | |
|---|---|---|---|---|---|
| tgggaatgtc | gaagaatacg | attacgttct | cgtatctata | ggacgccgtt | tgaatacaga | 60 |
| aaatattggc | ttggataaag | ctggtgttat | ttgtgatgaa | cgcggagtca | tccctaccga | 120 |
| tgccacaatg | cgcacaaacg | tacctaacat | ttatgctatt | ggagatatca | caggaaaatg | 180 |
| gcaacttgcc | catgtagctt | ctcatcaagg | aatcattgca | gcacggaata | tagctggcca | 240 |
| taaagaggaa | atcgattact | ctgccgtccc | ttctgtgatc | tttaccttcc | ctgaagtcgc | 300 |
| ttcagtaggc | ctctccccaa | cagcagctca | acaacaaaaa | atccccgtca | agtaacaaa | 360 |
| attcccattt | cgagctattg | gaaaagcggt | cgcaatgggc | gaggccgatg | gatttgcagc | 420 |
| cattatcagc | catgagacta | ctcagcagat | cctaggagct | tatgtgattg | gccctcatgc | 480 |
| ctcatcactg | atttccgaaa | ttaccctagc | agttcgtaat | gaactgactc | ttccttgtat | 540 |
| ttacgaaact | atccacgcac | atccaacctt | agcagaagtt | tgggctgaaa | gtgcgttgtt | 600 |
| agctgctgat | accccattac | atatgccccc | tgctaaaaaa | tgaccgattc | agaatctcct | 660 |
| actcctaaaa | aatctatacc | cgccagattc | cctaagtggc | tacgccagaa | actcccttta | 720 |
| gggcgggtat | ttgctcaaac | tgataatact | atcaaaaata | aagggcttcc | tacagtctgt | 780 |
| gaggaagcct | cttgtccgaa | tcgcacccat | tgttggtcta | gacatacagc | gtacctatct | 840 |
| agc | | | | | | 843 |

<210> SEQ ID NO 11
<211> LENGTH: 1474
<212> TYPE: DNA
<213> ORGANISM: Chlamydia trachomatis

<400> SEQUENCE: 11

| | | | | | |
|---|---|---|---|---|---|
| acagaaggga | cggcagagta | atcgatttcc | tctttatggc | cagctatatt | ccgtgctgca | 60 |
| atgattcctt | gatgagaagc | tacatgggca | agttgccatt | ttcctgtgat | atctccaata | 120 |
| gcataaatgt | taggtacgtt | tgtgcgcatt | gtggcatcgg | tagggatgac | tccgcgttca | 180 |
| tcacaaataa | caccagcttt | atccaagcca | atattttctg | tattcaaacg | gcgtcctata | 240 |
| gatacgagaa | cgtaatcgta | ttcttcgaca | ttcccattga | tagttaaccg | aacgcgatct | 300 |
| cctatatcct | caatatttga | tacagaggct | tctagtacga | aacggagtcc | ttgtcgggtg | 360 |
| aatttatcga | acatggtttt | tgaaatatct | ggattattca | aagcaaggat | ttgagagctt | 420 |
| gcttcgatca | cagaaacttc | ggagcctaac | gtatggaata | aggaagcgaa | ttcgcaaccg | 480 |
| atcacaccac | cgccaataat | ggccattttt | tgagggattt | ctttgaggtt | tagcacgcct | 540 |
| gttgagcata | aaatccgagg | agattctgcg | gaaaaaggaa | tcccgggaa | agctcgtggt | 600 |
| tcagagccgg | tggctaggat | aatggagtgc | gctttgatta | cagaagggtt | ttctcctaag | 660 |
| atttttactt | ctgttgaaga | gatcaaagag | cctcttccag | agaagacagt | gatcttattg | 720 |
| ctgcgaatga | gaccattaag | tccatcgcg | atgctacgga | ctacgaatc | cttcctttgt | 780 |
| accatagcgg | gatagttgat | gctgaatcct | tctacatgaa | tcccaaactg | gtcagcatgg | 840 |
| cgtatttggg | taacgacttc | agctcctgct | aagagggctt | tagaaggaat | acaccctcgg | 900 |
| tttaaacagg | ttccgccagc | ctctcgcttt | tcgattagcg | cagttttgag | tcctgcttga | 960 |

```
gcggcagtga ttgctgcaac atagcctcct ggccccgctc cgataactac acagtcgaaa    1020
gcttcattca taacatttcc tcttcaatga gtgtttagga ttgcaacgat ccatatgaga    1080
tgattatctg aaggaagagg attctccttc caagcctttc taggaaaggg aaagagaggt    1140
ccttcagaca aatacatttc ccggattgta catctgggtg gataaaatct caatgaggag    1200
aagtggtagc aggagagaaa aaataggaac gtaagagtgt tatttcgaat gctcagggag    1260
agagcggtac ccacgataag caagcagaat cccgactagt gcatagatgt atgagcgatt    1320 cttttggccag gagagaacga gtccagagcc tgtcgaaaac aagagaatca tgagcgaaaa    1380
ggtaaggaaa ccgcaaccca agaagagagc tgcagtcggc caatattgta gccagtccca    1440
ctgggagggg gcaggctctt gaacaggctc ctca                                1474

<210> SEQ ID NO 12
<211> LENGTH: 2017
<212> TYPE: DNA
<213> ORGANISM: Chlamydia trachomatis

<400> SEQUENCE: 12
ataagcattc tcatctaccc agaagtagaa gtcaaaacct tcataagtat ctaaaaagac      60
tcgcatataa tcttcgatac catccggagg cgctcctgcg atccatattc catggatgat     120
tttctcaaca ggtacacgat ggcctttaaa ttctgttttg atggtttcaa gaacaccttc     180
aatcggagtc gtcttaggtt tttcttcggc tttctgttcc ttagcttttg cctgtttagg     240
ctgagcctgc gatgatgctg gaagcttctt ctgaatggca tcgacgtatt ttccttgttg     300
aatcaaggaa ttctgtcccg cttccgaatt tttatctggc atagagttgt aagcactaat     360
gacctttttc agtttattta ataggtcttt aacagtagat ttctgttcag gagtaattcc     420 tagttttttct tctatgttct tgggagtaag atcgtatttg ctagcatcaa gattttctat     480 cttttccagaa gaagcttcct ccttcttctc ttctatagca cgcttttttc tcgataaaac     540
agctgctgta ggaggaactg cactagcaga aatcgttttt accccccccc ctctgaacag     600
agtacgtacg aacgttcact ggctgtgtaa taaacttcgt cttttctctta cgaggagagg     660 ttttgtcgtt acttcctgtt ctttagagat tgtagtgacc ttattctctg aagtagaagt     720
ctctgccgtc tcgtgccgaa ttcggcacga gaagccatgt tatctttgct tagatcaatg     780
ccttcttgtt ttttgaattc atcaagcatc cagttgatga tgactccgtc gaagtcgtct     840
cctcccaagt gagtatcccc gttggttgag agaacttcaa aaactccgtc accgatttcc     900
aagatagaaa tatcgaaagt tcctcctcct aagtcgaaga cggcgatttt tttatctcct     960
tccttatcaa taccataagc aagagcggcc gctgttggtt caggaataat gcgtttaaca    1020
tctaatcctg cgatacgtcc agcatctttt gtagaagctc tttgagaatc gttaaagtaa    1080
gctggtacgg taatgactgc ttccgttact gtttctccga gataagcctc agcagtttcc    1140
ttcatcttca tgaggatctg agcgccgatt tcttctggag tgtacagttt ttgttccaca    1200
tcaaagaccg catctccttt cgagttagga gcaactttgt aggggactgt tttaatttca    1260
gattcgactt cagagaattt tctaccgatg aatcgcttag tagaagccaa tgttttttca    1320
ggattggtta ctgcctgacg ttttgcagga attccaacaa gagtttcgcc acctttaaaa    1380
gcaacgatag aaggagtagt acgagttcct tcagaagagg caataacttt aggttggcca    1440
ccttccataa cagagacgca agagttggtc gtccctaggt cgataccaat aattttgtta    1500
gactttcttt tttcgctcat attgaacacc taatttctag gataattatt cttttttcttc    1560 gttaccgtct gagtttcctt tagcaggaag ttttgctact ttcactttgg ctacgcgaat    1620
```

```
aggacgatct cctatcttat aacctttagt aaattcctcc aagatagtcc cttctggaat    1680
tgttgtggtt tcttcgattt ctacagcttc atgcaggtac ggattaaata gttctccttt    1740
cgaggaatat tcaaccacac ctttctcttc gaagatttgc ttaaattgtt gaaggatcat    1800
ttggaatcct atagcccaat ttttttacttc ttcagaggtt tgagaagcga atcccaaagc   1860
cttttccata ctttcgatag aaggaaggaa atccataaga gcattttcta cagcatactg    1920
catcatttct gtgcgttctt tctgtagtcg ttttcttgag ttttctgctt cagcgagagc    1980
catcagatat cgatcattct gttcttgcct cgtgccg                             2017

<210> SEQ ID NO 13
<211> LENGTH: 1171
<212> TYPE: DNA
<213> ORGANISM: Chlamydia trachomatis

<400> SEQUENCE: 13
ggtaaacgag ttaaaacaag agcatacagg gctaacggac tcgcctttag tgaaaaaagc      60
tgaggagcag attagtcaag cacaaaaaga tattcaagag atcaaaccta gtggttcgga    120
tattcctatc gttggtccga gtgggtcagc tgcttccgca ggaagtgcgg caggagcgtt    180
gaaatcctct aacaattcag gaagaatttc cttgttgctt gatgatgtag acaatgaaat    240
ggcagcgatt gcactgcaag gttttcgatc tatgatcgaa caatttaatg taaacaatcc    300
tgcaacagct aaagagctac aagctatgga ggctcagctg actgcgatgt cagatcaact    360
ggttggtgcg gatggcgagc tcccagccga aatacaagca atcaaagatg ctcttgcgca    420
agctttgaaa caaccatcag cagatggttt ggctacagct atgggacaag tggcttttgc    480
agctgccaag gttggaggag ctccgcagg aacagctggc actgtccaga tgaatgtaaa    540
acagctttac aagacagcgt tttcttcgac ttcttccagc tcttatgcag cagcactttc    600
cgatggatat tctgcttaca aaacactgaa ctctttatat tccgaaagca gaagcggcgt    660
gcagtcagct attagtcaaa ctgcaaatcc cgcgctttcc agaagcgttt ctcgttctgg    720
catagaaagt caaggacgca gtgcagatgc tagccaaaga gcagcagaaa ctattgtcag    780
agatagccaa acgttaggtg atgtatatag ccgcttacag gttctggatt ctttgatgtc    840
tacgattgtg agcaatccgc aagcaaatca agaagagatt atgcagaagc tcacggcatc    900
tattagcaaa gctccacaat ttgggtatcc tgctgttcag aattctgcgg atagcttgca    960
gaagtttgct cgcgcaattgg aaagagagtt tgttgatggg gaacgtagtc tcgcagaatc   1020
tcaagagaat gcgtttagaa aacagcccgc tttcattcaa caggtgttgg taaacattgc   1080
ttctctattc tctggttatc tttccttaacg tgtgattgaa gtttgtgaat gagggggagc   1140
caaaaaagaa tttcttttttt ggctcttttt t                                  1171

<210> SEQ ID NO 14
<211> LENGTH: 877
<212> TYPE: DNA
<213> ORGANISM: Chlamydia trachomatis

<400> SEQUENCE: 14
cagagaattc tcgacatact atctaatcgg atatgtaaag ctgctttaca tcccttgaac     60
tagaaataaa atggaaataa aaagcccaga acaagagaag ttgttctggg ctgacagaag   120
ctgtcagatc atttttaataa gattgatgac aactacgaca agttcctgga tccaaaaaag   180
aatctaaaaa gccatacaaa gattgcgtta cttcttgcga tgcctctaac actttatcag   240
```

```
cgtcatcttt gagaagcatc tcaatgagcg cttttcttc tctagcatgc cgcacatccg      300
cttcttcatg ttctgtgaaa tatgcatagt cttcaggatt ggaaaatcca aagtactcag      360
tcaatccacg aattttctct ctagcgatac gtggaattg actctcataa gaatacaaag       420
cagccactcc tgcagctaaa gaatctcctg tacaccaccg cacgaaagta gctactttcg      480
cttttgctgc ttcactaggc tcatgagcct ctaactcttc tggagtaact cctagagcaa      540
acacaaactg cttccacaaa tcaatatgat tagggtaacc gttctcttca tccatcaagt      600
tatctaacaa taacttacgc gcctctaaat catcgcaacg actatgaatc gcagataaat      660
atttaggaaa ggctttgata tgtaaataat agtctttggc atacgcctgt aattgctctt      720
tagtaagctc ccccttcgac catttcacat aaaacgtgtg ttctagcata tgcttatttt      780
gaataattaa atctaactga tctaaaaaat tcataaacac ctccatcatt tcttttcttg      840
actccacgta accgcttgca aaaaggtcc gtataag                                877

<210> SEQ ID NO 15
<211> LENGTH: 396
<212> TYPE: DNA
<213> ORGANISM: Chlamydia trachomatis serovar E

<400> SEQUENCE: 15
tgtaccaaat atgagcttag atcaatctgt tgttgaactt tacacagata ctgccttctc       60
ttggagcgtg ggcgctcgag cagctttgtg ggagtgcgga tgtgcgactt tagggcttc      120 tttccaatac gctcaatcta aacctaaagt cgaagaatta aacgttctct gtaacgcagc      180
tgagtttact atcaataagc ctaaaggata tgtagggcaa gaattccctc ttgcactcat      240
agcaggaact gatgcagcga cgggcactaa agatgcctct attgattacc atgagtggca      300
agcaagttta gctctctctt acagattgaa tatgttcact ccctacattg gagttaaatg      360
gtctcgagca agttttgatg ccgatacgat tcgtat                                396

<210> SEQ ID NO 16
<211> LENGTH: 516
<212> TYPE: DNA
<213> ORGANISM: Chlamydia trachomatis serovar E

<400> SEQUENCE: 16
ctcaaaattt gacgatttct cagaatacag ggaatgttct gttttataac aacgtggcct       60 gttcggagg agctgttcgt atagaggatc atggtaatgt tctttttagaa gcttttggag      120 gagatattgt ttttaaagga aattcttctt tcagagcaca aggatccgat gccatctatt      180
ttgcaggtaa agaatcgcat attacagccc tgaatgctac ggaaggacat gctattgttt      240
tccacgacgc attagttttt gaaaatctag aagaaaggaa atctgctgaa gtattgttaa      300
tcaatagtcg agaaaatcca ggttacactg gatctattcg atttttagaa gcagaaagta      360
aagttcctca atgtattcat gtacaacaag gaagccttga gttgctaaat ggagctacat      420
tatgtagtta tggttttaaa caagatgctg gagctaagtt ggtattggct tctggatcta      480
aactgaagat tttagattca ggaactcctg tacaag                                516

<210> SEQ ID NO 17
<211> LENGTH: 723
<212> TYPE: DNA
<213> ORGANISM: Chlamydia trachomatis serovar E

<400> SEQUENCE: 17
ctccttttaa gggggacgat gtttacttga atggagactg cgcttttgtc aatgtctatg       60
```

-continued

```
caggggcaga gaacggctca attatctcag ctaatggcga caatttaacg attaccggac    120
aaaaccatac attatcattt acagattctc aagggccagt tcttcaaaat tatgccttca    180
tttcagcagg agagacactt actctgaaag atttttcgag tttgatgttc tcgaaaaatg    240
tttcttgcgg agaaaaggga atgatctcag ggaaaaccgt gagtatttcc ggagcaggcg    300
aagtgatttt ttgggataac tctgtggggt attctccttt gtctattgtg ccagcatcga    360
ctccaactcc tccagcacca gcaccagctc ctgctgcttc aagctcttta tctccaacag    420
ttagtgatgc tcggaaaggg tctatttttt ctgtagagac tagtttggag atctcaggcg    480
tcaaaaaagg ggtcatgttc gataataatg ccgggaattt tggaacagtt tttcgaggta    540
atagtaataa taatgctggt agtgggggta gtgggtctgc tacaacacca agttttacag    600
ttaaaaactg taaagggaaa gtttctttca cagataacgt agcctcctgt ggaggcggag    660
tagtctacaa aggaactgtg cttttcaaag acaatgaagg aggcatattc ttccgaggga    720
aca                                                                  723
```

<210> SEQ ID NO 18
<211> LENGTH: 1377
<212> TYPE: DNA
<213> ORGANISM: Chlamydia trachomatis serovar E

<400> SEQUENCE: 18

```
aaacagctaa tcgtcactac gctcacgtgg actgccctgg tcacgctgac tatgttaaaa     60
acatgatcac cggtgcggct caaatggacg gggctattct agtagtttct gcaacagacg    120
gagctatgcc tcaaactaaa gagcatattc ttttggcaag acaagttggg gttccttaca    180
tcgttgtttt tctcaataaa attgacatga tttccgaaga agacgctgaa ttggtcgact    240
tggttgagat ggagttggct gagcttcttg aagagaaagg atacaaaggg tgtccaatca    300
tcagaggttc tgctctgaaa gctttggaag ggatgctgc atacatagag aaagttcgag     360
agctaatgca agccgtcgat gataatatcc ctactccaga aagagaaatt gacaagcctt    420
tcttaatgcc tattgaggac gtgttctcta tctccggacg aggaactgta gtaactggac    480
gtattgagcg tggaattgtt aaagtttccg ataaagttca gttggtcggt cttagagata    540
ctaaagaaac gattgttact ggggttgaaa tgttcagaaa agaactccca gaaggtcgtg    600
caggagagaa cgttggattg ctcctcagag gtattggtaa gaacgatgtg gaaagaggaa    660
tggttgtttg cttgccaaac agtgttaaac ctcatacaca gtttaagtgt gctgtttacg    720
ttctgcaaaa agaagaaggt ggacgacata agcctttctt cacaggatat agacctcaat    780
tcttcttccg tacaacagac gttacaggtg tggtaactct gcctgaggga gttgagatgg    840
tcatgcctgg ggataacgtt gagtttgaag tgcaattgat tagccctgtg gctttagaag    900
aaggtatgag atttgcgatt cgtgaaggtg gtcgtacaat cggtgctgga actatttcta    960
agatcattgc ataaattaag tgatgtgttg gcgaggctga aaagccttgc ctttgggtgt   1020
gtagcttaga tggtagagca gtggcctcca aagccgccgg tcgggggttc gaatccctcc   1080
gcactcgtat taggtaactg aaagaagaat tcgcttatgg ggcaagatca ccgaagaaaa   1140
tttcttaaga aagtatcttt tgcaaaaaaa caagcagctt ttgcgggtaa ctttatcgaa   1200
gaaattaaga agattgagtg ggtaaataag cgaaatctta aaagatacgt caagattgtt   1260
ttgatgaata tttttggctt tggattttcc atctattgtg tggatttagc tcttcgaaag   1320
tccctttcat tgttcggtaa agtaacaagc tttttctttg gttgattcat gtttaag      1377
```

-continued

<210> SEQ ID NO 19
<211> LENGTH: 1736
<212> TYPE: DNA
<213> ORGANISM: Chlamydia trachomatis serovar E

<400> SEQUENCE: 19

```
gtagcggaac aaagccggac cacgaggcct catagaatat aaaaatacga ggagcttaaa     60
catgtcagat caagcaacga ccctcaagat taaacctttg ggagatagaa ttttagttaa    120
aagagaagaa gaagcttcca ctgcaagagg cggaatcatt cttcctgaca ctgccaagaa    180
aaagcaagat agagctgaag ttttagctct aggaacaggc aaaaaagatg ataaagggca    240
gcaacttcct tttgaagttc aggttggtga catcgtttta attgataaat attctggcca    300
agaactcact gtagaaggtg aagagtacgt catcgttcaa atgagcgaag ttatcgcagt    360
tctgcaataa aaactaagag agtgaagtaa gatttaaggg agcgcatcaa tggtcgctaa    420
aaacattaaa tacaacgaag aagccagaaa gaaaattcaa aaaggagtta agactttagc    480
tgaagctgta aaagtcactc tagggcctaa aggacgacat gttgtcatag ataaaagctt    540
cggatcccct caagtaacta aagatggtgt taccgttgcg aaagaagttg agcttgccga    600
caaacatgaa aatatgggcg ctcaaatggt caaagaagtc gccagcaaaa ctgctgacaa    660
agctggagac ggaactacaa cagctactgt tcttgctgaa gctatctata cagaaggatt    720
acgcaatgta acagctggag caaatccaat ggacctcaaa cgaggtattg ataaagctgt    780
taaggttgtt gttgatcaaa tcagaaaaat cagcaaacct gttcagcatc ataaagaaat    840
tgctcaagtt gcaacaattt ctgctaataa tgatgcagaa atcgggaatc tgattgctga    900
agcaatggag aaagttggta aaaacggctc tatcactgtt gaagaagcaa aggatttga    960
aaccgttttg gatgttgttg aaggaatgaa tttcaataga ggttacctct ctagctactt   1020
cgcaacaaat ccagaaactc aagaatgtgt attagaagac gctttggttc taatctacga   1080
taagaaaatt tctgggatca aagatttcct tcctgtttta caacaagttg ctgaatccgg   1140
ccgtcctctt cttattatag cagaagacat tgaaggcgaa gctttagcta ctttggtcgt   1200
gaacagaatt cgtggaggat tccgggtttg cgcagttaaa gctccaggct ttggagatag   1260
aagaaaagct atgttggaag acatcgctat cttaactggc ggtcaactca ttagcgaaga   1320
gttgggcatg aaattagaaa acgctaactt agctatgtta ggtaaagcta aaaaagttat   1380
cgtttctaag gaagacacga ccatcgtcga aggaatgggt gaaaaagaag ctttagaagc   1440
tcgttgcgaa agcatcaaaa aacaaattga agacagctct tctgattacg ataaagaaaa   1500
actccaagag cgtcttgcta agctctctgg tggagtagca gtcattcgcg ttggagctgc   1560
aacagagatt gagatgaaag agaaaaaaga tcgtgtagac gatgctcaac atgctacaat   1620
cgctgctgtt gaagaaggaa ttcttcctgg tggaggaaca gcattaatcc gttgtatccc   1680
tactcttgag gccttcttgc caatgttgac taatgaagat gagcaaattg gagctc       1736
```

<210> SEQ ID NO 20
<211> LENGTH: 1135
<212> TYPE: DNA
<213> ORGANISM: Chlamydia trachomatis serovar E

<400> SEQUENCE: 20

```
ggctcttgat gaaaaagagc ggcaggttat ggctctttat tactatgatg acttggtatt     60
aaaagaaatt gggaagattt taggagtgag cgagtcccga gtttctcaga tacactccaa    120
agctttattg aagttacgag gtacattgtc cagtctgctt tagtaactgt ctccagaaga    180
```

-continued

| | |
|---|---|
| tcctctttgt attttttccta tcaatattct attggagaag cgcgtcgttt ttttgacgag | 240 |
| gtgtctgcta tcgcttgcct tgctataaaa agaacaggat agataagatg ttgctagata | 300 |
| agtttatatg gatagatttt tatgcaacag ttaatcgata accttaagaa acggggtatt | 360 |
| ctagataatt cttctgcagg attagaaact cgtgccgaag tttgtggaga agagaaagaa | 420 |
| atctctctag cagactttcg tggtaagtat gtagtgctct tcttttatcc taaagatttc | 480 |
| acctatgtgt gtcctacaga attgcatgct tttcaagata gattggtaga ttttgaagag | 540 |
| cggggtgcag tcgtgcttgg ttgctccgtt gacgacattg agacacattc tcgttggctc | 600 |
| gctgtagcga gaaatgcagg aggaatagag ggaacagaat atcctctgtt agcagaccct | 660 |
| tcttttaaaa tatcagaagc ttttggtgtt ttgaatcctg aaggatcgct cgctttaaga | 720 |
| gcgactttcc ttatcgataa acatgggggtt gttcgtcatg cggttatcaa tgatcttcct | 780 |
| ttagggcgtt ccattgacga ggaattgcgt attttagatt cattgatctt ctttgagaac | 840 |
| cacggaatgg tttgtccagc taactggcgt tctggagagc gtggaatggt gccttctgaa | 900 |
| gagggattaa aagaatattt ccagacgatg gattaagcat ctttgaaagt aagaaagtcg | 960 |
| tacagatctt gatctgaaaa gagaagaagg cttttttaatt ttctgcagag agccagcgag | 1020 |
| gcttcaataa tgttgaagtc tccgccacca ggcaatgcta aggcgatgat attagttagt | 1080 |
| gaaatctgag tgttaaggaa ataaaggcca aagaagtagc tatcaataaa gaagc | 1135 |

<210> SEQ ID NO 21
<211> LENGTH: 731
<212> TYPE: DNA
<213> ORGANISM: Chlamydia trachomatis serovar E

<400> SEQUENCE: 21

| | |
|---|---|
| ttgaagacac tctttctccc ggagtcacag ttcttgaagc tgcaggagct caaatttctt | 60 |
| gtaataaagt agtttggact gtgaaagaac tgaatcctgg agagtctcta cagtataaag | 120 |
| ttctagtaag agcacaaact cctggacaat tcacaaataa tgttgttgtg aagagctgct | 180 |
| ctgactgtgg tacttgtact tcttgcgcag aagcgacaac ttactggaaa ggagttgctg | 240 |
| ctactcatat gtgcgtagta gatacttgtg accctgtttg tgtaggagaa atactgtttt | 300 |
| accgtatttg tgtcaccaac agaggttctg cagaagatac aaatgtttct ttaatgctta | 360 |
| aattctctaa agaactgcaa cctgtatcct tctctggacc aactaaagga acgattacag | 420 |
| gcaatacagt agtattcgat tcgttaccta gattaggttc taaagaaact gtagagtttt | 480 |
| ctgtaacatt gaaagcagtt acagctggag atgctcgtgg ggaagcgatt cttttcttccg | 540 |
| atacattgac tgttccagtt tctgatacag agaatacaca catctattaa tctttgattt | 600 |
| tatcgatgtg taggtgccgt ccagggattc ctgggcggct ttttttttgtt atctatatga | 660 |
| aaataaaaga gttcattttc ggtctcagag catattctag acgggttttt gaaaaaaata | 720 |
| agtgtttgtg t | 731 |

<210> SEQ ID NO 22
<211> LENGTH: 1181
<212> TYPE: DNA
<213> ORGANISM: Chlamydia trachomatis serovar E

<400> SEQUENCE: 22

| | |
|---|---|
| ctatcgtctg aatgctgaac tgaaacatct ttttgattta gacgcgttag ccgatgctat | 60 |
| ggatctatct cgagatctac agttttctta catgggtatt caaaatctgt atgatcgtta | 120 |

```
ttttaatcac cacgaagatt gccgtttaga aactccccaa attttttgga tgcgcgttgc      180
tatggggttg gcattgaatg agcaagacaa gacttcttgg gctattactt tttataattt      240
gctttcgaca ttccgatata caccagctac gccaaccttg ttcaattcag gtatgcggca      300
ttctcagtta agctcttgct atctttccac tgtacaagat aatttggtca atatctataa      360
ggtcattgct gataacgcta tgctatctaa gtgggcagga gggataggta atgattggac      420
ggcggttcgt gcaacagggg ctttaattaa aggaaccaat ggaagaagtc agggagtaat      480 tcctttatt aaggtgacaa atgatacagc agtcgcagtg aatcaaggtg gtaaacgcaa       540
gggagctgta tgcgtctatt tagaagtttg cacctcgac tacgaagatt tccttgaatt       600
gagaaagaat acaggggatg agcgtcgacg ggctcatgat gtcaatatag ctagctggat      660
tccagatctt ttcttcaaac gtttacagca aaaaggaca tggactctat tcagcccaga       720
tgatgttccg ggattacacg atgcttatgg ggaagaattt gagcgtttgt acgaagaata      780
tgagcggaag gttgataccg gagagattcg gttattcaag aaggtagaag ctgaagatct      840
gtggagaaaa atgctcagca tgcttttga acgggacac ccatggatga cttttaaaga       900
tccatccaac atccgttcgg ctcaagatca taaaggcgtg gtgcgttgtt ccaatctgtg      960
tacggagatt ttgttaaact gctcggagac agaaactgct gtttgtaatt taggatcgat     1020
taacttagtt caacatatcg taggggatgg gttagatgag gaaaaactct ctgagacgat     1080
ctctatagca gtccgtatgt tggataacgt gattgatatt aactttatc caacaaagga     1140 agctaaagag gcgaactttg ctcaccgcgc tattggatta g                          1181

<210> SEQ ID NO 23
<211> LENGTH: 167
<212> TYPE: DNA
<213> ORGANISM: Chlamydia trachomatis serovar E

<400> SEQUENCE: 23 ttaaaagat tttaaactaa aagaagatt tttaattata gttttcaaa atcatttga          60 tatttttaat gctgagataa acaagaaag cggaaactcc ttgcgacaaa gattttctgc      120
tcgagccctc ttccctgagg attttttagg ggagatccat tcttcca                   167

<210> SEQ ID NO 24
<211> LENGTH: 1265
<212> TYPE: DNA
<213> ORGANISM: Chlamydia trachomatis serovar E

<400> SEQUENCE: 24
caggttcttt ctagacgaac aaagaataat cctatgttga tagggagcc cggagttggg       60 aaaacagcaa tcgctgaagg acttgctctt cgcatagtgc aaggggatgt tccagagagt     120
ttaaaggaaa agcatctgta tgtactggat atgggagctt tgattgcagg tgccaagtat     180
cgaggagagt ttgaagagcg gttaaaaagt gtattgaagg gtgtagaagc ttctgaaggc     240
gagtgtatcc tattcattga tgaagtgcat actttagtag gagcgggagc tacagatgga     300
gctatggatg cagcgaatct attaaagcct gctttagcac gaggcacttt gcattgtatt     360
ggcgctacga ctttgaatga ataccaaaaa tatatagaga agacgcggc tttggaacgg     420 cgttccagc ctattttgt aacagaacct tctttggaag atgctgtatt cattctccgg      480
gggttaaggg aaaaatatga aatttttcat ggtgtgcgca ttacagaagg ggctttgaat     540
gcagctgtag ttcttcctta tcgttacatc acagaccgat tcttcctga taaggcgatt     600 gacctaattg atgaggctgc gagtttaatc cgtatgcaaa taggaagttt acctctgcct     660
```

| | |
|---|---|
| attgatgaaa aggaaagaga attatcagct ttaatcgtga aacaagaagc tattaaacgc | 720 |
| gagcaagcac cagcttatca ggaagaggct gaagacatgc aaaaagcaat tgaccgggtt | 780 |
| aaggaagagc tggccgcttt acgcttgcgc tgggatgaag aaaaaggatt aattgcagga | 840 |
| ttaaaagaaa agaagaatgc tttagaaaat ttaaaatttg ccgaagagga agctgagcgt | 900 |
| actgccgatt acaatcgggt agcagaacta cgctatagtt tgattccttc tttggaggaa | 960 |
| gaaattcatt tagctgagga agctttaaat caaagagatg gcgcctgct tcaagaggaa | 1020 |
| gttgatgagc ggttgattgc gcaagttgtt gcgaattgga ctggaatccc tgtgcaaaaa | 1080 |
| atgttggagg gagaatctga aaagttattg gtgttgagga gtctttagaa gaaagggttg | 1140 |
| tcggacagcc tttcgctatt gccgcagtca gtgattcgat tcgagctgct cgagtaggat | 1200 |
| tgagtgatcc gcagcgtctc cctcacaagg gaatattagc tggcgcggcg aaccgctggc | 1260 |
| gaaac | 1265 |

<210> SEQ ID NO 25
<211> LENGTH: 463
<212> TYPE: DNA
<213> ORGANISM: Chlamydia trachomatis serovar E

<400> SEQUENCE: 25

| | |
|---|---|
| atgacgaaca accccatgtt tatcgataag gaaagtcgct cttaaagcga gcgatccttc | 60 |
| aggattcaaa acaccaaaag cttctgatat tttaaaagaa gggtctgcta acagaggata | 120 |
| ttctgttccc tctattcctc ctgcatttct cgctacagcg agccaacgag aatgtgtctc | 180 |
| aatgtcgtca acggagcaac caagcacgac tgcaccccgc tcttcaaaat ctaccaatct | 240 |
| atcttgaaaa gcatgcaatt ctgtaggaca cataggtg aaatctttag gataaaagaa | 300 |
| gagcactaca tacttaccac gaaagtctgc tagagagatt tctttctctt ctccacaaac | 360 |
| aacggcttta ccagaaaaat ccggagcctg tcttccaatt agtgatccca taatactcct | 420 |
| cctagaaaga aacaacgcac cagagaggat ttgaacctct gac | 463 |

<210> SEQ ID NO 26
<211> LENGTH: 636
<212> TYPE: DNA
<213> ORGANISM: Chlamydia trachomatis serovar E

<400> SEQUENCE: 26

| | |
|---|---|
| ggtagaaaat tctctgaagt cgaatctgaa attaaaacag tcccctacaa agttgctcct | 60 |
| aactcgaaag gagatgcggt cttttgatgtg aacaaaaac tgtacactcc agaagaaatc | 120 |
| ggcgctcaga tcctcatgaa gatgaaggaa actgctgagg cttatctcgg agaaacagta | 180 |
| acggaagcag tcattaccgt accagcttac tttaacgatt ctcaaagagc ttctacaaaa | 240 |
| gatgctggac gtatcgcagg attagatgtt aaacgcatta ttcctgaacc aacagcggcc | 300 |
| gctcttgctt atggtattga taggaaagga gataaaaaaa tcgccgtctt cgacttagga | 360 |
| ggaggaactt tcgatatttc tatcttggaa atcggtgacg gagttttttga agttctctca | 420 |
| accaacgggg atactcactt gggaggagac gacttcgacg gagtcatcat caactggatg | 480 |
| cttgatgaat tcaaaaaaca gaaggcatt gatctaagca agataacat ggctttgcaa | 540 |
| agattgaaag atgctgctga aaaagcaaaa atagaattgt ctggtgtatc gtctactgaa | 600 |
| atcaatcagc cattcatcac tatcgacgct aatgga | 636 |

<210> SEQ ID NO 27

-continued

<211> LENGTH: 1797
<212> TYPE: DNA
<213> ORGANISM: Chlamydia trachomatis serE

<400> SEQUENCE: 27
atgcatcacc atcaccatca catgagcatc aggggagtag gaggcaacgg gaatagtcga 60
atcccttctc ataatgggga tggatcgaat cgcagaagtc aaaatacgaa gggtaataat 120
aaagttgaag atcgagtttg ttctctatat tcatctcgta gtaacgaaaa tagagaatct 180
ccttatgcag tagtagacgt cagctctatg atcgagagca ccccaacgag tggagagacg 240
acaagagctt cgcgtggagt gctcagtcgt ttccaaagag gtttagtacg aatagctgac 300
aaagtaagac gagctgttca gtgtgcgtgg agttcagtct ctacaagcag atcgtctgca 360
acaagagccg cagaatccgg atcaagtagt cgtactgctc gtggtgcaag ttctgggtat 420
agggagtatt ctccttcagc agctagaggg ctgcgtctta tgttcacaga tttctggaga 480
actcgggttt tacgccagac ctctcctatg gctggagttt ttgggaatct tgatgtgaac 540
gaggctcgtt tgatggctgc gtacacaagt gagtgcgcgg atcatttaga agcgaaggag 600
ttggctggcc ctgacggggt agcggccgcc cgggaaattg ctaaaagatg ggagaaaaga 660
gttagagatc tacaagataa aggtgctgca cgaaaattat taaatgatcc tttaggccga 720
cgaacaccta attatcagag caaaaatcca ggtgagtata ctgtagggaa ttccatgttt 780
tacgatggtc ctcaggtagc gaatctccag aacgtcgaca ctggtttttg gctggacatg 840
agcaatctct cagacgttgt attatccaga gagattcaaa caggacttcg agcacgagct 900
actttggaag aatccatgcc gatgttagag aatttagaag agcgttttag acgtttgcaa 960
gaaacttgtg atgcggctcg tactgagata gaagaatcgg gatggactcg agagtccgca 1020
tcaagaatgg aaggcgatga ggcgcaagga ccttctagag tacaacaagc ttttcagagc 1080
tttgtaaatg aatgtaacag catcgagttc tcatttggga gctttggaga gcatgtgcga 1140
gttctctgcg ctagagtatc acgaggatta gctgccgcag gagaggcgat tcgccgttgc 1200
ttctcttgtt gtaaaggatc gacgcatcgc tacgctcctc gcgatgacct atctcctgaa 1260
ggtgcatcgt tagcagagac tttggctaga ttcgcagatg atatgggaat agagcgaggt 1320
gctgatggaa cctacgatat tcctttggta gatgattgga gaagaggggt tcctagtatt 1380
gaaggagaag gatctgactc gatctatgaa atcatgatgc ctatctatga agttatgaat 1440
atggatctag aaacacgaag atcttttgcg gtacagcaag ggcactatca ggacccaaga 1500
gcttcagatt atgacctccc acgtgctagc gactatgatt tgcctagaag cccatatcct 1560
actccacctt tgcctcctag atatcagcta cagaatatgg atgtagaagc agggttccgt 1620
gaggcagttt atgcttcttt tgtagcagga atgtacaatt atgtagtgac acagccgcaa 1680
gagcgtattc ccaatagtca gcaggtggaa gggattctgc gtgatatgct taccaacggg 1740
tcacagacat ttagagacct gatgaagcgt tggaatagag aagtcgatag ggaataa 1797

<210> SEQ ID NO 28
<211> LENGTH: 1983
<212> TYPE: DNA
<213> ORGANISM: Chlamydia trachomatis serE

<400> SEQUENCE: 28
atgcatcacc atcaccatca catggaatca ggaccagaat cagtttcttc taatcagagc 60
tcgatgaatc caattattaa tgggcaaatc gcttctaatt cggagaccaa agagtccacg 120
aaggcgtccg aagcgagtcc ttcagcatcg tcctctgtaa gcagctggag ttttttatcc 180

-continued

| | |
|---|---|
| tcagcaaaga atgcattaat ctctcttcgt gatgccatct tgaataaaaa ttccagtcca | 240 |
| acagactctc tctctcaatt agaggcctct acttctacct ctacggttac acgtgtagcg | 300 |
| gcaaaagatt atgatgaggc taaatcgaat tttgatacgg cgaaaagtgg attagagaac | 360 |
| gctaagacac ttgctgaata cgaaacgaaa atggctgatt tgatggcagc tctccaagat | 420 |
| atggagcgtt tagctaattc agatcctagt aacaatcata ccgaagaagt aaataatatt | 480 |
| aagaaagcgc tcgaagcaca aaaagatact attgataagc tgaataaact cgttacgctg | 540 |
| caaaatcaga ataaatcttt aacagaagtg ttgaaaacaa ctgactctgc agatcagatt | 600 |
| ccagcgatta atagtcagtt agagatcaac aaaaattctg cagatcaaat tatcaaagat | 660 |
| ctggaaagac aaaacataag ttatgaagct gttctcacta acgcaggaga ggttatcaaa | 720 |
| gcttcttctg aagcgggaat taagttagga caagctttgc agtctattgt ggatgctggg | 780 |
| gaccaaagtc aggctgcagt tctgcaagca cagcaaaata atagcccaga taatattgca | 840 |
| gccacgaagg aattaattga tgctgctgaa acgaaggtaa acgagttaaa acaagagcat | 900 |
| acagggctaa cggactcgcc tttagtgaaa aagctgagg agcagattag tcaagcacaa | 960 |
| aaagatattc aagagatcaa acctagtggt tcggatattc ctatcgttgg tccgagtggg | 1020 |
| tcagctgctt ccgcaggaag tgcggcagga gcgttgaaat cctctaacaa ttcaggaaga | 1080 |
| atttccttgt tgcttgatga tgtagacaat gaaatggcag cgattgcact gcaaggtttt | 1140 |
| cgatctatga tcgaacaatt taatgtaaac aatcctgcaa cagctaaaga gctacaagct | 1200 |
| atggaggctc agctgactgc gatgtcagat caactggttg gtgcggatgg cgagctccca | 1260 |
| gccgaaatac aagcaatcaa agatgctctt gcgcaagctt tgaaacaacc atcagcagat | 1320 |
| ggtttggcta cagctatggg acaagtggct tttgcagctg ccaaggttgg aggaggctcc | 1380 |
| gcaggaacag ctggcactgt ccagatgaat gtaaaacagc tttacaagac agcgttttct | 1440 |
| tcgacttctt ccagctctta tgcagcagca ctttccgatg gatattctgc ttacaaaaca | 1500 |
| ctgaactctt tatattccga aagcagaagc ggcgtgcagt cagctattag tcaaactgca | 1560 |
| aatcccgcgc tttccagaag cgtttctcgt tctggcatag aaagtcaagg acgcagtgca | 1620 |
| gatgctagcc aaagagcagc agaaactatt gtcagagata gccaaacgtt aggtgatgta | 1680 |
| tatagccgct tacaggttct ggattctttg atgtctacga ttgtgagcaa tccgcaagca | 1740 |
| aatcaagaag agattatgca gaagctcacg gcatctatta gcaaagctcc acaatttggg | 1800 |
| tatcctgctg ttcagaattc tgcggatagc ttgcagaagt ttgctgcgca attggaagga | 1860 |
| gagtttgttg atggggaacg tagtctcgca gaatctcaag agaatgcgtt tagaaaacag | 1920 |
| cccgctttca ttcaacaggt gttggtaaac attgcttctc tattctctgg ttatctttct | 1980 |
| taa | 1983 |

<210> SEQ ID NO 29
<211> LENGTH: 1224
<212> TYPE: DNA
<213> ORGANISM: Chlamydia trachomatis serE

<400> SEQUENCE: 29

| | |
|---|---|
| gtaactttc aacattttc acaatgacaa gaataaaagc aaaagaaag gctgccgata | 60 |
| aaataaaagt tttactgcga gaacagaaga ctaaaactat ctggacgaat aagccggatg | 120 |
| cgcaggataa ttgcgcataa acacttaa tagagagtga tcttatgtct aaaacaccat | 180 |
| tatccatagc tcatccttgg catgggccag tattaacacg cgatgattat gaatctcttt | 240 |

```
gttgctatat agaaatcact ccagccgact ccgttaaatt cgaactggat aaagaaactg     300
gtatcctaaa agtggatcgg ccacaaaagt tttctaactt ttgtccttgc ttatacgggc     360
tgttacctaa gacttattgt ggagatcttt ctggagaata cagtggtcaa caaagtaaca     420
gagagaatat caaaggcgat ggcgatcctc ttgatatctg tgtgttaacg aaaaaaata      480 ttacacaagg gaacatcctc ttgcaagcgc gtcctatcgg agggattcgt attttagact     540
cggaagaagc cgatgataaa atcatcgctg ttctagaaga tgatttagtc tatggcaata     600
tagaagatat ttctgaatgc ccaggcacag ttttggacat gatccaacac tatttcttaa     660
cctataaagc tactccagaa agcttaattc aagcaaaacc agctaaaatt gaaattgtag     720
gtttatacgg caaaaaagaa gctcaaaaag tcattcgtct tgctcacgaa gactattgca     780 atcttttat gtaaatcgac agaaaaagaa aaggctgttg tgggagattc cacaacggcc      840
cctcctaacc aagttttttt catcctaggg gactttatga agcaaataga taactttgaa     900
caaattcatc tctcgtgccg aattcggcac gagattaaaa caaagctctc aaaaagagtt     960
ggtatcccga attcattcag cagttcccgg tgccaaagtt aaagagatac gcttttatt     1020 aggatagtta tggacgcaca agaaaagaaa tacgacgcat cagccatcac cgttttagaa    1080
ggattgcaag ctgttcgtga gcgtcctgga atgtacattg gtgatacagg agttaccgga    1140
ttgcatcact tggtttatga agtggtggat aacagtatcg atgaggcaat ggcgggtttt    1200
tgtaccgagg tcgttgttcg cata                                           1224

<210> SEQ ID NO 30
<211> LENGTH: 883
<212> TYPE: DNA
<213> ORGANISM: Chlamydia trachomatis serE

<400> SEQUENCE: 30
atgttgacta acatggcgac catcagaaac tctgtgaaga cattgaacag aattgaattg      60
gatcttgaag cttctaattc tggtcttacg aaaaaagaga tcgctttatt aacgaaaaga     120
catcgcaagt tgcttaacaa cctggaaggt gttcgtcata tgaactctct cccagggctt     180
ttaattgtaa ttgacccggg ctatgagcgc attgctgtcg cagaagctgg aaaactaggc     240
attcctgtaa tggccttagt tgatacaaac tgcgatccaa caccaatcaa ccacgttatt     300
ccttgcaacg atgattccat taagagtatc cgtctggttg tcaatgtact aaagacgct      360 gttattgatg cgaagaagcg ttcaggcatc gaaattttat ctccagtacg tcctgtagaa     420
agacctgcag aagaagctgt ggaagagttg cctcttccaa caggtgaagc tcaagatgaa     480
gcttcttcta aagaaggttt tttactttgg gcagatattg acaattgcgg ggcattgaaa     540
tgagcgactt ctccatggaa acattgaaaa atttaagaca gcagacaggt gtaggcctga     600
ctaaatgtaa agaggctcta gagcatgcta agggcaattt agaagatgct gttgtttatt     660
tacgtaagct tggtcttgcc tctgcaggca aaaagaaca ccgagaaaca aagaaggcg      720 taattgctgc actcgttgat gaacgtggtg cggcacttgt tgaagtcaac gttgaaactg     780
attttgttgc taacaacagt gttttccgag cattcgttac aggtttgtta tccgatcttc     840
ttgaccacaa gcttagcgat gttgaagctt tagctcgcgt aat                      883

<210> SEQ ID NO 31
<211> LENGTH: 393
<212> TYPE: DNA
<213> ORGANISM: Chlamydia trachomatis serE

<400> SEQUENCE: 31
```

-continued

| agttgaaaaa ggctgtttct tgcattcaaa aaactatcga gcaagagaga tctattttgt | 60 |
| ttgttggaac aaaaaaacag gcaaaacaga tcattagaga agctgctatc gaatgtggcg | 120 |
| aattctttgc ttcagagaga tggttgggtg gcatgttgac taacatggcg accatcagaa | 180 |
| actctgtgaa gacattgaac agaattgaat tggatcttga agcttctaat tctggtctta | 240 |
| cgaaaaaaga gatcgcttta ttaacgaaaa gacatcgcaa gttgcttaac aacctggaag | 300 |
| gtgttcgtca tatgaactct ctcccagggc ttttaattgt aattgacccg ggctatgagc | 360 |
| gcattgctgt cgcagaagct ggaaaactag gca | 393 |

<210> SEQ ID NO 32
<211> LENGTH: 2577
<212> TYPE: DNA
<213> ORGANISM: Chlamydia trachomatis serE

<400> SEQUENCE: 32

| attacggagg ccatacggta tcttctcgag gaggatttca agggatatgc gtacgaatag | 60 |
| ccgatttatt ccgtaactgt ttctctcgta atagaggcac tactactacg ccatctcgaa | 120 |
| ctgttatcac tcaggcagat atttatcatc cgactatttc tggacaagga gctcaaccta | 180 |
| ttgtctctac aggagataag aaattagata gcgcaattat tcaagcagat ttgcgtgcgc | 240 |
| agaataaaca gactttggct acacatattc aaagtaagct aggttctatg gagggacaat | 300 |
| ctcctcaaga ttataaagct ggtgcgtata gtgcgctaag attgatgctg tttactccag | 360 |
| gcgaaactac tgtgagtagc gagcgggaac gtcaagcgtg cgttacgggt cgggatctct | 420 |
| gggaacaggc tgcaggagat cttgctacca atgggaatac agatgggctt atgttaatgg | 480 |
| ctaacctatc tgtgggaggg aagcatgtgc ctgcggggca tttaagagaa tacatggata | 540 |
| ctgtaaaggg tacgtttact gatgagaacg aggctacaga tcctacggta gatgccattt | 600 |
| tagatttagc agcaaaaatc gatgcgacgg aattctctag tcctggttca gggcaagtca | 660 |
| ttcttaatta tataggaaat tatggacaag tcgtttttaga aaacgaggag atgaaccttc | 720 |
| ttgttttaga agatcaaaat gggcaagatc ctcaacgtgt tcaagataac tcaaaagagt | 780 |
| tacaaaaact gttagaaaat gctcgaaaaa cagatcctga gttatatttc caaacactaa | 840 |
| ctgtcataac ttcttctgtt ttcttagact aaagagaagg tatacggtgt tcggtccttt | 900 |
| caactattaa gaggaagtag tggtgagtag cataagccct agggggga attctgggcc | 960 |
| agagggattt tctagtgcat ctcgaggcga tgagattgat gatgtaccag atagtgaaga | 1020 |
| gggagagcta gaagagcgcg tttcggatca tgcagagtct atcattaccg agagctcgga | 1080 |
| aacgctgttt cgtactactt cttcatcagg ggtcagtgaa gatcttcagc aacacgttag | 1140 |
| cttggaggaa tctccacgac aacgaggttt ccttggacgg atccgtgatg cagtagcttc | 1200 |
| tatttggaag cgtcgtgttg cacgaaggaa tgaaaactat gatgtgaaaa agcagaaga | 1260 |
| gcagcaaggg attgtgcaat atctgcagga ttcgaaaatg cctgctttaa cgcgtgccta | 1320 |
| tcgccatctc cgtgctttca attctgcatg cttacgtacg attcgtgagt ttttcgctac | 1380 |
| cattttcgt gctttaaggg atgcgtatta tcgacattgt acacgttctg ggatcaactt | 1440 |
| ttgtggagct gataaagact ctttagaagt tcttgttgcg gtgggtttgc ttttgcgtat | 1500 |
| ggctacctta cgctctttg aacatgtcgg tgggaattac gaagatcgat tagtaaataa | 1560 |
| tgatgctccg gtgacaggtg cggggagaac tcttgttgat gatgctgtag acgatattga | 1620 |
| atcgatttta aatacgagaa ccaactggcc tcaacatgtc atgataggt tttctcgtgg | 1680 |

-continued

```
tctcgttcaa ttatgtgcga ctccttataa tgcgacttct caagaatgtt tcaagtcgat   1740
tgttcgttta gaaaaagaag acccttcttc agattattct caagctttat tattagcagg   1800
gataatagat cgcttggcgg agaaagcccc tatggctgca aagtatgttt tggatgcatt   1860
gcgtgttcga acttcggagc tcataggaga actcattatt ctcgatttgc ttcctcctgt   1920
atggaaggtt ggccgcggag gcgtattccc tcctgtgaat gagcagctcg ttgtgcaaat   1980
tgttaatgca aacgtagaac gattgcattc cactttcgct catgagccac aagcttattt   2040
gcgtatgatc gaaggtttgg taaccaattt ctttttctta cctagcgagg aagatccttc   2100
ttcggttggg aatatctaag aacattttct aatagggaag aggataaata gcgtgaaata   2160
atactgatta tgtgaagaat aggcaaaaag acctaaatcc ttatatgcta ttagattctc   2220
gtttccctac agattattat ttacgtatcc tagaattagt catccgggat gcttcttgta   2280
aattggtata taaccgacgc ctgcatatgt tggaggcgat ccctcttgat caaaaacttt   2340
ctactgatca agagggggaa tcaagtattt tacgagaagt gattagcgag ctacttgcgc   2400
attctgggga aagttatgcg atttcagctc aattacttgc cgtaatcgat atttatttaa   2460
aacaagagca accgtcgaat tcatggttcg ctcgaatctt tcggaagaga gagcgggcta   2520
gaaaacgaca aacaattaat aagttgcttt tgttaaaaag tatcctattt tttgaac      2577
```

<210> SEQ ID NO 33
<211> LENGTH: 554
<212> TYPE: DNA
<213> ORGANISM: Chlamydia trachomatis serE

<400> SEQUENCE: 33

```
ttctttatta aaaaaaactt tctcttttct ctcagacttc ttatgagtca agaaactcaa     60
cgagtcttgg tgtatggaga aggatttttt agaaaatgtt tatcgtcatt tccgttaccg    120
tttttttaaa ttaagtgtac ttccagctct tctcggactc tggctatttt ttactcctaa    180
tattcttaac tatttggatt cttctgttat tttatcagat aaaatttgcg gcgtcctttt    240
aattttatta tcagctttat ccttttataa tcctgttatt ttgcaactag gcatttttat    300
tgggctctgg gtttctttct tttcttgttc ttccgaccta cttcctttag tatttgctca    360
tgattcgcta ctaggttttg ccacactagc tattattttt ctactcccta atcgtcctga    420
agatctagaa gttggtccta ctattccaga aacttgccat tataatcctt cttccggagg    480
gaaaagagct gcggttctta tttttgcttt tgtaggatgg ttacaaagtc gctacttaac    540
ttccgcggca cgag                                                      554
```

<210> SEQ ID NO 34
<211> LENGTH: 1433
<212> TYPE: DNA
<213> ORGANISM: Chlamydia trachomatis serE

<400> SEQUENCE: 34

```
ctgcacgaaa attattaaat gatcctttag gccgacgaac acctaattat cagagcaaaa     60
atccaggtga gtatactgta gggaattcca tgttttacga tggtcctcag gtagcgaatc    120
tccagaacgt cgacactggt ttttggctgg acatgagcaa tctctcagac gttgtattat    180
ccagagagat tcaaacagga cttcgagcac gagctacttt ggaagaatcc atgccgatgt    240
tagagaattt agaagagcgt tttagacgtt tgcaagaaac ttgtgatgcg gctcgtactg    300
agatagaaga atcgggatgg actcgagagt ccgcatcaag aatggaaggc gatgaggcgc    360
aaggaccttc tagagcacaa caagcttttc agagctttgt aaatgaatgt aacagcatcg    420
```

```
agttctcatt tgggagcttt ggagagcatg tgcgagttct ctgcgctaga gtatcacgag    480
gattagctgc cgcaggagag gcgattcgcc gttgcttctc ttgttgtaaa ggatcgacgc    540
atcgctacgc tcctcgcgat gacctatctc ctgaaggtgc atcgttagca gagactttgg    600
ctagattcgc agatgatatg ggaatagagc gaggtgctga tggaacctac gatattcctt    660
tggtagatga ttggagaaga ggggttccta gtattgaagg agaaggatct gactcgatct    720
atgaaatcat gatgcctatc tatgaagtta tgaatatgga tctagaaaca cgaagatctt    780
ttgcggtaca gcaagggcac tatcaggacc aagagcttc agattatgac ctcccacgtg    840
ctagcgacta tgatttgcct agaagcccat atcctactcc acctttgcct cctagatatc    900
agctacagaa tatggatgta gaagcagggt tccgtgaggc agtttatgct tcttttgtag    960
caggaatgta caattatgta gtgacacagc cgcaagagcg tattcccaat agtcagcagg   1020
tggaagggat tctgcgtgat atgcttacca acgggtcaca gacatttaga gacctgatga   1080
agcgttggaa tagagaagtc gatagggaat aaactggtat ctaccatagg tttgtagcaa   1140
aaaactaagc ccaccaagaa gaattctct ttggtgggct tctttttta ttcaaaaaag    1200
aaagccctct tcaagattat accaagatgg gatgtataat ctgaaaggaa ggcgttttat   1260
tctctatcca tatgatggtg gtggtatcct cctttagagg agcagcagtc tccatgacgt   1320
tttttgaagc agcacttcaa gaagtttagg cagaccataa ccccagcgat tcccgttact   1380
acataagctg cttgtgtcca catggttcct tcaccaagca ggtgagtaag tag          1433
```

<210> SEQ ID NO 35
<211> LENGTH: 196
<212> TYPE: DNA
<213> ORGANISM: Chlamydia trachomatis

<400> SEQUENCE: 35

```
ctcgtgccga tgatacagca gtcgcagtga atcaaggtgg taaacgcaag ggagctgtat     60
gcgtctattt agaagtttgg cacctcgact acgaagattt ccttgaattg agaaagaata    120
caggggatga gcgtcgacgg gctcatgatg tcaatatagc tagctggatt ccagatcttt    180
tcttcaaacg tttaca                                                    196
```

<210> SEQ ID NO 36
<211> LENGTH: 1990
<212> TYPE: DNA
<213> ORGANISM: Chlamydia trachomatis

<400> SEQUENCE: 36

```
ttcactaggc tcatgagcct ctaactcttc tggagtaact cctagagcaa acacaaactg     60
cttccacaaa tcaatatgat tagggtaacc gttctcttca tccatcaagt tatctaacaa    120
taacttacgc gcctctaaat catcgcaacg actatgaatc gcagataaat atttaggaaa    180
ggctttgata tgtaaataat agtctttggc atacgcctgt aattgctctt tagtaagctc    240
cccttcgac catttcacat aaaacgtgtg ttctagcata tgcttatttt gaataattaa    300
atctaactga tctaaaaaat tcataaacac ctccatcatt tcttttcttg actccacgta    360
accgcttgca aaaaggtcc gtataagtcc tctgtttcat ctatgcgcaa agaacaatac    420
tcttctcgag aagtaggatg tgaatggtag accatattag gtgcctgctc tatcaccgct    480
aacggtgttt gctcattccc ctctcccata caaacaacag ccgcaactgc taaggcatct    540
acaagattac tttgcgtcat ctgtaagaga cgaccgaaac aatctagcga tcctatatag    600
```

| | |
|---|---:|
| ttgtgtaatg gagaaaatcc ataccaacac agcccgatac ccagtactcc acgccgcatt | 660 |
| ggagtagtat ggctatctgt aatgattacg cctagctctt tcactcgaaa ataatttctt | 720 |
| aaccattctc cgatgcgatt acacgatccc aaaatatctt taggatataa acaaaaggc | 780 |
| tggtccgtat tcgattcatc aatccctgca gaaggaatca aaataccttc ttttttcgtt | 840 |
| agatatatcc cgcttttctc acaaaacaaa taagcatccg cttctttttt tatcagctct | 900 |
| gctttgcaca ttcttgcatc agcgacagcg ccttcacata aactcacaat ctttgaagag | 960 |
| acaactacca cactccgttc ttgcagaggc ggcaaagcct cttgcaagat ctcttgaagc | 1020 |
| gaatcatgtg caaatacttt acgtgttttg atcggagtta ttttcataat aataaatact | 1080 |
| gaaatcctct gtattacaaa tacattcctt cttccatcct gataatcgcg tgatagggaa | 1140 |
| gaaagtatcg ccccaatatt cctttttgat atgtgtgaca aaacaagctt tcagaaggtt | 1200 |
| ttgttggaaa aactttcaa agagctccgc tcccccaatt aaaaacggat gattcaaaga | 1260 |
| tagtgtccca tactctgcaa aggaagaaac tcctatgcat tgtggtggat gcatcctgcg | 1320 |
| agaaaagaca acgatatccc gcccatgctt atacttgtct ggaagagact cccaagtctt | 1380 |
| tcgtcccata tgatgggat gatttcgaat ggtttctgca aaaaaacgta gatcttcggg | 1440 |
| ataactccaa gggagcttgc ctaaagctcc catcactcct ctgggatcaa tagcaacgat | 1500 |
| acctgttgct tggatcatac aaacatacca gcccaagcag cagcggctaa ggcacgtctg | 1560 |
| ttaccttcaa cctgatgcac gcgtagataa tcaactcctc gatcatgaag agatacagaa | 1620 |
| cagccgatcg tttcccaatc acgatcgtta ctattaaatc ggcccaacat actcaaacac | 1680 |
| gatttctag aatggcctat taatacagga cactctaaaa cacgtttaaa ctgctttact | 1740 |
| ccatccatca ataacatcga ctgaacggga gtcttcccaa atcctattcc tggatcgaaa | 1800 |
| acaacttgcc aacttgtatc taaacctact tgagcaaatt gttctaactg ggactctccc | 1860 |
| caacgcaaca tttgctcaat aggagattct tcataagaaa gtacaaatc tggtcttgga | 1920 |
| ggcagcgaac acgaatgatt tattaatagc cgtagcccaa actccttcgc caaatgagcc | 1980 |
| atttccaaag | 1990 |

<210> SEQ ID NO 37
<211> LENGTH: 2093
<212> TYPE: DNA
<213> ORGANISM: Chlamydia trachomatis

<400> SEQUENCE: 37

| | |
|---|---:|
| cagaaactct atccgcatac cttcttcggc aaattgatac caattttgcc tcttctcagg | 60 |
| aacgtactat agctcagtat attgtaggca acctctcccc agaaggactc tttttagaaa | 120 |
| atcctagtct tgtggctgca gatttaaacg tttccgaaca ccttttccac aaggtatggc | 180 |
| aacgtatcca acaattacat cctttaggag tcggagcgcc ttccctacag tcctactggg | 240 |
| tatcgctact acagacatct ccccataagg aggctttagc tattattcgc aaccatttcc | 300 |
| ctagattagc tcgttgtgat ttcactacta tcgctaggaa aatgcatgca accacaacag | 360 |
| agattcttac atttcttaga cacgcttttg cttccatccc ttggtgtcca gcagcaggct | 420 |
| tttccgagac actgcacccc cctgctccag cgcttcctga tgcctacctt tccttctcgc | 480 |
| gaaactctta ttgggatgtc tctattaata aagattgtct cccctctatt agactcaacg | 540 |
| acaccgtact agatatctat ccttctcttc ctcgtgaaga aaagaccac ctatcgcaac | 600 |
| aaatccgagc agcaaacaa ttgcttcgca atgtaaaaaa acgagaagaa acgttattgg | 660 |
| ctatccttcg agttctcatc ccctaccaag aagagttcct tcttaaaaaa cgcacctctc | 720 |

```
ctaaagctttt ttctgtaaaa caaatagctc gcgaactctc tcttcatgaa gctaccgttt      780
gtcgcgccat tgataataaa acgttagcaa ccctgttgg attactccct atgcgatcgc        840
tatttccaca gcggttgga tcctgccccg atcaatctaa agcaactatt ttgcattgga        900
tccaccagtg gatttctaca gaaaaacatc ctctatctga tgcagctatt agccaaaaaa      960
ttattgagaa gggcatcccc tgcgcacgac gcacagtagc caaatatcgt tcgcaactga      1020
atatcccacc tgcgcaccaa cgcaaacacc tatgctctgt tttaacaaca acacgcacag      1080
agaattctcg acatactatc taatcggata tgtaaagctg cttacatcc cttgaactag       1140
aaataaaatg gaaataaaaa gcccagaaca agagaagttg ttctgggctg acagaagctg     1200
tcagatcatt ttaataagat tgatgacaac tacgacaagt tcctggatcc aaaaaagaat      1260
ctaaaaagcc atacaaagat tgcgttactt cttgcgatgc ctctaacact ttatcagcgt      1320
catctttgag aagcatctca atgagcgctt tttcttctct agcatgccgc acatccgctt      1380
cttcatgttc tgtgaaatat gcatagtctt caggattgga aaatccaaag tactcagtca     1440
atccacgaat tttctctcta gcgatacgtt gaatttgact ctcataagaa tacaaagcag      1500
ccactcctgc agctaaagaa tctcctgtac accaccgcac gaaagtagct actttcgctt      1560
ttgctgcttc actaggctca tgagcctcta actcttctgg agtaactcct agagcaaaca      1620
caaactgctt ccacaaatca atatgattag ggtaaccgtt ctcttcatcc atcaagttat      1680
ctaacaataa cttacgcgcc tctaaatcat cgcaacgact atgaatcgca gataaatatt      1740
taggaaaggc tttgatatgt aaataatagt ctttggcata cgcctgtaat tgctcttag       1800
taagctcccc cttcgaccat ttcacataaa acgtgtgttc tagcatatgc ttattttgaa      1860
taattaaatc taactgatct aaaaaattca taaacacctc catcatttct tttcttgact      1920
ccacgtaacc gcttgcaaaa aaggtccgta taagtcctct gtttcatcta tgcgcaaaga     1980
acaatactct tctcgagaag taggatgtga atggtagacc atattaggtg cctgctctat     2040
caccgctaac ggtgtttgct cattcccctc tcccatacaa acaacagccg caa            2093
```

<210> SEQ ID NO 38
<211> LENGTH: 1834
<212> TYPE: DNA
<213> ORGANISM: Chlamydia trachomatis

<400> SEQUENCE: 38

```
ctctacttct acctctacgg ttacacgtgt agcggcaaaa gattatgatg aggctaaatc       60
gaattttgat acggcgaaaa gtggattaga gaacgctaag acacttgctg aatacgaaac     120
gaaaatggct gatttgatgg cagctctcca agatatggag cgtttagcta attcagatcc     180
tagtaacaat cataccgaag aagtaaataa tattaagaaa gcgctcgaag cacaaaaaga    240
tactattgat aagctgaata actcgttac gctgcaaaat cagaataaat ctttaacaga      300
agtgttgaaa acaactgact ctgcagatca gattccagcg attaatagtc agttagagat     360
caacaaaaat tctgcagatc aaattatcaa agatctggaa agacaaaaca taagttatga     420
agctgttctc actaacgcag agagggttat caaagcttct tctgaagcgg gaattaagtt     480
aggacaagct ttgcagtcta ttgtggatgc tggggaccaa agtcaggctg cagttctgca    540
agcacagcaa ataatagcc cagataatat tgcagccacg aaggaattaa ttgatgctgc      600
tgaaacgaag gtaaacgagt taaaacaaga gcatacaggg ctaacggact cgcctttagt     660
gaaaaaagct gaggagcaga ttagtcaagc acaaaaagat attcaagaga tcaaacctag    720
```

```
tggttcggat attcctatcg ttggtccgag tgggtcagct gcttccgcag gaagtgcggc      780
aggagcgttg aaatcctcta acaattcagg aagaatttcc ttgttgcttg atgatgtaga      840
caatgaaatg gcagcgattg cactgcaagg ttttcgatct atgatcgaac aatttaatgt      900
aaacaatcct gcaacagcta aagagctaca agctatggag gctcagctga ctgcgatgtc      960
agatcaactg gttggtgcgg atggcgagct cccagccgaa atacaagcaa tcaaagatgc     1020
tcttgcgcaa gctttgaaac aaccatcagc agatggtttg gctacagcta tgggacaagt     1080
ggcttttgca gctgccaagg ttggaggagg ctccgcagga acagctggca ctgtccagat     1140
gaatgtaaaa cagctttaca agacagcgtt ttcttcgact tcttccagct cttatgcagc     1200
agcactttcc gatggatatt ctgcttacaa acactgaac tctttatatt ccgaaagcag      1260
aagcggcgtg cagtcagcta ttagtcaaac tgcaaatccc gcgctttcca gaagcgtttc     1320
tcgttctggc atagaaagtc aaggacgcag tgcagatgct agccaaagag cagcagaaac     1380
tattgtcaga gatagccaaa cgttaggtga tgtatatagc cgcttacagg ttctggattc     1440
tttgatgtct acgattgtga gcaatccgca agcaaatcaa gaagagatta tgcagaagct     1500
cacggcatct attagcaaag ctccacaatt tgggtatcct gctgttcaga attctgcgga     1560
tagcttgcag aagtttgctg cgcaattgga aagagagttt gttgatgggg aacgtagtct     1620
cgcagaatct caagagaatg cgtttagaaa acagcccgct ttcattcaac aggtgttggt     1680
aaacattgct tctctattct ctggttatct ttcttaacgt gtgattgaag tttgtgaatg     1740
agggggagcc aaaaagaat tcttttttg gctctttttt cttttcaaag gaatctcgtg       1800
tctacagaag tcttttcagc acgagcggca cgag                                 1834

<210> SEQ ID NO 39
<211> LENGTH: 1180
<212> TYPE: DNA
<213> ORGANISM: Chlamydia trachomatis

<400> SEQUENCE: 39
agaaatttct caaaaatcaa agttttttac atttaagggg catcttacca ccacaacaac       60
cttctatgag cagaaactat ccattaaata aaagtaatta aatataacaa aaacatcttg      120 attattttg ttaaaagaaa tacttaatga gttttattta attaacgaaa cgaaaagctt       180
gctaatgaaa attattcaca cagctatcga atttgctccg gtaatcaaag ccggaggcct      240
gggagacgcg ctatacggac tagcaaaagc tttagccgct aatcacacaa cggaagtggt      300
aatcccttta taccctaaat tatttacttt gcccaaagaa caagatcttt gctcgatcca      360
aaaattatct tattttttg ctggagagca agaagcaact gctttctcct acttttatga      420
aggaattaaa gtaactctat tcaaactcga cacacagcca gagttattcg agaatgcgga      480
aacaatctac acaagcgatg atgccttccg tttttgcgct ttttctgctg ctgcggcctc      540
ctacatccaa aaagaaggag ccaatatcgt tcatttacac gattggcata caggattagt      600
tgctggacta ctcaaacaac agccctgctc tcaattacaa agattgttc ttaccctaca      660 taattttggt tatcgaggct atacaacacg agaaatatta gaagcctcct ctttgaatga      720 atttttatatc agccagtacc aactatttcg cgatccacaa acttgtgtgt tgctaaaagg     780
agctttatac tgttcagatt tcgtgactac ggtttctcct acatacgcca aagaaattct      840
tgaagattat ccgattacg aaattcacga tgccattact gctagacaac atcatctccg       900
cgggatttta aatggaatcg acacgacaat ttggggggcct gaaacggatc ccaatttagc     960
gaaaaactac actaaagagc ttttcgagac ccttcaatt tttttgaag ctaaagccga       1020
```

```
gaataaaaaa gccttgtacg aaagattagg cctctcttta gaacactctc cttgcgtgtg   1080
cattatttct agaattgctg agcagaaagg tcctcacttt atgaaacagg ccattctcca   1140
tgcactagaa aacgcttaca cgctcattat tataggtacc                         1180
```

<210> SEQ ID NO 40
<211> LENGTH: 1297
<212> TYPE: DNA
<213> ORGANISM: Chlamydia trachomatis

<400> SEQUENCE: 40

```
agaaacttct ataggagggg atgtgatcga cataggtacg tgtgagttat gggatatcga     60
tttgttgtat aatggataag aaattctctg aagataaaga ggctcctcca actaaaagac    120
cattaacatc agggcagagg gcaagtgagc gagcattatc ggctttcaca gatcctccgt    180
aaagaatggg ggtgcgttcc gcaatatctt tggaaaagag agaagcaatc gttttctac     240 agaaagcatg ggtttcctga actagatcag gatgagctac ttttccggtg cctatagccc    300
agactggttc ataagctaga atgaaagagg cttgctcagg gagtttagat aatcctatag    360
tcagttgatt taaaagaata tcttgagttg ctccagattc ttgttcttct aaagtttctc    420
caatacacag aactggaatc attccactat ggatagctgc agcagctttt tcagcaagta    480
caggattttg ttcatgaaag atatgacgtc tttcggaatg tccgatgaga acaaaatcga    540
ctccgatatc tttgagcatt ggggctgaaa tctcaccagt aaaagctcct gagtcagctt    600
catgagtggt ttgggctcca agaaagatgg gggaatcgct tacagcttgt tgacaagctg    660
acagcagtgt gaaggagga atgattcctg taatgatttg gggattagac agaatgtcac    720
tagagatgaa acttttaaa aaggtctgag cttcggtaag cgtcttgttc attttccaat    780
taccgaaaac aaattgcttt gatggctcag agtggagaag gtgggcccaa gttggaaatg    840
gttttctgtg agtttctttg tctgtaaaca tgagatttgc tgaataacct gtgcatgtat    900
tttgtttgta agatagatca aagcgtaata ctcgatttct gcaaggaag gcttattttt      960 atatgattta ttttctattg ctttgatata aatctcttgg atatgctaat cttcctgtct   1020
tacttttttc tgtgaatttg cttaaatagt tggttttagc cccttttgtta tatgaaggtg   1080 aaaatttgtg gtattacgca tcctgatgat gctcgggaag ctgccaaagc gggagccgat   1140
tacattggca tgattttttgc taaagattct cgaagatgtg tgagtgaaga aaaagcaaag   1200
tatatcgtag aggctataca ggaagggaat tcggaacctg ttggagtatt cccagagcat   1260
tcagtagaag aaatttagc tattactgag acgacag                              1297
```

<210> SEQ ID NO 41
<211> LENGTH: 1141
<212> TYPE: DNA
<213> ORGANISM: Chlamydia trachomatis

<400> SEQUENCE: 41

```
ctttccataa gttctttctt tcaatgattc tagcttattc ttgctgctct ttaagtgggg     60
gggggtatgc agcagaaatc atgattcctc aaggaattta cgatggggag acgttaactg    120
tatcatttcc ctatactgtt ataggagatc cgagtgggac tactgttttt tctgcaggag    180
agttaacgtt aaaaaatctt gacaattcta ttgcagcttt gcctttaagt tgttttggga    240
acttattagg gagttttact gttttaggga gaggacactc gttgactttc gagaacatac    300
ggacttctac aaatggagct gcactaagtg acagcgctaa tagcgggtta tttactattg    360
```

```
agggttttaa agaattatct ttttccaatt gcaactcatt acttgccgta ctgcctgctg    420
caacgactaa taatggtagc cagactccga cgacaacatc tacaccgtct aatggtacta    480
tttattctaa aacagatctt ttgttactca ataatgagaa gttctcattc tatagtaatt    540
tagtctctgg agatggggga gctatagatg ctaagagctt aacggttcaa ggaattagca    600
agctttgtgt cttccaagaa atactgctc aagctgatgg gggagcttgt caagtagtca     660
ccagtttctc tgctatggct aacgaggctc ctattgcctt tatagcgaat gttgcaggag    720
taagaggggg agggattgct gctgttcagg atgggcagca gggagtgtca tcatctactt    780
caacagaaga tccagtagta agttttttcca gaaatactgc ggtagagttt gatgggaacg   840
tagcccgagt aggaggaggg atttactcct acgggaacgt tgctttcctg aataatggaa    900
aaaccttgtt tctcaacaat gttgcttctc ctgtttacat tgctgctgag caaccaacaa    960
atggacaggc ttctaatacg agtgataatt acggagatgg aggagctatc ttctgtaaga   1020
atggtgcgca agcagcagga tccaataact ctggatcagt ttcctttgat ggagagggag   1080
tagttttctt tagtagcaat gtagctgctg ggaaaggggg agctatttat gccaaaaagc   1140
t                                                                  1141

<210> SEQ ID NO 42
<211> LENGTH: 822
<212> TYPE: DNA
<213> ORGANISM: Chlamydia trachomatis

<400> SEQUENCE: 42
cggcacgagt gtatgctgaa caagcagaag ggcccactga gaacgagcct ctgagaaaaa     60
aagcttttat taaaaaatta aaaaaatact ttacaaaact tattctgtag gttgagaaag    120
agcttcaacg taagcattcc aaagctccgt acttacaata ttattgcgga tagagcgaat    180
taattctctt tttagtgatg gaagaggttt ttttgggggctg aagcgagcca aaagatcttt  240
atcgccaact tgacgagcta actctaacac ccgttcgata tcggttttg tgaaattcac     300 aaagtctctg cgcttttttag aacctcgagg agctcgtggt ttagggctaa tggatctggg   360
agtgatagaa tcgatcacaa acgtctttaa catttttaac agttgctcag gagcagagtt    420
cttcattttt tttaaagtaa aatgatgcat gtagccgcct gttggccctg ggagataacg    480
acaaagatca ttttctttac ttcctccgac tttgctaatc gctttagtta tgagctgctc    540
tatttcttct tggatagtaa tctgtgccgt agccatgaat agctcctag tgggtagtct     600 agttctacag atggtagttt ttgctttatt aattgtaata gtcaactaag tctgtttttt    660
tcgatttaat gttcagtcga aataaaaatc aattagtgtt tatcttttgg tgaattctat    720
agtggttttt gcttttttcg caatctcatt ttagagattt ttttgatttg gacaaaagaa    780
aataaagtac ttcagattgt tttctaagtt tgtttgcata aa                       822

<210> SEQ ID NO 43
<211> LENGTH: 1634
<212> TYPE: DNA
<213> ORGANISM: Chlamydia trachomatis

<400> SEQUENCE: 43
ataaaaaatt aaattttggc tactccctgc tcctaataga atttcaccag aggagcttgc     60
tactgttatt gcatttcttc taggaggatt agctgacgta ctggtaccat ttgcattagt    120
tacattagtc acaatatttt cattaaaaat aatagcatgg cggtcggcag aaattttgga   180
gttactggtt ccgtctatat agatagcgcc ccccttatta ttggcgatat tgtttataaa    240
```

```
gtaggtaggg ccattatcca ctagggtaac tacaggagcg taaatagctc cgccataatt      300
ttttgtgata ttgtcactaa aaaagatcct accacgattg cctgtaacat ctaggcgagt      360
agttacttta attgctcctc catcagaagc ttctgaagaa gctgtttcta cattttt aaa     420 gcagcgattg ttatagaaaa cgatgttacc acgatttcct gttagagaac agatagggga     480
gaagatcgct cctcctgcac aacaggcgtt attgatgaag aagagatcgc agttattact     540
ctcaaaagaa ttgctcgttc cagcatagat agcgccacct tttcctgctg tattagtttg     600
aatacagatg ttgtccataa agagaaaaca agactgattc tcgctcacaa caaaggtatt     660
agcggtacta atggctcctc cttggacata agaaaagttc ttcataaatc cgaccacatc     720
atgattatga tttatgtaaa gattttgagc atgaatggct ccgccttctc ttatttatc      780 agcagcataa ggatttctcc atgtaaatag tctgcaacaa gtattatttt caaagattac     840
aggacctatt gtatcacgaa ctccacggt aggagaattg ggactcgcat aaccaatcgc      900
accaccactt tcagggtgta gattttttgc aaaataaata ccttctttt gtgtatcaaa     960 aaagcttagg taatctgtta ttgtgacagc agctccttca ttgggagttt tttgtagaat     1020
agccagtatg tagcgtaggt tatcgagata gcagttagtg agattgtgag tgtctcctgt     1080
caaactaatt ttatttgata gcgactcttt cgtaggatct ggaactgagt tgggcataag     1140
aaagattcta gaaggaacct ctctagctag tcctgatagg gagtttccga taggaaaaa     1200 gaaaacgct tttttcataa ttaaaagacc agagctcctc ctgcattgat gtagtgtgag     1260
acagtggaag tagccacttc tgcttgatag ttagcaaata gtttcagatg agaaaatttg     1320
agggagtgag aacctctccc ataaaaggaa tgtttagcta atggggtatt tgtggtgacc     1380
caagaaccgt tattttggat taatagtgtg ttgagtagag gacgtttcca gtagagggtg     1440
ggttggtaag ctagttccat ttcccaagag agtgttggcc atgtatcaga agaataagct     1500
cctttgattc ctattggaga gacaacggca gtatgggctt gctctaatgt aaataatcta     1560
gctagatcac cgctttctcg gatagaagct ggttctgttc gagagaataa agcctgagca     1620
aatggggtga gcat                                                      1634

<210> SEQ ID NO 44
<211> LENGTH: 1862
<212> TYPE: DNA
<213> ORGANISM: Chlamydia trachomatis

<400> SEQUENCE: 44
gttagctttc cctccaggga tttgcaattt aatgatttta atgattttt tattcgacat       60 attcaaccct ttcatttggc aagacatgga gtcatagtta gagggtctat gtatgcttct     120
ctaacaagca atatagaagt atatggccat ggaagatatg agtatcgaga tacttctcga     180
ggttatggtt tgagtgcagg aagtaaagtc cggttctaaa atattggtt agatagttaa      240 gtgttagcga tgccttttc tttgagatct acatcatttt gttttttagc ttgtttgtgt     300
tcctattcgt atggattcgc gagctctcct caagtgttaa cacctaatgt aaccactcct     360 tttaagggg acgatgttta cttgaatgga gactgcgctt ttgtcaatgt ctatgcaggg     420
gcagagaacg gctcaattat ctcagctaat ggcgacaatt taacgattac cggacaaaac     480
catacattat catttacaga ttctcaaggg ccagttcttc aaaattatgc cttcatttca     540
gcaggagaga cacttactct gaaagatttt tcgagtttga tgttctcgaa aaatgtttct     600
tgcggagaaa agggaatgat ctcagggaaa accgtgagta tttccggagc aggcgaagtg     660
```

```
attttttggg ataactctgt ggggtattct cctttgtcta ttgtgccagc atcgactcca    720
actcctccag caccagcacc agctcctgct gcttcaagct ctttatctcc aacagttagt    780
gatgctcgga aagggtctat tttttctgta gagactagtt tggagatctc aggcgtcaaa    840
aaagggtcta tgttcgataa taatgccggg aattttggaa cagttttcg aggtaatagt     900 aataataatg ctggtagtgg gggtagtggg tctgctacaa caccaagttt tacagttaaa    960
aactgtaaag ggaaagtttc tttcacagat aacgtagcct cctgtggagg cggagtagtc    1020
tacaaaggaa ctgtgctttt caaagacaat gaaggaggca tattcttccg agggaacaca    1080
gcatacgatg atttagggat tcttgctgct actagtcggg atcagaatac ggagacagga    1140
ggcggtggag gagttatttg ctctccagat gattctgtaa agtttgaagg caataaaggt    1200
tctattgttt ttgattacaa ctttgcaaaa ggcagaggcg gaagcatcct aacgaaagaa    1260
ttctctcttg tagcagatga ttcggttgtc tttagtaaca atacagcaga aaaaggcggt    1320
ggagctattt atgctcctac tatcgatata agcacgaatg gaggatcgat tctgtttgaa    1380
agaaaccgag ctgcagaagg aggcgccatc tgcgtgagtg aagcaagctc tggttcaact    1440
ggaaatctta ctttaagcgc ttctgatggg gatattgttt tttctgggaa tatgacgagt    1500
gatcgtcctg gagagcgcag cgcagcaaga atcttaagtg atggaacgac tgtttcttta    1560
aatgcttccg gactatcgaa gctgatcttt tatgatcctg tagtacaaaa taattcagca    1620
gcgggtgcat cgacaccatc accatcttct tcttctatgc ctggtgctgt cacgattaat    1680
cagtccggta atggatctgt gattttttacc gccgagtcat tgactccttc agaaaaactt    1740
caagttctta actctacttc taacttccca ggagctctga ctgtgtcagg aggggagttg    1800
gttgtgacgg aaggagctac cttaactact gggaccatta cagccacctc tggctcgtgc    1860
cg                                                                   1862

<210> SEQ ID NO 45
<211> LENGTH: 1668
<212> TYPE: DNA
<213> ORGANISM: Chlamydia trachomatis

<400> SEQUENCE: 45
agaaaatccg atagcagaaa tagaagaatt cgatgtggtt gcgaacaaag ctcaagattg     60
ggatgtcgat gtagctatgt caaattcttt tggttttggc ggacacaatt caacgatatt    120
attttcgagg tatgaacctt cattatgatg aaaactaagc acgaatattc ttttggcgtt    180
attcctatca gatttttttgg tactccggat agaagtacct taaaggcttg ttttatctgc    240
catacagatg ggaaacattg gggtttccct aaggggcatg ctgaggaaaa agaaggccct    300
caggaagctg ctgagagaga acttgtagaa gaaactggtt tggggattgt taattttttc    360
ccaaaaatat ttgtggaaaa ttattccttt aatgacaaag aagaaatctt gtacgtaaaa    420
gaggtaactt attttcttgc agaggttaaa gcgaagtac atgctgatcc tgatgagatc     480
tgtgatgtgc agtggctaag ctttcaagaa ggtttacgcc ttttaaattt cccagaaatt    540
cgtaatattg ttacggaagc agatgaattt gttcaaagtt atctatttgc ttcataaagt    600
cccctaggat gaaaaaaact tggttaggag gggccgttgt ggaatctccc acaacagcct    660
tttctttttc tgtcgattta cataaaaaga ttgcaatagt cttcgtgagc aagacgaatg    720 acttttgag cttcttttt gccgtataaa cctacaattt caattttagc tggttttgct    780
tgaattaagc tttctggagt agctttatag gttaagaaat agtgttggat catgtccaaa    840
actgtgcctg ggcattcaga aatatcttct atattgccat agactaaatc atcttctaga    900
```

-continued

```
acagcgatga tttatcatc ggcttcttcc gagtctaaaa tacgaatccc tccgatagga      960
cgcgcttgca agaggatgtt cccttgtgta atattttttt ccgttaacac acagatatca    1020
agaggatcgc catcgccttt gatattctct ctgttacttt gttgaccact gtattctcca    1080
gaaagatctc cacaataagt cttaggtaac agcccgtata agcaaggaca aaagttagaa    1140
aactttgtg gccgatccac ttttaggata ccagtttctt tatccagttc gaatttaacg     1200
gagtcggctg gagtgatttc tatatagcaa caaagagatt cataatcatc gcgtgttaat    1260
actggcccat gccaaggatg agctatggat aatggtgttt tagacataag atcactctct    1320
attaaagtgt tttatgcgca attatcctgc gcatccggct tattcgtcca gatagttta    1380
gtcttctgtt ctcgcagtaa aactttatt ttatcggcag cctttctttt tgcttttatt     1440
cttgtcattg tgaaaaatgt tgaaaagtta ctcgtggcaa cctttcagac aggttttttg    1500
tacgaaagac gagagtgatt gtactgcaaa ataatatgag ccggacgtag gatatgaaat    1560
actctttgca aatagaagac ctacatattg aaggatatga acaggttttg aaagttactt    1620
gcgagtctgt acagttagtt gctgtaattg ctattcatca gacaaaag                1668
```

<210> SEQ ID NO 46
<211> LENGTH: 2010
<212> TYPE: DNA
<213> ORGANISM: Chlamydia trachomatis

<400> SEQUENCE: 46

```
atatcaaagt tgggcaaatg acagagccgc tcaaggacca gcaataatc cttgggacaa       60
catcaacacc tgtcgcagcc aaaatgacag cttctgatgg aatatcttta acagtctcca    120
ataattcatc aaccaatgct tctattacaa ttggtttgga tgcggaaaaa gcttaccagc    180
ttattctaga aaagttggga gatcaaattc ttgatggaat tgctgatact attgttgata    240
gtacagtcca agatatttta gacaaaatca aaacagaccc ttctctaggt ttgttgaaag    300
cttttaacaa ctttccaatc actaataaaa ttcaatgcaa cgggttattc actcccagta    360
acattgaaac tttattagga ggaactgaaa taggaaaatt cacagtcaca cccaaaagct    420
ctgggagcat gttcttagtc tcagcagata ttattgcatc aagaatggaa ggcggcgttg    480
ttctagcttt ggtacgagaa ggtgattcta agccctgcgc gattagttat ggatactcat    540
caggcattcc taatttatgt agtctaagaa ccagtattac taatacagga ttgactccga    600
caacgtattc attacgtgta ggcggtttag aaagcggtgt ggtatgggtt aatgcccttt    660
ctaatggcaa tgatatttta ggaataacaa atacttctaa tgtatctttt ttagaggtaa    720
tacctcaaac aaacgcttaa acaattttta ttggattttt cttataggtt ttatatttag    780
agaaaacagt tcgaattacg gggtttgtta tgcaaaataa agaaaagtg agggacgatt     840
ttattaaaat tgtaaagat gtgaaaaag atttccccga attagaccta aaaatacgag       900
taaacaagga aaagtaact ttcttaaatt ctcccttaga actctaccat aaaagtgtct      960
cactaattct aggactgctt caacaaatag aaactctttt aggattattc ccagactctc    1020
ctgttcttga aaaattagag gataacagtt taaagctaaa aaaggctttg attatgctta    1080
tcttgtctag aaaagacatg ttttccaagg ctgaatagac aacttactct aacgttggag    1140
ttgatttgca caccttagtt ttttgctctt ttaagggagg aactggaaaa acaacacttt    1200
ctctaaacgt gggatgcaac ttggcccaat ttttagggaa aaaagtgtta cttgctgacc    1260
tagacccgca atccaattta tcttctggat tggggctag tgtcagaagt gaccaaaaag    1320
```

```
gcttgcacga catagtatac acatcaaacg atttaaaatc aatcatttgc gaaacaaaaa    1380
aagatagtgt ggacctaatt cctgcatcat tttcatccga acagtttaga gaattggata    1440
ttcatagagg acctagtaac aacttaaagt tatttctgaa tgagtactgc gctccttttt    1500
atgacatctg cataatagac actccaccta gcctaggagg gttaacgaaa gaagcttttg    1560
ttgcaggaga caaattaatt gcttgtttaa ctccagaacc tttttctatt ctagggttac    1620
aaaagatacg tgaattctta agttcggtcg gaaaacctga agaagaacac attcttggaa    1680
tagctttgtc ttttttgggat gatcgtaact cgactaacca aatgtatata gacattatcg    1740
agtctattta caaaaacaag cttttttcaa caaaaattcg tcgagatatt tctctcagcc    1800
gttctcttct aaagaagat tctgtagcta atgtctatcc aaattctagg gccgcagaag    1860
atattctgaa gttaacgcat gaaatagcaa atattttgca tatcgaatat gaacgagatt    1920
actctcagag gacaacgtga acaaactaaa aaagaagcg gatgtctttt ttaaaaaaaa    1980
tcaaactgcc gcttctctag attttaagaa                                    2010

<210> SEQ ID NO 47
<211> LENGTH: 2044
<212> TYPE: DNA
<213> ORGANISM: Chlamydia trachomatis

<400> SEQUENCE: 47
gtcatcaaga aaagattggg aacctatccg tagtttggtt aaagagcatg gtatgcgaca     60
ttgtcagctt atggctatag ctccgacagc gacgatctcc aacattatag gagtaactca    120
atctattgag ccaacgtaca aacatttgtt tgtgaagtct aatttgtccg gagaattcac    180
gattccaaat gtgtatttaa ttgagaagtt gaagaaatta ggtatctggg atgctgatat    240
gttagatgac ctgaaatatt ttgatgggtc tttattggaa atcgagcgta taccagatca    300
cttaaaacat attttcttga cagcttttga gattgaacca gaatggatta tcgaatgcgc    360
gtctcgaaga caaaaatgga ttgatatggg gcaatccctc aacctttatc ttgcccagcc    420
agacgggaaa aaactgtcga atatgtattt aacggcttgg aaaaaaggtt tgaaaaactac    480 gtattatctg agatcttcat cagcaacgac cgttgaaaaa tcttttgtag atattaataa    540
gagaggaatt cagcctcgtt ggatgaagaa taagtctgct tcggcaggaa ttattgttga    600
aagagcgaag aaagcacctg tctgttcttt ggaagaaggg tgtgaagcat gtcagtaatt    660
aatcatataa attaacaata aaattaacg ttcttatgca agcagatatt ttagatggaa    720
aacagaaacg cgttaatcta aatagcaagc gtctagtgaa ctgcaaccag gtcgatgtca    780
accaacttgt tcctattaag tacaaatggg cttgggaaca ttatttgaat ggctgcgcaa    840
ataactggct ccctacagag atccccatgg ggaaagacat cgaattatgg aagtcggatc    900
gtctttctga agatgagcgg cgagtcattc ttttgaattt aggtttttc agcaccgcag    960 agagcttggt tgggaataat attgttctag caatttttaa acatgtaact aatccggaag   1020
cgagacaata tcttttaaga caagcttttg aagaagcggt tcacacgcac acattttttgt   1080 atatttgtga gtcactcgga ttagacgaga agaaatttt caatgcctat aacgagcgtg   1140
ctgcgattaa ggccaaagat gatttccaga tggaaatcac tggcaaggta ttggatccta   1200
attttcgcac ggactctgtt gagggtctac aggagtttgt taaaaactta gtaggatact   1260
acatcattat ggaagggatt ttcttctata gtgggtttgt gatgatcctt tccttccaca   1320
gacaaaataa gatgattggt attggagaac aaatatcaata catcttaaga gatgagacaa   1380
tccacttgaa ctttggtatt gatttgatca acgggataaa agaagagaac ccggggattt   1440
```

-continued

```
ggactccaga gttacagcaa gaaattgtcg aattaattaa gcgagctgtc gatttagaaa   1500
ttgagtatgc gcaagactgt ctccctagag ggattttggg attgagagct tcgatgttca   1560
tcgattatgt gcagcatatt gcagaccgtc gtttggaaag aatcggatta aaacctattt   1620
atcatacgaa aaacccattc ccttggatga gcgaaacaat agaccttaat aaagagaaaa   1680
acttctttga acaagggtt atagaatatc aacatgcagc aagcttaact tggtagtcct   1740
gatatcaaaa taggagaaag cctcaaccat agagttgagg ctttttttg tcatacggta   1800 acctgataag aatttttaga ttttcaggtt agaagtaaat gtatttaccc atgaatttt    1860 tttaatttc tcataatatc ttgtagccct tttattaaaa tggaaaaggc tagtcacctc    1920
tcctatgact actgttagag tggtgagatt tggggttgga gcaggtgtag cctttcgcat   1980
acgaagtatt ttcctgtgaa accacaagat ttgaaacttc cctattttg ggaagaacgt    2040 tctc                                                                2044
```

<210> SEQ ID NO 48
<211> LENGTH: 3734
<212> TYPE: DNA
<213> ORGANISM: Chlamydia trachomatis

<400> SEQUENCE: 48

```
gttattcgct tctactccat tagaagtccc taatgctaaa ctcaccattt ttcctccttt     60
ccgttaaaac aggaaagaaa ttgtacagaa acatttttt aaagaaatca aaagccatt     120 tgcaggcaga tatcaggcca tttatatcaa aaacagaaag aatgattagg ataaaactt     180 gtcttgccat cgttccagag agcattgaga agccgttttt attataaata cattgcacta    240
agaatcttaa aatcgaacag acaacacaat ggctcgaaca gactgatcca cacgcactaa    300
ttcaaatgca aaaacttct aaaatgaaca cagcaagctt gataaaaaca tataaagaa      360 ttggatcata gagctttacg agaagggggg cactgcaatc tgtctcgacc aaatagcaat    420
gcaaacagat aaataccct aatcattggg aaaaattgag tgtagaatag cctctttctc     480
ttcctctatt tgttgcttag ctaacgcgat ttcttcttta gagatatctg caagtctctg    540
cttatccaaa aagccttgtc tctcatttc aatacaaat ctgtccagag aaactttttt      600
tggctctcca ccatagctag aaattctagt aagaacagca cctagcatca cagatccaaa    660
aacaaccagg gtaaccacta cgtcaatcat aggaagcgta gtccaacctg ccccaataaa    720
taaggctgct cctgtaacta tgaataaaat actaagaata ccgagcgcaa gcacagcaat    780
acgttcgcta caacaagaaa ctctcgcttt agaagcgcta tccaccaaag gagcctctgg    840
catataactt ctaagaggta cactatctcc aacaaaactc atggcatccc cttaaggta     900 aaagagaagc tttcctctaa atagaaaagc gtatcgtcaa ctcttttata gatctaaaaa    960
gtcttgcttt ccttaatccc acccatgaaa tttagcataa aaaccatcca acatattcac   1020
acgctcttct aaaaggccta tttccctatt tttctgagtc tctaaaaccc tataatggct   1080
ggaaattttc cgcgcacttt ccttggcttc ttgtaatagc tgatctgaat tgcgtatcac   1140
agataacagg taagaaacta atccaaaagc tcctatacaa gaaccaataa ttgcagctct   1200
cccactactc ctaaaactaa ggaagaatag actccccaa gacaaagaaa aactcctcct    1260
aaagctgcaa gcaaacttgt tagaacaact acaaataact ggtatgtttt agaacggtga   1320 ataaggagt tgttagccac attttcactg tacctcagtt tttgctgaac aacaattccc    1380 taaaaattg gtaggacgcc aaacgttcat aattactcta cttggaaacc attaataatt   1440
```

```
atatcagact ttcttccaat acacatttca acccactttg aagctgttct attttttttct    1500 gagcaagctc taaatctttg ctcttttgag caagcaatcc ttcaacttct ttcaaatctt    1560
cttctgcttc atatagaagt tcttgataag ataacactaa tccaggagtc acggcctctg    1620
gagctaactc agatgactct gaagggagtc tcgtcggttt taaagaaaac ccatacatat    1680
aaactagact tcctcctata caggcagaac ccagtgtcat tgctaataag ctaagaatag    1740
gagcaaaaag agagaccaca cttcctgaaa aagaagcag aagagcacca cctaaaactg     1800
ctagtacccc taataccaag gcacctattg ccaacaattg ctctttacgg cttgtagtag    1860
tctgagcacc gatagtttca gtatgatcgg cacgcaatgg tttgctggaa ttacaacaaa    1920
aagaaatatt aaacatggcg cctctatttc gcaaaaaaaa ggccaacatg ctacaggaaa    1980
gctaattaaa gtaaaaattt ttatatattt caatggtagt taaataccta atctacccaa    2040
ccaaaagatg tctaaatgac aaaaaaataa tcgtatttat attatcatga gacacttata    2100
gtcacgtctg cttcattcag ctcaaattct aatgaaaaat cggatttaga agaaaataga    2160
ctcgaagagt cagaactagc caaaatgttt gttctaattc tattttgcaa tccccgacta    2220
caagaccaat agagaaacgt taaccctact cctaaagcca cagaaccaat cataatcgct    2280
ccaataccta aaccggcaaa cacaagcgac gatcccccgc aaagcaaaca aagcaaggct    2340
acacaactta aaatagcaaa aattcctaag gaaacggcaa attctatatt tcctcttcgt    2400
ttgcaataaa tatgcgtctt atacagacac aactctgcgg ggctctccag agttggagcg    2460
caagaggaac aaaaaagata agacattgtc gactccggac caaaaaaagg cgagataata    2520
cgcgagatgg taaaaataca gaatatttt tgacatagaa aaccctaacc ctcctttcat     2580
cgcgtgagac tagagtgtaa acaagatgc gaaagcaagg ttcgctatgt ttggaaacaa     2640
acctccacac ggtcccggat tatcaaaaca agtcttccag ggatatgtta gagaacgtcc    2700
tatccatacc aaagcaacat atagacgtct tttgtgaaaa gactgaatag aggaatctaa    2760
gaagcttggt tagcgtctat agatgcttta agagcagctt tttccttttc agcactatcc    2820
aaccatcttg tgtagctaga taaaactaag cgcacatcgg acaataaagc ttgctcattt    2880
ttctctaatc tgtccaaaca atcaatctca acttctattg ccttagcttc caaagcttgg    2940
agatcgtccg taagacctcg cagaaacatc ttattaatga agagacgga gaccaaagcg     3000 tccttctctt ctgaaagatt acgcaaacgt tgctcagcca aaacatttt tgcttctaag     3060 ctagcataag aggatcgaca cataagacga gatattcccg cacccacaca agcagatcca    3120
ataattaatg cagcaatacc tattgcagta aatatgacat tgctagcgca caaaaccaaa    3180
gctaataccc cagcgacaac aactaaagcc cctacgatag ctaaagctat atccaaaatt    3240
ttggaacaag tattcccttt tgttgaagac gaagtagatt ttatctctac gcaggaagct    3300
gttggcaatg gtaaagaaga agcgtctccg ctaatagtag tactcatttt tccacatttt    3360 tattttaaa acggaaaaac tgtatcagaa cggcgcttta ttcgcaaatc attataaatc     3420
cgcaacatgc agaactaaag cgccgtaagc aaaaggaacc cctaactctc agatgcaata    3480
tctgaggagt cttaattat tttttacgac gggatgcctg cacctgcagc cgctctgata     3540
atgtcttatt ctcagatctc aatttacaca actctgctgt taattgactg caagtgttct    3600
gactttgttg caaccgctgt ttaaacccct ctgtctgatg acgaatttct tgttcagcat    3660
cctcctcaat ggagcaaact gtttcggcat aacgcttaca caaatctaat atttgttctt    3720
ccaactcttg gcaa                                                      3734
```

<210> SEQ ID NO 49
<211> LENGTH: 2937
<212> TYPE: DNA
<213> ORGANISM: Chlamydia pneumoniae

<400> SEQUENCE: 49

| | | | | | |
|---|---|---|---|---|---|
| atgcctcttt | ctttcaaatc | ttcatctttt | tgtctacttg | cctgtttatg | tagtgcaagt | 60 |
| tgcgcgtttg | ctgagactag | actcggaggg | aactttgttc | ctccaattac | gaatcagggt | 120 |
| gaagagatct | tactcacttc | agattttgtt | tgttcaaact | tcttggggc | gagttttca | 180 |
| agttcctta | tcaatagttc | cagcaatctc | tccttattag | gaagggcct | ttccttaacg | 240 |
| tttacctctt | gtcaagctcc | tacaaatagt | aactatgcgc | tactttctgc | cgcagagact | 300 |
| ctgaccttca | agaattttc | ttctataaac | tttacaggga | accaatcgac | aggacttggc | 360 |
| ggcctcatct | acgaaaaga | tattgttttc | caatctatca | aagatttgat | cttcactacg | 420 |
| aaccgtgttg | cctattctcc | agcatctgta | actacgtcgg | caactcccgc | aatcactaca | 480 |
| gtaactacag | gagcctctgc | tctccaacct | acagactcac | tcactgtcga | aaacatatcc | 540 |
| caatcgatca | agttttttgg | gaaccttgcc | aacttcggct | ctgcaattag | cagttctccc | 600 |
| acggcagtcg | ttaaattcat | caataacacc | gctaccatga | gcttctccca | taacttact | 660 |
| tcgtcaggag | gcggcgtgat | ttatggagga | agctctctcc | ttttgaaaa | caattctgga | 720 |
| tgcatcatct | tcaccgccaa | ctcctgtgtg | aacagcttaa | aaggcgtcac | cccttcatca | 780 |
| ggaacctatg | ctttaggaag | tggcggagcc | atctgcatcc | ctacgggaac | tttcgaatta | 840 |
| aaaaacaatc | aggggaagtg | caccttctct | tataatggta | caccaaatga | tgcgggtgcg | 900 |
| atctacgccg | aaacctgcaa | catcgtaggg | aaccagggtg | ccttgctcct | agatagcaac | 960 |
| actgcagcga | gaaatggcgg | agccatctgt | gctaaagtgc | tcaatattca | aggacgcggt | 1020 |
| cctattgaat | tctctagaaa | ccgcgcggag | aagggtggag | ctatttcat | aggcccctct | 1080 |
| gttgagacc | ctgcgaagca | aacatcgaca | cttacgattt | tggcttccga | aggtgatatt | 1140 |
| gcgttccaag | gaaacatgct | caatacaaaa | cctggaatcc | gcaatgccat | cactgtagaa | 1200 |
| gcaggggag | agattgtgtc | tctatctgca | caaggaggct | cacgtcttgt | attttatgat | 1260 |
| cccattacac | atagcctccc | aaccacaagt | ccgtctaata | aagacattac | aatcaacgct | 1320 |
| aatgcgcgtt | caggatctgt | agtctttaca | gtaagggac | tctcctctac | agaactcctg | 1380 |
| ttgcctgcca | acacgacaac | tatacttcta | ggaacagtca | gatcgctag | tggagaactg | 1440 |
| aagattactg | acaatgcggt | tgtcaatgtt | cttggcttcg | ctactcaggg | ctcaggtcag | 1500 |
| cttaccctgg | gctctggagg | aaccttaggg | ctggcaacac | ccacgggagc | acctgccgct | 1560 |
| gtagacttta | cgattggaaa | gttagcattc | gatccttttt | ccttcctaaa | aagagatttt | 1620 |
| gtttcagcat | cagtaaatgc | aggcacaaaa | acgtcactt | taacaggagc | tctggttctt | 1680 |
| gatgaacatg | acgttacaga | tctttatgat | atggtgtcat | acaatctcc | agtagcaatt | 1740 |
| cctatcgctg | ttttcaaagg | agcaaccgtt | actaagacag | gatttcctga | tggggagatt | 1800 |
| gcgactccaa | gccactacgg | ctaccaagga | aagtggtcct | acacatggtc | ccgtcccctg | 1860 |
| ttaattccag | ctcctgatgg | aggatttcct | ggaggtccct | ctcctagcgc | aaatactctc | 1920 |
| tatgctgtat | ggaattcaga | cactctcgtg | cgttctacct | atatcttaga | tcccgagcgt | 1980 |
| tacggagaaa | ttgtcagcaa | cagcttatgg | atttccttct | taggaaatca | ggcattctct | 2040 |
| gatattctcc | aagatgttct | tttgatagat | catcccgggt | tgtccataac | cgcgaaagct | 2100 |
| ttaggagcct | atgtcgaaca | cacaccaaga | caaggacatg | agggcttttc | aggtcgctat | 2160 |

```
ggaggctacc aagctgcgct atctatgaac tacacggacc acactacgtt aggactttct   2220
ttcgggcagc tttatggaaa actaacgcc aacccctacg attcacgttg ctcagaacaa    2280
atgtatttac tctcgttctt tggtcaattc cctatcgtga ctcaaaagag cgaggcctta   2340
atttcctgga aagcagctta tggttattcc aaaaatcacc taaataccac ctacctcaga   2400
cctgacaaag ctccaaaatc tcaagggcaa tggcataaca atagttacta tgttcttatt   2460
tctgcagaac atcctttcct aaactggtgt cttcttacaa gacctctggc tcaagcttgg   2520
gatctttcag gtttatttc cgcagaattc ctaggtggtt ggcaaagtaa gttcacagaa    2580
actggagatc tgcaacgtag ctttagtaga ggtaaagggt acaatgtttc cctaccgata   2640
ggatgttctt ctcaatggtt cacaccattt aagaaggctc cttctacact gaccatcaaa   2700
cttgcctaca agcctgatat ctatcgtgtc aaccctcaca atattgtgac tgtcgtctca   2760
aaccaagaga gcacttcgat ctcaggagca atctacgcc gccacggttt gtttgtacaa    2820
atccatgatg tagtagatct caccgaggac actcaggcct ttctaaacta tacctttgac   2880
gggaaaaatg gatttacaaa ccaccgagtg tctacaggac taaaatccac attttaa     2937

<210> SEQ ID NO 50
<211> LENGTH: 801
<212> TYPE: DNA
<213> ORGANISM: Chlamydia pneumoniae

<400> SEQUENCE: 50
atgcattcaa aatttctttc tcgaagaaaa aaaaatagtt ctcataagga ggaaacctct     60
tgggattgta tagcctcaag ttacaataag atagtccaag ataaagggca ctactatcat    120
agagaaacta tccttcccca actcctgcct tcactcacct taggttcaaa agttctgta    180 ttggatattg gctgcggtca aggttttta gaaagggccc ttcctaagga atgtcgttat    240
ctaggcatag atatctcttc tagattgatt gctctagcaa agaaaatgcg atcggtaaac    300
tctcatcagt ttaaggttgc agatcttagc aaacgcctag agttcgtaga accgacatta    360
ttctctcatg cagtagcaat cctctcccctt caaaatatgg aattccccgg agaggctata   420
cgtaatacag ctacgctcct cgaaccactc gggcaatttt ttatagtttt aaaccatcct    480
tgttttcgta ttcctagggc atcatcctgg cactatgatg aaaataaaaa agctatctct   540
cgtcatatag atcgttatct ctccccaatg aaaatcccaa tcatggctca cccaggacaa   600
aaagattcgc cttctaccct ctccttcac tttcctctaa gctattggtt taaagaactg     660
tcttctcatg gattcttagt ttcaggtctt gaggaatgga catcttcaaa acctcaaca    720 ggaaaacgag ctaaggcaga aaacctttgt cgaaaggaat ttccattatt ccttatgatt   780
tcatgcatta agataaaata a                                              801

<210> SEQ ID NO 51
<211> LENGTH: 252
<212> TYPE: DNA
<213> ORGANISM: Chlamydia pneumoniae

<400> SEQUENCE: 51
atgaaacaac aacacaatcg taaggcttta tctcgcaaga ttggcacagt gaaaaaacaa     60
gccaaatttg caggaagctt tttagatgag attaaaaaaa ttgaatgggt aagcaagcac    120
gatcttaaga aatacataaa agtagttctt atcagtatt ttggttttgg atttgctatt    180
tatttcgtag atcttgtgtt gcgtaagtca atcacatgtt tagatggtat aacaaccttt    240
ttgttcggtt aa                                                       252
```

<210> SEQ ID NO 52
<211> LENGTH: 1185
<212> TYPE: DNA
<213> ORGANISM: Chlamydia pneumoniae

<400> SEQUENCE: 52

| | | | | | |
|---|---|---|---|---|---|
| atgtcaaaag | aaacttttca | acgtaataag | ccccatatca | atattgggac | gatcgggcac | 60 |
| gttgaccatg | gtaaaactac | gctaacagcg | gcaattacac | gcgcgctatc | agggatgga | 120 |
| ttggcctctt | tccgtgacta | tagttcaatt | gacaatactc | cagaagaaaa | ggctcgtgga | 180 |
| attactatca | acgcttctca | cgttgaatac | gaaaccccaa | atcgtcacta | cgctcacgta | 240 |
| gactgccctg | gtcacgctga | ctatgttaaa | aatatgatta | caggcgccgc | tcaaatggac | 300 |
| ggagctatcc | tagtcgtttc | agctacagac | ggagctatgc | cacaaactaa | agaacatatc | 360 |
| ttgctagctc | gccaggttgg | agttccttat | atcgttgttt | tcttgaataa | agtagatatg | 420 |
| atctctcaag | aagatgctga | acttattgac | cttgttgaga | tggaacttag | tgagcttctt | 480 |
| gaagaaaaag | gctacaaagg | atgccctatt | atccgtggtt | ctgctttgaa | agctcttgaa | 540 |
| ggtgatgcaa | attatatcga | aaaagttcga | gaacttatgc | aagctgtgga | tgacaacatc | 600 |
| cctacaccag | aaagagaaat | tgataagcct | tcttaatgc | ctatcgaaga | cgtattctca | 660 |
| atctctggtc | gtggtactgt | ggttacagga | agaatcgagc | gtggaatcgt | taaagtttct | 720 |
| gataaagttc | agctcgtggg | attaggagag | actaaagaaa | caatcgttac | tggagtcgaa | 780 |
| atgttcagga | agaacttcc | tgaaggtcgt | gcaggagaaa | acgttggttt | actcctcaga | 840 |
| ggtattggaa | agaacgatgt | tgaaagaggt | atggtggttt | gtcagcctaa | cagcgtgaag | 900 |
| cctcatacga | aatttaagtc | agctgtttac | gttcttcaga | aagaagaagg | cggacgtcat | 960 |
| aagcctttct | tcagcggata | cagacctcag | ttcttcttcc | gtactacaga | cgtgacagga | 1020 |
| gtcgtaactc | ttcctgaagg | aactgaaatg | gtaatgcctg | gagataacgt | tgagcttgat | 1080 |
| gttgagctca | ttggaacagt | tgctcttgaa | gaaggaatga | gatttgcaat | tcgtgaaggt | 1140 |
| ggtcgtacta | tcggcgctgg | aacgatttca | aagatcaatg | cttaa | | 1185 |

<210> SEQ ID NO 53
<211> LENGTH: 1431
<212> TYPE: DNA
<213> ORGANISM: Chlamydia pneumoniae

<400> SEQUENCE: 53

| | | | | | |
|---|---|---|---|---|---|
| atgagaatcg | tacaagtcgc | tgtagaattc | actccaatcg | ttaaagtagg | cggtctaggc | 60 |
| gatgctgtag | ctagtctatc | taaggagtta | gcgaaacaaa | atgatgtgga | agtacttctc | 120 |
| cctcattatc | ctttaatttc | caaattctct | tcgtctcaag | ttctttccga | gcgttctttc | 180 |
| tattatgaat | ttttaggcaa | gcagcaagcc | tctgcaattt | cttattctta | cgagggtctt | 240 |
| acgcttacta | taattacgtt | ggattcacaa | atagagcttt | tctcaaccac | gtccgtgtac | 300 |
| tctgagaata | tgttgtacg | tttctctgct | tttgcagctg | cagctgcagc | ttatcttcaa | 360 |
| gaagcggatc | ctgctgacat | tgtgcacttg | catgactggc | atgtaggttt | acttgcgggt | 420 |
| ttattaaaaa | acccttttaaa | ccctgtgcat | tcgaagattt | tctttactat | ccataatttt | 480 |
| ggttatcgag | ggtattgtag | tacgcagcta | ttagcagcgt | cgcaaattga | tgattttcat | 540 |
| ttgagtcact | accaactatt | tcgcgatccg | caaacttctg | ttctaatgaa | gggagctctc | 600 |
| tattgttcgg | attacattac | gacagtgtct | cttacttatg | tgcaggaaat | tataaacgac | 660 |

```
tattctgatt acgaacttca tgatgcgatt ctagcaagaa attctgtatt ttctgggatc      720
atcaatggca ttgatgaaga cgtttggaac ccgaagacag atcctgcttt agctgtacag      780
tacgatgcaa gcctattaag cgaacctgac gttctcttta ctaaaaaaga agagaacaga      840
gcggtattat atgagaagtt ggggatcagt tcagactatt ttcctttgat tgtgtgatc       900
tcacgcattg ttgaggaaaa gggtcctgaa tttatgaaag agattattct ccatgctatg      960
gagcacagtt atgcctttat cttgattggg acaagtcaaa tgaggttct  tcttaatgag     1020
ttccgtaact acaagattg tttagcgagc tcccccaaca ttcgtttgat cttggacttt      1080
aatgatcctt tagccaggct aacttatgct gctgccgata tgatctgcat cccttcacat     1140
agggaggctt gtggacttac ccagctgata gcgatgcgtt atggcacagt tcctttagtt     1200
cgtaaaactg gagggcttgc tgatacagtg attcctgggg taaatggttt cactttcttt     1260
gatacaaaca ttttaatga atttcgggct atgcttagca acgctgtaac gacgtatcgt      1320
caggagcctg acgtttggtt gaatttgatt gagtcgggaa tgcttcgggc ctctggctta     1380
gatgccatgg ctaagcatta cgtaaatctt tatcaatctt tactctcatg a              1431

<210> SEQ ID NO 54
<211> LENGTH: 1041
<212> TYPE: DNA
<213> ORGANISM: Chlamydia pneumoniae

<400> SEQUENCE: 54
atggaagcag atattttaga tggaaagctc aaacgggttg aggtaagtaa aaaaggattg       60
gtgaattgta atcaagtaga tgtcaatcag ctagtcccta tcaagtataa atgggcttgg      120
gaacattacc tcaatggatg tgcaaacaac tggcttccta ctgaagttcc tatggcaaga      180
gatatcgagt tgtggaaatc agatgaactg tctgaagacg aacgcagggt cattttgtta      240
aacctaggat ttttcagtac cgcggaaagc ctagtcggaa ataacatcgt tcttgctatc      300
ttcaaacata tcacaaaccc tgaagcaaga cagtatttac tgcgtcaagc ttttgaggaa      360
gccgtacata cacatacatt tctctatatt tgcgaatctt taggacttga tgaaggcgaa      420
gtattcaatg cctataatga aagagcctca attagggcta agatgatttt tcaaaatgaca     480
ttaacagtcg atgtccttga tcctaatttt tctgtacagt cttcagaagg ccttgggcag      540
ttcattaaaa acttagtagg atactatatc attatggaag gaatcttctt ctatagtggt      600
tttgtaatga ttctctcttt ccatagacaa aataaaatga caggaattgg agaacagtac      660
caatacatcc tcagagatga aaccatacat ttaaattttg gaatcgatct tatcaatgga      720
attaaagaag aaaaccccga gtttggact  acgaactac aagaagaaat cgtcgctctt       780
attgaaaaag ctgtagagct tgaaattgag tacgctaaag attgcttacc tcgaggaatc      840
ttgggattaa gatcttcgat gtttatagat tacgttcgtc atattgcaga tcgtcgttta      900
gagagaattg ggttgaagcc tatctatcac tccagaaatc ctttcccttg gatgagcgaa      960
accatggatc tgaataaaga aaagaatttc tttgaaaccc gggttaccga ataccaaacc     1020
gctggtaatt taagttggta a                                                1041

<210> SEQ ID NO 55
<211> LENGTH: 3135
<212> TYPE: DNA
<213> ORGANISM: Chlamydia pneumoniae

<400> SEQUENCE: 55
atggtcgaag ttgaagaaaa gcattacacc atcgtcaaac gtaatggaat gtttgtccca       60
```

```
tttaatcaag atcggatttt ccaggctttg gaggcagctt ttcgagatac gcgtagctta      120
gaaactagtt ctccactacc taaagactta aagaatccta ttgcgcaaat tactcataaa      180
gtcgtgaagg aagtcctcgc taaaatttca gaaggtcagg tagtcactgt agagagaatc      240
caggatcttg tagaaagtca gctctatatt agcgggttgc aggatgtggc tcgcgattat      300
attgtttaca gggaccaacg caaggcagag cgcggtaact cttcgtccat aattgccatc      360
atacgtagag acgggggaag cgctaaattt aatcctatga agatctctgc agctctcgaa      420
aaagcattca gagcgacgct ccaaattaat gggatgactc ctcctgcaac actatccgaa      480
attaatgacc ttacccttag gatcgttgaa gatgtcctaa gccttcatgg tgaagaagct      540
attaatctgg aagagatcca agatattgtt gaaaagcaac ttatggttgc cggctattat      600
gatgtggcca agaattatat tttatataga gaagctcgtg cacgagcccg tgctaataaa      660
gatcaagatg gacaagaaga gtttgtcccc caagaggaaa cgtacgttgt tcaaaaagaa      720
gacggcacca cctaccttct gagaaaaaca gatttagaaa gaggttttc ttgggcatgc      780 aaacgctttc ctaaaactac agattctcaa ctgcttgcag atatggcatt tatgaatttg      840
tattcaggaa tcaaagaaga cgaggtcacc acagcatgca tcatggcggc acgtgccaat      900
atcgagagag aacctgatta cgcttttatc gcagcagaac tcctcacgag ttccttgtat      960
gaagagacct taggatgcag ctctcaagac cccaattat cagaaataca taaaaaacat      1020 tttaagaat acatcctcaa tggagaagag tatcgcttga atcctcaatt aaaggattat      1080
gatctcgatg ctcttagtga agtcctagac ctctctagag accaacagtt ttcctatatg      1140
ggagtccaaa atctctacga tcgctatttt aatctgcatg aaggacgacg tttagagact      1200
gcgcagatct tttggatgcg ggtttctatg ggcttagcct taaatgaagg agaacaaaag      1260
aattttgggg caatcacttt ctataatctg ttatccacat tccgctatac cccagcaact      1320
cctacattgt ttaactccgg aatgcgtcat tcccaactca gttcatgcta tctttccaca      1380
gtaaaagatg acctaagtca catttataag gtgatttctg ataatgcttt gctttctaaa      1440
tgggcagggg gaattggaaa tgattggaca gatgtccgtg ctacaggagc tgtaattaag      1500
ggaaccaatg gaaagagtca aggcgtcatt cccttcatta aggttgccaa tgatactgca      1560
attgcagtga atcaggggg caaacgtaaa ggtgctatgt gcgtatattt agaaaactgg      1620
cacttggatt acgaagactt tttagaattg cggaagaata caggagatga gcgtcgtaga      1680
actcacgata tcaatacagc aagctggatt cctgatctct tctttaagag actagaaaaa      1740 aaggcatgt ggacactctt tagccccgat gatgtcccag gtttacacga agcctatggg      1800
ttagagtttg aaaagcttta tgaagaatat gaacgtaagg ttgaatctgg ggaaatccgt      1860
ctttataaaa aagtagaagc cgaagtgctg tggcgtaaaa tgttaagcat gctttacgaa      1920
acagggcatc cttggattac atttaaagat ccttcgaata ttcgctcaaa ccaagatcat      1980
gttggcgtcg tacgctgttc taatctatgt acagagattt tattgaactg ttcggaatca      2040
gagactgcag tttgtaattt aggttccata aacttggtag aacatatccg taatgacaag      2100
ttagatgaag aaaaattaaa agaaactatc tcaatagcca tccgtatttt ggataacgtt      2160
attgacctga acttctaccc tacaccagag gctaaacaag ccaacctaac tcacagagct      2220
gtggggttgg gggttatggg attccaggat gttctttacg agttgaacat tagctatgcc      2280
tcacaagaag ctgtcgaatt ttctgacgag tgctcggaga tcatcgcata ctacgctatt      2340
ctagcctcga gcttactcgc gaaagaacga ggtacatatg cttcttattc aggatctaag      2400
```

-continued

```
tgggatcgtg ggtatctacc cttagatact atcgagcttc tcaaagaaac tcgcggagag    2460
cataatgttc ttgtagacac atcaagtaaa aaagattgga ctccagttcg tgatactatc    2520
cagaaatacg gaatgagaaa tagccaggtc atggcaattg ctcctacagc aacgatctcg    2580
aatatcatag gggtcaccca atctatagag cccatgtata acatctctt tgtaaagtcc     2640 aacctttccg gagagtttac gatccccaac acctacctga ttaaaaaact taaggaatta    2700
ggactttggg atgcagaaat gttagatgat ctaaaatatt ttgacggatc tctattggaa    2760
attgaaagga tccctaatca cttgaaaaag cttttcctta cggcatttga aatcgaaccc    2820
gagtggatta tagagtgtac ctctagaaga cagaaatgga ttgatatggg agtttctcta    2880
aatctgtatc ttgctgagcc agatggtaaa aaactctcca atatgtatct cacggcttgg    2940
aaaaaaggat taaagactac ctattattta agatctcaag ctgcaacatc agtagagaaa    3000
tcatttatag atatcaataa acgcggcatt cagcctcgtt ggatgaaaaa taaatcagcg    3060
tccacaagta ttgtggtcga agaaaaaaca accccgtttt gttcaatgga agaaggttgc    3120
gaatcttgtc aataa                                                    3135
```

```
<210> SEQ ID NO 56
<211> LENGTH: 1386
<212> TYPE: DNA
<213> ORGANISM: Chlamydia pneumoniae

<400> SEQUENCE: 56
atgatgagct ctaagcgtac ctcgaaaata gcggtgcttt caatttatt aacatttact      60 cactctatag ggttcgcaaa tgcgaattcg tccgtaggtc ttggcacggt ctacattaca    120
tccgaggttg taaagaagcc tcagaaagga tcagaaagga acaagccaa aaagaacct     180 cgtgctcgta aaggatactt agtcccttct tcaaggactc tttcagctcg agcccaaaag    240
atgaaaaact cctctcgtaa agagtcttca ggtggttgta acgaaatttc tgcaaattct    300
acacccagat ctgtaaaatt acgaagaaac aaacgtgcag aacaaaaggc agctaaacaa    360
ggattttcag cttttttctaa cctaactttg aaaagcctac ttcctaaaact tccttcaaaa    420 caaaaaactt caattcacga gagagaaaaa gcaacctcaa gatttgttaa tgagtctcag    480
cttagttccg cacgaaaacg ctactgcaca ccatcttcag ccgctccttc cctattttta    540
gaaacagaaa tcgttcgagc tcctgtagaa agaactaaag aacttcaaga taatgaaatt    600
catattcctg tagtgcaagt ccaaacgaac cccaaagaac aaaatacaaa gacaactaaa    660
cagttggcat cccaagcctc gattcaacaa tctgaaggaa ccgagcaatc attgcgagag    720
ctcgcccaag gtgctagcct acctgtctta gtgcgctcta atcctgaagt gtctgtacaa    780
agacaaaaag aagagttatt aaaagaactc gtagctgaac gtagacaatg taaaagaaag    840
tctgtaagac aagctcttga agctcgttct ttaactaaga agttgctag aggcggttct    900 gtgacctcga ctttacgata cgatccgaa aaagcggcgg aaatcaaaag tagacgcaat    960
tgcaaagtaa gtcctgaagc acgtgaacaa aaatattcat cttgcaaaag agatgctcgc    1020
gctaatggga acaagacaa gacaactcct agtgaagatg cttctcaaga agaacaacaa    1080
actggggcag gactcgtacg caagactcct aaatctcagg ttgcaagtaa tgctcagaac    1140
ttctaccgaa attctaaaaa tacaaacata gatagctatc ttacagctaa ccaatacagc    1200
tgtagttctg aagaaacaga ttggccatgt tcttcctgcg tctctaaacg cagaactcac    1260
aacagtatat ctgtatgtac catggtagtt actgtcattg cgatgatcgt agggggcttg    1320
attatagcta atgctacaga atctcaaaca acatcagatc caactcctcc aactcctact    1380
```

-continued ccatag                                                              1386

<210> SEQ ID NO 57
<211> LENGTH: 1731
<212> TYPE: DNA
<213> ORGANISM: Chlamydia pneumoniae

<400> SEQUENCE: 57
atgacagatt ttcctactca cttcaaagga cccaaactta accccattaa agtaaatcca      60
aactttttg agaggaatcc taaagtcgca agggtactgc aaattacagc cgtagtctta     120
ggaatcattg ccctcttatc cggtatagta ctcattatag gcacccctct cggagctcct    180
ataagtatga tcctcggcgg atgtctttta gcttctggag gcgccttatt tgttggtggt    240
acgattgcta cgatattgca agctagaaat agttataaga aggccgtgaa ccaaaagaaa    300
ctctcagagc ctttgatgga acgccccgaa ttgaaagcct tagattattc cctagatctg    360
aaagaggtat gggacctaca tcattctgtt gtcaaacatc ttaaaaaatt agacctgaat    420
ctttccaaaa cccaaaggga agttctaaat caaatcaaaa ttgatgatga gggaccctcc    480
ctagggaat gcgccgctat gatttcagaa aactacgacg catgcttaaa gatgctcgcg    540
tatcgtgagg agctcctgaa agaacaaacc aataccaag agacacgatt caatcagaac    600
ctcactcata gaaataaagt tttgctctcc atcctctcaa ggatcacgga caatatttct    660
aaagcgggcg gggtcttttc tttgaaattt tccacgctaa gctcgcggat gtcacgaatt    720
cataccacca ccactgtgat tctggcttta agtgccgttg tttctgtcat ggtcgtagca    780
gctctaattc caggtggcat tttagcacta cctatacttt tggctgttgc tatttctgca    840
ggagtgattg tcaccggact ttcctatcta gttcgtcaga ttttaagtaa caccaagcgt    900
aatcgtcagg atttttataa agattttgta aaaaatgtag atatagagct tcttaaccaa    960
acggtaactt tacagcgatt cctctttgaa atgctcaaag tgttctgaa agaagaagaa   1020
gaagtctcct agaaggtca agattggtat acacaataca taaccaatgc acccatagaa   1080
aaagattga tcgaagagat cagagttacc tacaaagaga tcgatgctca gaccaaaaaa   1140
atgaagacag acttggagtt cttagaaaat gaggtgcgtt ccgggagact gtctgtagcg   1200
tccccgtcgg aagatccaag tgaaactcct atttttactc aaggtaagga gtttgcaaag   1260
ttacgtcgcc aaacctctca gaatatatcc acgatttatg gtccggacaa tgaaaatatt   1320
gatcccgaat tttccttacc ctggatgcct aaaaaagaag aagaaataga ccatagctta   1380
gaacctgtta caaagttgga acccggttca agagaagagt tgttgttggt agaggggtc    1440
aacccaacct taagagaact caatatgaga attgcacttc tacaacaaca actatcaagt   1500
gtccgaaaat ggagacaccc tcgaggggaa cattacggga atgttatcta ttcagataca   1560
gaactcgatc gtattcagat gctagaaggc gcattttata atcacctcag gaagctcaa    1620
gaggaaatca cccagtctct cggagacctt gttgacattc aaaaccgtat tttagggatc   1680
atagttgaag gggactcaga ttcaagaaca gaagaagagc ctcaggaata g            1731

<210> SEQ ID NO 58
<211> LENGTH: 1086
<212> TYPE: DNA
<213> ORGANISM: Chlamydia pneumoniae

<400> SEQUENCE: 58
atgcaacaaa ctgtaattgt agcaatgtca ggaggcgtgg attcttctgt cgttgcctat     60

-continued

| | |
|---|---|
| ttattcaaaa aatttaccaa ttataaggtt attggcctct tcatgaagaa ttgggaagag | 120 |
| gatagcgaag gcggcctttg ctcgtctact aaagattatg aagatgtcga gagggtatgt | 180 |
| cttcagctcg atatcccttaa ttacaccgta tcttttgcta agaatatag agaaagagtg | 240 |
| ttcgctcgtt tcctcaagga atactcttta ggctacactc ctaaccccga cattctttgt | 300 |
| aaccgagaaa tcaaatttga ccttctacaa agaaagtcc aggaacttgg cggagattac | 360 |
| ctcgctacag ggcactactg ccgattaaat accgagctcc aagaaaccca actccttaga | 420 |
| ggttgcgatc ctcaaaaaga tcagagctat tttttatcag gaactcctaa aagtgctctt | 480 |
| cacaatgtgc tctttcctct tggggaaatg aataagactg aagttcgtgc gattgcagct | 540 |
| caagcagctc ttcccacagc agaaaaaaaa gatagtacag gcatttgctt tatagggaag | 600 |
| cgccctttta aagagttcct agagaagttt cttcccaata aaacaggcaa cgttatcgat | 660 |
| tgggatacca aggaaattgt agggcaacat cagggagctc actattatac tatagggcag | 720 |
| cggcgaggac ttgatcttgg aggatccgag aaaccctgtt atgttgtggg aaaaaatata | 780 |
| gaggaaaata gcatttatat tgtgaggggg gaagaccatc cccagctcta cctacgggaa | 840 |
| ttaacagcta gagagctcaa ttggtttacc cctcctaaat ccggatgtca ctgtagcgct | 900 |
| aaagtccgct accgttctcc tgatgaagct tgcacgatag attatagctc aggtgacgag | 960 |
| gtcaaggtgc gattttcaca acccgtcaag gcggtaactc caggacaaac aatagcgttt | 1020 |
| tatcaaggag atacctgcct tggtagtgga gttatcgacg ttcctatgat tccaagtgag | 1080 |
| ggctag | 1086 |

<210> SEQ ID NO 59
<211> LENGTH: 4830
<212> TYPE: DNA
<213> ORGANISM: Chlamydia pneumoniae

<400> SEQUENCE: 59

| | |
|---|---|
| atggtagcga aaaaaacagt acgatcttat aggtcttcat tttctcattc cgtaatagta | 60 |
| gcaatattgt cagcaggcat tgcttttgaa gcacattcct tacacagctc agaactagat | 120 |
| ttaggtgtat tcaataaaca gtttgaggaa cattctgctc atgttgaaga ggctcaaaca | 180 |
| tctgttttaa agggatcaga tcctgtaaat ccctctcaga agaatccga gaaggttttg | 240 |
| tacactcaag tgcctcttac ccaaggaagc tctggagaga gtttggatct cgccgatgct | 300 |
| aatttcttag agcatttttca gcatcttttt gaagagacta cagtatttgg tatcgatcaa | 360 |
| aagctggttt ggtcagattt agatactagg aattttccc aacccactca agaacctgat | 420 |
| acaagtaatg ctgtaagtga gaaaatctcc tcagatacca agagaatag aaaagaccta | 480 |
| gagactgaag atccttcaaa aaaaagtggc cttaaagaag tttcatcaga tctccctaaa | 540 |
| agtcctgaaa ctgcagtagc agctatttct gaagatcttg aaatctcaga aacatttca | 600 |
| gcaagagatc ctcttcaggg tttagcattt ttttataaaa atacatcttc tcagtctatc | 660 |
| tctgaaaagg attcttcatt tcaaggaatt atcttttctg gttcaggagc taattcaggg | 720 |
| ctaggttttg aaaatcttaa ggcgccgaaa tctggggctg cagtttattc tgatcgagat | 780 |
| attgttttg aaaatcttgt taaggattg agttttatat cttgtgaatc tttagaagat | 840 |
| ggctctgccg caggtgtaaa cattgttgtg acccattgtg gtgatgtaac tctcactgat | 900 |
| tgtgccactg gtttagacct tgaagcttta cgtctggtta agatttttc tcgtggagga | 960 |
| gctgttttca ctgctcgcaa ccatgaagtg caaaataacc ttgcaggtgg aattctatcc | 1020 |
| gttgtaggca ataaggagc tattgttgta gagaaaaata gtgctgagaa gtccaatgga | 1080 |

-continued

| | |
|---|---|
| ggagcttttg cttgcggaag ttttgtttac agtaacaacg aaaacaccgc cttgtggaaa | 1140 |
| gaaaatcaag cattatcagg aggagccata tcctcagcaa gtgatattga tattcaaggg | 1200 |
| aactgtagcg ctattgaatt ttcaggaaac cagtctctaa ttgctcttgg agagcatata | 1260 |
| gggcttacag attttgtagg tggaggagct ttagctgctc aagggacgct taccttaaga | 1320 |
| aataatgcag tagtgcaatg tgttaaaaac acttctaaaa cacatggtgg agctatttta | 1380 |
| gcaggtactg ttgatctcaa cgaaacaatt agcgaagttg cctttaagca gaatacagca | 1440 |
| gctctaactg gaggtgcttt aagtgcaaat gataaggtta taattgcaaa taactttgga | 1500 |
| gaaattcttt ttgagcaaaa cgaagtgagg aatcacggag gagccattta ttgtggatgt | 1560 |
| cgatctaatc ctaagttaga acaaaaggat tctggagaga acatcaatat tattggaaac | 1620 |
| tccggagcta tcacttttt aaaaaataag gcttctgttt tagaagtgat gacacaagct | 1680 |
| gaagattatg ctggtggagg cgctttatgg gggcataatg ttcttctaga ttccaatagt | 1740 |
| gggaatattc aatttatagg aaatataggt ggaagtacct tctggatagg agaatatgtc | 1800 |
| ggtggtggtg cgattctctc tactgataga gtgacaattt ctaataactc tggagatgtt | 1860 |
| gtttttaaag gaaacaaagg ccaatgtctt gctcaaaaat atgtagctcc tcaagaaaca | 1920 |
| gctcccgtgg aatcagatgc ttcatctaca aataaagacg agaagagcct taatgcttgt | 1980 |
| agtcatggag atcattatcc tcctaaaact gtagaagagg aagtgccacc ttcattgtta | 2040 |
| gaagaacatc ctgttgtttc ttcgacagat attcgtggtg gtgggccat tctagctcaa | 2100 |
| catatcttta ttacagataa tacaggaaat ctgagattct ctgggaacct tggtggtggt | 2160 |
| gaagagtctt ctactgtcgg tgatttagct atcgtaggag gaggtgcttt gctttctact | 2220 |
| aatgaagtta atgtttgcag taaccaaaat gttgtttttt ctgataacgt gacttcaaat | 2280 |
| ggttgtgatt caggggggagc tattttagct aaaaaagtag atatctccgc gaaccactcg | 2340 |
| gttgaatttg tctctaatgg ttcagggaaa ttcggtggtg ccgtttgcgc tttaaacgaa | 2400 |
| tcagtaaaca ttacggacaa tggctcggca gtatcattct ctaaaaatag aacacgtctt | 2460 |
| ggcggtgctg gagttgcagc tcctcaaggc tctgtaacga tttgtggaaa tcagggaaac | 2520 |
| atagcattta agagaacttt tgtttttggc tctgaaaatc aaagatcagg tggaggagct | 2580 |
| atcattgcta actcttctgt aaatattcag gataacgcag gagatatcct atttgtaagt | 2640 |
| aactctacgg gatcttatgg aggtgctatt tttgtaggat cttttggttgc ttctgaaggc | 2700 |
| agcaacccac gaacgcttac aattacaggc aacagtgggg atatcctatt tgctaaaaat | 2760 |
| agcacgcaaa cagccgcttc tttatcagaa aaagattcct ttggtggagg ggccatctat | 2820 |
| acacaaaacc tcaaaattgt aaagaatgca gggaacgttt cttttctatgg caacagagct | 2880 |
| cctagtggtg ctggtgtcca aattgcagac ggaggaactg tttgtttaga ggcttttgga | 2940 |
| ggagatatct atttgaagg gaatatcaat tttgatggga gtttcaatgc gattcactta | 3000 |
| tgcgggaatg actcaaaaat cgtagagctt tctgctgttc aagataaaaa tattattttc | 3060 |
| caagatgcaa ttacttatga agagaacaca attcgtggct tgccagataa agatgtcagt | 3120 |
| cctttaagtg ccccttcatt aattttaac tccaagccac aagatgacag cgctcaacat | 3180 |
| catgaaggga cgatacggtt ttctcgaggg gtatctaaaa ttcctcagat tgctgctata | 3240 |
| caagagggaa ccttagcttt atcacaaaac gcagagcttt ggttggcagg acttaaacag | 3300 |
| gaaacaggaa gttctatcgt attgtctgcg ggatctattc tccgtatttt tgattcccag | 3360 |
| gttgatagca gtgcgcctct tcctacagaa aataaagagg agactcttgt ttctgccgga | 3420 |

-continued

```
gttcaaatta acatgagctc tcctacaccc aataaagata aagctgtaga tactccagta        3480
cttgcagata tcataagtat tactgtagat ttgtcttcat tgttcctga gcaagacgga        3540 actcttcctc ttcctcctga aattatcatt cctaagggaa caaaattaca ttctaatgcc        3600
atagatctta agattataga tcctaccaat gtgggatatg aaaatcatgc tcttctaagt        3660
tctcataaag atattccatt aatttctctt aagacagcgg aaggaatgac agggacgcct        3720
acagcagatg cttctctatc taatataaaa atagatgtat ctttaccttc gatcacacca        3780
gcaacgtatg gtcacacagg agtttggtct gaaagtaaaa tggaagatgg aagacttgta        3840
gtcggttggc aacctacggg atataagtta atcctgaga agcaagggc tctagttttg         3900 aataatctct ggagtcatta tacagatctt agagctctta agcaggagat ctttgctcat        3960
catacgatag ctcaaagaat ggagttagat ttctcgacaa atgtctgggg atcaggatta        4020
ggtgttgttg aagattgtca gaacatcgga gagtttgatg ggttcaaaca tcatctcaca        4080
gggtatgccc taggcttgga tacacaacta gttgaagact tcttaattgg aggatgtttc        4140
tcacagttct ttggtaaaac tgaaagccaa tcctacaaag ctaagaacga tgtgaagagt        4200
tatatgggag ctgcttatgc ggggatttta gcaggtcctt ggttaataaa aggagctttt        4260
gtttacggta atataaacaa cgatttgact acagattacg gtactttagg tatttcaaca        4320
ggttcatgga taggaaaagg gtttatcgca ggcacaagca ttgattaccg ctatattgta        4380
aatcctcgac ggtttatatc ggcaatcgta tccacagtgg ttccttttgt agaagccgag        4440
tatgtccgta tagatcttcc agaaattagc gaacagggta aagaggttag aacgttccaa        4500
aaaactcgtt ttgagaatgt cgccattcct tttggatttg ctttagaaca tgcttattcg        4560
cgtggctcac gtgctgaagt gaacagtgta cagcttgctt acgtctttga tgtatatcgt        4620
aagggacctg tctctttgat tacactcaag gatgctgctt attcttggaa gagttatggg        4680
gtagatattc cttgtaaagc ttggaaggct cgcttgagca ataatacgga atggaattca        4740
tatttaagta cgtatttagc gtttaattat gaatggagag aagatctgat agcttatgac        4800
ttcaatggtg gtatccgtat tattttctag                                         4830
```

<210> SEQ ID NO 60
<211> LENGTH: 591
<212> TYPE: DNA
<213> ORGANISM: Chlamydia pneumoniae

<400> SEQUENCE: 60

```
atgacactct ccctagttgg aaaggaagcc cctgattttg ttgcgcaagc tgttgttaat         60
ggcgaaacgt gtaccgtatc tttaaaagat tatttaggaa agtatgttgt gcttttcttc        120
tatcctaaag atttttactta cgtgtgtcct acggaattgc acgcatttca agatgcttta       180
ggagaattcc acacccgagg agctgaagtc ataggctgtt ccgtggatga cattgccacc       240
catcaacagt ggttagctac taagaaaaag caaggtggta tcgaaggtat tacctatcct        300
cttctctcag acgaagataa agtcatttca agaagttatc atgtgttaaa acccgaagaa       360
gaattatctt tcagaggagt tttcctgatt gataaaggtg aatcatccg tcatcttgta         420 gtgaatgatc ttcctctagg ccgttctata agaagaac ttagaaccct agatgcttta          480
atcttctttg aaactaatgg cttagtctgt cctgcaaatt ggcatgaagg agagcgagcg        540
atggctccaa atgaagaagg actgcaaaat tatttcggga ctatagacta g                591
```

<210> SEQ ID NO 61
<211> LENGTH: 1983

<210> TYPE: DNA
<213> ORGANISM: Chlamydia pneumoniae

<400> SEQUENCE: 61

```
atgagtgaac acaaaaaatc aagcaaaatt ataggtatag acttaggcac aacaaactcc      60
tgcgtatctg ttatggaagg aggacaagct aaagtaatta catcatccga aggaacaaga     120
accacgccat cgatcgttgc cttcaaaggt aatgagaaat tagtgggat tccagcaaaa      180
cgtcaagcag tgacaaatcc agaaaaaact ctcggctcta caaaacgctt tattggccgt     240
aagtactctg aagtagcttc ggaaatccaa accgttcctt atacagtcac ctccggatct     300
aaaggtgatg ccgttttcga agttgatggc aaacaataca ctccagaaga aattggcgca     360
caaatcttaa tgaaaatgaa agagacagca gaagcttatc taggcgaaac tgtcacagaa     420
gcagtgatca ccgtccccgc atacttcaat gattctcaac gagcatccac aaaagatgct     480
ggacgcattg caggtctaga tgtaaaacgt atcattccag aacctaccgc agcagctctt     540
gcctacggaa tcgataaagt cggtgataaa aaaatcgctg tcttcgacct tggtggagga     600
acttttgata tctccatcct agaaatcggt gatggcgtct tcgaagttct atctacaaat     660
ggagatactc tcctcggtgg agacgacttt gatgaagtca ttatcaaatg gatgatcgaa     720
gaattcaaaa acaagaagg cattgatctt agcaaagata tatggcctt acaaagactt      780
aaagatgctg ctgagaaagc aaaaatagaa cttcaggag tctcttccac agaaatcaat     840
cagccattca tcacaatgga tgcacaagga cctaaacacc ttgcattgac actcacacgt     900
gcgcaattcg agaaactcgc agcctctcta atcgaaagaa caaaatctcc atgcatcaaa     960
gcactcagtg acgcaaaact ttccgctaag gatatcgatg atgttctctt agttggaggt    1020
atgtcaagaa tgcccgcagt gcaagaaact gtaaaagaac tcttcggcaa agagcctaat    1080
aaaggagtca accccgacga agttgttgct attggagccg caattcaagg tggtgttctt    1140
ggcggagaag ttaaggatgt tctacttcta gacgttatcc ccctatctct gggtatcgaa    1200
actctaggag gcgtcatgac gactctggta gagagaaata ctacaatccc tacacagaaa    1260
aaacaaatct tctccacagc tgctgataac cagcctgcgg ttaccatcgt agttctccaa    1320
ggagagcgtc ccatggccaa agataacaag gaaatcggaa gattcgatct tacagatatc    1380
cctccggctc ctcgaggcca tcctcaaatc gaagtctcct tcgatatcga tgcaaacgga    1440
attttccatg tctcagctaa agatgttgcc agcggtaaag aacagaaaat tcgtatcgaa    1500
gcaagctcag gacttcaaga agatgaaatc caaagaatgg ttcgagatgc cgaaattaat    1560
aaggaagaag ataaaaaacg tcgtgaagct tcagatgcta aaaatgaagc cgatagcatg    1620
atcttcagag ccgaaaaagc tattaaagat tataaggagc aaattcctga aactttagtt    1680
aaagaaatcg aagagcgaat cgaaaacgtg cgcaacgcac tcaaagatga cgctcctatt    1740
gaaaaaatta agaggttac tgaagaccta agcaagcata tgcaaaaaat tggagagtct    1800
atgcaatcgc agtctgcatc agcagcagca tcatcggcag ccaatgctaa aggtggacct    1860
aacatcaata cagaagattt gaaaaaacat agtttcagta cgaagcctcc ttcaaataac    1920
ggttcttcag aagaccatat cgaagaagct gatgtagaaa ttattgataa cgacgataag    1980
taa                                                                 1983
```

<210> SEQ ID NO 62
<211> LENGTH: 1860
<212> TYPE: DNA
<213> ORGANISM: Chlamydia pneumoniae

<400> SEQUENCE: 62

```
atgaaaaaag ggaaattagg agccatagtt tttggccttc tatttacaag tagtgttgct      60
ggttttcta aggatttgac taaagacaac gcttatcaag atttaaatgt catagagcat     120
ttaatatcgt taaaatatgc cctttacca tggaaggaac tattatttgg ttgggattta     180
tctcagcaaa cacagcaagc tcgcttgcaa ctggtcttag aagaaaaacc aacaaccaac    240
tactgccaga aggtactctc taactacgtg agatcattaa acgattatca tgcagggatt    300
acgttttatc gtactgaaag tgcgtatatc ccttacgtat tgaagttaag tgaagatggt    360
catgtctttg tagtcgacgt acagactagc caagggata tttacttagg ggatgaaatc     420
cttgaagtag atggaatggg gattcgtgag gctatcgaaa gccttcgctt tggacgaggg    480
agtgccacag actattctgc tgcagttcgt tccttgacat cgcgttccgc cgcttttgga    540
gatgcggttc cttcaggaat tgccatgttg aaacttcgcc gacccagtgg tttgatccgt    600
tcgacaccgg tccgttggcg ttatactcca gagcatatcg agatttttc tttagttgct     660
cctttgattc ctgaacataa acctcaatta cctacacaaa gttgtgtgct attccgttcc    720
ggggtaaatt cacagtcttc tagtagctct ttattcagtt cctacatggt gccttatttc    780
tgggaagaat tgcgggttca aaataagcag cgttttgaca gtaatcacca tagggagc     840
cgtaatggat ttttacctac gtttggtcct attctttggg aacaagacaa ggggccctat    900
cgttcctata tctttaaagc aaaagattct cagggcaatc cccatcgcat aggatttta    960
agaatttctt cttatgtttg gactgattta gaaggacttg aagaggatca taaggatagt   1020
ccttgggagc tctttggaga gatcatcgat catttggaaa aagagactga tgctttgatt   1080
attgatcaga cccataatcc tggaggcagt gttttctatc tctattcgtt actatctatg   1140
ttaacagatc atcctttaga tactcctaaa catagaatga ttttcactca ggatgaagtc   1200
agctcggctt tgcactggca agatctacta gaagatgtct tcacagatga gcaggcagtt   1260
gccgtgctag gggaaactat ggaaggatat tgcatggata tgcatgctgt agcctctctt   1320
caaaacttct ctcagagtgt ccttctcttcc tgggtttcag gtgatattaa cctttcaaaa   1380
cctatgcctt tgctaggatt tgcacaggtt cgacctcatc ctaaacatca atatactaaa   1440
cctttgtta tgttgataga cgaggatgac ttctcttgtg gagatttagc gcctgcaatt    1500
ttgaaggata atggccgcgc tactctcatt ggaaagccaa cagcaggagc tggaggtttt   1560
gtattccaag tcactttccc taaccgttct ggaattaaag gtctttctttt aacaggatct   1620
ttagctgtta ggaaagatgg tgagtttatt gaaaacttag gagtggctcc tcatattgat   1680
ttaggattta cctccaggga tttgcaaact tccaggttta ctgattacgt tgaggcagtg   1740
aaaactatag ttttaacttc tttgtctgag aacgctaaga gagtgaaga gcagacttct   1800
ccgcaagaga cgcctgaagt tattcgagtc tcttatccca caacgacttc tgcttcgtaa   1860
```

<210> SEQ ID NO 63
<211> LENGTH: 1956
<212> TYPE: DNA
<213> ORGANISM: Chlamydia pneumoniae

<400> SEQUENCE: 63

```
atggttaatc ctattggtcc aggtcctata gacgaaacag aacgcacacc tcccgcagat      60
cttctgctc aaggattgga ggcgagtgca gcaaataaga gtgcggaagc tcaaagaata     120
gcaggtgcgg aagctaagcc taaagaatct aagaccgatt ctgtagagcg atggagcatc    180
ttgcgttctg cagtgaatgc tctcatgagt ctggcagata agctgggtat tgcttctagt    240
```

-continued

```
aacagctcgt cttctactag cagatctgca gacgtggact caacgacagc gaccgcacct      300
acgcctcctc cacccacgtt tgatgattat aagactcaag cgcaaacagc ttacgatact      360
atctttacct caacatcact agctgacata caggctgctt tggtgagcct ccaggatgct      420
gtcactaata taaggatac agcggctact gatgaggaaa ccgcaatcgc tgcggagtgg       480
gaaactaaga atgccgatgc agttaaagtt ggcgcgcaaa ttacagaatt agcgaaatat     540
gcttcggata ccaagcgat tcttgactct ttaggtaaac tgacttcctt cgacctctta      600
caggctgctc ttctccaatc tgtagcaaac aataacaaag cagctgagct tcttaaagag     660
atgcaagata acccagtagt cccagggaaa acgcctgcaa ttgctcaatc tttagttgat    720
cagacagatg ctacagcgac acagatagag aaagatggaa atgcgattag ggatgcatat    780
tttgcaggac agaacgctag tggagctgta gaaaatgcta atctaataa cagtataagc     840 aacatagatt cagctaaagc agcaatcgct actgctaaga cacaaatagc tgaagctcag    900
aaaaagttcc ccgactctcc aattcttcaa gaagcggaac aaatggtaat acaggctgag   960
aaagatctta aaaatatcaa acctgcagat ggttctgatg ttccaaatcc aggaactaca    1020
gttggaggct ccaagcaaca aggaagtagt attggtagta ttcgtgtttc catgctgtta    1080
gatgatgctg aaaatgagac cgcttccatt ttgatgtctg ggtttcgtca gatgattcac    1140
atgttcaata cggaaaatcc tgattctcaa gctgcccaac aggagctcgc agcacaagct   1200
agagcagcga aagccgctgg agatgacagt gctgctgcag cgctggcaga tgctcagaaa   1260
gctttagaag cggctctagg taaagctggg caacaacagg gcatactcaa tgctttagga    1320
cagatcgctt ctgctgctgt tgtgagcgca ggagttcctc ccgctgcagc aagttctata   1380
gggtcatctg taaaacagct ttacaagacc tcaaaatcta caggttctga ttataaaaca   1440
cagatatcag caggttatga tgcttacaaa tccatcaatg atgcctatgg tagggcacga    1500
aatgatgcga ctcgtgatgt gataaacaat gtaagtaccc ccgctctcac acgatccgtt   1560
cctagagcac gaacagaagc tcgaggacca gaaaaaacag atcaagccct cgctagggtg   1620
atttctggca atagcagaac tcttggagat gtctatagtc aagtttcggc actacaatct   1680
gtaatgcaga tcatccagtc gaatcctcaa gcgaataatg aggagatcag acaaaagctt    1740
acatcggcag tgacaaagcc tccacagttt ggctatcctt atgtgcaact ttctaatgac   1800
tctacacaga agttcatagc taaattagaa agtttgtttg ctgaaggatc taggacagca    1860
gctgaaataa aagcactttc ctttgaaacg aactccttgt ttattcagca ggtgctggtc    1920
aatatcggct ctctatattc tggttatctc caataa                               1956
```

<210> SEQ ID NO 64
<211> LENGTH: 264
<212> TYPE: DNA
<213> ORGANISM: Chlamydia pneumoniae

<400> SEQUENCE: 64

```
atgagtcaaa aaataaaaa ctctgctttt atgcatcccg tgaatatttc cacagattta      60
gcagttatag ttggcaaggg acctatgccc agaaccgaaa ttgtaaagaa agtttgggaa    120
tacattaaaa aacacaactg tcaggatcaa aaaaataaac gtaatatcct tcccgatgcg    180
aatcttgcca aagtctttgg ctctagtgat cctatcgaca tgttccaaat gaccaaagcc    240
ctttccaaac atattgtaaa ataa                                            264
```

<210> SEQ ID NO 65

<211> LENGTH: 978
<212> TYPE: PRT
<213> ORGANISM: Chlamydia pneumoniae

<400> SEQUENCE: 65

```
Met Pro Leu Ser Phe Lys Ser Ser Phe Cys Leu Leu Ala Cys Leu
                 5                  10                  15

Cys Ser Ala Ser Cys Ala Phe Ala Glu Thr Arg Leu Gly Gly Asn Phe
             20                  25                  30

Val Pro Pro Ile Thr Asn Gln Gly Glu Glu Ile Leu Leu Thr Ser Asp
         35                  40                  45

Phe Val Cys Ser Asn Phe Leu Gly Ala Ser Phe Ser Ser Phe Ile
     50                  55                  60

Asn Ser Ser Asn Leu Ser Leu Leu Gly Lys Gly Leu Ser Leu Thr
 65                  70                  75                  80

Phe Thr Ser Cys Gln Ala Pro Thr Asn Ser Asn Tyr Ala Leu Leu Ser
             85                  90                  95

Ala Ala Glu Thr Leu Thr Phe Lys Asn Phe Ser Ser Ile Asn Phe Thr
            100                 105                 110

Gly Asn Gln Ser Thr Gly Leu Gly Gly Leu Ile Tyr Gly Lys Asp Ile
        115                 120                 125

Val Phe Gln Ser Ile Lys Asp Leu Ile Phe Thr Thr Asn Arg Val Ala
    130                 135                 140

Tyr Ser Pro Ala Ser Val Thr Thr Ser Ala Thr Pro Ala Ile Thr Thr
145                 150                 155                 160

Val Thr Thr Gly Ala Ser Ala Leu Gln Pro Thr Asp Ser Leu Thr Val
                165                 170                 175

Glu Asn Ile Ser Gln Ser Ile Lys Phe Phe Gly Asn Leu Ala Asn Phe
            180                 185                 190

Gly Ser Ala Ile Ser Ser Pro Thr Ala Val Val Lys Phe Ile Asn
        195                 200                 205

Asn Thr Ala Thr Met Ser Phe Ser His Asn Phe Thr Ser Ser Gly Gly
    210                 215                 220

Gly Val Ile Tyr Gly Gly Ser Ser Leu Leu Phe Glu Asn Asn Ser Gly
225                 230                 235                 240

Cys Ile Ile Phe Thr Ala Asn Ser Cys Val Asn Ser Leu Lys Gly Val
                245                 250                 255

Thr Pro Ser Ser Gly Thr Tyr Ala Leu Gly Ser Gly Gly Ala Ile Cys
            260                 265                 270

Ile Pro Thr Gly Thr Phe Glu Leu Lys Asn Lys Asn Gln Gly Lys Cys Thr
        275                 280                 285

Phe Ser Tyr Asn Gly Thr Pro Asn Asp Ala Gly Ala Ile Tyr Ala Glu
    290                 295                 300

Thr Cys Asn Ile Val Gly Asn Gln Gly Ala Leu Leu Leu Asp Ser Asn
305                 310                 315                 320

Thr Ala Ala Arg Asn Gly Gly Ala Ile Cys Ala Lys Val Leu Asn Ile
                325                 330                 335

Gln Gly Arg Gly Pro Ile Glu Phe Ser Arg Asn Arg Ala Glu Lys Gly
            340                 345                 350

Gly Ala Ile Phe Ile Gly Pro Ser Val Gly Asp Pro Ala Lys Gln Thr
        355                 360                 365

Ser Thr Leu Thr Ile Leu Ala Ser Glu Gly Asp Ile Ala Phe Gln Gly
    370                 375                 380

Asn Met Leu Asn Thr Lys Pro Gly Ile Arg Asn Ala Ile Thr Val Glu
```

```
            385                 390                 395                 400
Ala Gly Gly Glu Ile Val Ser Leu Ser Ala Gln Gly Gly Ser Arg Leu
                    405                 410                 415
Val Phe Tyr Asp Pro Ile Thr His Ser Leu Pro Thr Thr Ser Pro Ser
                420                 425                 430
Asn Lys Asp Ile Thr Ile Asn Ala Asn Gly Ala Ser Gly Ser Val Val
            435                 440                 445
Phe Thr Ser Lys Gly Leu Ser Ser Thr Glu Leu Leu Leu Pro Ala Asn
        450                 455                 460
Thr Thr Thr Ile Leu Leu Gly Thr Val Lys Ile Ala Ser Gly Glu Leu
465                 470                 475                 480
Lys Ile Thr Asp Asn Ala Val Val Asn Val Leu Gly Phe Ala Thr Gln
                485                 490                 495
Gly Ser Gly Gln Leu Thr Leu Gly Ser Gly Thr Leu Gly Leu Ala
                500                 505                 510
Thr Pro Thr Gly Ala Pro Ala Val Asp Phe Thr Ile Gly Lys Leu
            515                 520                 525
Ala Phe Asp Pro Phe Ser Phe Leu Lys Arg Asp Phe Val Ser Ala Ser
        530                 535                 540
Val Asn Ala Gly Thr Lys Asn Val Thr Leu Thr Gly Ala Leu Val Leu
545                 550                 555                 560
Asp Glu His Asp Val Thr Asp Leu Tyr Asp Met Val Ser Leu Gln Ser
                565                 570                 575
Pro Val Ala Ile Pro Ile Ala Val Phe Lys Gly Ala Thr Val Thr Lys
                580                 585                 590
Thr Gly Phe Pro Asp Gly Glu Ile Ala Thr Pro Ser His Tyr Gly Tyr
                595                 600                 605
Gln Gly Lys Trp Ser Tyr Thr Trp Ser Arg Pro Leu Leu Ile Pro Ala
            610                 615                 620
Pro Asp Gly Gly Phe Pro Gly Gly Pro Ser Pro Ser Ala Asn Thr Leu
625                 630                 635                 640
Tyr Ala Val Trp Asn Ser Asp Thr Leu Val Arg Ser Thr Tyr Ile Leu
                645                 650                 655
Asp Pro Glu Arg Tyr Gly Glu Ile Val Ser Asn Ser Leu Trp Ile Ser
                660                 665                 670
Phe Leu Gly Asn Gln Ala Phe Ser Asp Ile Leu Gln Asp Val Leu Leu
            675                 680                 685
Ile Asp His Pro Gly Leu Ser Ile Thr Ala Lys Ala Leu Gly Ala Tyr
            690                 695                 700
Val Glu His Thr Pro Arg Gln Gly His Glu Gly Phe Ser Gly Arg Tyr
705                 710                 715                 720
Gly Gly Tyr Gln Ala Ala Leu Ser Met Asn Tyr Thr Asp His Thr Thr
                725                 730                 735
Leu Gly Leu Ser Phe Gly Gln Leu Tyr Gly Lys Thr Asn Ala Asn Pro
                740                 745                 750
Tyr Asp Ser Arg Cys Ser Glu Gln Met Tyr Leu Leu Ser Phe Phe Gly
            755                 760                 765
Gln Phe Pro Ile Val Thr Gln Lys Ser Glu Ala Leu Ile Ser Trp Lys
        770                 775                 780
Ala Ala Tyr Gly Tyr Ser Lys Asn His Leu Asn Thr Thr Tyr Leu Arg
785                 790                 795                 800
Pro Asp Lys Ala Pro Lys Ser Gln Gly Gln Trp His Asn Asn Ser Tyr
                805                 810                 815
```

-continued

```
Tyr Val Leu Ile Ser Ala Glu His Pro Phe Leu Asn Trp Cys Leu Leu
            820                 825                 830

Thr Arg Pro Leu Ala Gln Ala Trp Asp Leu Ser Gly Phe Ile Ser Ala
        835                 840                 845

Glu Phe Leu Gly Gly Trp Gln Ser Lys Phe Thr Glu Thr Gly Asp Leu
    850                 855                 860

Gln Arg Ser Phe Ser Arg Gly Lys Gly Tyr Asn Val Ser Leu Pro Ile
865                 870                 875                 880

Gly Cys Ser Ser Gln Trp Phe Thr Pro Phe Lys Lys Ala Pro Ser Thr
                885                 890                 895

Leu Thr Ile Lys Leu Ala Tyr Lys Pro Asp Ile Tyr Arg Val Asn Pro
            900                 905                 910

His Asn Ile Val Thr Val Val Ser Asn Gln Glu Ser Thr Ser Ile Ser
        915                 920                 925

Gly Ala Asn Leu Arg Arg His Gly Leu Phe Val Gln Ile His Asp Val
    930                 935                 940

Val Asp Leu Thr Glu Asp Thr Gln Ala Phe Leu Asn Tyr Thr Phe Asp
945                 950                 955                 960

Gly Lys Asn Gly Phe Thr Asn His Arg Val Ser Thr Gly Leu Lys Ser
                965                 970                 975

Thr Phe
```

<210> SEQ ID NO 66
<211> LENGTH: 266
<212> TYPE: PRT
<213> ORGANISM: Chlamydia pneumoniae

<400> SEQUENCE: 66

```
Met His Ser Lys Phe Leu Ser Arg Arg Lys Lys Asn Ser Ser His Lys
                 5                  10                  15

Glu Glu Thr Ser Trp Asp Cys Ile Ala Ser Ser Tyr Asn Lys Ile Val
             20                  25                  30

Gln Asp Lys Gly His Tyr Tyr His Arg Glu Thr Ile Leu Pro Gln Leu
         35                  40                  45

Leu Pro Ser Leu Thr Leu Gly Ser Lys Ser Ser Val Leu Asp Ile Gly
     50                  55                  60

Cys Gly Gln Gly Phe Leu Glu Arg Ala Leu Pro Lys Glu Cys Arg Tyr
 65                  70                  75                  80

Leu Gly Ile Asp Ile Ser Ser Arg Leu Ile Ala Leu Ala Lys Lys Met
                 85                  90                  95

Arg Ser Val Asn Ser His Gln Phe Lys Val Ala Asp Leu Ser Lys Arg
            100                 105                 110

Leu Glu Phe Val Glu Pro Thr Leu Phe Ser His Ala Val Ala Ile Leu
        115                 120                 125

Ser Leu Gln Asn Met Glu Phe Pro Gly Glu Ala Ile Arg Asn Thr Ala
    130                 135                 140

Thr Leu Leu Glu Pro Leu Gly Gln Phe Ile Val Leu Asn His Pro
145                 150                 155                 160

Cys Phe Arg Ile Pro Arg Ala Ser Ser Trp His Tyr Asp Glu Asn Lys
                165                 170                 175

Lys Ala Ile Ser Arg His Ile Asp Arg Tyr Leu Ser Pro Met Lys Ile
            180                 185                 190

Pro Ile Met Ala His Pro Gly Gln Lys Asp Ser Pro Ser Thr Leu Ser
        195                 200                 205
```

-continued

```
Phe His Phe Pro Leu Ser Tyr Trp Phe Lys Glu Leu Ser Ser His Gly
    210                 215                 220

Phe Leu Val Ser Gly Leu Glu Trp Thr Ser Ser Lys Thr Ser Thr
225                 230                 235                 240

Gly Lys Arg Ala Lys Ala Glu Asn Leu Cys Arg Lys Glu Phe Pro Leu
                245                 250                 255

Phe Leu Met Ile Ser Cys Ile Lys Ile Lys
            260                 265

<210> SEQ ID NO 67
<211> LENGTH: 83
<212> TYPE: PRT
<213> ORGANISM: Chlamydia pneumoniae

<400> SEQUENCE: 67

Met Lys Gln Gln His Asn Arg Lys Ala Leu Ser Arg Lys Ile Gly Thr
                  5                  10                  15

Val Lys Lys Gln Ala Lys Phe Ala Gly Ser Phe Leu Asp Glu Ile Lys
                 20                  25                  30

Lys Ile Glu Trp Val Ser Lys His Asp Leu Lys Lys Tyr Ile Lys Val
             35                  40                  45

Val Leu Ile Ser Ile Phe Gly Phe Gly Phe Ala Ile Tyr Phe Val Asp
         50                  55                  60

Leu Val Leu Arg Lys Ser Ile Thr Cys Leu Asp Gly Ile Thr Thr Phe
65                  70                  75                  80

Leu Phe Gly

<210> SEQ ID NO 68
<211> LENGTH: 394
<212> TYPE: PRT
<213> ORGANISM: Chlamydia pneumoniae

<400> SEQUENCE: 68

Met Ser Lys Glu Thr Phe Gln Arg Asn Lys Pro His Ile Asn Ile Gly
                  5                  10                  15

Thr Ile Gly His Val Asp His Gly Lys Thr Thr Leu Thr Ala Ala Ile
                 20                  25                  30

Thr Arg Ala Leu Ser Gly Asp Gly Leu Ala Ser Phe Arg Asp Tyr Ser
             35                  40                  45

Ser Ile Asp Asn Thr Pro Glu Glu Lys Ala Arg Gly Ile Thr Ile Asn
         50                  55                  60

Ala Ser His Val Glu Tyr Glu Thr Pro Asn Arg His Tyr Ala His Val
65                  70                  75                  80

Asp Cys Pro Gly His Ala Asp Tyr Val Lys Asn Met Ile Thr Gly Ala
                 85                  90                  95

Ala Gln Met Asp Gly Ala Ile Leu Val Val Ser Ala Thr Asp Gly Ala
                100                 105                 110

Met Pro Gln Thr Lys Glu His Ile Leu Leu Ala Arg Gln Val Gly Val
            115                 120                 125

Pro Tyr Ile Val Val Phe Leu Asn Lys Val Asp Met Ile Ser Gln Glu
        130                 135                 140

Asp Ala Glu Leu Ile Asp Leu Val Glu Met Glu Leu Ser Glu Leu Leu
145                 150                 155                 160

Glu Glu Lys Gly Tyr Lys Gly Cys Pro Ile Ile Arg Gly Ser Ala Leu
                165                 170                 175
```

-continued

```
Lys Ala Leu Glu Gly Asp Ala Asn Tyr Ile Glu Lys Val Arg Glu Leu
                180                 185                 190

Met Gln Ala Val Asp Asp Asn Ile Pro Thr Pro Arg Glu Ile Asp
            195                 200                 205

Lys Pro Phe Leu Met Pro Ile Glu Asp Val Phe Ser Ile Ser Gly Arg
210                 215                 220

Gly Thr Val Val Thr Gly Arg Ile Glu Arg Gly Ile Val Lys Val Ser
225                 230                 235                 240

Asp Lys Val Gln Leu Val Gly Leu Gly Glu Thr Lys Glu Thr Ile Val
                245                 250                 255

Thr Gly Val Glu Met Phe Arg Lys Glu Leu Pro Glu Gly Arg Ala Gly
                260                 265                 270

Glu Asn Val Gly Leu Leu Arg Gly Ile Gly Lys Asn Asp Val Glu
                275                 280                 285

Arg Gly Met Val Val Cys Gln Pro Asn Ser Val Lys Pro His Thr Lys
            290                 295                 300

Phe Lys Ser Ala Val Tyr Val Leu Gln Lys Glu Gly Gly Arg His
305                 310                 315                 320

Lys Pro Phe Phe Ser Gly Tyr Arg Pro Gln Phe Phe Arg Thr Thr
                325                 330                 335

Asp Val Thr Gly Val Val Thr Leu Pro Glu Gly Thr Glu Met Val Met
            340                 345                 350

Pro Gly Asp Asn Val Glu Leu Asp Val Glu Leu Ile Gly Thr Val Ala
        355                 360                 365

Leu Glu Glu Gly Met Arg Phe Ala Ile Arg Glu Gly Arg Thr Ile
    370                 375                 380

Gly Ala Gly Thr Ile Ser Lys Ile Asn Ala
385                 390
```

<210> SEQ ID NO 69
<211> LENGTH: 476
<212> TYPE: PRT
<213> ORGANISM: Chlamydia pneumoniae

<400> SEQUENCE: 69

```
Met Arg Ile Val Gln Val Ala Val Glu Phe Thr Pro Ile Val Lys Val
                5                   10                  15

Gly Gly Leu Gly Asp Ala Val Ala Ser Leu Ser Lys Glu Leu Ala Lys
            20                  25                  30

Gln Asn Asp Val Glu Val Leu Leu Pro His Tyr Pro Leu Ile Ser Lys
        35                  40                  45

Phe Ser Ser Ser Gln Val Leu Ser Glu Arg Ser Phe Tyr Tyr Glu Phe
    50                  55                  60

Leu Gly Lys Gln Gln Ala Ser Ala Ile Ser Tyr Ser Tyr Glu Gly Leu
65                  70                  75                  80

Thr Leu Thr Ile Ile Thr Leu Asp Ser Gln Ile Glu Leu Phe Ser Thr
                85                  90                  95

Thr Ser Val Tyr Ser Glu Asn Asn Val Val Arg Phe Ser Ala Phe Ala
            100                 105                 110

Ala Ala Ala Ala Tyr Leu Gln Glu Ala Asp Pro Ala Asp Ile Val
        115                 120                 125

His Leu His Asp Trp His Val Gly Leu Leu Ala Gly Leu Leu Lys Asn
    130                 135                 140

Pro Leu Asn Pro Val His Ser Lys Ile Val Phe Thr Ile His Asn Phe
145                 150                 155                 160
```

-continued

```
Gly Tyr Arg Gly Tyr Cys Ser Thr Gln Leu Leu Ala Ala Ser Gln Ile
                165                 170                 175

Asp Asp Phe His Leu Ser His Tyr Gln Leu Phe Arg Asp Pro Gln Thr
            180                 185                 190

Ser Val Leu Met Lys Gly Ala Leu Tyr Cys Ser Asp Tyr Ile Thr Thr
        195                 200                 205

Val Ser Leu Thr Tyr Val Gln Glu Ile Ile Asn Asp Tyr Ser Asp Tyr
    210                 215                 220

Glu Leu His Asp Ala Ile Leu Ala Arg Asn Ser Val Phe Ser Gly Ile
225                 230                 235                 240

Ile Asn Gly Ile Asp Glu Asp Val Trp Asn Pro Lys Thr Asp Pro Ala
                245                 250                 255

Leu Ala Val Gln Tyr Asp Ala Ser Leu Leu Ser Glu Pro Asp Val Leu
            260                 265                 270

Phe Thr Lys Lys Glu Asn Arg Ala Val Leu Tyr Glu Lys Leu Gly
        275                 280                 285

Ile Ser Ser Asp Tyr Phe Pro Leu Ile Cys Val Ile Ser Arg Ile Val
    290                 295                 300

Glu Glu Lys Gly Pro Glu Phe Met Lys Glu Ile Ile Leu His Ala Met
305                 310                 315                 320

Glu His Ser Tyr Ala Phe Ile Leu Ile Gly Thr Ser Gln Asn Glu Val
                325                 330                 335

Leu Leu Asn Glu Phe Arg Asn Leu Gln Asp Cys Leu Ala Ser Ser Pro
            340                 345                 350

Asn Ile Arg Leu Ile Leu Asp Phe Asn Asp Pro Leu Ala Arg Leu Thr
        355                 360                 365

Tyr Ala Ala Ala Asp Met Ile Cys Ile Pro Ser His Arg Glu Ala Cys
    370                 375                 380

Gly Leu Thr Gln Leu Ile Ala Met Arg Tyr Gly Thr Val Pro Leu Val
385                 390                 395                 400

Arg Lys Thr Gly Gly Leu Ala Asp Thr Val Ile Pro Gly Val Asn Gly
                405                 410                 415

Phe Thr Phe Phe Asp Thr Asn Asn Phe Asn Glu Phe Arg Ala Met Leu
            420                 425                 430

Ser Asn Ala Val Thr Thr Tyr Arg Gln Glu Pro Asp Val Trp Leu Asn
        435                 440                 445

Leu Ile Glu Ser Gly Met Leu Arg Ala Ser Gly Leu Asp Ala Met Ala
    450                 455                 460

Lys His Tyr Val Asn Leu Tyr Gln Ser Leu Leu Ser
465                 470                 475

<210> SEQ ID NO 70
<211> LENGTH: 346
<212> TYPE: PRT
<213> ORGANISM: Chlamydia pneumoniae

<400> SEQUENCE: 70

Met Glu Ala Asp Ile Leu Asp Gly Lys Leu Lys Arg Val Glu Val Ser
                5                   10                  15

Lys Lys Gly Leu Val Asn Cys Asn Gln Val Asp Val Asn Gln Leu Val
            20                  25                  30

Pro Ile Lys Tyr Lys Trp Ala Trp Glu His Tyr Leu Asn Gly Cys Ala
        35                  40                  45

Asn Asn Trp Leu Pro Thr Glu Val Pro Met Ala Arg Asp Ile Glu Leu
```

-continued

```
                50                  55                  60
Trp Lys Ser Asp Glu Leu Ser Glu Asp Glu Arg Arg Val Ile Leu Leu
 65                  70                  75                  80

Asn Leu Gly Phe Phe Ser Thr Ala Glu Ser Leu Val Gly Asn Asn Ile
                 85                  90                  95

Val Leu Ala Ile Phe Lys His Ile Thr Asn Pro Glu Ala Arg Gln Tyr
                100                 105                 110

Leu Leu Arg Gln Ala Phe Glu Ala Val His Thr His Thr Phe Leu
                115                 120                 125

Tyr Ile Cys Glu Ser Leu Gly Leu Asp Glu Gly Glu Val Phe Asn Ala
130                 135                 140

Tyr Asn Glu Arg Ala Ser Ile Arg Ala Lys Asp Asp Phe Gln Met Thr
145                 150                 155                 160

Leu Thr Val Asp Val Leu Asp Pro Asn Phe Ser Val Gln Ser Ser Glu
                165                 170                 175

Gly Leu Gly Gln Phe Ile Lys Asn Leu Val Gly Tyr Tyr Ile Ile Met
                180                 185                 190

Glu Gly Ile Phe Phe Tyr Ser Gly Phe Val Met Ile Leu Ser Phe His
                195                 200                 205

Arg Gln Asn Lys Met Thr Gly Ile Gly Glu Gln Tyr Gln Tyr Ile Leu
210                 215                 220

Arg Asp Glu Thr Ile His Leu Asn Phe Gly Ile Asp Leu Ile Asn Gly
225                 230                 235                 240

Ile Lys Glu Glu Asn Pro Glu Val Trp Thr Thr Glu Leu Gln Glu Glu
                245                 250                 255

Ile Val Ala Leu Ile Glu Lys Ala Val Glu Leu Glu Ile Glu Tyr Ala
                260                 265                 270

Lys Asp Cys Leu Pro Arg Gly Ile Leu Gly Leu Arg Ser Ser Met Phe
                275                 280                 285

Ile Asp Tyr Val Arg His Ile Ala Asp Arg Arg Leu Glu Arg Ile Gly
                290                 295                 300

Leu Lys Pro Ile Tyr His Ser Arg Asn Pro Phe Pro Trp Met Ser Glu
305                 310                 315                 320

Thr Met Asp Leu Asn Lys Glu Lys Asn Phe Phe Glu Thr Arg Val Thr
                325                 330                 335

Glu Tyr Gln Thr Ala Gly Asn Leu Ser Trp
                340                 345
```

<210> SEQ ID NO 71
<211> LENGTH: 1044
<212> TYPE: PRT
<213> ORGANISM: Chlamydia pneumoniae

<400> SEQUENCE: 71

```
Met Val Glu Val Glu Lys His Tyr Thr Ile Val Lys Arg Asn Gly
                 5                  10                  15

Met Phe Val Pro Phe Asn Gln Asp Arg Ile Phe Gln Ala Leu Glu Ala
                20                  25                  30

Ala Phe Arg Asp Thr Arg Ser Leu Glu Thr Ser Ser Pro Leu Pro Lys
                35                  40                  45

Asp Leu Glu Glu Ser Ile Ala Gln Ile Thr His Lys Val Val Lys Glu
                50                  55                  60

Val Leu Ala Lys Ile Ser Glu Gly Gln Val Val Thr Val Glu Arg Ile
 65                  70                  75                  80
```

```
Gln Asp Leu Val Glu Ser Gln Leu Tyr Ile Ser Gly Leu Gln Asp Val
                85                   90                   95

Ala Arg Asp Tyr Ile Val Tyr Arg Asp Gln Arg Lys Ala Glu Arg Gly
           100                  105                 110

Asn Ser Ser Ile Ile Ala Ile Ile Arg Arg Asp Gly Gly Ser Ala
           115                 120                 125

Lys Phe Asn Pro Met Lys Ile Ser Ala Ala Leu Glu Lys Ala Phe Arg
    130                 135                 140

Ala Thr Leu Gln Ile Asn Gly Met Thr Pro Pro Ala Thr Leu Ser Glu
145                 150                 155                 160

Ile Asn Asp Leu Thr Leu Arg Ile Val Glu Asp Val Leu Ser Leu His
                165                 170                 175

Gly Glu Glu Ala Ile Asn Leu Glu Glu Ile Gln Asp Ile Val Glu Lys
            180                 185                 190

Gln Leu Met Val Ala Gly Tyr Tyr Asp Val Ala Lys Asn Tyr Ile Leu
            195                 200                 205

Tyr Arg Glu Ala Arg Ala Arg Ala Arg Ala Asn Lys Asp Gln Asp Gly
    210                 215                 220

Gln Glu Glu Phe Val Pro Gln Glu Glu Thr Tyr Val Val Gln Lys Glu
225                 230                 235                 240

Asp Gly Thr Thr Tyr Leu Leu Arg Lys Thr Asp Leu Glu Lys Arg Phe
                245                 250                 255

Ser Trp Ala Cys Lys Arg Phe Pro Lys Thr Asp Ser Gln Leu Leu
            260                 265                 270

Ala Asp Met Ala Phe Met Asn Leu Tyr Ser Gly Ile Lys Glu Asp Glu
        275                 280                 285

Val Thr Thr Ala Cys Ile Met Ala Ala Arg Ala Asn Ile Glu Arg Glu
        290                 295                 300

Pro Asp Tyr Ala Phe Ile Ala Ala Glu Leu Leu Thr Ser Ser Leu Tyr
305                 310                 315                 320

Glu Glu Thr Leu Gly Cys Ser Ser Gln Asp Pro Asn Leu Ser Glu Ile
            325                 330                 335

His Lys Lys His Phe Lys Glu Tyr Ile Leu Asn Gly Glu Glu Tyr Arg
            340                 345                 350

Leu Asn Pro Gln Leu Lys Asp Tyr Asp Leu Asp Ala Leu Ser Glu Val
        355                 360                 365

Leu Asp Leu Ser Arg Asp Gln Gln Phe Ser Tyr Met Gly Val Gln Asn
370                 375                 380

Leu Tyr Asp Arg Tyr Phe Asn Leu His Glu Gly Arg Arg Leu Glu Thr
385                 390                 395                 400

Ala Gln Ile Phe Trp Met Arg Val Ser Met Gly Leu Ala Leu Asn Glu
                405                 410                 415

Gly Glu Gln Lys Asn Phe Trp Ala Ile Thr Phe Tyr Asn Leu Leu Ser
            420                 425                 430

Thr Phe Arg Tyr Thr Pro Ala Thr Pro Thr Leu Phe Asn Ser Gly Met
        435                 440                 445

Arg His Ser Gln Leu Ser Ser Cys Tyr Leu Ser Thr Val Lys Asp Asp
    450                 455                 460

Leu Ser His Ile Tyr Lys Val Ile Ser Asp Asn Ala Leu Leu Ser Lys
465                 470                 475                 480

Trp Ala Gly Gly Ile Gly Asn Asp Trp Thr Asp Val Arg Ala Thr Gly
                485                 490                 495

Ala Val Ile Lys Gly Thr Asn Gly Lys Ser Gln Gly Val Ile Pro Phe
```

-continued

```
            500                 505                 510
Ile Lys Val Ala Asn Asp Thr Ala Ile Ala Val Asn Gln Gly Gly Lys
        515                 520                 525

Arg Lys Gly Ala Met Cys Val Tyr Leu Glu Asn Trp His Leu Asp Tyr
    530                 535                 540

Glu Asp Phe Leu Glu Leu Arg Lys Asn Thr Gly Asp Glu Arg Arg Arg
545                 550                 555                 560

Thr His Asp Ile Asn Thr Ala Ser Trp Ile Pro Asp Leu Phe Phe Lys
                565                 570                 575

Arg Leu Glu Lys Lys Gly Met Trp Thr Leu Phe Ser Pro Asp Asp Val
            580                 585                 590

Pro Gly Leu His Glu Ala Tyr Gly Leu Glu Phe Glu Lys Leu Tyr Glu
        595                 600                 605

Glu Tyr Glu Arg Lys Val Glu Ser Gly Glu Ile Arg Leu Tyr Lys Lys
    610                 615                 620

Val Glu Ala Glu Val Leu Trp Arg Lys Met Leu Ser Met Leu Tyr Glu
625                 630                 635                 640

Thr Gly His Pro Trp Ile Thr Phe Lys Asp Pro Ser Asn Ile Arg Ser
                645                 650                 655

Asn Gln Asp His Val Gly Val Arg Cys Ser Asn Leu Cys Thr Glu
            660                 665                 670

Ile Leu Leu Asn Cys Ser Glu Ser Glu Thr Ala Val Cys Asn Leu Gly
        675                 680                 685

Ser Ile Asn Leu Val Glu His Ile Arg Asn Asp Lys Leu Asp Glu Glu
    690                 695                 700

Lys Leu Lys Glu Thr Ile Ser Ile Ala Ile Arg Ile Leu Asp Asn Val
705                 710                 715                 720

Ile Asp Leu Asn Phe Tyr Pro Thr Pro Glu Ala Lys Gln Ala Asn Leu
                725                 730                 735

Thr His Arg Ala Val Gly Leu Gly Val Met Gly Phe Gln Asp Val Leu
            740                 745                 750

Tyr Glu Leu Asn Ile Ser Tyr Ala Ser Gln Glu Ala Val Glu Phe Ser
        755                 760                 765

Asp Glu Cys Ser Glu Ile Ile Ala Tyr Tyr Ala Ile Leu Ala Ser Ser
    770                 775                 780

Leu Leu Ala Lys Glu Arg Gly Thr Tyr Ala Ser Tyr Ser Gly Ser Lys
785                 790                 795                 800

Trp Asp Arg Gly Tyr Leu Pro Leu Asp Thr Ile Glu Leu Leu Lys Glu
                805                 810                 815

Thr Arg Gly Glu His Asn Val Leu Val Asp Thr Ser Lys Lys Asp
            820                 825                 830

Trp Thr Pro Val Arg Asp Thr Ile Gln Lys Tyr Gly Met Arg Asn Ser
        835                 840                 845

Gln Val Met Ala Ile Ala Pro Thr Ala Thr Ile Ser Asn Ile Ile Gly
    850                 855                 860

Val Thr Gln Ser Ile Glu Pro Met Tyr Lys His Leu Phe Val Lys Ser
865                 870                 875                 880

Asn Leu Ser Gly Glu Phe Thr Ile Pro Asn Thr Tyr Leu Ile Lys Lys
                885                 890                 895

Leu Lys Glu Leu Gly Leu Trp Asp Ala Glu Met Leu Asp Asp Leu Lys
            900                 905                 910

Tyr Phe Asp Gly Ser Leu Leu Glu Ile Glu Arg Ile Pro Asn His Leu
        915                 920                 925
```

```
Lys Lys Leu Phe Leu Thr Ala Phe Glu Ile Glu Pro Glu Trp Ile Ile
    930                 935                 940
Glu Cys Thr Ser Arg Arg Gln Lys Trp Ile Asp Met Gly Val Ser Leu
945                 950                 955                 960
Asn Leu Tyr Leu Ala Glu Pro Asp Gly Lys Lys Leu Ser Asn Met Tyr
            965                 970                 975
Leu Thr Ala Trp Lys Lys Gly Leu Lys Thr Thr Tyr Tyr Leu Arg Ser
            980                 985                 990
Gln Ala Ala Thr Ser Val Glu Lys Ser Phe Ile Asp Ile Asn Lys Arg
            995                 1000                1005
Gly Ile Gln Pro Arg Trp Met Lys Asn Lys Ser Ala Ser Thr Ser Ile
    1010                1015                1020
Val Val Glu Arg Lys Thr Thr Pro Val Cys Ser Met Glu Glu Gly Cys
1025                1030                1035                1040
Glu Ser Cys Gln
```

<210> SEQ ID NO 72
<211> LENGTH: 461
<212> TYPE: PRT
<213> ORGANISM: Chlamydia pneumoniae

<400> SEQUENCE: 72

```
Met Met Ser Ser Lys Arg Thr Ser Lys Ile Ala Val Leu Ser Ile Leu
                5                   10                  15
Leu Thr Phe Thr His Ser Ile Gly Phe Ala Asn Ala Asn Ser Ser Val
            20                  25                  30
Gly Leu Gly Thr Val Tyr Ile Thr Ser Glu Val Val Lys Lys Pro Gln
        35                  40                  45
Lys Gly Ser Glu Arg Lys Gln Ala Lys Lys Glu Pro Arg Ala Arg Lys
    50                  55                  60
Gly Tyr Leu Val Pro Ser Ser Arg Thr Leu Ser Ala Arg Ala Gln Lys
65                  70                  75                  80
Met Lys Asn Ser Ser Arg Lys Glu Ser Ser Gly Gly Cys Asn Glu Ile
                85                  90                  95
Ser Ala Asn Ser Thr Pro Arg Ser Val Lys Leu Arg Arg Asn Lys Arg
            100                 105                 110
Ala Glu Gln Lys Ala Ala Lys Gln Gly Phe Ser Ala Phe Ser Asn Leu
        115                 120                 125
Thr Leu Lys Ser Leu Leu Pro Lys Leu Pro Ser Lys Gln Lys Thr Ser
    130                 135                 140
Ile His Glu Arg Glu Lys Ala Thr Ser Arg Phe Val Asn Glu Ser Gln
145                 150                 155                 160
Leu Ser Ser Ala Arg Lys Arg Tyr Cys Thr Pro Ser Ser Ala Ala Pro
                165                 170                 175
Ser Leu Phe Leu Glu Thr Glu Ile Val Arg Ala Pro Val Glu Arg Thr
            180                 185                 190
Lys Glu Leu Gln Asp Asn Glu Ile His Ile Pro Val Val Gln Val Gln
        195                 200                 205
Thr Asn Pro Lys Glu Gln Asn Thr Lys Thr Thr Lys Gln Leu Ala Ser
    210                 215                 220
Gln Ala Ser Ile Gln Gln Ser Glu Gly Thr Glu Gln Ser Leu Arg Glu
225                 230                 235                 240
Leu Ala Gln Gly Ala Ser Leu Pro Val Leu Val Arg Ser Asn Pro Glu
                245                 250                 255
```

```
Val Ser Val Gln Arg Gln Lys Glu Leu Leu Lys Glu Leu Val Ala
            260                 265                 270

Glu Arg Arg Gln Cys Lys Arg Lys Ser Val Arg Gln Ala Leu Glu Ala
            275                 280                 285

Arg Ser Leu Thr Lys Lys Val Ala Arg Gly Gly Ser Val Thr Ser Thr
            290                 295                 300

Leu Arg Tyr Asp Pro Glu Lys Ala Ala Glu Ile Lys Ser Arg Arg Asn
305                 310                 315                 320

Cys Lys Val Ser Pro Glu Ala Arg Glu Gln Lys Tyr Ser Ser Cys Lys
                325                 330                 335

Arg Asp Ala Arg Ala Asn Gly Lys Gln Asp Lys Thr Thr Pro Ser Glu
            340                 345                 350

Asp Ala Ser Gln Glu Gln Gln Thr Gly Ala Gly Leu Val Arg Lys
            355                 360                 365

Thr Pro Lys Ser Gln Val Ala Ser Asn Ala Gln Asn Phe Tyr Arg Asn
            370                 375                 380

Ser Lys Asn Thr Asn Ile Asp Ser Tyr Leu Thr Ala Asn Gln Tyr Ser
385                 390                 395                 400

Cys Ser Ser Glu Glu Thr Asp Trp Pro Cys Ser Ser Cys Val Ser Lys
                405                 410                 415

Arg Arg Thr His Asn Ser Ile Ser Val Cys Thr Met Val Val Thr Val
            420                 425                 430

Ile Ala Met Ile Val Gly Ala Leu Ile Ile Ala Asn Ala Thr Glu Ser
            435                 440                 445

Gln Thr Thr Ser Asp Pro Thr Pro Thr Pro Thr Pro
            450                 455                 460

<210> SEQ ID NO 73
<211> LENGTH: 576
<212> TYPE: PRT
<213> ORGANISM: Chlamydia pneumoniae

<400> SEQUENCE: 73

Met Thr Asp Phe Pro Thr His Phe Lys Gly Pro Lys Leu Asn Pro Ile
                5                   10                  15

Lys Val Asn Pro Asn Phe Phe Glu Arg Asn Pro Lys Val Ala Arg Val
            20                  25                  30

Leu Gln Ile Thr Ala Val Val Leu Gly Ile Ile Ala Leu Leu Ser Gly
        35                  40                  45

Ile Val Leu Ile Ile Gly Thr Pro Leu Gly Ala Pro Ile Ser Met Ile
    50                  55                  60

Leu Gly Gly Cys Leu Leu Ala Ser Gly Gly Ala Leu Phe Val Gly Gly
65                  70                  75                  80

Thr Ile Ala Thr Ile Leu Gln Ala Arg Asn Ser Tyr Lys Lys Ala Val
                85                  90                  95

Asn Gln Lys Lys Leu Ser Glu Pro Leu Met Glu Arg Pro Glu Leu Lys
            100                 105                 110

Ala Leu Asp Tyr Ser Leu Asp Leu Lys Glu Val Trp Asp Leu His His
        115                 120                 125

Ser Val Val Lys His Leu Lys Lys Leu Asp Leu Asn Leu Ser Lys Thr
    130                 135                 140

Gln Arg Glu Val Leu Asn Gln Ile Lys Ile Asp Asp Glu Gly Pro Ser
145                 150                 155                 160

Leu Gly Glu Cys Ala Ala Met Ile Ser Glu Asn Tyr Asp Ala Cys Leu
```

```
                    165                 170                 175
Lys Met Leu Ala Tyr Arg Glu Glu Leu Lys Glu Gln Thr Gln Tyr
            180                 185                 190
Gln Glu Thr Arg Phe Asn Gln Asn Leu Thr His Arg Asn Lys Val Leu
            195                 200                 205
Leu Ser Ile Leu Ser Arg Ile Thr Asp Asn Ile Ser Lys Ala Gly Gly
            210                 215                 220
Val Phe Ser Leu Lys Phe Ser Thr Leu Ser Ser Arg Met Ser Arg Ile
225                 230                 235                 240
His Thr Thr Thr Thr Val Ile Leu Ala Leu Ser Ala Val Val Ser Val
                245                 250                 255
Met Val Val Ala Ala Leu Ile Pro Gly Gly Ile Leu Ala Leu Pro Ile
            260                 265                 270
Leu Leu Ala Val Ala Ile Ser Ala Gly Val Ile Val Thr Gly Leu Ser
            275                 280                 285
Tyr Leu Val Arg Gln Ile Leu Ser Asn Thr Lys Arg Asn Arg Gln Asp
            290                 295                 300
Phe Tyr Lys Asp Phe Val Lys Asn Val Asp Ile Glu Leu Leu Asn Gln
305                 310                 315                 320
Thr Val Thr Leu Gln Arg Phe Leu Phe Glu Met Leu Lys Gly Val Leu
                325                 330                 335
Lys Glu Glu Glu Val Ser Leu Glu Gly Gln Asp Trp Tyr Thr Gln
            340                 345                 350
Tyr Ile Thr Asn Ala Pro Ile Glu Lys Arg Leu Ile Glu Glu Ile Arg
            355                 360                 365
Val Thr Tyr Lys Glu Ile Asp Ala Gln Thr Lys Lys Met Lys Thr Asp
            370                 375                 380
Leu Glu Phe Leu Glu Asn Glu Val Arg Ser Gly Arg Leu Ser Val Ala
385                 390                 395                 400
Ser Pro Ser Glu Asp Pro Ser Glu Thr Pro Ile Phe Thr Gln Gly Lys
                405                 410                 415
Glu Phe Ala Lys Leu Arg Arg Gln Thr Ser Gln Asn Ile Ser Thr Ile
            420                 425                 430
Tyr Gly Pro Asp Asn Glu Asn Ile Asp Pro Glu Phe Ser Leu Pro Trp
            435                 440                 445
Met Pro Lys Lys Glu Glu Ile Asp His Ser Leu Glu Pro Val Thr
            450                 455                 460
Lys Leu Glu Pro Gly Ser Arg Glu Glu Leu Leu Leu Val Glu Gly Val
465                 470                 475                 480
Asn Pro Thr Leu Arg Glu Leu Asn Met Arg Ile Ala Leu Leu Gln Gln
            485                 490                 495
Gln Leu Ser Ser Val Arg Lys Trp Arg His Pro Arg Gly Glu His Tyr
            500                 505                 510
Gly Asn Val Ile Tyr Ser Asp Thr Glu Leu Asp Arg Ile Gln Met Leu
            515                 520                 525
Glu Gly Ala Phe Tyr Asn His Leu Arg Glu Ala Gln Glu Glu Ile Thr
            530                 535                 540
Gln Ser Leu Gly Asp Leu Val Asp Ile Gln Asn Arg Ile Leu Gly Ile
545                 550                 555                 560
Ile Val Glu Gly Asp Ser Asp Ser Arg Thr Glu Glu Pro Gln Glu
                565                 570                 575

<210> SEQ ID NO 74
```

```
<211> LENGTH: 361
<212> TYPE: PRT
<213> ORGANISM: Chlamydia pneumoniae

<400> SEQUENCE: 74
```

Met Gln Gln Thr Val Ile Val Ala Met Ser Gly Gly Val Asp Ser Ser
                5                  10                  15
Val Val Ala Tyr Leu Phe Lys Lys Phe Thr Asn Tyr Lys Val Ile Gly
            20                  25                  30
Leu Phe Met Lys Asn Trp Glu Glu Asp Ser Glu Gly Gly Leu Cys Ser
        35                  40                  45
Ser Thr Lys Asp Tyr Glu Asp Val Glu Arg Val Cys Leu Gln Leu Asp
    50                  55                  60
Ile Pro Tyr Tyr Thr Val Ser Phe Ala Lys Glu Tyr Arg Glu Arg Val
65                  70                  75                  80
Phe Ala Arg Phe Leu Lys Glu Tyr Ser Leu Gly Tyr Thr Pro Asn Pro
                85                  90                  95
Asp Ile Leu Cys Asn Arg Glu Ile Lys Phe Asp Leu Leu Gln Lys Lys
            100                 105                 110
Val Gln Glu Leu Gly Gly Asp Tyr Leu Ala Thr Gly His Tyr Cys Arg
        115                 120                 125
Leu Asn Thr Glu Leu Gln Glu Thr Gln Leu Leu Arg Gly Cys Asp Pro
    130                 135                 140
Gln Lys Asp Gln Ser Tyr Phe Leu Ser Gly Thr Pro Lys Ser Ala Leu
145                 150                 155                 160
His Asn Val Leu Phe Pro Leu Gly Glu Met Asn Lys Thr Glu Val Arg
                165                 170                 175
Ala Ile Ala Ala Gln Ala Ala Leu Pro Thr Ala Glu Lys Lys Asp Ser
            180                 185                 190
Thr Gly Ile Cys Phe Ile Gly Lys Arg Pro Phe Lys Glu Phe Leu Glu
        195                 200                 205
Lys Phe Leu Pro Asn Lys Thr Gly Asn Val Ile Asp Trp Asp Thr Lys
    210                 215                 220
Glu Ile Val Gly Gln His Gln Gly Ala His Tyr Tyr Thr Ile Gly Gln
225                 230                 235                 240
Arg Arg Gly Leu Asp Leu Gly Gly Ser Glu Lys Pro Cys Tyr Val Val
                245                 250                 255
Gly Lys Asn Ile Glu Glu Asn Ser Ile Tyr Ile Val Arg Gly Glu Asp
            260                 265                 270
His Pro Gln Leu Tyr Leu Arg Glu Leu Thr Ala Arg Glu Leu Asn Trp
        275                 280                 285
Phe Thr Pro Pro Lys Ser Gly Cys His Cys Ser Ala Lys Val Arg Tyr
    290                 295                 300
Arg Ser Pro Asp Glu Ala Cys Thr Ile Asp Tyr Ser Ser Gly Asp Glu
305                 310                 315                 320
Val Lys Val Arg Phe Ser Gln Pro Val Lys Ala Val Thr Pro Gly Gln
                325                 330                 335
Thr Ile Ala Phe Tyr Gln Gly Asp Thr Cys Leu Gly Ser Gly Val Ile
            340                 345                 350
Asp Val Pro Met Ile Pro Ser Glu Gly
        355                 360

```
<210> SEQ ID NO 75
<211> LENGTH: 1609
<212> TYPE: PRT
```

<213> ORGANISM: Chlamydia pneumoniae

<400> SEQUENCE: 75

Met Val Ala Lys Lys Thr Val Arg Ser Tyr Arg Ser Ser Phe Ser His
                5                   10                  15

Ser Val Ile Val Ala Ile Leu Ser Ala Gly Ile Ala Phe Glu Ala His
            20                  25                  30

Ser Leu His Ser Ser Glu Leu Asp Leu Gly Val Phe Asn Lys Gln Phe
        35                  40                  45

Glu Glu His Ser Ala His Val Glu Glu Ala Gln Thr Ser Val Leu Lys
    50                  55                  60

Gly Ser Asp Pro Val Asn Pro Ser Gln Lys Glu Ser Glu Lys Val Leu
65                  70                  75                  80

Tyr Thr Gln Val Pro Leu Thr Gln Gly Ser Ser Gly Glu Ser Leu Asp
                85                  90                  95

Leu Ala Asp Ala Asn Phe Leu Glu His Phe Gln His Leu Phe Glu Glu
            100                 105                 110

Thr Thr Val Phe Gly Ile Asp Gln Lys Leu Val Trp Ser Asp Leu Asp
        115                 120                 125

Thr Arg Asn Phe Ser Gln Pro Thr Gln Glu Pro Asp Thr Ser Asn Ala
    130                 135                 140

Val Ser Glu Lys Ile Ser Ser Asp Thr Lys Glu Asn Arg Lys Asp Leu
145                 150                 155                 160

Glu Thr Glu Asp Pro Ser Lys Lys Ser Gly Leu Lys Glu Val Ser Ser
                165                 170                 175

Asp Leu Pro Lys Ser Pro Glu Thr Ala Val Ala Ala Ile Ser Glu Asp
            180                 185                 190

Leu Glu Ile Ser Glu Asn Ile Ser Ala Arg Asp Pro Leu Gln Gly Leu
        195                 200                 205

Ala Phe Phe Tyr Lys Asn Thr Ser Ser Gln Ser Ile Ser Glu Lys Asp
    210                 215                 220

Ser Ser Phe Gln Gly Ile Ile Phe Ser Gly Ser Gly Ala Asn Ser Gly
225                 230                 235                 240

Leu Gly Phe Glu Asn Leu Lys Ala Pro Lys Ser Gly Ala Ala Val Tyr
                245                 250                 255

Ser Asp Arg Asp Ile Val Phe Glu Asn Leu Val Lys Gly Leu Ser Phe
            260                 265                 270

Ile Ser Cys Glu Ser Leu Glu Asp Gly Ser Ala Ala Gly Val Asn Ile
        275                 280                 285

Val Val Thr His Cys Gly Asp Val Thr Leu Thr Asp Cys Ala Thr Gly
    290                 295                 300

Leu Asp Leu Glu Ala Leu Arg Leu Val Lys Asp Phe Ser Arg Gly Gly
305                 310                 315                 320

Ala Val Phe Thr Ala Arg Asn His Glu Val Gln Asn Asn Leu Ala Gly
                325                 330                 335

Gly Ile Leu Ser Val Val Gly Asn Lys Gly Ala Ile Val Val Glu Lys
            340                 345                 350

Asn Ser Ala Glu Lys Ser Asn Gly Gly Ala Phe Ala Cys Gly Ser Phe
        355                 360                 365

Val Tyr Ser Asn Asn Glu Asn Thr Ala Leu Trp Lys Glu Asn Gln Ala
    370                 375                 380

Leu Ser Gly Gly Ala Ile Ser Ser Ala Ser Asp Ile Asp Ile Gln Gly
385                 390                 395                 400

-continued

```
Asn Cys Ser Ala Ile Glu Phe Ser Gly Asn Gln Ser Leu Ile Ala Leu
            405                 410                 415
Gly Glu His Ile Gly Leu Thr Asp Phe Val Gly Gly Ala Leu Ala
        420                 425                 430
Ala Gln Gly Thr Leu Thr Leu Arg Asn Asn Ala Val Val Gln Cys Val
            435                 440                 445
Lys Asn Thr Ser Lys Thr His Gly Gly Ala Ile Leu Ala Gly Thr Val
    450                 455                 460
Asp Leu Asn Glu Thr Ile Ser Glu Val Ala Phe Lys Gln Asn Thr Ala
465                 470                 475                 480
Ala Leu Thr Gly Gly Ala Leu Ser Ala Asn Asp Lys Val Ile Ile Ala
                485                 490                 495
Asn Asn Phe Gly Glu Ile Leu Phe Glu Gln Asn Glu Val Arg Asn His
            500                 505                 510
Gly Gly Ala Ile Tyr Cys Gly Cys Arg Ser Asn Pro Lys Leu Glu Gln
            515                 520                 525
Lys Asp Ser Gly Glu Asn Ile Asn Ile Ile Gly Asn Ser Gly Ala Ile
    530                 535                 540
Thr Phe Leu Lys Asn Lys Ala Ser Val Leu Glu Val Met Thr Gln Ala
545                 550                 555                 560
Glu Asp Tyr Ala Gly Gly Gly Ala Leu Trp Gly His Asn Val Leu Leu
                565                 570                 575
Asp Ser Asn Ser Gly Asn Ile Gln Phe Ile Gly Asn Ile Gly Gly Ser
            580                 585                 590
Thr Phe Trp Ile Gly Glu Tyr Val Gly Gly Ala Ile Leu Ser Thr
        595                 600                 605
Asp Arg Val Thr Ile Ser Asn Asn Ser Gly Asp Val Val Phe Lys Gly
    610                 615                 620
Asn Lys Gly Gln Cys Leu Ala Gln Lys Tyr Val Ala Pro Gln Glu Thr
625                 630                 635                 640
Ala Pro Val Glu Ser Asp Ala Ser Ser Thr Asn Lys Asp Glu Lys Ser
                645                 650                 655
Leu Asn Ala Cys Ser His Gly Asp His Tyr Pro Pro Lys Thr Val Glu
            660                 665                 670
Glu Glu Val Pro Pro Ser Leu Leu Glu Glu His Pro Val Val Ser Ser
        675                 680                 685
Thr Asp Ile Arg Gly Gly Gly Ala Ile Leu Ala Gln His Ile Phe Ile
    690                 695                 700
Thr Asp Asn Thr Gly Asn Leu Arg Phe Ser Gly Asn Leu Gly Gly Gly
705                 710                 715                 720
Glu Glu Ser Ser Thr Val Gly Asp Leu Ala Ile Val Gly Gly Gly Ala
                725                 730                 735
Leu Leu Ser Thr Asn Glu Val Asn Val Cys Ser Asn Gln Asn Val Val
            740                 745                 750
Phe Ser Asp Asn Val Thr Ser Asn Gly Cys Asp Ser Gly Gly Ala Ile
        755                 760                 765
Leu Ala Lys Lys Val Asp Ile Ser Ala Asn His Ser Val Glu Phe Val
    770                 775                 780
Ser Asn Gly Ser Gly Lys Phe Gly Gly Ala Val Cys Ala Leu Asn Glu
785                 790                 795                 800
Ser Val Asn Ile Thr Asp Asn Gly Ser Ala Val Ser Phe Ser Lys Asn
                805                 810                 815
Arg Thr Arg Leu Gly Gly Ala Gly Val Ala Ala Pro Gln Gly Ser Val
```

```
                   820             825              830
Thr Ile Cys Gly Asn Gln Gly Asn Ile Ala Phe Lys Glu Asn Phe Val
            835             840             845
Phe Gly Ser Glu Asn Gln Arg Ser Gly Gly Ala Ile Ile Ala Asn
850             855             860
Ser Ser Val Asn Ile Gln Asp Asn Ala Gly Asp Ile Leu Phe Val Ser
865             870             875             880
Asn Ser Thr Gly Ser Tyr Gly Gly Ala Ile Phe Val Gly Ser Leu Val
            885             890             895
Ala Ser Glu Gly Ser Asn Pro Arg Thr Leu Thr Ile Thr Gly Asn Ser
            900             905             910
Gly Asp Ile Leu Phe Ala Lys Asn Ser Thr Gln Thr Ala Ala Ser Leu
            915             920             925
Ser Glu Lys Asp Ser Phe Gly Gly Ala Ile Tyr Thr Gln Asn Leu
930             935             940
Lys Ile Val Lys Asn Ala Gly Asn Val Ser Phe Tyr Gly Asn Arg Ala
945             950             955             960
Pro Ser Gly Ala Gly Val Gln Ile Ala Asp Gly Gly Thr Val Cys Leu
            965             970             975
Glu Ala Phe Gly Gly Asp Ile Leu Phe Glu Gly Asn Ile Asn Phe Asp
            980             985             990
Gly Ser Phe Asn Ala Ile His Leu Cys Gly Asn Asp Ser Lys Ile Val
            995             1000            1005
Glu Leu Ser Ala Val Gln Asp Lys Asn Ile Ile Phe Gln Asp Ala Ile
    1010            1015            1020
Thr Tyr Glu Glu Asn Thr Ile Arg Gly Leu Pro Asp Lys Asp Val Ser
1025            1030            1035            1040
Pro Leu Ser Ala Pro Ser Leu Ile Phe Asn Ser Lys Pro Gln Asp Asp
            1045            1050            1055
Ser Ala Gln His His Glu Gly Thr Ile Arg Phe Ser Arg Gly Val Ser
            1060            1065            1070
Lys Ile Pro Gln Ile Ala Ala Ile Gln Glu Gly Thr Leu Ala Leu Ser
            1075            1080            1085
Gln Asn Ala Glu Leu Trp Leu Ala Gly Leu Lys Gln Glu Thr Gly Ser
    1090            1095            1100
Ser Ile Val Leu Ser Ala Gly Ser Ile Leu Arg Ile Phe Asp Ser Gln
1105            1110            1115            1120
Val Asp Ser Ser Ala Pro Leu Pro Thr Glu Asn Lys Glu Glu Thr Leu
            1125            1130            1135
Val Ser Ala Gly Val Gln Ile Asn Met Ser Ser Pro Thr Pro Asn Lys
            1140            1145            1150
Asp Lys Ala Val Asp Thr Pro Val Leu Ala Asp Ile Ile Ser Ile Thr
            1155            1160            1165
Val Asp Leu Ser Ser Phe Val Pro Glu Gln Asp Gly Thr Leu Pro Leu
    1170            1175            1180
Pro Pro Glu Ile Ile Ile Pro Lys Gly Thr Lys Leu His Ser Asn Ala
1185            1190            1195            1200
Ile Asp Leu Lys Ile Ile Asp Pro Thr Asn Val Gly Tyr Glu Asn His
            1205            1210            1215
Ala Leu Leu Ser Ser His Lys Asp Ile Pro Leu Ile Ser Leu Lys Thr
            1220            1225            1230
Ala Glu Gly Met Thr Gly Thr Pro Thr Ala Asp Ala Ser Leu Ser Asn
            1235            1240            1245
```

```
Ile Lys Ile Asp Val Ser Leu Pro Ser Ile Thr Pro Ala Thr Tyr Gly
    1250                1255                1260

His Thr Gly Val Trp Ser Glu Ser Lys Met Glu Asp Gly Arg Leu Val
1265                1270                1275                1280

Val Gly Trp Gln Pro Thr Gly Tyr Lys Leu Asn Pro Glu Lys Gln Gly
                1285                1290                1295

Ala Leu Val Leu Asn Asn Leu Trp Ser His Tyr Thr Asp Leu Arg Ala
            1300                1305                1310

Leu Lys Gln Glu Ile Phe Ala His His Thr Ile Ala Gln Arg Met Glu
        1315                1320                1325

Leu Asp Phe Ser Thr Asn Val Trp Gly Ser Gly Leu Gly Val Val Glu
    1330                1335                1340

Asp Cys Gln Asn Ile Gly Glu Phe Asp Gly Phe Lys His His Leu Thr
1345                1350                1355                1360

Gly Tyr Ala Leu Gly Leu Asp Thr Gln Leu Val Glu Asp Phe Leu Ile
                1365                1370                1375

Gly Gly Cys Phe Ser Gln Phe Phe Gly Lys Thr Glu Ser Gln Ser Tyr
            1380                1385                1390

Lys Ala Lys Asn Asp Val Lys Ser Tyr Met Gly Ala Ala Tyr Ala Gly
        1395                1400                1405

Ile Leu Ala Gly Pro Trp Leu Ile Lys Gly Ala Phe Val Tyr Gly Asn
    1410                1415                1420

Ile Asn Asn Asp Leu Thr Thr Asp Tyr Gly Thr Leu Gly Ile Ser Thr
1425                1430                1435                1440

Gly Ser Trp Ile Gly Lys Gly Phe Ile Ala Gly Thr Ser Ile Asp Tyr
                1445                1450                1455

Arg Tyr Ile Val Asn Pro Arg Arg Phe Ile Ser Ala Ile Val Ser Thr
            1460                1465                1470

Val Val Pro Phe Val Glu Ala Glu Tyr Val Arg Ile Asp Leu Pro Glu
        1475                1480                1485

Ile Ser Glu Gln Gly Lys Glu Val Arg Thr Phe Gln Lys Thr Arg Phe
    1490                1495                1500

Glu Asn Val Ala Ile Pro Phe Gly Phe Ala Leu Glu His Ala Tyr Ser
1505                1510                1515                1520

Arg Gly Ser Arg Ala Glu Val Asn Ser Val Gln Leu Ala Tyr Val Phe
                1525                1530                1535

Asp Val Tyr Arg Lys Gly Pro Val Ser Leu Ile Thr Leu Lys Asp Ala
            1540                1545                1550

Ala Tyr Ser Trp Lys Ser Tyr Gly Val Asp Ile Pro Cys Lys Ala Trp
        1555                1560                1565

Lys Ala Arg Leu Ser Asn Asn Thr Glu Trp Asn Ser Tyr Leu Ser Thr
    1570                1575                1580

Tyr Leu Ala Phe Asn Tyr Glu Trp Arg Glu Asp Leu Ile Ala Tyr Asp
1585                1590                1595                1600

Phe Asn Gly Gly Ile Arg Ile Ile Phe
                1605

<210> SEQ ID NO 76
<211> LENGTH: 196
<212> TYPE: PRT
<213> ORGANISM: Chlamydia pneumoniae

<400> SEQUENCE: 76

Met Thr Leu Ser Leu Val Gly Lys Glu Ala Pro Asp Phe Val Ala Gln
```

```
                 5                  10                 15
Ala Val Val Asn Gly Glu Thr Cys Thr Val Ser Leu Lys Asp Tyr Leu
                20                 25                 30

Gly Lys Tyr Val Val Leu Phe Phe Tyr Pro Lys Asp Phe Thr Tyr Val
                35                 40                 45

Cys Pro Thr Glu Leu His Ala Phe Gln Asp Ala Leu Gly Glu Phe His
                50                 55                 60

Thr Arg Gly Ala Glu Val Ile Gly Cys Ser Val Asp Asp Ile Ala Thr
65                  70                 75                     80

His Gln Gln Trp Leu Ala Thr Lys Lys Gln Gly Gly Ile Glu Gly
                85                 90                 95

Ile Thr Tyr Pro Leu Leu Ser Asp Glu Asp Lys Val Ile Ser Arg Ser
                100                105                110

Tyr His Val Leu Lys Pro Glu Glu Glu Leu Ser Phe Arg Gly Val Phe
                115                120                125

Leu Ile Asp Lys Gly Gly Ile Ile Arg His Leu Val Val Asn Asp Leu
            130                135                140

Pro Leu Gly Arg Ser Ile Glu Glu Leu Arg Thr Leu Asp Ala Leu
145                 150                155                160

Ile Phe Phe Glu Thr Asn Gly Leu Val Cys Pro Ala Asn Trp His Glu
                165                170                175

Gly Glu Arg Ala Met Ala Pro Asn Glu Gly Leu Gln Asn Tyr Phe
                180                185                190

Gly Thr Ile Asp
            195

<210> SEQ ID NO 77
<211> LENGTH: 619
<212> TYPE: PRT
<213> ORGANISM: Chlamydia pneumoniae

<400> SEQUENCE: 77

Met Lys Lys Gly Lys Leu Gly Ala Ile Val Phe Gly Leu Leu Phe Thr
                5                  10                 15

Ser Ser Val Ala Gly Phe Ser Lys Asp Leu Thr Lys Asp Asn Ala Tyr
                20                 25                 30

Gln Asp Leu Asn Val Ile Glu His Leu Ile Ser Leu Lys Tyr Ala Pro
            35                 40                 45

Leu Pro Trp Lys Glu Leu Leu Phe Gly Trp Asp Leu Ser Gln Gln Thr
    50                 55                 60

Gln Gln Ala Arg Leu Gln Leu Val Leu Glu Glu Lys Pro Thr Thr Asn
65              70                 75                     80

Tyr Cys Gln Lys Val Leu Ser Asn Tyr Val Arg Ser Leu Asn Asp Tyr
                85                 90                 95

His Ala Gly Ile Thr Phe Tyr Arg Thr Glu Ser Ala Tyr Ile Pro Tyr
                100                105                110

Val Leu Lys Leu Ser Glu Asp Gly His Val Phe Val Val Asp Val Gln
                115                120                125

Thr Ser Gln Gly Asp Ile Tyr Leu Gly Asp Glu Ile Leu Glu Val Asp
            130                135                140

Gly Met Gly Ile Arg Glu Ala Ile Glu Ser Leu Arg Phe Gly Arg Gly
145                 150                155                160

Ser Ala Thr Asp Tyr Ser Ala Ala Val Arg Ser Leu Thr Ser Arg Ser
                165                170                175
```

```
Ala Ala Phe Gly Asp Ala Val Pro Ser Gly Ile Ala Met Leu Lys Leu
            180                 185                 190

Arg Arg Pro Ser Gly Leu Ile Arg Ser Thr Pro Val Arg Trp Arg Tyr
        195                 200                 205

Thr Pro Glu His Ile Gly Asp Phe Ser Leu Val Ala Pro Leu Ile Pro
    210                 215                 220

Glu His Lys Pro Gln Leu Pro Thr Gln Ser Cys Val Leu Phe Arg Ser
225                 230                 235                 240

Gly Val Asn Ser Gln Ser Ser Ser Ser Leu Phe Ser Ser Tyr Met
                245                 250                 255

Val Pro Tyr Phe Trp Glu Glu Leu Arg Val Gln Asn Lys Gln Arg Phe
            260                 265                 270

Asp Ser Asn His His Ile Gly Ser Arg Asn Gly Phe Leu Pro Thr Phe
            275                 280                 285

Gly Pro Ile Leu Trp Glu Gln Asp Lys Gly Pro Tyr Arg Ser Tyr Ile
    290                 295                 300

Phe Lys Ala Lys Asp Ser Gln Gly Asn Pro His Arg Ile Gly Phe Leu
305                 310                 315                 320

Arg Ile Ser Ser Tyr Val Trp Thr Asp Leu Glu Gly Leu Glu Glu Asp
                325                 330                 335

His Lys Asp Ser Pro Trp Glu Leu Phe Gly Glu Ile Ile Asp His Leu
            340                 345                 350

Glu Lys Glu Thr Asp Ala Leu Ile Ile Asp Gln Thr His Asn Pro Gly
            355                 360                 365

Gly Ser Val Phe Tyr Leu Tyr Ser Leu Leu Ser Met Leu Thr Asp His
        370                 375                 380

Pro Leu Asp Thr Pro Lys His Arg Met Ile Phe Thr Gln Asp Glu Val
385                 390                 395                 400

Ser Ser Ala Leu His Trp Gln Asp Leu Leu Glu Asp Val Phe Thr Asp
                405                 410                 415

Glu Gln Ala Val Ala Val Leu Gly Glu Thr Met Glu Gly Tyr Cys Met
            420                 425                 430

Asp Met His Ala Val Ala Ser Leu Gln Asn Phe Ser Gln Ser Val Leu
            435                 440                 445

Ser Ser Trp Val Ser Gly Asp Ile Asn Leu Ser Lys Pro Met Pro Leu
        450                 455                 460

Leu Gly Phe Ala Gln Val Arg Pro His Pro Lys His Gln Tyr Thr Lys
465                 470                 475                 480

Pro Leu Phe Met Leu Ile Asp Glu Asp Phe Ser Cys Gly Asp Leu
                485                 490                 495

Ala Pro Ala Ile Leu Lys Asp Asn Gly Arg Ala Thr Leu Ile Gly Lys
            500                 505                 510

Pro Thr Ala Gly Ala Gly Phe Val Phe Gln Val Thr Phe Pro Asn
            515                 520                 525

Arg Ser Gly Ile Lys Gly Leu Ser Leu Thr Gly Ser Leu Ala Val Arg
        530                 535                 540

Lys Asp Gly Glu Phe Ile Glu Asn Leu Gly Val Ala Pro His Ile Asp
545                 550                 555                 560

Leu Gly Phe Thr Ser Arg Asp Leu Gln Thr Ser Arg Phe Thr Asp Tyr
                565                 570                 575

Val Glu Ala Val Lys Thr Ile Val Leu Thr Ser Leu Ser Glu Asn Ala
            580                 585                 590

Lys Lys Ser Glu Glu Gln Thr Ser Pro Gln Glu Thr Pro Glu Val Ile
```

```
                595                 600                 605
Arg Val Ser Tyr Pro Thr Thr Thr Ser Ala Ser
    610                 615

<210> SEQ ID NO 78
<211> LENGTH: 651
<212> TYPE: PRT
<213> ORGANISM: Chlamydia pneumoniae

<400> SEQUENCE: 78

Met Val Asn Pro Ile Gly Pro Gly Pro Ile Asp Glu Thr Glu Arg Thr
                  5                  10                  15

Pro Pro Ala Asp Leu Ser Ala Gln Gly Leu Glu Ala Ser Ala Ala Asn
             20                  25                  30

Lys Ser Ala Glu Ala Gln Arg Ile Ala Gly Ala Glu Ala Lys Pro Lys
         35                  40                  45

Glu Ser Lys Thr Asp Ser Val Glu Arg Trp Ser Ile Leu Arg Ser Ala
     50                  55                  60

Val Asn Ala Leu Met Ser Leu Ala Asp Lys Leu Gly Ile Ala Ser Ser
 65                  70                  75                  80

Asn Ser Ser Ser Thr Ser Arg Ser Ala Asp Val Asp Ser Thr Thr
                 85                  90                  95

Ala Thr Ala Pro Thr Pro Pro Pro Thr Phe Asp Asp Tyr Lys Thr
            100                 105                 110

Gln Ala Gln Thr Ala Tyr Asp Thr Ile Phe Thr Ser Thr Ser Leu Ala
        115                 120                 125

Asp Ile Gln Ala Ala Leu Val Ser Leu Gln Asp Ala Val Thr Asn Ile
    130                 135                 140

Lys Asp Thr Ala Ala Thr Asp Glu Glu Thr Ala Ile Ala Ala Glu Trp
145                 150                 155                 160

Glu Thr Lys Asn Ala Asp Ala Val Lys Val Gly Ala Gln Ile Thr Glu
                165                 170                 175

Leu Ala Lys Tyr Ala Ser Asp Asn Gln Ala Ile Leu Asp Ser Leu Gly
            180                 185                 190

Lys Leu Thr Ser Phe Asp Leu Leu Gln Ala Ala Leu Leu Gln Ser Val
        195                 200                 205

Ala Asn Asn Asn Lys Ala Ala Glu Leu Leu Lys Glu Met Gln Asp Asn
    210                 215                 220

Pro Val Pro Gly Lys Thr Pro Ala Ile Ala Gln Ser Leu Val Asp
225                 230                 235                 240

Gln Thr Asp Ala Thr Ala Thr Gln Ile Glu Lys Asp Gly Asn Ala Ile
                245                 250                 255

Arg Asp Ala Tyr Phe Ala Gly Gln Asn Ala Ser Gly Ala Val Glu Asn
            260                 265                 270

Ala Lys Ser Asn Ser Ile Ser Asn Ile Asp Ser Ala Lys Ala Ala
        275                 280                 285

Ile Ala Thr Ala Lys Thr Gln Ile Ala Glu Ala Gln Lys Lys Phe Pro
    290                 295                 300

Asp Ser Pro Ile Leu Gln Glu Ala Glu Gln Met Val Ile Gln Ala Glu
305                 310                 315                 320

Lys Asp Leu Lys Asn Ile Lys Pro Ala Asp Gly Ser Asp Val Pro Asn
                325                 330                 335

Pro Gly Thr Thr Val Gly Gly Ser Lys Gln Gln Gly Ser Ser Ile Gly
            340                 345                 350
```

```
Ser Ile Arg Val Ser Met Leu Leu Asp Asp Ala Glu Asn Glu Thr Ala
        355                 360                 365
Ser Ile Leu Met Ser Gly Phe Arg Gln Met Ile His Met Phe Asn Thr
        370                 375                 380
Glu Asn Pro Asp Ser Gln Ala Ala Gln Gln Glu Leu Ala Ala Gln Ala
385                 390                 395                 400
Arg Ala Ala Lys Ala Ala Gly Asp Asp Ser Ala Ala Ala Ala Leu Ala
                405                 410                 415
Asp Ala Gln Lys Ala Leu Glu Ala Ala Leu Gly Lys Ala Gly Gln Gln
            420                 425                 430
Gln Gly Ile Leu Asn Ala Leu Gly Gln Ile Ala Ser Ala Ala Val Val
        435                 440                 445
Ser Ala Gly Val Pro Pro Ala Ala Ser Ser Ile Gly Ser Ser Val
450                 455                 460
Lys Gln Leu Tyr Lys Thr Ser Lys Ser Thr Gly Ser Asp Tyr Lys Thr
465                 470                 475                 480
Gln Ile Ser Ala Gly Tyr Asp Ala Tyr Lys Ser Ile Asn Asp Ala Tyr
                485                 490                 495
Gly Arg Ala Arg Asn Asp Ala Thr Arg Asp Val Ile Asn Asn Val Ser
                500                 505                 510
Thr Pro Ala Leu Thr Arg Ser Val Pro Arg Ala Arg Thr Glu Ala Arg
            515                 520                 525
Gly Pro Glu Lys Thr Asp Gln Ala Leu Ala Arg Val Ile Ser Gly Asn
        530                 535                 540
Ser Arg Thr Leu Gly Asp Val Tyr Ser Gln Val Ser Ala Leu Gln Ser
545                 550                 555                 560
Val Met Gln Ile Ile Gln Ser Asn Pro Gln Ala Asn Asn Glu Glu Ile
                565                 570                 575
Arg Gln Lys Leu Thr Ser Ala Val Thr Lys Pro Pro Gln Phe Gly Tyr
            580                 585                 590
Pro Tyr Val Gln Leu Ser Asn Asp Ser Thr Gln Lys Phe Ile Ala Lys
        595                 600                 605
Leu Glu Ser Leu Phe Ala Gly Gly Ser Arg Thr Ala Ala Glu Ile Lys
610                 615                 620
Ala Leu Ser Phe Glu Thr Asn Ser Leu Phe Ile Gln Gln Val Leu Val
625                 630                 635                 640
Asn Ile Gly Ser Leu Tyr Ser Gly Tyr Leu Gln
                645                 650

<210> SEQ ID NO 79
<211> LENGTH: 87
<212> TYPE: PRT
<213> ORGANISM: Chlamydia pneumoniae

<400> SEQUENCE: 79

Met Ser Gln Lys Asn Lys Asn Ser Ala Phe Met His Pro Val Asn Ile
                5                   10                  15
Ser Thr Asp Leu Ala Val Ile Val Gly Lys Gly Pro Met Pro Arg Thr
            20                  25                  30
Glu Ile Val Lys Lys Val Trp Glu Tyr Ile Lys Lys His Asn Cys Gln
        35                  40                  45
Asp Gln Lys Asn Lys Arg Asn Ile Leu Pro Asp Ala Asn Leu Ala Lys
    50                  55                  60
Val Phe Gly Ser Ser Asp Pro Ile Asp Met Phe Gln Met Thr Lys Ala
65                  70                  75                  80
```

Leu Ser Lys His Ile Val Lys
              85

<210> SEQ ID NO 80
<211> LENGTH: 3048
<212> TYPE: DNA
<213> ORGANISM: Chlamydia trachomatis serovar D

<400> SEQUENCE: 80

| | |
|---|---|
| atgccttttt ctttgagatc tacatcattt tgttttttag cttgtttgtg ttcctattcg | 60 |
| tatggattcg cgagctctcc tcaagtgtta acacctaatg taaccactcc ttttaagggg | 120 |
| gacgatgttt acttgaatgg agactgcgct tttgtcaatg tctatgcagg ggcagagaac | 180 |
| ggctcaatta tctcagctaa tggcgacaat ttaacgatta ccggacaaaa ccatacatta | 240 |
| tcatttacag attctcaagg ccagttctt caaaattatg ccttcatttc agcaggagag | 300 |
| acacttactc tgaaagattt ttcgagtttg atgttctcga aaatgtttc ttgcggagaa | 360 |
| aagggaatga tctcagggaa aaccgtgagt atttccggag caggcgaagt gatttttgg | 420 |
| gataactctg tggggtattc tcctttgtct attgtgccag catcgactcc aactcctcca | 480 |
| gcaccagcac cagctcctgc tgcttcaagc tctttatctc aacagttag tgatgctcgg | 540 |
| aaagggtcta ttttttctgt agagactagt ttggagatct caggcgtcaa aaagggtc | 600 |
| atgttcgata taatgccgg gaattttgga acagttttc gaggtaatag taataataat | 660 |
| gctggtagtg ggggtagtgg gtctgctaca acaccaagtt ttacagttaa aaactgtaaa | 720 |
| gggaaagttt ctttcacaga taacgtagcc tcctgtggag gcggagtagt ctacaaagga | 780 |
| actgtgcttt tcaaagacaa tgaaggaggc atattcttcc gagggaacac agcatacgat | 840 |
| gatttaggga ttcttgctgc tactagtcgg gatcagaata cggagacagg aggcggtgga | 900 |
| ggagttattt gctctccaga tgattctgta aagtttgaag gcaataaagg ttctattgtt | 960 |
| tttgattaca actttgcaaa aggcagaggc ggaagcatcc taacgaaaga attctctctt | 1020 |
| gtagcagatg attccggttgt ctttagtaac aatacagcag aaaaggcgg tggagctatt | 1080 |
| tatgctccta ctatcgatat aagcacgaat ggaggatcga ttctatttga agaaaccga | 1140 |
| gctgcagaag gaggcgccat ctgcgtgagt gaagcaagct ctggttcaac tggaaatctt | 1200 |
| actttaagcg cttctgatgg ggatattgtt ttttctggga atatgacgag tgatcgtcct | 1260 |
| ggagagcgca cgcagcaag aatcttaagt gatggaacga ctgtttcttt aaatgcttcc | 1320 |
| ggactatcga agctgatctt ttatgatcct gtagtacaaa ataattcagc agcgggtgca | 1380 |
| tcgacaccat caccatcttc ttcttctatg cctggtgctg tcacgattaa tcagtccggt | 1440 |
| aatggatctg tgatttttac cgccgagtca ttgactcctt cagaaaaact tcaagttctt | 1500 |
| aactctactt ctaacttccc aggagctctg actgtgtcag gaggggagtt ggttgtgacg | 1560 |
| gaaggagcta ccttaactac tgggaccatt acagccacct ctggacgagt gactttagga | 1620 |
| tccggagctt cgttgtctgc cgttgcaggt gctgcaaata ataattatac ttgtacagta | 1680 |
| tctaagttgg ggattgattt agaatccttt ttaactccta actataagac ggccatactg | 1740 |
| ggtgcggatg aacagttac tgttaacagc ggctctactt tagacctagt gatggagagt | 1800 |
| gaggcagagg tatatgataa tccgcttttt gtgggatcgc tgacaattcc ttttgttact | 1860 |
| ctatcttcta gtagtgctag taacggagtt acaaaaaatt ctgtcactat taatgatgca | 1920 |
| gacgctgcgc actatgggta tcaaggctct tggtctgcag attggacgaa accgcctctg | 1980 |
| gctcctgatg ctaaggggat ggtacctcct aataccaata acactctgta tctgacatgg | 2040 |

-continued agacctgctt cgaattacgg tgaatatcga ctggatcctc agagaaaggg agaactagta 2100
cccaactctc tttgggtagc gggatctgca ttaagaacct ttactaatgg tttgaaagaa 2160
cactatgttt ctagagatgt tggatttgta gcatctctgc atgctctcgg ggattatatt 2220
ttgaattata cgcaagatga tcgggatggc tttttagcta gatatggggg attccaggcg 2280
accgcagcct cccattatga aaatgggtca atatttggag tggcttttgg acaactctat 2340
ggtcagacaa agagcagaat gtattactct aaagatgctg ggaacatgac gatgttgtcc 2400
tgtttcggaa gaagttacgt agatattaaa ggaacagaaa ctgttatgta ttgggagacg 2460
gcttatggct attctgtgca cagaatgcat acgcagtatt ttaatgacaa aacgcagaag 2520
ttcgatcatt cgaaatgtca ttggcacaac aataactatt atgcgtttgt gggtgccgag 2580
cataatttct tagagtactg cattcctact cgtcagttcg ctagagatta tgagcttaca 2640
gggtttatgc gttttgaaat ggccggagga tggtccagtt ctacacgaga aactggctcc 2700
ctaactagat atttcgctcg cgggtcaggg cataatatgt cgcttccaat aggaattgta 2760
gctcatgcag tttctcatgt gcgaagatct cctccttcta aactgacact aaatatggga 2820
tatagaccag acatttggcg tgtcactcca cattgcaata tggaaattat tgctaacgga 2880
gtgaagacac ctatacaagg atctccgctg gcacggcatg ccttcttctt agaagtgcat 2940
gatactttgt atattcatca ttttggaaga gcctatatga actattcgct ggatgctcgt 3000
cgtcgacaaa cggcacattt tgtatccatg ggcttgaata gaatcttt 3048

<210> SEQ ID NO 81
<211> LENGTH: 1038
<212> TYPE: DNA
<213> ORGANISM: Chlamydia trachomatis serovar D

<400> SEQUENCE: 81
atgcaagcag atattttaga tggaaaacag aaacgcgtta atctaaatag caagcgtcta 60
gtgaactgca accaggtcga tgtcaaccaa cttgttccta ttaagtacaa atgggcttgg 120
gaacattatt tgaatggctg cgcaaataac tggctcccta cagagatccc catggggaaa 180
gacatcgaat tatggaagtc ggatcgtctt tctgaagatg agcggcgagt cattcttttg 240
aatttaggtt ttttcagcac cgcagagagc ttggttggga ataatattgt tctagcaatt 300
tttaaacatg taactaatcc ggaagcgaga caatatcttt taagacaagc ttttgaagaa 360
gcggttcaca cgcacacatt tttgtatatt tgtgagtcac tcggattaga cgagaaagaa 420
attttcaatg cctataacga gcgtgctgcg attaaggcca aagatgattt ccagatggaa 480
atcactggca aggtattaga tcctaatttt cgcacggact ctgttgaggg tctacaggag 540
tttgttaaaa acttagtagg atactacatc attatggaag ggattttctt ctatagtggg 600
tttgtgatga tcctttcctt ccacagacaa aataagatga ttggtattgg agaacaatat 660
caatacatct taagagatga gacaatccac ttgaactttg gtattgattt gatcaacggg 720
ataaaagaag agaacccgga gatttggact ccagagttac agcaagaaat tgtcgaatta 780
attaagcgag ctgtcgattt agaaattgag tatgcgcaag actgtctccc tagagggatt 840
ttgggattga gagcttcgat gttcatcgat tatgtgcagc atattgcaga ccgtcgtttg 900
gaaagaatcg gattaaaacc tatttatcat acgaaaaacc cattcccttg gatgagcgaa 960
acaatagacc ttaataaaga gaaaaacttc tttgaaacaa gggttataga atatcaacat 1020
gcagcaagct taacttgg 1038

<210> SEQ ID NO 82
<211> LENGTH: 3159
<212> TYPE: DNA
<213> ORGANISM: Chlamydia trachomatis serovar D

<400> SEQUENCE: 82

| | | | | | |
|---|---|---|---|---|---|
| atgtttacaa | ggatagttat | ggtcgatcta | caagaaaagc | aatgcacaat | tgttaagcgc | 60 |
| aatggaatgt | ttgttccttt | cgatcggaac | cgtatttttc | aggctttaga | agcagctttt | 120 |
| cgagacactc | gcagaattga | tgatcatatg | cctttgcctg | aagatctgga | aagttccata | 180 |
| cgctcgataa | cgcatcaggt | agttaaagaa | gttgtgcaaa | agattacaga | tggacaagtg | 240 |
| gttactgtag | agcgtatcca | agatatggtt | gaaagccaac | tatatgtgaa | tggtttgcaa | 300 |
| gatgttgctc | gcgattatat | tgtctatcgc | gatgaccgta | aagcgcatcg | gaaaaaatct | 360 |
| tggcaaagcc | tatccgttgt | tcgtcgttgt | gggactgttg | tacactttaa | tcctatgaaa | 420 |
| atttccgccg | ctttggaaaa | agctttccga | gctaccgata | agactgaggg | gatgactcca | 480 |
| agttctgtgc | gagaggaaat | caatgctttg | acgcaaaaca | ttgtcgcgga | aatagaagaa | 540 |
| tgttgtcctc | aacaggatag | acgcattgat | atcgagaaga | ttcaagatat | tgttgaacag | 600 |
| caactaatgg | ttgttgggca | ttatgctgtt | gcaaagaact | atattcttta | tcgagaagct | 660 |
| cgcgctcgtg | ttcgtgataa | cagagaagag | acgggagta | cagaaaagac | tatagcagaa | 720 |
| gaagctgttg | aggtgctcag | taaagacggt | tctacctata | caatgacgca | ttcgcagttg | 780 |
| ttggctcatt | tagcgcgcgc | ttgtagtcgt | tttccagaaa | cgacagatgc | ggcgctgctt | 840 |
| accgatatgg | ctttcgcaaa | tttctattcc | ggtatcaaag | agtctgaagt | agtactggcc | 900 |
| tgtattatgg | cggctcgtgc | caatattgaa | aaggagcctg | attatgcctt | tgttgctgca | 960 |
| gagctcttac | ttgacgttgt | atataaggaa | gcgttaggga | aatcgaaata | tgctgaggat | 1020 |
| ttagaacaag | cacatcgcga | tcatttcaaa | cgctacatcg | cagaagggga | tacctatcgt | 1080 |
| ctgaatgctg | aactgaaaca | tcttttttgat | ttagacgcgt | tagccgatgc | tatggatcta | 1140 |
| tctcgagatc | tacagttttc | ttacatgggt | attcaaaatc | tgtatgatcg | ttatttaat | 1200 |
| caccacgaag | gttgccgttt | agaaactccc | caaatttttt | ggatgcgcgt | tgctatgggg | 1260 |
| ttggcattga | tgagcaaga | caagacttct | tgggctatta | cttttttataa | tttgctttcg | 1320 |
| acattccgat | atacaccagc | tacgccaacc | ttgttcaatt | caggtatgcg | gcattctcag | 1380 |
| ttaagctctt | gctatctttc | cactgtacaa | gataatttgg | tcaatatcta | taaggtcatt | 1440 |
| gctgataacg | ctatgctatc | taagtgggca | ggagggata | gtaatgattg | gacggcgatt | 1500 |
| cgtgcaacag | ggctttaat | taaggaacc | aatggaagaa | gtcagggagt | aattcctttt | 1560 |
| attaaggtga | caaatgatac | agcagtcgca | gtgaatcaag | tggtaaacg | caagggagct | 1620 |
| gtatgcgtct | atttagaagt | ttggcacctc | gactacgaag | atttccttga | attgagaaag | 1680 |
| aatacagggg | atgagcgtcg | acgggctcat | gatgtcaata | tagctagctg | gattccagat | 1740 |
| cttttcttca | aacgtttaca | gcaaaaaggg | acatggactc | tattcagccc | agatgatgtt | 1800 |
| ccgggattac | acgatgctta | tgggaagaa | tttgagcgtt | tgtacgaaga | atatgagcgg | 1860 |
| aaggttgata | ccggagagat | tcggttattc | aagaaggtag | aagctgaaga | tctgtggaga | 1920 |
| aaaatgctca | gcatgctttt | tgaaacggga | cacccatgga | tgactttaa | agatccatcc | 1980 |
| aacatccgtt | cggctcaaga | tcataaaggc | gtggtgcgtt | gttccaatct | gtgtacggag | 2040 |
| attttgttaa | actgctcgga | gacagaaact | gctgtttgta | atttaggatc | gattaactta | 2100 |
| gttcaacata | tcgtagggga | tgggttagat | gaggaaaaac | tctctgagac | gatctctata | 2160 |

```
gcagtccgta tgttggataa cgtgattgat attaactttt atccaacaaa ggaagctaaa     2220
gaggcgaact tgctcaccg cgctattgga ttaggggtga tgggattcca agatgccttg     2280
tataagctag atataagcta tgcttcgcaa gaagctgtag aatttgctga ctacagttca     2340
gagttgattt cttactatgc gattcaagct tcttgtctgc tcgctaaaga acgaggcact     2400
tacagctctt ataaaggatc gaaatgggat agaggtttgc tccctattga tacgattcag     2460
ttgttagcga actatcgagg agaagcaaat ctccagatgg atacgtcatc aagaaaagat     2520
tgggaaccta tccgtagttt ggttaaagag catggtatgc gacattgtca gcttatggct     2580
atagctccga cagcgacgat ctccaacatt ataggagtaa ctcaatctat tgagccaacg     2640
tacaaacatt tgtttgtgaa gtctaatttg tccggagaat tcacgattcc aaatgtgtat     2700
ttaattgaga agttgaagaa attaggtatc tgggatgctg atatgttaga tgacctgaaa     2760
tattttgatg ggtctttatt ggaaatcgag cgtataccag atcacttaaa acatattttc     2820
ttgacagctt ttgagattga accagaatgg attatcgaat gcgcgtctcg aagacaaaaa     2880
tggattgata tggggcaatc cctcaacctt tatcttgccc agccagacgg gaaaaaactg     2940
tcgaatatgt atttaacggc ttggaaaaaa ggtttgaaaa ctacgtatta tctgagatct     3000
tcatcagcaa cgaccgttga aaaatctttt gtagatatta ataagagagg aattcagcct     3060
cgttggatga agaataagtc tgcttcggca ggaattattg ttgaaagagc gaagaaagca     3120
cctgtctgtt ctttggaaga agggtgtgaa gcatgtcag                             3159

<210> SEQ ID NO 83
<211> LENGTH: 4593
<212> TYPE: DNA
<213> ORGANISM: Chlamydia trachomatis serovar D

<400> SEQUENCE: 83
atgagttccg agaaagatat aaaaagcacc tgttctaagt tttctttgtc tgtagtagca       60
gctatccttg cctctgttag cgggttagct agttgcgtag atcttcatgc tggaggacag      120
tctgtaaatg agctggtata tgtaggccct caagcggttt tattgttaga ccaaattcga      180
gatctattcg ttgggtctaa agatagtcag gctgaaggac agtataggtt aattgtagga      240
gatccaagtt ctttccaaga gaaagatgcg gatactcttc ccgggaaggt agagcaaagt      300
actttgttct cagtaaccaa tcccgtggtt ttccaaggtg tggaccaaca ggatcaagtc      360
tcttcccaag ggtaaatttg tagttttacg agcagcaacc ttgattctcc tcgtgacgga      420
gaatcttttt taggtattgc ttttgttggg gatagtagta aggctggaat cacattaact      480
gacgtgaaag cttctttgtc tggagcggct ttatattcta cagaagatct tatctttgaa      540
aagattaagg gtggattgga atttgcatca tgttcttctc tagaacaggg gggagcttgt      600
gcagctcaaa gtattttgat tcatgattgt caaggattgc aggttaaaca ctgtactaca      660
gccgtgaatg ctgagggtc tagtgcgaat gatcatcttg gatttggagg aggcgctttc      720
tttgttacgg gttctctttc tggagagaaa agtctctata tgcctgcagg agatatggta      780
gttgcgaatt gtgatggggc tatatctttt gaaggaaaca gcgcgaactt tgctaatgga      840
ggagcgattg ctgcctctgg gaaagtgctt tttgtcgcta atgataaaaa gacttctttt      900
atagagaacc gagctttgtc tggaggagcg attgcagcct cttctgatat tgcctttcaa      960
aactgcgcag aactagtttt caaaggcaat tgtgcaattg aacagagga taaaggttct     1020 ttaggtggag gggctatatc ttctctaggc accgttcttt tgcaagggaa tcacgggata     1080
```

```
acttgtgata agaatgagtc tgcttcgcaa ggaggcgcca tttttggcaa aaattgtcag    1140
atttctgaca acgaggggcc agtggttttc agagatagta cagcttgctt aggaggaggc    1200
gctattgcag ctcaagaaat tgtttctatt cagaacaatc aggctgggat ttccttcgag    1260
ggaggtaagg ctagtttcgg aggaggtatt gcgtgtggat cttttttcttc cgcaggtggt   1320 gcttctgttt tagggaccat tgatatttcg aagaatttag gcgcgatttc gttctctcgt    1380
actttatgta cgacctcaga tttaggacaa atggagtacc aggaggagg agctctatt     1440 ggtgaaaata tttctctttc tgagaatgct ggtgtgctca cctttaaaga caacattgtg    1500
aagacttttg cttcgaatgg gaaaattctg ggaggaggag cgattttagc tactggtaag    1560
gtggaaatta ctaataattc cgaaggaatt tcttttacag gaaatgcgag agctccacaa    1620
gctcttccaa ctcaagagga gtttccttta ttcagcaaaa agaagggcg accactctct     1680 tcaggatatt ctgggggagg agcgattttta ggaagagaag tagctattct ccacaacgct   1740
gcagtagtat ttgagcaaaa tcgtttgcag tgcagcgaag aagaagcgac attattaggt    1800
tgttgtggag gaggcgctgt tcatgggatg gatagcactt cgattgttgg caactcttca    1860
gtaagatttg gtaataatta cgcaatggga caaggagtct caggaggagc tcttttatct    1920
aaaacagtgc agttagctgg gaatggaagc gtcgatttt ctcgaaatat gctagtttg      1980 ggaggaggag ctcttcaagc ttctgaagga aattgtgagc tagttgataa cggctatgtg    2040
ctattcagag ataatcgagg gagggtttat ggggtgcta tttcttgctt acgtggagat     2100
gtagtcattt ctggaaacaa gggtagagtt gaatttaaag acaacatagc aacacgtctt    2160
tatgtggaag aaactgtaga aaaggttgaa gaggtagagc cagctcctga gcaaaaagac    2220
aataatgagc tttctttctt agggagagca gaacagagtt ttattactgc agctaatcaa    2280
gctcttttcg catctgaaga tggggattta tcacctgagt catccatttc ttctgaagaa    2340
cttgcgaaaa gaagagagtg tgctggagga gctattttttg caaaacgggt tcgtattgta   2400
gataaccaag aggccgttgt attctcgaat aacttctctg atatttatgg cggcgccatt    2460
tttacaggtt ctcttcgaga agaggataag ttagatgggc aaatccctga gtcttgatc     2520 tcaggcaatg caggggatgt tgttttttcc ggaaattcct cgaagcgtga tgagcatctt    2580
cctcatacag gtgggggagc catttgtact caaaatttga cgatttctca gaatacaggg    2640
aatgttctgt tttataacaa cgtggcctgt tcgggaggag ctgttcgtat agaggatcat    2700
ggtaatgttc ttttagaagc ttttggagga gatattgttt ttaaaggaaa ttcttctttc    2760
agagcacaag gatccgatgc tatctatttt gcaggtaaag aatcgcatat tacagccctg    2820
aatgctacgg aaggacatgc tattgttttc cacgacgcat tagttttttga aaatctagaa   2880 gaaaggaaat ctgctgaagt attgttaatc aatagtcgag aaaatccagg ttacactgga    2940
tctattcgat ttttagaagc agaaagtaaa gttcctcaat gtattcatgt acaacaagga    3000
agccttgagt tgctaaatgg agccacatta tgtagttatg gttttaaaca agatgctgga    3060
gctaagttgg tattggctgc tggagctaaa ctgaagattt tagattcagg aactcctgta    3120
caacaagggc atgctatcag taaacctgaa gcagaaatcg agtcatcttc tgaaccagag    3180
ggtgcacatt ctcttggat tgcgaagaat gctcaaacaa cagttcctat ggttgatatc     3240
catactattt ctgtagattt agcctccttc tcttctagtc aacaggaggg gacagtagaa    3300
gctcctcagg ttattgttcc tggaggaagt tatgttcgat ctggagagct taatttggag    3360
ttagttaaca caacaggtac tggttatgaa aatcatgctt tattgaagaa tgaggctaaa    3420
gttccattga tgtctttcgt tgcttctggt gatgaagctt cagccgaaat cagtaacttg    3480
```

-continued

```
tcggtttctg atttacagat tcatgtagta actccagaga ttgaagaaga cacatacggc    3540
catatgggag attggtctga ggctaaaatt caagatggaa ctcttgtcat tagttggaat    3600
cctactggat atcgattaga tcctcaaaaa gcagggcctt tagtatttaa tgcattatgg    3660
gaagaagggg ctgtcttgtc tgctctgaaa atgcacgct ttgctcataa tctcactgct     3720
cagcgtatgg aattcgatta ttctacaaat gtgtgggat tcgcctttgg tggtttccga     3780
actctatctg cagagaatct ggttgctatt gatggataca aaggagctta tggtggtgct    3840
tctgctggag tcgatattca attgatgaa gattttgttc taggagttag tggagctgct     3900
ttcctaggta aaatggatag tcagaagttt gatgcggagg tttctcggaa gggagttgtt    3960
ggttctgtat atacaggatt tttagctgga tcctggttct tcaaaggaca atatagcctt    4020
ggagaaacac agaacgatat gaaaacgcgt tatggagtac taggagagtc gagtgcttct    4080
tggacatctc gaggagtact ggcagatgct ttagttgaat accgaagttt agttggtcct    4140
gtgagaccta ctttttatgc tttgcatttc aatccttatg tcgaagtatc ttatgcttct    4200
atgaaattcc ctggctttac agaacaagga agagaagcgc gttctttga agacgcttcc     4260 cttaccaata tcaccattcc tttagggatg aagtttgaat tggcgttcat aaaaggacag    4320
ttttcagagg tgaactcttt gggaataagt tatgcatggg aagcttatcg aaaagtagaa    4380
ggaggcgcgg tgcagctttt agaagctggg tttgattggg agggagctcc aatggatctt    4440
cctagacagg agctgcgtgt cgctctggaa aataatacgg aatggagttc ttacttcagc    4500
acagtcttag gattaacagc ttttttgtgga ggatttactt ctacagatag taaactagga    4560
tatgaggcga atactggatt gcgattgatc ttt                                 4593
```

<210> SEQ ID NO 84
<211> LENGTH: 1422
<212> TYPE: DNA
<213> ORGANISM: Chlamydia trachomatis serovar D

<400> SEQUENCE: 84

```
atgaaaatta ttcacacagc tatcgaattt gctccggtaa tcaaagccgg aggcctggga     60
gacgcgctat acggactagc aaaagcttta gccgctaatc acacaacgga agtggtaatc    120
cctttatacc ctaaattatt tactttgccc aaagaacaag atctttgctc gatccaaaaa    180
ttatcttatt tttttgctgg agagcaagaa gcaactgctt tctcctactt ttatgaagga    240
attaaagtaa ctctattcaa actcgacaca cagccagagt tattcgagaa tgcggaaaca    300
atctacacaa gcgatgatgc cttccgtttt tgcgcttttt ctgctgctgc ggcctcctac    360
atccaaaaag aaggagccaa tatcgttcat ttacacgatt ggcatacagg attagttgct    420
ggactactca acaacagcc tgctctcaa ttacaaaaga ttgttcttac cctacataat      480
tttggttatc gaggctatac aacacgagaa atattagaag cctcctcttt gaatgaattt    540
tatatcagcc agtaccaact atttcgcgat ccacaaactt gtgtgttgct aaaaggagct    600
ttatactgtt cagatttcgt gactacggtt tctcctacat acgccaaaga aattcttgaa    660
gattattccg attacgaaat tcacgatgcc attactgcta gacaacatca tctccgcggg    720
atttttaatg aatcgacac gacaatttgg gggcctgaaa cggatcccaa tttagcgaaa    780
aactacacta aagagctttt cgagacccct tcaatttttt ttgaagctaa agccgagaat    840
aaaaaagcct tgtacgaaag attaggcctc tctttagaac actctccttg cgtgtgcatt    900
atttctagaa ttgctgagca gaaaggtcct cactttatga acaggccat tctccatgca    960
```

-continued

```
ctagaaaacg cttacacgct cattattata ggtacctgct acgggaatca attgcatgaa   1020
gaatttgcaa atcttcaaga atcattagcg aattcccctg atgtaaggat tcttttgact   1080
tatagtgatg tgctggcacg acaaattttc gccgctgcag atatgatctg cattccttct   1140
atgtttgaac catgtggact cacacaaatg attggaatgc gttacgggac tgtaccgtta   1200
gtaagagcta caggaggact agcagatact gtagcaaatg gaatcaatgg attttccttc   1260
tttaatccgc atgacttcta tgaattccga aacatgcttt cggaagcagt gacaacctac   1320
cgtaccaacc acgacaagtg gcaacatatt gtacgtgctt gtctagattt ttcttcagac   1380
ctagaaactg ccgccaataa atatttagaa atttataaac aa                      1422
```

<210> SEQ ID NO 85
<211> LENGTH: 1179
<212> TYPE: DNA
<213> ORGANISM: Chlamydia trachomatis serovar D

<400> SEQUENCE: 85

```
atgaaaaaac tcttgaaatc ggtattagta tttgccgctt tgagttctgc ttcctccttg     60
caagctctgc ctgtggggaa tcctgctgaa ccaagcctta tgatcgacgg aattctgtgg    120
gaaggtttcg gcggagatcc ttgcgatcct tgcgccactt ggtgtgacgc tatcagcatg    180
cgtgttggtt actacggaga ctttgttttc gaccgtgttt tgaaaactga tgtgaataaa    240
gaatttcaga tgggtgccaa gcctacaact gatacaggca atagtgcagc tccatccact    300
cttacagcaa gagagaatcc tgcttacggc cgacatatgc aggatgctga gatgtttaca    360
aatgccgctt gcatggcatt gaatatttgg gatcgttttg atgtattctg tacattagga    420
gccaccagtg gatatcttaa aggaaactct gcttctttca atttagttgg attgtttgga    480
gataatgaaa atcaaaaaac ggtcaaagcg gagtctgtac caaatatgag ctttgatcaa    540
tctgttgttg agttgtatac agatactact tttgcgtgga gcgtcggcgc tcgcgcagct    600
ttgtgggaat gtggatgtgc aactttagga gcttcattcc aatatgctca atctaaacct    660
aaagtagaag aattaaacgt tctctgcaat gcagcagagt ttactattaa taaacctaaa    720
gggtatgtag gtaaggagtt tcctcttgat cttacagcag gaacagatgc tgcgacagga    780
actaaggatg cctctattga ttaccatgaa tggcaagcaa gtttagctct ctcttacaga    840
ctgaatatgt tcactcccta cattggagtt aaatggtctc gagcaagctt tgatgccgat    900
acgattcgta tagcccagcc aaaatcagct acagctattt ttgatactac cacgcttaac    960
ccaactattg ctggagctgg cgatgtgaaa actggcgcag agggtcagct cggagacaca   1020
atgcaaatcg tttccttgca attgaacaag atgaaatcta gaaaatcttg cggtattgca   1080
gtaggaacaa ctattgtgga tgcagacaaa tacgcagtta cagttgagac tcgcttgatc   1140
gatgagagag cagctcacgt aaatgcacaa ttccgcttc                          1179
```

<210> SEQ ID NO 86
<211> LENGTH: 585
<212> TYPE: DNA
<213> ORGANISM: Chlamydia trachomatis serovar D

<400> SEQUENCE: 86

```
atgggatcac tagttggaag acaggctccg gatttttctg gtaaagccgt tgtttgtgga     60
gaagagaaag aaatctctct agcagacttt cgtggtaagt atgtagtgct cttcttttat    120
cctaaagatt ttacctatgt ttgtcctaca gaattgcatg cttttcaaga tagattggta    180
gattttgaag agcgaggtgc agtcgtgctt ggttgctccg ttgacgacat tgagacacat    240
```

-continued

```
tctcgttggc tcgctgtagc gagaaatgca ggaggaatag agggaacaga atatcctctg      300
ttagcagacc cttcttttaa aatatcagaa gcttttggtg ttttgaatcc tgaaggatcg      360
ctcgctttaa gagcgacttt ccttatcgat aaatatgggg ttgttcgtca tgcggttatc      420
aatgatcttc ctttagggcg ttccattgac gaggaattgc gtattttaga ttcattgatc      480
ttctttgaga accacggaat ggtttgtcca gctaactggc gttctggaga gcgtggaatg      540
gtgccttctg aagagggatt aaaagaatat tccagacga tggat                       585
```

<210> SEQ ID NO 87
<211> LENGTH: 258
<212> TYPE: DNA
<213> ORGANISM: Chlamydia trachomatis serovar D

<400> SEQUENCE: 87

```
atgagtcaaa ataagaactc tgctttcatg cagcctgtga acgtatccgc tgatttagct       60
gccatcgttg gtgcaggacc tatgcctcgc acagagatca ttaagaaaat gtgggattac      120
attaagaaga atggccttca agatcctaca acaaaacgta atatcaatcc cgatgataaa      180
ttggctaaag ttttttggaac tgaaaaacct atcgatatgt ccaaatgac aaaaatggtt      240 tctcaacaca tcattaaa                                                    258
```

<210> SEQ ID NO 88
<211> LENGTH: 1182
<212> TYPE: DNA
<213> ORGANISM: Chlamydia trachomatis serovar D

<400> SEQUENCE: 88

```
atgtcaaaag aaacttttca acgtaataag cctcatatca acatagggac cattggccac       60
gttgaccatg gtaagactac gttgacagct gctattacgc gtgcgttgtc tggagatggg      120
ttggctgatt tcgtgatta tagctctatt gacaacactc ctgaagaaaa agctcgcggt      180
attacaatta acgcttccca cgttgagtac gaaacagcta atcgtcacta cgctcacgtg      240
gactgccctg gtcacgctga ctatgttaaa aacatgatca ccgtgcagc tcaaatggac      300 ggggctattc tagtagtttc tgcaacagac ggagctatgc ctcaaactaa agagcatatt      360
cttttggcaa gacaagttgg ggttccttac atcgttgttt ttctcaataa aattgacatg      420
atttccgaag aagacgctga attggtcgac ttagttgaga tggagttggt tgagcttctt      480
gaagagaaag gatacaaagg gtgtccaatc atcagaggtt ctgctctgaa agctttggaa      540
ggggatgctg catacataga gaaagttcga gagctaatgc aagccgtcga tgataacatc      600
cctactccag aaagagaaat tgacaagcct tccttaatgc ctattgagga cgtattctct      660
atctccggac gaggaactgt agtaactgga cgtattgagc gtggaattgt taaagttttcc      720 gataaagttc agttggtcgg tcttagagat actaaagaaa cgattgttac tggggttgaa      780
atgttcagaa agaactccc agaaggtcgt gcaggagaga acgttggatt gctcctcaga      840
ggtattggta gaacgatgt ggaaagagga atggttgttt gcttgccaaa cagtgttaaa      900
cctcatacac agttcaagtg tgctgtttac gttttgcaaa agaagaagg tggacgacat      960 aagcctttct tcacaggata tagacctcaa ttcttcttcc gtacaacaga cgtcacaggt     1020
gtggtaactc tgcctgaggg aattgagatg gtcatgcctg gggataacgt tgagtttgaa     1080
gtgcaattga ttagccctgt ggcttttagaa gaaggtatga gatttgcgat tcgtgaaggt     1140
ggtcgtacaa tcggtgctgg aactatttct aagatcattg ca                        1182
```

-continued

<210> SEQ ID NO 89
<211> LENGTH: 246
<212> TYPE: DNA
<213> ORGANISM: Chlamydia trachomatis serovar D

<400> SEQUENCE: 89
atggggcaag atcaccgaag aaaatttctt aagaaagtat cttttgtaaa aaaacaagca 60
gcttttgcgg gtaactttat cgaagaaatt aagaagattg agtgggtaaa taagcgagat 120
cttaaaagat acgtcaagat tgttttgatg aatatttttg gctttggatt ttccatctat 180
tgtgtggatt tagctcttcg aaagtccctt tcattgttcg gtaaagtaac aagctttttc 240
tttggt 246

<210> SEQ ID NO 90
<211> LENGTH: 1137
<212> TYPE: DNA
<213> ORGANISM: Chlamydia trachomatis serovar D

<400> SEQUENCE: 90
atggtgatcc ctaaggtgga tctaggagaa agtgccgtca tgatgggtta caagcttact 60
tcgcaacttg ctatgctttc gatcttattg actttcaccc atactatggg tcatgcaagt 120
cagatgagcc aaactcttcc tactattata gaagcacaag cggaagaggc attgcaggct 180
gacaggggag ttgctggaca ggctcttaaa aaacttcgta aaaaaagatg tgcttctaga 240
aaatctgcat gtaaggcttc ttttaagaaa aaggatttct tttcttgtat tacaaatgga 300
ttgttctctg gaaatcatga gcagcgttta actgcgaaaa aagagaacaa ggctcgaggt 360
aaagagcctc gagtagtggt tcaaacgact aaaaaacgac aaataactca gtctgagaaa 420
gaatttttcg attggctatg taatagtaaa agagaaagaa agcttctcaa gaaaaagcct 480
gtaaatactt ctcttgctaa gagtgaagaa ttgagtccta aagaagcagc aatagctgct 540
gctcgagctt ctctttctcc agaagaaaaa cgtcaattga ttcgtgagtg gttagcagaa 600
gaaaagactg ctcgtaaatc tgggcgtgcg gcttgtgcgg taagtgagaa tcttaaaaga 660
gacggaagta ttacttctac attgcgctat gatgcggaga aagctttgac tacacgtgta 720
aaacgcaatg aaaattctgt aaatgctaga gcaagacaac gagccgctct tcaaaaagcc 780
aagaaagcaa agacggagaa acctgaggct gatgagaaag ctgcagaagc tgttgccgca 840
gctccaacca aacaggcgca taaggagcca gagaattact tcgcagctac agcttctaca 900
aataatacta atgttatgtc ctatctaaat gctcatcaat accgttgtga ttcttcggag 960
acggactggc cttgctcttc ttgtgttacg aaacgccgag ctaacttcgg tatttctgtg 1020
tgtactatgg tggttaccgt cattgctatg atcgtaggag ctgttatcat ttctaatgct 1080
acagactcta ccgttgcggg ctcctcggga acaggaggag gaggctcaac gcaacca 1137

<210> SEQ ID NO 91
<211> LENGTH: 1689
<212> TYPE: DNA
<213> ORGANISM: Chlamydia trachomatis serovar D

<400> SEQUENCE: 91
atggtttatt ttagagctca tcaacctagg catacgccta aaacatttcc tttggaagtt 60
caccattcgt tctccgataa gcatcctcaa attgctaaag ctatgcggat tacggggata 120
gccctcgcag ctctatctct gctcgctgta gtcgcctgcg ttattgccgt ctctgcggga 180
ggagctgcca ttcctcttgc tgtcattagt ggaattgctg taatgtctgg cctcttatcc 240

-continued

```
gctgccacca ttatctgttc tgcaaaaaag gctttggctc aacgaaaaca aaaacaacta      300
gaagagtcgc ttccgttaga taatgcgacc gagcatgtga gttacctgac ctcagacacc      360
tcttatttta atcaatggga atccttaggt gctctaaata agcagttgtc tcagattgac      420
ttaactattc aagctcccga aaaaaaacta ttaaaagaag ttcttggttc cagatacgat      480
tccattaatc actccatcga agagatctcc gatcgcttta cgaaaatgct ctctcttctt      540
cgattaagag aacattttta tcgaggagaa gagcgttatg cccctatttt aagcccctcct     600 ctacttaaca agaatcgttt gctgacccaa atcacatcca atatgattag gatgctacca      660
aaatccggtg gtgttttttc cctcaaagcc aatacactaa gtcatgccag ccgcacacta      720
tatacagtat aaaagtcgc tttatcctta ggagttctcg ctggagtcgc tgctcttatc       780
atctttcttc ccctagcct gccttttatc gctgttatag gagtatcttc cttagcattg       840
gggatggcat ctttccttat gattcggggc attaagtatt tgctcgaaca ttctcctctg      900
aatagaaagc aactagctaa agatattcaa aaaaccattg gcccagatgt cttggcctct      960
atggttcatt accagcatca attactatca catctacatg aaactctatt agatgaagcc     1020
atcacagcta gatggagcga gcccttcttt attgaacacg ctaatcttaa ggcaaaaatt     1080
gaagatttga caaaacaata tgatatattg aacgcagcct ttaataaatc tttacaacaa     1140
gatgaggcgc tccgttctca attagagaaa cgagcttact tattcccaat tcctaataac     1200
gacgaaaatg ctaaaactaa agaatcgcag cttctagact cagaaaatga ttcaaattct     1260
gaatttcagg agattataaa taaggacta gaagctgcca ataaacgacg agctgacgct      1320
aagtcaaaat tctatacgga agacgaaacc tctgacaaaa tattctctat atggaaaccc     1380
acaaagaact tggcattaga agatttgtgg agagtgcatg aagcttgcaa tgaagagcaa     1440
caagctctcc tcttagaaga ttatatgagt tataaaacct cagaatgtca agctgcactc     1500
caaaaagtga gtcaagaact gaaggcggca caaaaatcat tcgcagtcct agaaaagcat     1560
gctctagaca gatcttatga atccagtgta gccacgatgg atttagctag agcgaatcaa     1620
gaaacacacc ggcttctgaa catcctctct gaattacaac aactagcaca atacctgtta     1680
gataatcac                                                            1689
```

<210> SEQ ID NO 92
<211> LENGTH: 1074
<212> TYPE: DNA
<213> ORGANISM: Chlamydia trachomatis serovar D

<400> SEQUENCE: 92

```
gtgcgtaaaa ctgtcattgt tgctatgtct ggaggagtgg attcctcggt tgttgcttat       60
ctcttaaaga agcaagggga gtataatgtt gttgggctct tcatgaaaaa ttggggagag      120
caggacgaga atggtgagtg tactgcaacc aaagattttc gcgatgtaga gcggatcgca      180
gaacaattgt ccattccata ttacacagtt tccttttcta aggaatataa agagcgagtg      240
tttttctaga ttctaagaga atatgcgaac ggctacactc ccaatcctga tgtgttatgc      300
aatcgagaaa tcaaatttga tttattacag aagaaggtac gtgagctaaa aggtgatttt      360
ttagccacgg gacattattg tcgaggaggg gctgatggaa ctggtttgtc cagaggaata      420
gaccccaata agaccaaag ttatttctta tgtggcactc ctaaggatgc tttatccaat       480
gtacttttcc ccctgggagg tatgtataaa acggaggtac gtcgaattgc tcaagaagct      540
ggtttagcta ccgccacaaa aaaagatagc acagggattt gcttcattgg taaacggcct      600
```

-continued

```
tttaagagtt tccttgagca gtttgtagca gactctcctg gagacattat tgattttgat      660
acacaacagg tagtcggccg acatgaagga gcccattatt atacgattgg acagcgtcga      720
gggttaaaca taggaggaat ggaaaagcct tgttatgttc ttagcaagaa tatggaaaag      780
aatattgttt acattgtaag gggtgaagat catcctttac tttatcgaca agagctttta      840
gctaaggaac ttaattggtt tgttcccttg caggagccta tgatctgtag tgctaaagtt      900
cggtacagat cccctgacga gaaatgttct gtatatcctt tggaagatgg aacggtaaaa      960
gtgattttcg atgtccctgt gaaagctgtc acccctggac agactgtagc tttctaccag     1020
ggggacattt gtttaggagg aggagtgatt gaagtgccta tgattcatca gctg            1074
```

<210> SEQ ID NO 93
<211> LENGTH: 801
<212> TYPE: DNA
<213> ORGANISM: Chlamydia trachomatis serovar D

<400> SEQUENCE: 93

```
atgtccagaa aaccggcttc taactcatcc cggaacacca aacggtcctc agacacttcc       60
tgggaagtca ttgcccaaga ttataataaa gccgttgatc gcgatggaca tttctatcat      120
aaggaagtga ttctccctaa tctcctttct aagctacata tttcccgctc atcgtctctg      180
gttgatgtag gatgtggtca agggattttg gagaagcatt acccaaaaca tctcccttat      240
ctaggaatcg atcttcccc tagtctgctg cgttttgcaa agaaaagcgc ttcctcaaaa       300
tcacgtcgct tcttcatca cgatatgacg caaccggtac cagcagatca tcatgagcag       360
ttttcccatg ctacagcaat cctttctctt cagaatatgg aatctccaga caagctatc       420
gcacacacag cgaatctttt ggctcctcaa ggtaggttgt ttattgttct caaccatcca      480
tgctttcgca tccctaggct tcttcatgg ctttatgatg agcctaaaaa actcttatct       540
agaaaaatag accgctatct ctctcctgtg gcggttccta tcgttgtgca tcctggagaa      600
aaacattctg agacgacata ttctttccat ttccccttaa gctattgggt acaagcttta      660
tctaatcaca atcttctgat tgatagtatg aagaatgga tctcccctaa aaaatcctca       720
gggaagaggg ctcgagcaga aaatctttgt cgcaaggagt ttccgctttt cttgtttatc      780
tcagcattaa aaatatcaaa a                                                801
```

<210> SEQ ID NO 94
<211> LENGTH: 2601
<212> TYPE: DNA
<213> ORGANISM: Chlamydia trachomatis serovar D

<400> SEQUENCE: 94

```
atggagaaat tttcagatgc agtaagcgaa gccttagaaa aggcgtttga gttagctaaa       60
aactctaagc attcctacgt gacagaaaac catttgctga aagtctttt gcaaaatcca       120
ggttccctat tttgtttggt cattaaggat gtgcacggta atcttggttt gcttacttct      180
gctgtggacg acgccttacg cagagaacca actgtagtcg agggaaccgc tgttgctagt      240
ccttctccaa gttacagca gttgttgctc aatgcgcatc aagaagctag aagtatgggt       300
gacgaatatc tatcagggga tcatttgtta ctagcttttt ggcgatcgac taaagagcct      360
tttgcttctt ggagaaaaac tgtaaaaact acctctgaag cgttgaaaga attaattact      420
aaattaagac aaggaagtcg tatggactca cctagtgctg aagaaaatct gaaaggatta      480
gagaaatact gcaaaaattt gactgtactt gcaagagaag gcaagcttga tcctgtgatt      540
ggtcgagatg aagagattag acgtacgata caggttcttt ctagacgaac aaagaataat      600
```

-continued

| | |
|---|---|
| cctatgttga tagggagcc cggagttggg aaaacagcaa tcgctgaagg acttgctctt | 660 |
| cgcatagtgc aaggggatgt tccagagagt ttaaaggaaa agcatctgta tgtactggat | 720 |
| atgggagctt tgattgcagg tgccaagtat cgaggagagt ttgaagagcg gttaaaaagt | 780 |
| gtattgaagg gtgtagaagc ttctgaaggc gagtgtatcc tattcattga tgaagtgcat | 840 |
| actttagtag gagcgggagc tacagatgga gctatggatg cagcgaatct attaaagcct | 900 |
| gctttagcac gaggcacttt gcattgtatt ggcgctacga ctttgaatga ataccaaaaa | 960 |
| tatatagaga aagacgcggc tttgaacgg cgtttccagc ctattttgt aacagaacct | 1020 |
| tctttggaag atgctgtatt cattctccgg gggttaaggg aaaaatatga aattttcat | 1080 |
| ggtgtgcgca ttacagaagg ggctttgaat gcagctgtag ttctttctta tcgttacatc | 1140 |
| acagaccgat tcttcctga taaggcgatt gacctaattg atgaggctgc gagtttaatc | 1200 |
| cgtatgcaaa taggaagttt acctctgcct attgatgaaa aggaaagaga attatcagct | 1260 |
| ttaatcgtga acaagaagc tattaaacgc gagcaagcac cagcttatca ggaagaggct | 1320 |
| gaagacatgc aaaagcaat tgaccgggtt aaggaagagc tggccgcttt acgcttgcgc | 1380 |
| tgggatgaag aaaaaggatt aattacagga ttaaaagaaa agaagaatgc tttagaaaat | 1440 |
| ttaaaatttg ccgaagagga agctgagcgt actgccgatt acaatcgggt ggcagaacta | 1500 |
| cgctatagtt tgattccttc tttggaggaa gaaattcatt tagctgagga agctttaaat | 1560 |
| caaagagatg ggcgcctgct tcaagagaa gttgatgagc ggttgattgc gcaagttgtt | 1620 |
| gcgaattgga ctggaatccc tgtgcaaaaa atgttggagg gagaatctga aaagttattg | 1680 |
| gtgttggagg agtctttaga agaaaggggtt gttggacaac ctttcgctat tgccgcagtc | 1740 |
| agtgattcga ttcgagctgc tcgagtagga ttgagtgatc cgcagcgtcc tctaggagtg | 1800 |
| tttctatttc ttggacctac aggggtaggg aaaactgagc ttgctaaagc attagcagag | 1860 |
| cttttattta ataaggaaga agcgatgatt cggtttgaca tgaccgaata tatgaaaaaa | 1920 |
| cattccgttt ccaaattgat aggatctcct ccagggtatg taggatatga agaaggaggg | 1980 |
| agtctctcag aagcttaag aagacgacct tattctgttg ttcttttga tgagatagaa | 2040 |
| aaagcagata agaagtatt taatatttta ttgcagattt ttgatgatgg gattcttacg | 2100 |
| gatagcaaga agcgtaaggt aaattgtaag aatgctcttt tcattatgac atcaaatatt | 2160 |
| ggttcgcaag agcttgctga ttattgtact aagaaaggaa ctatcgtaga caaagaagct | 2220 |
| gtgctatctg ttgttgcccc tgcgcttaaa aattatttta gtccagaatt tatcaatcgt | 2280 |
| atcgatgaca ttctgccttt cgttcctttg actacggaag acattgtaaa aattgtcggt | 2340 |
| attcaaatga atcgggttgc tttacgtttg ctggaaagaa aaatttcgtt aacttgggat | 2400 |
| gattctttag tgctatttct cagtgagcaa ggttatgaca gcgcttttgg agctcgccct | 2460 |
| ctgaagcgtt tgatacagca aaaagtagtg actatgttgt ctaaagctct tttgaaagga | 2520 |
| gatatcaaac ctggaatggc ggtggagctt actatggcaa aagatgtagt tgtgtttaaa | 2580 |
| attaaaacaa atccagctgt g | 2601 |

<210> SEQ ID NO 95
<211> LENGTH: 1016
<212> TYPE: PRT
<213> ORGANISM: Chlamydia trachomatis serovar D

<400> SEQUENCE: 95

Met Pro Phe Ser Leu Arg Ser Thr Ser Phe Cys Phe Leu Ala Cys Leu
            5                   10                15

-continued

```
Cys Ser Tyr Ser Tyr Gly Phe Ala Ser Ser Pro Gln Val Leu Thr Pro
             20                  25                  30

Asn Val Thr Thr Pro Phe Lys Gly Asp Asp Val Tyr Leu Asn Gly Asp
         35                  40                  45

Cys Ala Phe Val Asn Val Tyr Ala Gly Ala Glu Asn Gly Ser Ile Ile
     50                  55                  60

Ser Ala Asn Gly Asp Asn Leu Thr Ile Thr Gly Gln Asn His Thr Leu
 65                  70                  75                  80

Ser Phe Thr Asp Ser Gln Gly Pro Val Leu Gln Asn Tyr Ala Phe Ile
                 85                  90                  95

Ser Ala Gly Glu Thr Leu Thr Leu Lys Asp Phe Ser Ser Leu Met Phe
             100                 105                 110

Ser Lys Asn Val Ser Cys Gly Glu Lys Gly Met Ile Ser Gly Lys Thr
         115                 120                 125

Val Ser Ile Ser Gly Ala Gly Glu Val Ile Phe Trp Asp Asn Ser Val
     130                 135                 140

Gly Tyr Ser Pro Leu Ser Ile Val Pro Ala Ser Thr Pro Thr Pro Pro
145                 150                 155                 160

Ala Pro Ala Pro Ala Pro Ala Ala Ser Ser Ser Leu Ser Pro Thr Val
                 165                 170                 175

Ser Asp Ala Arg Lys Gly Ser Ile Phe Ser Val Glu Thr Ser Leu Glu
             180                 185                 190

Ile Ser Gly Val Lys Lys Gly Val Met Phe Asp Asn Asn Ala Gly Asn
         195                 200                 205

Phe Gly Thr Val Phe Arg Gly Asn Ser Asn Asn Asn Ala Gly Ser Gly
     210                 215                 220

Gly Ser Gly Ser Ala Thr Thr Pro Ser Phe Thr Val Lys Asn Cys Lys
225                 230                 235                 240

Gly Lys Val Ser Phe Thr Asp Asn Val Ala Ser Cys Gly Gly Gly Val
                 245                 250                 255

Val Tyr Lys Gly Thr Val Leu Phe Lys Asp Asn Glu Gly Gly Ile Phe
             260                 265                 270

Phe Arg Gly Asn Thr Ala Tyr Asp Asp Leu Gly Ile Leu Ala Ala Thr
         275                 280                 285

Ser Arg Asp Gln Asn Thr Glu Thr Gly Gly Gly Gly Val Ile Cys
     290                 295                 300

Ser Pro Asp Asp Ser Val Lys Phe Glu Gly Asn Lys Gly Ser Ile Val
305                 310                 315                 320

Phe Asp Tyr Asn Phe Ala Lys Gly Arg Gly Gly Ser Ile Leu Thr Lys
                 325                 330                 335

Glu Phe Ser Leu Val Ala Asp Asp Ser Val Val Phe Ser Asn Asn Thr
             340                 345                 350

Ala Glu Lys Gly Gly Ala Ile Tyr Ala Pro Thr Ile Asp Ile Ser
         355                 360                 365

Thr Asn Gly Gly Ser Ile Leu Phe Glu Arg Asn Arg Ala Ala Glu Gly
     370                 375                 380

Gly Ala Ile Cys Val Ser Glu Ala Ser Ser Gly Ser Thr Gly Asn Leu
385                 390                 395                 400

Thr Leu Ser Ala Ser Asp Gly Asp Ile Val Phe Ser Gly Asn Met Thr
                 405                 410                 415

Ser Asp Arg Pro Gly Glu Arg Ser Ala Ala Arg Ile Leu Ser Asp Gly
             420                 425                 430
```

-continued

```
Thr Thr Val Ser Leu Asn Ala Ser Gly Leu Ser Lys Leu Ile Phe Tyr
        435                 440                 445

Asp Pro Val Gln Asn Asn Ser Ala Ala Gly Ala Ser Thr Pro Ser
    450                 455                 460

Pro Ser Ser Ser Ser Met Pro Gly Ala Val Thr Ile Asn Gln Ser Gly
465                 470                 475                 480

Asn Gly Ser Val Ile Phe Thr Ala Glu Ser Leu Thr Pro Ser Glu Lys
                485                 490                 495

Leu Gln Val Leu Asn Ser Thr Ser Asn Phe Pro Gly Ala Leu Thr Val
            500                 505                 510

Ser Gly Gly Glu Leu Val Val Thr Glu Gly Ala Thr Leu Thr Thr Gly
        515                 520                 525

Thr Ile Thr Ala Thr Ser Gly Arg Val Thr Leu Gly Ser Gly Ala Ser
    530                 535                 540

Leu Ser Ala Val Ala Gly Ala Ala Asn Asn Tyr Thr Cys Thr Val
545                 550                 555                 560

Ser Lys Leu Gly Ile Asp Leu Glu Ser Phe Leu Thr Pro Asn Tyr Lys
                565                 570                 575

Thr Ala Ile Leu Gly Ala Asp Gly Thr Val Thr Val Asn Ser Gly Ser
            580                 585                 590

Thr Leu Asp Leu Val Met Glu Ser Glu Ala Glu Val Tyr Asp Asn Pro
        595                 600                 605

Leu Phe Val Gly Ser Leu Thr Ile Pro Phe Val Thr Leu Ser Ser Ser
    610                 615                 620

Ser Ala Ser Asn Gly Val Thr Lys Asn Ser Val Thr Ile Asn Asp Ala
625                 630                 635                 640

Asp Ala Ala His Tyr Gly Tyr Gln Gly Ser Trp Ser Ala Asp Trp Thr
                645                 650                 655

Lys Pro Pro Leu Ala Pro Asp Ala Lys Gly Met Val Pro Pro Asn Thr
            660                 665                 670

Asn Asn Thr Leu Tyr Leu Thr Trp Arg Pro Ala Ser Asn Tyr Gly Glu
        675                 680                 685

Tyr Arg Leu Asp Pro Gln Arg Lys Gly Glu Leu Val Pro Asn Ser Leu
    690                 695                 700

Trp Val Ala Gly Ser Ala Leu Arg Thr Phe Thr Asn Gly Leu Lys Glu
705                 710                 715                 720

His Tyr Val Ser Arg Asp Val Gly Phe Val Ala Ser Leu His Ala Leu
                725                 730                 735

Gly Asp Tyr Ile Leu Asn Tyr Thr Gln Asp Asp Arg Asp Gly Phe Leu
            740                 745                 750

Ala Arg Tyr Gly Gly Phe Gln Ala Thr Ala Ala Ser His Tyr Glu Asn
        755                 760                 765

Gly Ser Ile Phe Gly Val Ala Phe Gly Gln Leu Tyr Gly Gln Thr Lys
    770                 775                 780

Ser Arg Met Tyr Tyr Ser Lys Asp Ala Gly Asn Met Thr Met Leu Ser
785                 790                 795                 800

Cys Phe Gly Arg Ser Tyr Val Asp Ile Lys Gly Thr Glu Thr Val Met
                805                 810                 815

Tyr Trp Glu Thr Ala Tyr Gly Tyr Ser Val His Arg Met His Thr Gln
            820                 825                 830

Tyr Phe Asn Asp Lys Thr Gln Lys Phe Asp His Ser Lys Cys His Trp
        835                 840                 845

His Asn Asn Asn Tyr Tyr Ala Phe Val Gly Ala Glu His Asn Phe Leu
```

```
              850                 855                 860
Glu Tyr Cys Ile Pro Thr Arg Gln Phe Ala Arg Asp Tyr Glu Leu Thr
865                 870                 875                 880

Gly Phe Met Arg Phe Glu Met Ala Gly Gly Trp Ser Ser Ser Thr Arg
                885                 890                 895

Glu Thr Gly Ser Leu Thr Arg Tyr Phe Ala Arg Gly Ser Gly His Asn
            900                 905                 910

Met Ser Leu Pro Ile Gly Ile Val Ala His Ala Val Ser His Val Arg
                915                 920                 925

Arg Ser Pro Pro Ser Lys Leu Thr Leu Asn Met Gly Tyr Arg Pro Asp
930                 935                 940

Ile Trp Arg Val Thr Pro His Cys Asn Met Glu Ile Ala Asn Gly
945                 950                 955                 960

Val Lys Thr Pro Ile Gln Gly Ser Pro Leu Ala Arg His Ala Phe Phe
                965                 970                 975

Leu Glu Val His Asp Thr Leu Tyr Ile His His Phe Gly Arg Ala Tyr
            980                 985                 990

Met Asn Tyr Ser Leu Asp Ala Arg Arg Arg Gln Thr Ala His Phe Val
        995                 1000                1005

Ser Met Gly Leu Asn Arg Ile Phe
    1010                1015

<210> SEQ ID NO 96
<211> LENGTH: 346
<212> TYPE: PRT
<213> ORGANISM: Chlamydia trachomatis serovar D

<400> SEQUENCE: 96

Met Gln Ala Asp Ile Leu Asp Gly Lys Gln Lys Arg Val Asn Leu Asn
                5                   10                  15

Ser Lys Arg Leu Val Asn Cys Asn Gln Val Asp Val Asn Gln Leu Val
            20                  25                  30

Pro Ile Lys Tyr Lys Trp Ala Trp Glu His Tyr Leu Asn Gly Cys Ala
        35                  40                  45

Asn Asn Trp Leu Pro Thr Glu Ile Pro Met Gly Lys Asp Ile Glu Leu
    50                  55                  60

Trp Lys Ser Asp Arg Leu Ser Glu Asp Glu Arg Arg Val Ile Leu Leu
65                  70                  75                  80

Asn Leu Gly Phe Phe Ser Thr Ala Glu Ser Leu Val Gly Asn Asn Ile
                85                  90                  95

Val Leu Ala Ile Phe Lys His Val Thr Asn Pro Glu Ala Arg Gln Tyr
            100                 105                 110

Leu Leu Arg Gln Ala Phe Glu Glu Ala Val His Thr His Thr Phe Leu
        115                 120                 125

Tyr Ile Cys Glu Ser Leu Gly Leu Asp Glu Lys Glu Ile Phe Asn Ala
    130                 135                 140

Tyr Asn Glu Arg Ala Ala Ile Lys Ala Lys Asp Asp Phe Gln Met Glu
145                 150                 155                 160

Ile Thr Gly Lys Val Leu Asp Pro Asn Phe Arg Thr Asp Ser Val Glu
                165                 170                 175

Gly Leu Gln Glu Phe Val Lys Asn Leu Val Gly Tyr Tyr Ile Ile Met
            180                 185                 190

Glu Gly Ile Phe Phe Tyr Ser Gly Phe Val Met Ile Leu Ser Phe His
        195                 200                 205
```

```
Arg Gln Asn Lys Met Ile Gly Ile Gly Glu Gln Tyr Gln Tyr Ile Leu
    210                 215                 220

Arg Asp Glu Thr Ile His Leu Asn Phe Gly Ile Asp Leu Ile Asn Gly
225                 230                 235                 240

Ile Lys Glu Glu Asn Pro Glu Ile Trp Thr Pro Glu Leu Gln Gln Glu
                245                 250                 255

Ile Val Glu Leu Ile Lys Arg Ala Val Asp Leu Glu Ile Glu Tyr Ala
            260                 265                 270

Gln Asp Cys Leu Pro Arg Gly Ile Leu Gly Leu Arg Ala Ser Met Phe
        275                 280                 285

Ile Asp Tyr Val Gln His Ile Ala Asp Arg Arg Leu Glu Arg Ile Gly
    290                 295                 300

Leu Lys Pro Ile Tyr His Thr Lys Asn Pro Phe Pro Trp Met Ser Glu
305                 310                 315                 320

Thr Ile Asp Leu Asn Lys Glu Lys Asn Phe Phe Glu Thr Arg Val Ile
                325                 330                 335

Glu Tyr Gln His Ala Ala Ser Leu Thr Trp
            340                 345

<210> SEQ ID NO 97
<211> LENGTH: 1053
<212> TYPE: PRT
<213> ORGANISM: Chlamydia trachomatis serovar D

<400> SEQUENCE: 97

Met Phe Thr Arg Ile Val Met Val Asp Leu Gln Glu Lys Gln Cys Thr
                5                   10                  15

Ile Val Lys Arg Asn Gly Met Phe Val Pro Phe Asp Arg Asn Arg Ile
            20                  25                  30

Phe Gln Ala Leu Glu Ala Ala Phe Arg Asp Thr Arg Arg Ile Asp Asp
        35                  40                  45

His Met Pro Leu Pro Glu Asp Leu Glu Ser Ser Ile Arg Ser Ile Thr
    50                  55                  60

His Gln Val Val Lys Glu Val Gln Lys Ile Thr Asp Gly Gln Val
65                  70                  75                  80

Val Thr Val Glu Arg Ile Gln Asp Met Val Glu Ser Gln Leu Tyr Val
                85                  90                  95

Asn Gly Leu Gln Asp Val Ala Arg Asp Tyr Ile Val Tyr Arg Asp Asp
            100                 105                 110

Arg Lys Ala His Arg Lys Ser Trp Gln Ser Leu Ser Val Val Arg
        115                 120                 125

Arg Cys Gly Thr Val Val His Phe Asn Pro Met Lys Ile Ser Ala Ala
    130                 135                 140

Leu Glu Lys Ala Phe Arg Ala Thr Asp Lys Thr Glu Gly Met Thr Pro
145                 150                 155                 160

Ser Ser Val Arg Glu Glu Ile Asn Ala Leu Thr Gln Asn Ile Val Ala
                165                 170                 175

Glu Ile Glu Glu Cys Cys Pro Gln Gln Asp Arg Arg Ile Asp Ile Glu
            180                 185                 190

Lys Ile Gln Asp Ile Val Glu Gln Gln Leu Met Val Val Gly His Tyr
        195                 200                 205

Ala Val Ala Lys Asn Tyr Ile Leu Tyr Arg Glu Ala Arg Ala Arg Val
    210                 215                 220

Arg Asp Asn Arg Glu Glu Asp Gly Ser Thr Glu Lys Thr Ile Ala Glu
225                 230                 235                 240
```

-continued

Glu Ala Val Glu Val Leu Ser Lys Asp Gly Ser Thr Tyr Thr Met Thr
                245                 250                 255

His Ser Gln Leu Leu Ala His Leu Ala Arg Ala Cys Ser Arg Phe Pro
            260                 265                 270

Glu Thr Asp Ala Ala Leu Leu Thr Asp Met Ala Phe Ala Asn Phe
        275                 280                 285

Tyr Ser Gly Ile Lys Glu Ser Glu Val Val Leu Ala Cys Ile Met Ala
    290                 295                 300

Ala Arg Ala Asn Ile Glu Lys Glu Pro Asp Tyr Ala Phe Val Ala Ala
305                 310                 315                 320

Glu Leu Leu Asp Val Val Tyr Lys Glu Ala Leu Gly Lys Ser Lys
                325                 330                 335

Tyr Ala Glu Asp Leu Glu Gln Ala His Arg Asp His Phe Lys Arg Tyr
                340                 345                 350

Ile Ala Glu Gly Asp Thr Tyr Arg Leu Asn Ala Glu Leu Lys His Leu
            355                 360                 365

Phe Asp Leu Asp Ala Leu Ala Asp Ala Met Asp Leu Ser Arg Asp Leu
370                 375                 380

Gln Phe Ser Tyr Met Gly Ile Gln Asn Leu Tyr Asp Arg Tyr Phe Asn
385                 390                 395                 400

His His Glu Gly Cys Arg Leu Thr Pro Gln Ile Phe Trp Met Arg
                405                 410                 415

Val Ala Met Gly Leu Ala Leu Asn Glu Gln Asp Lys Thr Ser Trp Ala
                420                 425                 430

Ile Thr Phe Tyr Asn Leu Leu Ser Thr Phe Arg Tyr Thr Pro Ala Thr
            435                 440                 445

Pro Thr Leu Phe Asn Ser Gly Met Arg His Ser Gln Leu Ser Ser Cys
        450                 455                 460

Tyr Leu Ser Thr Val Gln Asp Asn Leu Val Asn Ile Tyr Lys Val Ile
465                 470                 475                 480

Ala Asp Asn Ala Met Leu Ser Lys Trp Ala Gly Gly Ile Gly Asn Asp
                485                 490                 495

Trp Thr Ala Ile Arg Ala Thr Gly Ala Leu Ile Lys Gly Thr Asn Gly
            500                 505                 510

Arg Ser Gln Gly Val Ile Pro Phe Ile Lys Val Thr Asn Asp Thr Ala
        515                 520                 525

Val Ala Val Asn Gln Gly Gly Lys Arg Lys Gly Ala Val Cys Val Tyr
    530                 535                 540

Leu Glu Val Trp His Leu Asp Tyr Glu Asp Phe Leu Glu Leu Arg Lys
545                 550                 555                 560

Asn Thr Gly Asp Glu Arg Arg Ala His Asp Val Asn Ile Ala Ser
                565                 570                 575

Trp Ile Pro Asp Leu Phe Phe Lys Arg Leu Gln Gln Lys Gly Thr Trp
            580                 585                 590

Thr Leu Phe Ser Pro Asp Val Pro Gly Leu His Asp Ala Tyr Gly
        595                 600                 605

Glu Glu Phe Glu Arg Leu Tyr Glu Glu Tyr Glu Arg Lys Val Asp Thr
    610                 615                 620

Gly Glu Ile Arg Leu Phe Lys Lys Val Glu Ala Glu Asp Leu Trp Arg
625                 630                 635                 640

Lys Met Leu Ser Met Leu Phe Glu Thr Gly His Pro Trp Met Thr Phe
                645                 650                 655

```
Lys Asp Pro Ser Asn Ile Arg Ser Ala Gln Asp His Lys Gly Val Val
            660                 665                 670

Arg Cys Ser Asn Leu Cys Thr Glu Ile Leu Leu Asn Cys Ser Glu Thr
        675                 680                 685

Glu Thr Ala Val Cys Asn Leu Gly Ser Ile Asn Leu Val Gln His Ile
    690                 695                 700

Val Gly Asp Gly Leu Asp Glu Glu Lys Leu Ser Glu Thr Ile Ser Ile
705                 710                 715                 720

Ala Val Arg Met Leu Asp Asn Val Ile Asp Ile Asn Phe Tyr Pro Thr
                725                 730                 735

Lys Glu Ala Lys Glu Ala Asn Phe Ala His Arg Ala Ile Gly Leu Gly
            740                 745                 750

Val Met Gly Phe Gln Asp Ala Leu Tyr Lys Leu Asp Ile Ser Tyr Ala
        755                 760                 765

Ser Gln Glu Ala Val Glu Phe Ala Asp Tyr Ser Ser Glu Leu Ile Ser
    770                 775                 780

Tyr Tyr Ala Ile Gln Ala Ser Cys Leu Leu Ala Lys Glu Arg Gly Thr
785                 790                 795                 800

Tyr Ser Ser Tyr Lys Gly Ser Lys Trp Asp Arg Gly Leu Leu Pro Ile
                805                 810                 815

Asp Thr Ile Gln Leu Leu Ala Asn Tyr Arg Gly Glu Ala Asn Leu Gln
            820                 825                 830

Met Asp Thr Ser Ser Arg Lys Asp Trp Glu Pro Ile Arg Ser Leu Val
        835                 840                 845

Lys Glu His Gly Met Arg His Cys Gln Leu Met Ala Ile Ala Pro Thr
    850                 855                 860

Ala Thr Ile Ser Asn Ile Ile Gly Val Thr Gln Ser Ile Glu Pro Thr
865                 870                 875                 880

Tyr Lys His Leu Phe Val Lys Ser Asn Leu Ser Gly Glu Phe Thr Ile
                885                 890                 895

Pro Asn Val Tyr Leu Ile Glu Lys Leu Lys Lys Leu Gly Ile Trp Asp
            900                 905                 910

Ala Asp Met Leu Asp Asp Leu Lys Tyr Phe Asp Gly Ser Leu Leu Glu
        915                 920                 925

Ile Glu Arg Ile Pro Asp His Leu Lys His Ile Phe Leu Thr Ala Phe
    930                 935                 940

Glu Ile Glu Pro Glu Trp Ile Ile Glu Cys Ala Ser Arg Arg Gln Lys
945                 950                 955                 960

Trp Ile Asp Met Gly Gln Ser Leu Asn Leu Tyr Leu Ala Gln Pro Asp
                965                 970                 975

Gly Lys Lys Leu Ser Asn Met Tyr Leu Thr Ala Trp Lys Lys Gly Leu
            980                 985                 990

Lys Thr Thr Tyr Tyr Leu Arg Ser Ser Ala Thr Thr Val Glu Lys
        995                 1000                1005

Ser Phe Val Asp Ile Asn Lys Arg Gly Ile Gln Pro Arg Trp Met Lys
    1010                1015                1020

Asn Lys Ser Ala Ser Ala Gly Ile Ile Val Glu Arg Ala Lys Lys Ala
1025                1030                1035                1040

Pro Val Cys Ser Leu Glu Glu Gly Cys Glu Ala Cys Gln
                1045                1050
```

<210> SEQ ID NO 98
<211> LENGTH: 1531
<212> TYPE: PRT

-continued

<213> ORGANISM: Chlamydia trachomatis serovar D

<400> SEQUENCE: 98

```
Met Ser Ser Glu Lys Asp Ile Lys Ser Thr Cys Ser Lys Phe Ser Leu
                5                   10                  15

Ser Val Val Ala Ala Ile Leu Ala Ser Val Ser Gly Leu Ala Ser Cys
            20                  25                  30

Val Asp Leu His Ala Gly Gly Gln Ser Val Asn Glu Leu Val Tyr Val
        35                  40                  45

Gly Pro Gln Ala Val Leu Leu Leu Asp Gln Ile Arg Asp Leu Phe Val
    50                  55                  60

Gly Ser Lys Asp Ser Gln Ala Glu Gly Gln Tyr Arg Leu Ile Val Gly
65                  70                  75                  80

Asp Pro Ser Ser Phe Gln Glu Lys Asp Ala Asp Thr Leu Pro Gly Lys
                85                  90                  95

Val Glu Gln Ser Thr Leu Phe Ser Val Thr Asn Pro Val Val Phe Gln
            100                 105                 110

Gly Val Asp Gln Gln Asp Gln Val Ser Ser Gln Gly Leu Ile Cys Ser
        115                 120                 125

Phe Thr Ser Ser Asn Leu Asp Ser Pro Arg Asp Gly Glu Ser Phe Leu
    130                 135                 140

Gly Ile Ala Phe Val Gly Asp Ser Ser Lys Ala Gly Ile Thr Leu Thr
145                 150                 155                 160

Asp Val Lys Ala Ser Leu Ser Gly Ala Ala Leu Tyr Ser Thr Glu Asp
                165                 170                 175

Leu Ile Phe Glu Lys Ile Lys Gly Gly Leu Glu Phe Ala Ser Cys Ser
            180                 185                 190

Ser Leu Glu Gln Gly Gly Ala Cys Ala Ala Gln Ser Ile Leu Ile His
        195                 200                 205

Asp Cys Gln Gly Leu Gln Val Lys His Cys Thr Thr Ala Val Asn Ala
    210                 215                 220

Glu Gly Ser Ser Ala Asn Asp His Leu Gly Phe Gly Gly Gly Ala Phe
225                 230                 235                 240

Phe Val Thr Gly Ser Leu Ser Gly Glu Lys Ser Leu Tyr Met Pro Ala
                245                 250                 255

Gly Asp Met Val Val Ala Asn Cys Asp Gly Ala Ile Ser Phe Glu Gly
            260                 265                 270

Asn Ser Ala Asn Phe Ala Asn Gly Gly Ala Ile Ala Ala Ser Gly Lys
        275                 280                 285

Val Leu Phe Val Ala Asn Asp Lys Lys Thr Ser Phe Ile Glu Asn Arg
    290                 295                 300

Ala Leu Ser Gly Gly Ala Ile Ala Ala Ser Ser Asp Ile Ala Phe Gln
305                 310                 315                 320

Asn Cys Ala Glu Leu Val Phe Lys Gly Asn Cys Ala Ile Gly Thr Glu
                325                 330                 335

Asp Lys Gly Ser Leu Gly Gly Gly Ala Ile Ser Ser Leu Gly Thr Val
            340                 345                 350

Leu Leu Gln Gly Asn His Gly Ile Thr Cys Asp Lys Asn Glu Ser Ala
        355                 360                 365

Ser Gln Gly Gly Ala Ile Phe Gly Lys Asn Cys Gln Ile Ser Asp Asn
    370                 375                 380

Glu Gly Pro Val Val Phe Arg Asp Ser Thr Ala Cys Leu Gly Gly Gly
385                 390                 395                 400
```

-continued

```
Ala Ile Ala Ala Gln Glu Ile Val Ser Ile Gln Asn Asn Gln Ala Gly
            405                 410                 415
Ile Ser Phe Glu Gly Gly Lys Ala Ser Phe Gly Gly Ile Ala Cys
        420                 425                 430
Gly Ser Phe Ser Ser Ala Gly Ala Ser Val Leu Gly Thr Ile Asp
        435                 440                 445
Ile Ser Lys Asn Leu Gly Ala Ile Ser Phe Ser Arg Thr Leu Cys Thr
        450                 455                 460
Thr Ser Asp Leu Gly Gln Met Glu Tyr Gln Gly Gly Ala Leu Phe
465                 470                 475                 480
Gly Glu Asn Ile Ser Leu Ser Glu Asn Ala Gly Val Leu Thr Phe Lys
                485                 490                 495
Asp Asn Ile Val Lys Thr Phe Ala Ser Asn Gly Lys Ile Leu Gly Gly
            500                 505                 510
Gly Ala Ile Leu Ala Thr Gly Lys Val Glu Ile Thr Asn Asn Ser Glu
            515                 520                 525
Gly Ile Ser Phe Thr Gly Asn Ala Arg Ala Pro Gln Ala Leu Pro Thr
        530                 535                 540
Gln Glu Glu Phe Pro Leu Phe Ser Lys Lys Gly Arg Pro Leu Ser
545                 550                 555                 560
Ser Gly Tyr Ser Gly Gly Gly Ala Ile Leu Gly Arg Glu Val Ala Ile
                565                 570                 575
Leu His Asn Ala Ala Val Val Phe Glu Gln Asn Arg Leu Gln Cys Ser
            580                 585                 590
Glu Glu Glu Ala Thr Leu Leu Gly Cys Cys Gly Gly Ala Val His
        595                 600                 605
Gly Met Asp Ser Thr Ser Ile Val Gly Asn Ser Ser Val Arg Phe Gly
        610                 615                 620
Asn Asn Tyr Ala Met Gly Gln Gly Val Ser Gly Gly Ala Leu Leu Ser
625                 630                 635                 640
Lys Thr Val Gln Leu Ala Gly Asn Gly Ser Val Asp Phe Ser Arg Asn
            645                 650                 655
Ile Ala Ser Leu Gly Gly Gly Ala Leu Gln Ala Ser Glu Gly Asn Cys
        660                 665                 670
Glu Leu Val Asp Asn Gly Tyr Val Leu Phe Arg Asp Asn Arg Gly Arg
        675                 680                 685
Val Tyr Gly Gly Ala Ile Ser Cys Leu Arg Gly Asp Val Val Ile Ser
        690                 695                 700
Gly Asn Lys Gly Arg Val Glu Phe Lys Asp Asn Ile Ala Thr Arg Leu
705                 710                 715                 720
Tyr Val Glu Glu Thr Val Glu Lys Val Glu Glu Val Glu Pro Ala Pro
                725                 730                 735
Glu Gln Lys Asp Asn Asn Glu Leu Ser Phe Leu Gly Arg Ala Glu Gln
            740                 745                 750
Ser Phe Ile Thr Ala Ala Asn Gln Ala Leu Phe Ala Ser Glu Asp Gly
        755                 760                 765
Asp Leu Ser Pro Glu Ser Ser Ile Ser Ser Glu Glu Leu Ala Lys Arg
        770                 775                 780
Arg Glu Cys Ala Gly Gly Ala Ile Phe Ala Lys Arg Val Arg Ile Val
785                 790                 795                 800
Asp Asn Gln Glu Ala Val Val Phe Ser Asn Asn Phe Ser Asp Ile Tyr
                805                 810                 815
Gly Gly Ala Ile Phe Thr Gly Ser Leu Arg Glu Glu Asp Lys Leu Asp
```

-continued

```
               820                 825                 830
Gly Gln Ile Pro Glu Val Leu Ile Ser Gly Asn Ala Gly Asp Val Val
           835                 840                 845
Phe Ser Gly Asn Ser Ser Lys Arg Asp Glu His Leu Pro His Thr Gly
850                 855                 860
Gly Gly Ala Ile Cys Thr Gln Asn Leu Thr Ile Ser Gln Asn Thr Gly
865                 870                 875                 880
Asn Val Leu Phe Tyr Asn Asn Val Ala Cys Ser Gly Ala Val Arg
               885                 890                 895
Ile Glu Asp His Gly Asn Val Leu Leu Glu Ala Phe Gly Gly Asp Ile
           900                 905                 910
Val Phe Lys Gly Asn Ser Ser Phe Arg Ala Gln Gly Ser Asp Ala Ile
           915                 920                 925
Tyr Phe Ala Gly Lys Glu Ser His Ile Thr Ala Leu Asn Ala Thr Glu
           930                 935                 940
Gly His Ala Ile Val Phe His Asp Ala Leu Val Phe Glu Asn Leu Glu
945                 950                 955                 960
Glu Arg Lys Ser Ala Glu Val Leu Leu Ile Asn Ser Arg Glu Asn Pro
               965                 970                 975
Gly Tyr Thr Gly Ser Ile Arg Phe Leu Glu Ala Glu Ser Lys Val Pro
           980                 985                 990
Gln Cys Ile His Val Gln Gln Gly Ser Leu Glu Leu Leu Asn Gly Ala
           995                1000                1005
Thr Leu Cys Ser Tyr Gly Phe Lys Gln Asp Ala Gly Ala Lys Leu Val
          1010                1015                1020
Leu Ala Ala Gly Ala Lys Leu Lys Ile Leu Asp Ser Gly Thr Pro Val
1025                1030                1035                1040
Gln Gln Gly His Ala Ile Ser Lys Pro Glu Ala Glu Ile Glu Ser Ser
               1045                1050                1055
Ser Glu Pro Glu Gly Ala His Ser Leu Trp Ile Ala Lys Asn Ala Gln
           1060                1065                1070
Thr Thr Val Pro Met Val Asp Ile His Thr Ile Ser Val Asp Leu Ala
           1075                1080                1085
Ser Phe Ser Ser Gln Gln Glu Gly Thr Val Glu Ala Pro Gln Val
           1090                1095                1100
Ile Val Pro Gly Gly Ser Tyr Val Arg Ser Gly Glu Leu Asn Leu Glu
1105                1110                1115                1120
Leu Val Asn Thr Thr Gly Thr Gly Tyr Glu Asn His Ala Leu Leu Lys
                1125                1130                1135
Asn Glu Ala Lys Val Pro Leu Met Ser Phe Val Ala Ser Gly Asp Glu
           1140                1145                1150
Ala Ser Ala Glu Ile Ser Asn Leu Ser Val Ser Asp Leu Gln Ile His
           1155                1160                1165
Val Val Thr Pro Glu Ile Glu Glu Asp Thr Tyr Gly His Met Gly Asp
           1170                1175                1180
Trp Ser Glu Ala Lys Ile Gln Asp Gly Thr Leu Val Ile Ser Trp Asn
1185                1190                1195                1200
Pro Thr Gly Tyr Arg Leu Asp Pro Gln Lys Ala Gly Ala Leu Val Phe
               1205                1210                1215
Asn Ala Leu Trp Glu Glu Gly Ala Val Leu Ser Ala Leu Lys Asn Ala
           1220                1225                1230
Arg Phe Ala His Asn Leu Thr Ala Gln Arg Met Glu Phe Asp Tyr Ser
           1235                1240                1245
```

-continued

Thr Asn Val Trp Gly Phe Ala Phe Gly Gly Phe Arg Thr Leu Ser Ala
1250                1255                1260

Glu Asn Leu Val Ala Ile Asp Gly Tyr Lys Gly Ala Tyr Gly Gly Ala
1265                1270                1275                1280

Ser Ala Gly Val Asp Ile Gln Leu Met Glu Asp Phe Val Leu Gly Val
                1285                1290                1295

Ser Gly Ala Ala Phe Leu Gly Lys Met Asp Ser Gln Lys Phe Asp Ala
            1300                1305                1310

Glu Val Ser Arg Lys Gly Val Val Ser Val Tyr Thr Gly Phe Leu
        1315                1320                1325

Ala Gly Ser Trp Phe Phe Lys Gly Gln Tyr Ser Leu Gly Glu Thr Gln
    1330                1335                1340

Asn Asp Met Lys Thr Arg Tyr Gly Val Leu Gly Glu Ser Ser Ala Ser
1345                1350                1355                1360

Trp Thr Ser Arg Gly Val Leu Ala Asp Ala Leu Val Glu Tyr Arg Ser
                1365                1370                1375

Leu Val Gly Pro Val Arg Pro Thr Phe Tyr Ala Leu His Phe Asn Pro
            1380                1385                1390

Tyr Val Glu Val Ser Tyr Ala Ser Met Lys Phe Pro Gly Phe Thr Glu
        1395                1400                1405

Gln Gly Arg Glu Ala Arg Ser Phe Glu Asp Ala Ser Leu Thr Asn Ile
    1410                1415                1420

Thr Ile Pro Leu Gly Met Lys Phe Glu Leu Ala Phe Ile Lys Gly Gln
1425                1430                1435                1440

Phe Ser Glu Val Asn Ser Leu Gly Ile Ser Tyr Ala Trp Glu Ala Tyr
                1445                1450                1455

Arg Lys Val Glu Gly Gly Ala Val Gln Leu Leu Glu Ala Gly Phe Asp
            1460                1465                1470

Trp Glu Gly Ala Pro Met Asp Leu Pro Arg Gln Glu Leu Arg Val Ala
        1475                1480                1485

Leu Glu Asn Asn Thr Glu Trp Ser Ser Tyr Phe Ser Thr Val Leu Gly
    1490                1495                1500

Leu Thr Ala Phe Cys Gly Gly Phe Thr Ser Thr Asp Ser Lys Leu Gly
1505                1510                1515                1520

Tyr Glu Ala Asn Thr Gly Leu Arg Leu Ile Phe
                1525                1530

<210> SEQ ID NO 99
<211> LENGTH: 474
<212> TYPE: PRT
<213> ORGANISM: Chlamydia trachomatis serovar D

<400> SEQUENCE: 99

Met Lys Ile Ile His Thr Ala Ile Glu Phe Ala Pro Val Ile Lys Ala
5 10 15

Gly Gly Leu Gly Asp Ala Leu Tyr Gly Leu Ala Lys Ala Leu Ala Ala
20 25 30

Asn His Thr Thr Glu Val Val Ile Pro Leu Tyr Pro Lys Leu Phe Thr
35 40 45

Leu Pro Lys Glu Gln Asp Leu Cys Ser Ile Gln Lys Leu Ser Tyr Phe
50 55 60

Phe Ala Gly Glu Gln Glu Ala Thr Ala Phe Ser Tyr Phe Tyr Glu Gly
65 70 75 80

Ile Lys Val Thr Leu Phe Lys Leu Asp Thr Gln Pro Glu Leu Phe Glu

```
                   85                  90                  95
Asn Ala Glu Thr Ile Tyr Thr Ser Asp Asp Ala Phe Arg Phe Cys Ala
               100                 105                 110
Phe Ser Ala Ala Ala Ser Tyr Ile Gln Lys Glu Gly Ala Asn Ile
           115                 120                 125
Val His Leu His Asp Trp His Thr Gly Leu Val Ala Gly Leu Leu Lys
       130                 135                 140
Gln Gln Pro Cys Ser Gln Leu Gln Lys Ile Val Leu Thr Leu His Asn
145                 150                 155                 160
Phe Gly Tyr Arg Gly Tyr Thr Thr Arg Glu Ile Leu Glu Ala Ser Ser
               165                 170                 175
Leu Asn Glu Phe Tyr Ile Ser Gln Tyr Gln Leu Phe Arg Asp Pro Gln
           180                 185                 190
Thr Cys Val Leu Leu Lys Gly Ala Leu Tyr Cys Ser Asp Phe Val Thr
       195                 200                 205
Thr Val Ser Pro Thr Tyr Ala Lys Glu Ile Leu Glu Asp Tyr Ser Asp
   210                 215                 220
Tyr Glu Ile His Asp Ala Ile Thr Ala Arg Gln His His Leu Arg Gly
225                 230                 235                 240
Ile Leu Asn Gly Ile Asp Thr Thr Ile Trp Gly Pro Glu Thr Asp Pro
               245                 250                 255
Asn Leu Ala Lys Asn Tyr Thr Lys Glu Leu Phe Glu Thr Pro Ser Ile
           260                 265                 270
Phe Phe Glu Ala Lys Ala Glu Asn Lys Lys Ala Leu Tyr Glu Arg Leu
       275                 280                 285
Gly Leu Ser Leu Glu His Ser Pro Cys Val Cys Ile Ile Ser Arg Ile
   290                 295                 300
Ala Glu Gln Lys Gly Pro His Phe Met Lys Gln Ala Ile Leu His Ala
305                 310                 315                 320
Leu Glu Asn Ala Tyr Thr Leu Ile Ile Ile Gly Thr Cys Tyr Gly Asn
               325                 330                 335
Gln Leu His Glu Glu Phe Ala Asn Leu Gln Glu Ser Leu Ala Asn Ser
           340                 345                 350
Pro Asp Val Arg Ile Leu Leu Thr Tyr Ser Asp Val Leu Ala Arg Gln
       355                 360                 365
Ile Phe Ala Ala Ala Asp Met Ile Cys Ile Pro Ser Met Phe Glu Pro
   370                 375                 380
Cys Gly Leu Thr Gln Met Ile Gly Met Arg Tyr Gly Thr Val Pro Leu
385                 390                 395                 400
Val Arg Ala Thr Gly Gly Leu Ala Asp Thr Val Ala Asn Gly Ile Asn
               405                 410                 415
Gly Phe Ser Phe Phe Asn Pro His Asp Phe Tyr Glu Phe Arg Asn Met
           420                 425                 430
Leu Ser Glu Ala Val Thr Thr Tyr Arg Thr Asn His Asp Lys Trp Gln
       435                 440                 445
His Ile Val Arg Ala Cys Leu Asp Phe Ser Ser Asp Leu Glu Thr Ala
   450                 455                 460
Ala Asn Lys Tyr Leu Glu Ile Tyr Lys Gln
465                 470

<210> SEQ ID NO 100
<211> LENGTH: 393
<212> TYPE: PRT
<213> ORGANISM: Chlamydia trachomatis serovar D
```

<400> SEQUENCE: 100

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Ala Thr Trp Cys Asp Ala Ile Ser Met Arg Val Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Lys Pro Thr Thr Asp Thr Gly Asn Ser Ala
                85                  90                  95

Ala Pro Ser Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
        115                 120                 125

Ile Trp Asp Arg Phe Asp Val Phe Cys Thr Leu Gly Ala Thr Ser Gly
    130                 135                 140

Tyr Leu Lys Gly Asn Ser Ala Ser Phe Asn Leu Val Gly Leu Phe Gly
145                 150                 155                 160

Asp Asn Glu Asn Gln Lys Thr Val Lys Ala Glu Ser Val Pro Asn Met
                165                 170                 175

Ser Phe Asp Gln Ser Val Val Glu Leu Tyr Thr Asp Thr Phe Ala
            180                 185                 190

Trp Ser Val Gly Ala Arg Ala Ala Leu Trp Glu Cys Gly Cys Ala Thr
        195                 200                 205

Leu Gly Ala Ser Phe Gln Tyr Ala Gln Ser Lys Pro Lys Val Glu Glu
    210                 215                 220

Leu Asn Val Leu Cys Asn Ala Ala Glu Phe Thr Ile Asn Lys Pro Lys
225                 230                 235                 240

Gly Tyr Val Gly Lys Glu Phe Pro Leu Asp Leu Thr Ala Gly Thr Asp
                245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile
        275                 280                 285

Gly Val Lys Trp Ser Arg Ala Ser Phe Asp Ala Asp Thr Ile Arg Ile
    290                 295                 300

Ala Gln Pro Lys Ser Ala Thr Ala Ile Phe Asp Thr Thr Thr Leu Asn
305                 310                 315                 320

Pro Thr Ile Ala Gly Ala Gly Asp Val Lys Thr Gly Ala Glu Gly Gln
                325                 330                 335

Leu Gly Asp Thr Met Gln Ile Val Ser Leu Gln Leu Asn Lys Met Lys
            340                 345                 350

Ser Arg Lys Ser Cys Gly Ile Ala Val Gly Thr Thr Ile Val Asp Ala
        355                 360                 365

Asp Lys Tyr Ala Val Thr Val Glu Thr Arg Leu Ile Asp Glu Arg Ala
    370                 375                 380

Ala His Val Asn Ala Gln Phe Arg Phe
385                 390

<210> SEQ ID NO 101
<211> LENGTH: 195
<212> TYPE: PRT
<213> ORGANISM: Chlamydia trachomatis serovar D

<400> SEQUENCE: 101

Met Gly Ser Leu Val Gly Arg Gln Ala Pro Asp Phe Ser Gly Lys Ala
                 5                  10                  15

Val Val Cys Gly Glu Glu Lys Glu Ile Ser Leu Ala Asp Phe Arg Gly
             20                  25                  30

Lys Tyr Val Val Leu Phe Phe Tyr Pro Lys Asp Phe Thr Tyr Val Cys
         35                  40                  45

Pro Thr Glu Leu His Ala Phe Gln Asp Arg Leu Val Asp Phe Glu Glu
     50                  55                  60

Arg Gly Ala Val Val Leu Gly Cys Ser Val Asp Asp Ile Glu Thr His
 65                  70                  75                  80

Ser Arg Trp Leu Ala Val Ala Arg Asn Ala Gly Gly Ile Glu Gly Thr
                 85                  90                  95

Glu Tyr Pro Leu Leu Ala Asp Pro Ser Phe Lys Ile Ser Glu Ala Phe
            100                 105                 110

Gly Val Leu Asn Pro Glu Gly Ser Leu Ala Leu Arg Ala Thr Phe Leu
        115                 120                 125

Ile Asp Lys Tyr Gly Val Val Arg His Ala Val Ile Asn Asp Leu Pro
    130                 135                 140

Leu Gly Arg Ser Ile Asp Glu Glu Leu Arg Ile Leu Asp Ser Leu Ile
145                 150                 155                 160

Phe Phe Glu Asn His Gly Met Val Cys Pro Ala Asn Trp Arg Ser Gly
                165                 170                 175

Glu Arg Gly Met Val Pro Ser Glu Glu Gly Leu Lys Glu Tyr Phe Gln
            180                 185                 190

Thr Met Asp
        195

<210> SEQ ID NO 102
<211> LENGTH: 86
<212> TYPE: PRT
<213> ORGANISM: Chlamydia trachomatis serovar D

<400> SEQUENCE: 102

Met Ser Gln Asn Lys Asn Ser Ala Phe Met Gln Pro Val Asn Val Ser
                 5                  10                  15

Ala Asp Leu Ala Ala Ile Val Gly Ala Gly Pro Met Pro Arg Thr Glu
             20                  25                  30

Ile Ile Lys Lys Met Trp Asp Tyr Ile Lys Lys Asn Gly Leu Gln Asp
         35                  40                  45

Pro Thr Asn Lys Arg Asn Ile Asn Pro Asp Asp Lys Leu Ala Lys Val
     50                  55                  60

Phe Gly Thr Glu Lys Pro Ile Asp Met Phe Gln Met Thr Lys Met Val
 65                  70                  75                  80

Ser Gln His Ile Ile Lys
                 85

<210> SEQ ID NO 103
<211> LENGTH: 394
<212> TYPE: PRT
<213> ORGANISM: Chlamydia trachomatis serovar D

<400> SEQUENCE: 103

```
Met Ser Lys Glu Thr Phe Gln Arg Asn Lys Pro His Ile Asn Ile Gly
              5                   10                  15

Thr Ile Gly His Val Asp His Gly Lys Thr Thr Leu Thr Ala Ala Ile
             20                  25                  30

Thr Arg Ala Leu Ser Gly Asp Gly Leu Ala Asp Phe Arg Asp Tyr Ser
             35                  40                  45

Ser Ile Asp Asn Thr Pro Glu Glu Lys Ala Arg Gly Ile Thr Ile Asn
 50                  55                  60

Ala Ser His Val Glu Tyr Glu Thr Ala Asn Arg His Tyr Ala His Val
 65                  70                  75                  80

Asp Cys Pro Gly His Ala Asp Tyr Val Lys Asn Met Ile Thr Gly Ala
             85                  90                  95

Ala Gln Met Asp Gly Ala Ile Leu Val Val Ser Ala Thr Asp Gly Ala
            100                 105                 110

Met Pro Gln Thr Lys Glu His Ile Leu Leu Ala Arg Gln Val Gly Val
            115                 120                 125

Pro Tyr Ile Val Val Phe Leu Asn Lys Ile Asp Met Ile Ser Glu Glu
130                 135                 140

Asp Ala Glu Leu Val Asp Leu Val Glu Met Glu Leu Val Glu Leu Leu
145                 150                 155                 160

Glu Glu Lys Gly Tyr Lys Gly Cys Pro Ile Ile Arg Gly Ser Ala Leu
            165                 170                 175

Lys Ala Leu Glu Gly Asp Ala Ala Tyr Ile Glu Lys Val Arg Glu Leu
            180                 185                 190

Met Gln Ala Val Asp Asp Asn Ile Pro Thr Pro Glu Arg Glu Ile Asp
            195                 200                 205

Lys Pro Phe Leu Met Pro Ile Glu Asp Val Phe Ser Ile Ser Gly Arg
            210                 215                 220

Gly Thr Val Val Thr Gly Arg Ile Glu Arg Gly Ile Val Lys Val Ser
225                 230                 235                 240

Asp Lys Val Gln Leu Val Gly Leu Arg Asp Thr Lys Glu Thr Ile Val
            245                 250                 255

Thr Gly Val Glu Met Phe Arg Lys Glu Leu Pro Glu Gly Arg Ala Gly
            260                 265                 270

Glu Asn Val Gly Leu Leu Leu Arg Gly Ile Gly Lys Asn Asp Val Glu
            275                 280                 285

Arg Gly Met Val Val Cys Leu Pro Asn Ser Val Lys Pro His Thr Gln
            290                 295                 300

Phe Lys Cys Ala Val Tyr Val Leu Gln Lys Glu Glu Gly Gly Arg His
305                 310                 315                 320

Lys Pro Phe Phe Thr Gly Tyr Arg Pro Gln Phe Phe Arg Thr Thr
            325                 330                 335

Asp Val Thr Gly Val Val Thr Leu Pro Glu Gly Ile Glu Met Val Met
            340                 345                 350

Pro Gly Asp Asn Val Glu Phe Glu Val Gln Leu Ile Ser Pro Val Ala
            355                 360                 365

Leu Glu Glu Gly Met Arg Phe Ala Ile Arg Glu Gly Arg Thr Ile
            370                 375                 380

Gly Ala Gly Thr Ile Ser Lys Ile Ile Ala
385                 390

<210> SEQ ID NO 104
<211> LENGTH: 82
```

```
<212> TYPE: PRT
<213> ORGANISM: Chlamydia trachomatis serovar D

<400> SEQUENCE: 104
```

Met Gly Gln Asp His Arg Arg Lys Phe Leu Lys Lys Val Ser Phe Val
5 10 15

Lys Lys Gln Ala Ala Phe Ala Gly Asn Phe Ile Glu Glu Ile Lys Lys
20 25 30

Ile Glu Trp Val Asn Lys Arg Asp Leu Lys Arg Tyr Val Lys Ile Val
35 40 45

Leu Met Asn Ile Phe Gly Phe Gly Phe Ser Ile Tyr Cys Val Asp Leu
50 55 60

Ala Leu Arg Lys Ser Leu Ser Leu Phe Gly Lys Val Thr Ser Phe Phe
65 70 75 80

Phe Gly

<210> SEQ ID NO 105
<211> LENGTH: 379
<212> TYPE: PRT
<213> ORGANISM: Chlamydia trachomatis serovar D

<400> SEQUENCE: 105

Met Val Ile Pro Lys Val Asp Leu Gly Glu Ser Ala Val Met Met Gly
5 10 15

Tyr Lys Leu Thr Ser Gln Leu Ala Met Leu Ser Ile Leu Leu Thr Phe
20 25 30

Thr His Thr Met Gly His Ala Ser Gln Met Ser Gln Thr Leu Pro Thr
35 40 45

Ile Ile Glu Ala Gln Ala Glu Glu Ala Leu Gln Ala Asp Arg Gly Val
50 55 60

Ala Gly Gln Ala Leu Lys Lys Leu Arg Lys Lys Arg Cys Ala Ser Arg
65 70 75 80

Lys Ser Ala Cys Lys Ala Ser Phe Lys Lys Lys Asp Phe Phe Ser Cys
85 90 95

Ile Thr Asn Gly Leu Phe Ser Gly Asn His Glu Gln Arg Leu Thr Ala
100 105 110

Lys Lys Glu Asn Lys Ala Arg Gly Lys Glu Pro Arg Val Val Val Gln
115 120 125

Thr Thr Lys Lys Arg Gln Ile Thr Gln Ser Glu Lys Glu Phe Phe Asp
130 135 140

Trp Leu Cys Asn Ser Lys Arg Glu Arg Lys Leu Leu Lys Lys Lys Pro
145 150 155 160

Val Asn Thr Ser Leu Ala Lys Ser Glu Glu Leu Ser Pro Lys Glu Ala
165 170 175

Ala Ile Ala Ala Ala Arg Ala Ser Leu Ser Pro Glu Glu Lys Arg Gln
180 185 190

Leu Ile Arg Glu Trp Leu Ala Glu Glu Lys Thr Ala Arg Lys Ser Gly
195 200 205

Arg Ala Ala Cys Ala Val Ser Glu Asn Leu Lys Arg Asp Gly Ser Ile
210 215 220

Thr Ser Thr Leu Arg Tyr Asp Ala Glu Lys Ala Leu Thr Thr Arg Val
225 230 235 240

Lys Arg Asn Glu Asn Ser Val Asn Ala Arg Ala Arg Gln Arg Ala Ala
245 250 255

Leu Gln Lys Ala Lys Lys Ala Lys Thr Glu Lys Pro Glu Ala Asp Glu

```
                260                 265                 270
Lys Ala Glu Ala Val Ala Ala Pro Thr Lys Gln Ala His Lys
        275                 280                 285

Glu Pro Glu Asn Tyr Phe Ala Ala Thr Ala Ser Thr Asn Asn Thr Asn
    290                 295                 300

Val Met Ser Tyr Leu Asn Ala His Gln Tyr Arg Cys Asp Ser Ser Glu
305                 310                 315                 320

Thr Asp Trp Pro Cys Ser Ser Cys Val Thr Lys Arg Arg Ala Asn Phe
                325                 330                 335

Gly Ile Ser Val Cys Thr Met Val Val Thr Val Ile Ala Met Ile Val
                340                 345                 350

Gly Ala Val Ile Ile Ser Asn Ala Thr Asp Ser Thr Val Ala Gly Ser
            355                 360                 365

Ser Gly Thr Gly Gly Gly Ser Thr Gln Pro
370                 375

<210> SEQ ID NO 106
<211> LENGTH: 563
<212> TYPE: PRT
<213> ORGANISM: Chlamydia trachomatis serovar D

<400> SEQUENCE: 106

Met Val Tyr Phe Arg Ala His Gln Pro Arg His Thr Pro Lys Thr Phe
                    5                  10                  15

Pro Leu Glu Val His His Ser Phe Ser Asp Lys His Pro Gln Ile Ala
                20                  25                  30

Lys Ala Met Arg Ile Thr Gly Ile Ala Leu Ala Ala Leu Ser Leu Leu
            35                  40                  45

Ala Val Val Ala Cys Val Ile Ala Val Ser Ala Gly Gly Ala Ala Ile
        50                  55                  60

Pro Leu Ala Val Ile Ser Gly Ile Ala Val Met Ser Gly Leu Leu Ser
65                  70                  75                  80

Ala Ala Thr Ile Ile Cys Ser Ala Lys Lys Ala Leu Ala Gln Arg Lys
                85                  90                  95

Gln Lys Gln Leu Glu Glu Ser Leu Pro Leu Asp Asn Ala Thr Glu His
            100                 105                 110

Val Ser Tyr Leu Thr Ser Asp Thr Ser Tyr Phe Asn Gln Trp Glu Ser
        115                 120                 125

Leu Gly Ala Leu Asn Lys Gln Leu Ser Gln Ile Asp Leu Thr Ile Gln
    130                 135                 140

Ala Pro Glu Lys Lys Leu Leu Lys Glu Val Leu Gly Ser Arg Tyr Asp
145                 150                 155                 160

Ser Ile Asn His Ser Ile Glu Glu Ile Ser Asp Arg Phe Thr Lys Met
                165                 170                 175

Leu Ser Leu Leu Arg Leu Arg Glu His Phe Tyr Arg Gly Glu Glu Arg
            180                 185                 190

Tyr Ala Pro Tyr Leu Ser Pro Pro Leu Leu Asn Lys Asn Arg Leu Leu
        195                 200                 205

Thr Gln Ile Thr Ser Asn Met Ile Arg Met Leu Pro Lys Ser Gly Gly
    210                 215                 220

Val Phe Ser Leu Lys Ala Asn Thr Leu Ser His Ala Ser Arg Thr Leu
225                 230                 235                 240

Tyr Thr Val Leu Lys Val Ala Leu Ser Leu Gly Val Leu Ala Gly Val
                245                 250                 255
```

```
Ala Ala Leu Ile Ile Phe Leu Pro Pro Ser Leu Pro Phe Ile Ala Val
            260                 265                 270

Ile Gly Val Ser Ser Leu Ala Leu Gly Met Ala Ser Phe Leu Met Ile
            275                 280                 285

Arg Gly Ile Lys Tyr Leu Leu Glu His Ser Pro Leu Asn Arg Lys Gln
            290                 295                 300

Leu Ala Lys Asp Ile Gln Lys Thr Ile Gly Pro Asp Val Leu Ala Ser
305                 310                 315                 320

Met Val His Tyr Gln His Gln Leu Leu Ser His Leu His Glu Thr Leu
            325                 330                 335

Leu Asp Glu Ala Ile Thr Ala Arg Trp Ser Glu Pro Phe Phe Ile Glu
            340                 345                 350

His Ala Asn Leu Lys Ala Lys Ile Glu Asp Leu Thr Lys Gln Tyr Asp
            355                 360                 365

Ile Leu Asn Ala Ala Phe Asn Lys Ser Leu Gln Gln Asp Glu Ala Leu
370                 375                 380

Arg Ser Gln Leu Glu Lys Arg Ala Tyr Leu Phe Pro Ile Pro Asn Asn
385                 390                 395                 400

Asp Glu Asn Ala Lys Thr Lys Glu Ser Gln Leu Leu Asp Ser Glu Asn
            405                 410                 415

Asp Ser Asn Ser Glu Phe Gln Glu Ile Ile Asn Lys Gly Leu Glu Ala
            420                 425                 430

Ala Asn Lys Arg Arg Ala Asp Ala Lys Ser Lys Phe Tyr Thr Glu Asp
            435                 440                 445

Glu Thr Ser Asp Lys Ile Phe Ser Ile Trp Lys Pro Thr Lys Asn Leu
            450                 455                 460

Ala Leu Glu Asp Leu Trp Arg Val His Glu Ala Cys Asn Glu Gln
465                 470                 475                 480

Gln Ala Leu Leu Leu Glu Asp Tyr Met Ser Tyr Lys Thr Ser Glu Cys
            485                 490                 495

Gln Ala Ala Leu Gln Lys Val Ser Gln Glu Leu Lys Ala Ala Gln Lys
            500                 505                 510

Ser Phe Ala Val Leu Glu Lys His Ala Leu Asp Arg Ser Tyr Glu Ser
            515                 520                 525

Ser Val Ala Thr Met Asp Leu Ala Arg Ala Asn Gln Glu Thr His Arg
            530                 535                 540

Leu Leu Asn Ile Leu Ser Glu Leu Gln Gln Leu Ala Gln Tyr Leu Leu
545                 550                 555                 560

Asp Asn His

<210> SEQ ID NO 107
<211> LENGTH: 358
<212> TYPE: PRT
<213> ORGANISM: Chlamydia trachomatis serovar D

<400> SEQUENCE: 107

Met Arg Lys Thr Val Ile Val Ala Met Ser Gly Gly Val Asp Ser Ser
                5                   10                  15

Val Val Ala Tyr Leu Leu Lys Lys Gln Gly Glu Tyr Asn Val Val Gly
            20                  25                  30

Leu Phe Met Lys Asn Trp Gly Glu Gln Asp Glu Asn Gly Glu Cys Thr
            35                  40                  45

Ala Thr Lys Asp Phe Arg Asp Val Glu Arg Ile Ala Glu Gln Leu Ser
        50                  55                  60
```

-continued

```
Ile Pro Tyr Tyr Thr Val Ser Phe Ser Lys Glu Tyr Lys Glu Arg Val
 65                  70                  75                  80

Phe Ser Arg Phe Leu Arg Glu Tyr Ala Asn Gly Tyr Thr Pro Asn Pro
                 85                  90                  95

Asp Val Leu Cys Asn Arg Glu Ile Lys Phe Asp Leu Leu Gln Lys Lys
            100                 105                 110

Val Arg Glu Leu Lys Gly Asp Phe Leu Ala Thr Gly His Tyr Cys Arg
        115                 120                 125

Gly Gly Ala Asp Gly Thr Gly Leu Ser Arg Gly Ile Asp Pro Asn Lys
    130                 135                 140

Asp Gln Ser Tyr Phe Leu Cys Gly Thr Pro Lys Asp Ala Leu Ser Asn
145                 150                 155                 160

Val Leu Phe Pro Leu Gly Gly Met Tyr Lys Thr Glu Val Arg Arg Ile
                165                 170                 175

Ala Gln Glu Ala Gly Leu Ala Thr Ala Thr Lys Lys Asp Ser Thr Gly
            180                 185                 190

Ile Cys Phe Ile Gly Lys Arg Pro Phe Lys Ser Phe Leu Glu Gln Phe
        195                 200                 205

Val Ala Asp Ser Pro Gly Asp Ile Ile Asp Phe Asp Thr Gln Gln Val
    210                 215                 220

Val Gly Arg His Glu Gly Ala His Tyr Tyr Thr Ile Gly Gln Arg Arg
225                 230                 235                 240

Gly Leu Asn Ile Gly Gly Met Glu Lys Pro Cys Tyr Val Leu Ser Lys
                245                 250                 255

Asn Met Glu Lys Asn Ile Val Tyr Ile Val Arg Gly Glu Asp His Pro
            260                 265                 270

Leu Leu Tyr Arg Gln Glu Leu Leu Ala Lys Glu Leu Asn Trp Phe Val
        275                 280                 285

Pro Leu Gln Glu Pro Met Ile Cys Ser Ala Lys Val Arg Tyr Arg Ser
    290                 295                 300

Pro Asp Glu Lys Cys Ser Val Tyr Pro Leu Glu Asp Gly Thr Val Lys
305                 310                 315                 320

Val Ile Phe Asp Val Pro Val Lys Ala Val Thr Pro Gly Gln Thr Val
                325                 330                 335

Ala Phe Tyr Gln Gly Asp Ile Cys Leu Gly Gly Val Ile Glu Val
            340                 345                 350

Pro Met Ile His Gln Leu
        355
```

<210> SEQ ID NO 108
<211> LENGTH: 267
<212> TYPE: PRT
<213> ORGANISM: Chlamydia trachomatis serovar D

<400> SEQUENCE: 108

```
Met Ser Arg Lys Pro Ala Ser Asn Ser Ser Arg Asn Thr Lys Arg Ser
                 5                  10                  15

Ser Asp Thr Ser Trp Glu Val Ile Ala Gln Asp Tyr Asn Lys Ala Val
             20                  25                  30

Asp Arg Asp Gly His Phe Tyr His Lys Glu Val Ile Leu Pro Asn Leu
         35                  40                  45

Leu Ser Lys Leu His Ile Ser Arg Ser Ser Leu Val Asp Val Gly
     50                  55                  60

Cys Gly Gln Gly Ile Leu Glu Lys His Leu Pro Lys His Leu Pro Tyr
 65                  70                  75                  80
```

-continued

```
Leu Gly Ile Asp Leu Ser Pro Ser Leu Leu Arg Phe Ala Lys Lys Ser
                85                  90                  95

Ala Ser Ser Lys Ser Arg Arg Phe Leu His His Asp Met Thr Gln Pro
            100                 105                 110

Val Pro Ala Asp His His Glu Gln Phe Ser His Ala Thr Ala Ile Leu
        115                 120                 125

Ser Leu Gln Asn Met Glu Ser Pro Glu Gln Ala Ile Ala His Thr Ala
    130                 135                 140

Asn Leu Leu Ala Pro Gln Gly Arg Leu Phe Ile Val Leu Asn His Pro
145                 150                 155                 160

Cys Phe Arg Ile Pro Arg Leu Ser Ser Trp Leu Tyr Asp Glu Pro Lys
                165                 170                 175

Lys Leu Leu Ser Arg Lys Ile Asp Arg Tyr Leu Ser Pro Val Ala Val
            180                 185                 190

Pro Ile Val Val His Pro Gly Glu Lys His Ser Glu Thr Thr Tyr Ser
        195                 200                 205

Phe His Phe Pro Leu Ser Tyr Trp Val Gln Ala Leu Ser Asn His Asn
    210                 215                 220

Leu Leu Ile Asp Ser Met Glu Glu Trp Ile Ser Pro Lys Lys Ser Ser
225                 230                 235                 240

Gly Lys Arg Ala Arg Ala Glu Asn Leu Cys Arg Lys Glu Phe Pro Leu
                245                 250                 255

Phe Leu Phe Ile Ser Ala Leu Lys Ile Ser Lys
            260                 265

<210> SEQ ID NO 109
<211> LENGTH: 867
<212> TYPE: PRT
<213> ORGANISM: Chlamydia trachomatis serovar D

<400> SEQUENCE: 109

Met Glu Lys Phe Ser Asp Ala Val Ser Glu Ala Leu Glu Lys Ala Phe
                  5                  10                  15

Glu Leu Ala Lys Asn Ser Lys His Ser Tyr Val Thr Glu Asn His Leu
             20                  25                  30

Leu Lys Ser Leu Leu Gln Asn Pro Gly Ser Leu Phe Cys Leu Val Ile
         35                  40                  45

Lys Asp Val His Gly Asn Leu Gly Leu Leu Thr Ser Ala Val Asp Asp
     50                  55                  60

Ala Leu Arg Arg Glu Pro Thr Val Val Glu Gly Thr Ala Val Ala Ser
 65                  70                  75                  80

Pro Ser Pro Ser Leu Gln Gln Leu Leu Leu Asn Ala His Gln Glu Ala
                 85                  90                  95

Arg Ser Met Gly Asp Glu Tyr Leu Ser Gly Asp His Leu Leu Leu Ala
            100                 105                 110

Phe Trp Arg Ser Thr Lys Glu Pro Phe Ala Ser Trp Arg Lys Thr Val
        115                 120                 125

Lys Thr Thr Ser Glu Ala Leu Lys Glu Leu Ile Thr Lys Leu Arg Gln
    130                 135                 140

Gly Ser Arg Met Asp Ser Pro Ser Ala Glu Glu Asn Leu Lys Gly Leu
145                 150                 155                 160

Glu Lys Tyr Cys Lys Asn Leu Thr Val Leu Ala Arg Glu Gly Lys Leu
                165                 170                 175

Asp Pro Val Ile Gly Arg Asp Glu Glu Ile Arg Arg Thr Ile Gln Val
```

-continued

```
                180                 185                 190
Leu Ser Arg Arg Thr Lys Asn Asn Pro Met Leu Ile Gly Glu Pro Gly
            195                 200                 205
Val Gly Lys Thr Ala Ile Ala Glu Gly Leu Ala Leu Arg Ile Val Gln
    210                 215                 220
Gly Asp Val Pro Glu Ser Leu Lys Glu Lys His Leu Tyr Val Leu Asp
225                 230                 235                 240
Met Gly Ala Leu Ile Ala Gly Ala Lys Tyr Arg Gly Glu Phe Glu Glu
                245                 250                 255
Arg Leu Lys Ser Val Leu Lys Gly Val Glu Ala Ser Glu Gly Glu Cys
            260                 265                 270
Ile Leu Phe Ile Asp Glu Val His Thr Leu Val Gly Ala Gly Ala Thr
        275                 280                 285
Asp Gly Ala Met Asp Ala Ala Asn Leu Leu Lys Pro Ala Leu Ala Arg
290                 295                 300
Gly Thr Leu His Cys Ile Gly Ala Thr Thr Leu Asn Glu Tyr Gln Lys
305                 310                 315                 320
Tyr Ile Glu Lys Asp Ala Ala Leu Glu Arg Arg Phe Gln Pro Ile Phe
                325                 330                 335
Val Thr Glu Pro Ser Leu Glu Asp Ala Val Phe Ile Leu Arg Gly Leu
            340                 345                 350
Arg Glu Lys Tyr Glu Ile Phe His Gly Val Arg Ile Thr Glu Gly Ala
        355                 360                 365
Leu Asn Ala Ala Val Val Leu Ser Tyr Arg Tyr Ile Thr Asp Arg Phe
370                 375                 380
Leu Pro Asp Lys Ala Ile Asp Leu Ile Asp Glu Ala Ala Ser Leu Ile
385                 390                 395                 400
Arg Met Gln Ile Gly Ser Leu Pro Leu Pro Ile Asp Glu Lys Glu Arg
                405                 410                 415
Glu Leu Ser Ala Leu Ile Val Lys Gln Glu Ala Ile Lys Arg Glu Gln
            420                 425                 430
Ala Pro Ala Tyr Gln Glu Glu Ala Glu Asp Met Gln Lys Ala Ile Asp
        435                 440                 445
Arg Val Lys Glu Glu Leu Ala Ala Leu Arg Leu Arg Trp Asp Glu Glu
450                 455                 460
Lys Gly Leu Ile Thr Gly Leu Lys Glu Lys Lys Asn Ala Leu Glu Asn
465                 470                 475                 480
Leu Lys Phe Ala Glu Glu Ala Glu Arg Thr Ala Asp Tyr Asn Arg
                485                 490                 495
Val Ala Glu Leu Arg Tyr Ser Leu Ile Pro Ser Leu Glu Glu Glu Ile
            500                 505                 510
His Leu Ala Glu Glu Ala Leu Asn Gln Arg Asp Gly Arg Leu Leu Gln
        515                 520                 525
Glu Glu Val Asp Glu Arg Leu Ile Ala Gln Val Ala Asn Trp Thr
    530                 535                 540
Gly Ile Pro Val Gln Lys Met Leu Glu Gly Glu Ser Glu Lys Leu Leu
545                 550                 555                 560
Val Leu Glu Glu Ser Leu Glu Glu Arg Val Val Gly Gln Pro Phe Ala
                565                 570                 575
Ile Ala Ala Val Ser Asp Ser Ile Arg Ala Ala Arg Val Gly Leu Ser
            580                 585                 590
Asp Pro Gln Arg Pro Leu Gly Val Phe Leu Phe Leu Gly Pro Thr Gly
        595                 600                 605
```

-continued

Val Gly Lys Thr Glu Leu Ala Lys Ala Leu Ala Glu Leu Leu Phe Asn
        610                 615                 620

Lys Glu Glu Ala Met Ile Arg Phe Asp Met Thr Glu Tyr Met Glu Lys
625                 630                 635                 640

His Ser Val Ser Lys Leu Ile Gly Ser Pro Pro Gly Tyr Val Gly Tyr
                645                 650                 655

Glu Glu Gly Gly Ser Leu Ser Glu Ala Leu Arg Arg Pro Tyr Ser
            660                 665                 670

Val Val Leu Phe Asp Glu Ile Glu Lys Ala Asp Lys Glu Val Phe Asn
                675                 680                 685

Ile Leu Leu Gln Ile Phe Asp Asp Gly Ile Leu Thr Asp Ser Lys Lys
            690                 695                 700

Arg Lys Val Asn Cys Lys Asn Ala Leu Phe Ile Met Thr Ser Asn Ile
705                 710                 715                 720

Gly Ser Gln Glu Leu Ala Asp Tyr Cys Thr Lys Gly Thr Ile Val
                725                 730                 735

Asp Lys Glu Ala Val Leu Ser Val Ala Pro Ala Leu Lys Asn Tyr
            740                 745                 750

Phe Ser Pro Glu Phe Ile Asn Arg Ile Asp Asp Ile Leu Pro Phe Val
                755                 760                 765

Pro Leu Thr Thr Glu Asp Ile Val Lys Ile Val Gly Ile Gln Met Asn
    770                 775                 780

Arg Val Ala Leu Arg Leu Leu Glu Arg Lys Ile Ser Leu Thr Trp Asp
785                 790                 795                 800

Asp Ser Leu Val Leu Phe Leu Ser Glu Gln Gly Tyr Asp Ser Ala Phe
                805                 810                 815

Gly Ala Arg Pro Leu Lys Arg Leu Ile Gln Gln Lys Val Val Thr Met
            820                 825                 830

Leu Ser Lys Ala Leu Leu Lys Gly Asp Ile Lys Pro Gly Met Ala Val
        835                 840                 845

Glu Leu Thr Met Ala Lys Asp Val Val Val Phe Lys Ile Lys Thr Asn
850                 855                 860

Pro Ala Val
865

<210> SEQ ID NO 110
<211> LENGTH: 1170
<212> TYPE: DNA
<213> ORGANISM: Chlamydia pneumoniae

<400> SEQUENCE: 110
atgaaaaaac tcttaaagtc ggcgttatta tccgccgcat tgctggttc tgttggctcc      60 ttacaagcct tgcctgtagg gaacccttct gatccaagct tattaattga tggtacaata     120
tgggaaggtg ctgcaggaga tccttgcgat ccttgcgcta cttggtgcga cgctattagc     180
ttacgtgctg gattttacgg agactatgtt ttcgaccgta tcttaaaagt agatgcacct     240
aaaacatttt ctatgggagc caagcctact ggatccgctg ctgcaaacta tactactgcc     300
gtagatagac ctaacccggc ctacaataag catttacacg atgcagagtg gttcactaat     360
gcaggcttca ttgccttaaa catttgggat cgctttgatg ttttctgtac tttaggagct     420
tctaatggtt acattagagg aaactctaca gcgttcaatc tcgttggttt attcggagtt     480
aaaggtacta ctgtaaatgc aaatgaacta ccaaacgttt cttaagtaa cggagttgtt     540 gaactttaca cagacaccctc tttctcttgg agcgtaggcg ctcgtggagc cttatgggaa    600

```
tgcggttgtg caactttggg agctgaattc caatatgcac agtccaaacc taaagttgaa      660
gaacttaatg tgatctgtaa cgtatcgcaa ttctctgtaa acaaacccaa gggctataaa      720
ggcgttgctt tccccttgcc aacagacgct ggcgtagcaa cagctactgg aacaaagtct      780
gcgaccatca attatcatga atggcaagta ggagcctctc tatcttacag actaaactct      840
ttagtgccat acattggagt acaatggtct cgagcaactt tgatgctga taacatccgc       900 attgctcagc aaaactacc tacagctgtt ttaaacttaa ctgcatggaa cccttcttta       960
ctaggaaatg ccacagcatt gtctactact gattcgttct cagacttcat gcaaattgtt     1020
tcctgtcaga tcaacaagtt taaatctaga aaagcttgtg gagttactgt aggagctact     1080
ttagttgatg ctgataaatg gtcacttact gcagaagctc gtttaattaa cgagagagct     1140
gctcacgtat ctggtcagtt cagattctaa                                       1170

<210> SEQ ID NO 111
<211> LENGTH: 2601
<212> TYPE: DNA
<213> ORGANISM: Chlamydia pneumoniae

<400> SEQUENCE: 111
atggagaaat tttccgatgc tgtctctgaa gctttagaga aggctttcga acttgctaaa       60
tcttcgaaac atacctatgt cacagaaaat cacctattac tggctttatt agaaaataca     120
gagtctctct tttatttggt aattaaggac attcatggga accctggttt gctcaatacg     180
gcagttaaag atgcgctctc acgagagccg actgtagttg aaggagaggt ggatcctaaa     240
ccttctccgg gttacaaaac ccttcttagg gatgccaaac aagaggcaaa gacattagga     300
gatgaataca tttctggaga tcatctgctg cttgcttttt ggagttcaaa caagagagcct     360 tttaattctt ggaagcaaac aacaaaagtt agtttttaaag atcttaagaa tctgattact     420
aaaatacgac gaggaaatcg tatggattcg ccaagcgctg aaagtaattt tcagggttta     480
gaaaagtatt gtaaaaattt aacagcatta gctcgtgaag gtaaactgga tcctgtgatc     540
ggtagagatg aagaaattcg tagaaccatc caagtgcttt cccgtagaac taaaaataac     600
cctatgctta ttggtgagcc gggtgtaggg aaaactgcta tagcagaagg attagctctt     660
aggcttatcc agggtgatgt tcctgaatct ctcaaaggta acagctttta tgtcttagat     720
atgggagctt tgattgcagg agctaagtat cgaggtgagt ttgaagaaag actaaagagt     780
gttttaaaag atgtagaatc tggagatggc gagcacatta tctttattga tgaggtgcat     840
actcttgttg gagcaggagc tactgatgga gctatggatg ctgcgaatct tttaaagcct     900
gcattagcaa gagggacgct acactgtatt ggcgcgacga cttttgaatga gtatcagaag     960 tatattgaaa aagatgctgc tttggaacgt cgatttcagc ctatttttgt gacagagcct    1020
tctttggagg atgctgtctt tattcttcgt ggactaagag aaaaatatga aattttccat    1080
ggagtcagga ttacagaggg ggctttgaat gccgcagtcc tactttccta tcgttatatc    1140
ccagatcgct tccttccaga taaggctatc gatttgatag atgaagcggc aagtttaatt    1200
cgcatgcaaa ttggtagtct tcctcttcct attgatgaaa aggagagaga gcttgctgct    1260
ttgatcgtta agcaagaggc tataaaacgc gagcaatctc cttcctatca agaagaggcg    1320
gatgctatgc agaagtctat agatgctttg agagaggaat tagcatctct acgtttgggt    1380
tgggatgaag agaagaagtt gatttcgggg ctcaaggaaa aaagaattc cttggaaagt    1440 atgaaatttt ctgaagagga ggcggagcgt gttgcagact ataatcgtgt agctgagctt    1500
```

-continued

```
cggtatagtt taattcccca acttgaagaa gaaatcaaac aggatgaagc ctctttaaat    1560
caaagagata accgtctcct tcaagaagaa gttgacgagc gattgattgc gcaagtggta    1620
gctaattgga cagggattcc tgtgcaaaaa atgctagaag gggaagctga gaaactgtta    1680
attcttgaag aatccttaga agaacgtgtg gtaggacagc cttttgcagt ctctgcggtt    1740
agtgattcta ttcgtgctgc acgtgtaggt ttaaatgatc ctcaacgtcc cttaggagtc    1800
tttttatttt tagggccaac aggggtagga aaaaccgagc ttgcaaaagc tcttgcagat    1860
cttcttttca ataaagagga agctatggtc cgcttcgata tgtcagagta tatggaaaag    1920
cattccattt ccaagcttat aggatcttct ccagggtatg tgggttatga ggaaggtggg    1980
agtctttctg aggctcttcg acgacgtccc tattcagtag ttctctttga tgagatagag    2040
aaagcagata aggaagttct aaatatcctt ttacaggttt ttgatgatgg gattcttacg    2100
gatgggaaaa aacgcaaagt aaattgtaaa aatgccttgt ttatcatgac atcaaatata    2160
ggttctccag aacttgcaga ttattgttca aaaaaggaa gtgagcttac gaaagaagcg    2220
attctttctg tagtctctcc agtattgaaa agatacttga gccctgaatt tatgaaccga    2280
attgatgaga tacttccttt tgttccatta acgaaagaag atatcgtgaa atagttggc    2340 attcaaatgc gaaggattgc ccagagatta aaggcacggc ggatcaattt atcttgggat    2400
gattctgtaa tattatttct tagtgaacag ggttatgaca gtgctttcgg agcccgccct    2460
ttaaaacgtt tgatccaaca aaaagttgtg atcttgcttt ctaaggcttt gcttaaagga    2520
gatattaaac ctgatacatc gattgagttg acgatggcaa agaggtgct cgtatttaaa    2580 aaagtggaaa ctccttctta g                                              2601
```

<210> SEQ ID NO 112
<211> LENGTH: 389
<212> TYPE: PRT
<213> ORGANISM: Chlamydia pneumoniae

<400> SEQUENCE: 112

```
Met Lys Lys Leu Leu Lys Ser Ala Leu Leu Ser Ala Ala Phe Ala Gly
              5                  10                  15

Ser Val Gly Ser Leu Gln Ala Leu Pro Val Gly Asn Pro Ser Asp Pro
          20                  25                  30

Ser Leu Leu Ile Asp Gly Thr Ile Trp Glu Gly Ala Ala Gly Asp Pro
      35                  40                  45

Cys Asp Pro Cys Ala Thr Trp Cys Asp Ala Ile Ser Leu Arg Ala Gly
  50                  55                  60

Phe Tyr Gly Asp Tyr Val Phe Asp Arg Ile Leu Lys Val Asp Ala Pro
65                  70                  75                  80

Lys Thr Phe Ser Met Gly Ala Lys Pro Thr Gly Ser Ala Ala Ala Asn
                  85                  90                  95

Tyr Thr Thr Ala Val Asp Arg Pro Asn Pro Ala Tyr Asn Lys His Leu
             100                 105                 110

His Asp Ala Glu Trp Phe Thr Asn Ala Gly Phe Ile Ala Leu Asn Ile
         115                 120                 125

Trp Asp Arg Phe Asp Val Phe Cys Thr Leu Gly Ala Ser Asn Gly Tyr
     130                 135                 140

Ile Arg Gly Asn Ser Thr Ala Phe Asn Leu Val Gly Leu Phe Gly Val
145                 150                 155                 160

Lys Gly Thr Thr Val Asn Ala Asn Glu Leu Pro Asn Val Ser Leu Ser
                 165                 170                 175
```

-continued

Asn Gly Val Val Glu Leu Tyr Thr Asp Thr Ser Phe Ser Trp Ser Val
            180                 185                 190

Gly Ala Arg Gly Ala Leu Trp Glu Cys Gly Cys Ala Thr Leu Gly Ala
        195                 200                 205

Glu Phe Gln Tyr Ala Gln Ser Lys Pro Lys Val Glu Glu Leu Asn Val
    210                 215                 220

Ile Cys Asn Val Ser Gln Phe Ser Val Asn Lys Pro Lys Gly Tyr Lys
225                 230                 235                 240

Gly Val Ala Phe Pro Leu Pro Thr Asp Ala Gly Val Ala Thr Ala Thr
                245                 250                 255

Gly Thr Lys Ser Ala Thr Ile Asn Tyr His Glu Trp Gln Val Gly Ala
            260                 265                 270

Ser Leu Ser Tyr Arg Leu Asn Ser Leu Val Pro Tyr Ile Gly Val Gln
        275                 280                 285

Trp Ser Arg Ala Thr Phe Asp Ala Asp Asn Ile Arg Ile Ala Gln Pro
    290                 295                 300

Lys Leu Pro Thr Ala Val Leu Asn Leu Thr Ala Trp Asn Pro Ser Leu
305                 310                 315                 320

Leu Gly Asn Ala Thr Ala Leu Ser Thr Thr Asp Ser Phe Ser Asp Phe
                325                 330                 335

Met Gln Ile Val Ser Cys Gln Ile Asn Lys Phe Lys Ser Arg Lys Ala
            340                 345                 350

Cys Gly Val Thr Val Gly Ala Thr Leu Val Asp Ala Asp Lys Trp Ser
        355                 360                 365

Leu Thr Ala Glu Ala Arg Leu Ile Asn Glu Arg Ala Ala His Val Ser
    370                 375                 380

Gly Gln Phe Arg Phe
385

<210> SEQ ID NO 113
<211> LENGTH: 866
<212> TYPE: PRT
<213> ORGANISM: Chlamydia pneumoniae

<400> SEQUENCE: 113

Met Glu Lys Phe Ser Asp Ala Val Ser Glu Ala Leu Glu Lys Ala Phe
                5                  10                  15

Glu Leu Ala Lys Ser Ser Lys His Thr Tyr Val Thr Glu Asn His Leu
            20                  25                  30

Leu Leu Ala Leu Leu Glu Asn Thr Glu Ser Leu Phe Tyr Leu Val Ile
        35                  40                  45

Lys Asp Ile His Gly Asn Pro Gly Leu Leu Asn Thr Ala Val Lys Asp
    50                  55                  60

Ala Leu Ser Arg Glu Pro Thr Val Val Glu Gly Val Asp Pro Lys
65                  70                  75                  80

Pro Ser Pro Gly Leu Gln Thr Leu Leu Arg Asp Ala Lys Gln Glu Ala
                85                  90                  95

Lys Thr Leu Gly Asp Glu Tyr Ile Ser Gly Asp His Leu Leu Leu Ala
            100                 105                 110

Phe Trp Ser Ser Asn Lys Glu Pro Phe Asn Ser Trp Lys Gln Thr Thr
        115                 120                 125

Lys Val Ser Phe Lys Asp Leu Lys Asn Leu Ile Thr Lys Ile Arg Arg
    130                 135                 140

Gly Asn Arg Met Asp Ser Pro Ser Ala Glu Ser Asn Phe Gln Gly Leu
145                 150                 155                 160

```
Glu Lys Tyr Cys Lys Asn Leu Thr Ala Leu Ala Arg Glu Gly Lys Leu
            165                 170                 175
Asp Pro Val Ile Gly Arg Asp Glu Ile Arg Arg Thr Ile Gln Val
        180                 185                 190
Leu Ser Arg Arg Thr Lys Asn Asn Pro Met Leu Ile Gly Glu Pro Gly
            195                 200                 205
Val Gly Lys Thr Ala Ile Ala Glu Gly Leu Ala Leu Arg Leu Ile Gln
    210                 215                 220
Gly Asp Val Pro Glu Ser Leu Lys Gly Lys Gln Leu Tyr Val Leu Asp
225                 230                 235                 240
Met Gly Ala Leu Ile Ala Gly Ala Lys Tyr Arg Gly Glu Phe Glu Glu
                245                 250                 255
Arg Leu Lys Ser Val Leu Lys Asp Val Glu Ser Gly Asp Gly Glu His
            260                 265                 270
Ile Ile Phe Ile Asp Glu Val His Thr Leu Val Gly Ala Gly Ala Thr
        275                 280                 285
Asp Gly Ala Met Asp Ala Ala Asn Leu Leu Lys Pro Ala Leu Ala Arg
    290                 295                 300
Gly Thr Leu His Cys Ile Gly Ala Thr Thr Leu Asn Glu Tyr Gln Lys
305                 310                 315                 320
Tyr Ile Glu Lys Asp Ala Ala Leu Glu Arg Arg Phe Gln Pro Ile Phe
                325                 330                 335
Val Thr Glu Pro Ser Leu Glu Asp Ala Val Phe Ile Leu Arg Gly Leu
            340                 345                 350
Arg Glu Lys Tyr Glu Ile Phe His Gly Val Arg Ile Thr Glu Gly Ala
        355                 360                 365
Leu Asn Ala Ala Val Leu Leu Ser Tyr Arg Tyr Ile Pro Asp Arg Phe
    370                 375                 380
Leu Pro Asp Lys Ala Ile Asp Leu Ile Asp Glu Ala Ala Ser Leu Ile
385                 390                 395                 400
Arg Met Gln Ile Gly Ser Leu Pro Leu Pro Ile Asp Glu Lys Glu Arg
                405                 410                 415
Glu Leu Ala Ala Leu Ile Val Lys Gln Glu Ala Ile Lys Arg Glu Gln
            420                 425                 430
Ser Pro Ser Tyr Gln Glu Glu Ala Asp Ala Met Gln Lys Ser Ile Asp
        435                 440                 445
Ala Leu Arg Glu Glu Leu Ala Ser Leu Arg Leu Gly Trp Asp Glu Glu
    450                 455                 460
Lys Lys Leu Ile Ser Gly Leu Lys Glu Lys Asn Ser Leu Glu Ser
465                 470                 475                 480
Met Lys Phe Ser Glu Glu Ala Glu Arg Val Ala Asp Tyr Asn Arg
                485                 490                 495
Val Ala Glu Leu Arg Tyr Ser Leu Ile Pro Gln Leu Glu Glu Ile
            500                 505                 510
Lys Gln Asp Glu Ala Ser Leu Asn Gln Arg Asp Asn Arg Leu Leu Gln
        515                 520                 525
Glu Glu Val Asp Glu Arg Leu Ile Ala Gln Val Ala Asn Trp Thr
    530                 535                 540
Gly Ile Pro Val Gln Lys Met Leu Glu Gly Ala Glu Lys Leu Leu
545                 550                 555                 560
Ile Leu Glu Glu Ser Leu Glu Glu Arg Val Val Gly Gln Pro Phe Ala
                565                 570                 575
```

-continued

| | | | | | | | | | | | |
|---|---|---|---|---|---|---|---|---|---|---|---|
| Val | Ser | Ala | Val | Ser | Asp | Ser | Ile | Arg | Ala | Ala | Arg | Val | Gly | Leu | Asn |
| | | | 580 | | | | | 585 | | | | | 590 | | |

Val Ser Ala Val Ser Asp Ser Ile Arg Ala Ala Arg Val Gly Leu Asn
         580                 585                 590

Asp Pro Gln Arg Pro Leu Gly Val Phe Leu Phe Leu Gly Pro Thr Gly
         595                 600                 605

Val Gly Lys Thr Glu Leu Ala Lys Ala Leu Ala Asp Leu Leu Phe Asn
    610                 615                 620

Lys Glu Glu Ala Met Val Arg Phe Asp Met Ser Glu Tyr Met Glu Lys
625                 630                 635                 640

His Ser Ile Ser Lys Leu Ile Gly Ser Ser Pro Gly Tyr Val Gly Tyr
                645                 650                 655

Glu Glu Gly Gly Ser Leu Ser Glu Ala Leu Arg Arg Pro Tyr Ser
                660                 665                 670

Val Val Leu Phe Asp Glu Ile Glu Lys Ala Asp Lys Glu Val Leu Asn
        675                 680                 685

Ile Leu Leu Gln Val Phe Asp Asp Gly Ile Leu Thr Asp Gly Lys Lys
        690                 695                 700

Arg Lys Val Asn Cys Lys Asn Ala Leu Phe Ile Met Thr Ser Asn Ile
705                 710                 715                 720

Gly Ser Pro Glu Leu Ala Asp Tyr Cys Ser Lys Lys Gly Ser Glu Leu
                725                 730                 735

Thr Lys Glu Ala Ile Leu Ser Val Val Ser Pro Val Leu Lys Arg Tyr
            740                 745                 750

Leu Ser Pro Glu Phe Met Asn Arg Ile Asp Glu Ile Leu Pro Phe Val
            755                 760                 765

Pro Leu Thr Lys Glu Asp Ile Val Lys Ile Val Gly Ile Gln Met Arg
    770                 775                 780

Arg Ile Ala Gln Arg Leu Lys Ala Arg Ile Asn Leu Ser Trp Asp
785                 790                 795                 800

Asp Ser Val Ile Leu Phe Leu Ser Glu Gln Gly Tyr Asp Ser Ala Phe
                805                 810                 815

Gly Ala Arg Pro Leu Lys Arg Leu Ile Gln Gln Lys Val Val Ile Leu
            820                 825                 830

Leu Ser Lys Ala Leu Leu Lys Gly Asp Ile Lys Pro Asp Thr Ser Ile
            835                 840                 845

Glu Leu Thr Met Ala Lys Glu Val Leu Val Phe Lys Lys Val Glu Thr
    850                 855                 860

Pro Ser
865

<210> SEQ ID NO 114
<211> LENGTH: 1179
<212> TYPE: DNA
<213> ORGANISM: Homo sapiens

<400> SEQUENCE: 114
taactctccc ctctcttctt aaaaaagagg ggagcctttt ttccttacaa agatacgcta      60 gcttttcct gaagaatctc atcaagagat atttgcattt tcccacggat aaaggcatcc     120
caaggaagcc ctggaatcac ttcatattct cccgttgcta gcattcgaca agggaaacca     180
aagattaaat cttccggtaa tccataggga ttgtggtccg aacacactcc ggaagaaaac     240
cattctcctt cttttggctg atatattgat cgagcagcct ctgctaaagc tcgtgctgca     300
gaagctgccg aagacttccc tcgtgcttcg attactgcac taccacgact ctgtacagaa     360
ggcaccataa tattctctaa ccaatcacga tccgctatcg tctctgcgat aggacggtca     420

```
ttaatcagag cttgcgtaaa atcaggcact tgtttggcgg agtgatttcc ccaaaccaca    480
acttgtgata cagccgataa aggtacttct gctctatgcg ataacatgct atgcatacga    540
ttctggtcca atcgtagcat cgcatgaaag ttctttctca ataatctggg agcatgattc    600
attgctatcc agcaattggt attcacaggg ttcccaacaa caaaaatctt tgcatcccgc    660
ttggctgttg tgttcaaagc ttttccttgc gtagcaaaaa tctccccatt tttctttaga    720
agatcccttc tctccattcc tgggcctcta ggaactgacc ctataaggaa tgccgcatca    780
atgccatcaa aagcatcatg caatgatgtc gttacctgca cacgctgtaa taagggaaa     840 gcaccatcat ctagctccat gcgcacacca gataaagccc tttctgttcc aggaatatcg    900
tagatacgca gatcgatgcc acaatcaagg ccaaaaacat ctccatgagc cagagaaaat    960
agaaagctat aggctatttg ccctgttcct cctgttactg ctacactcac tgtttgagaa   1020
accataagcc accctctctt tacttttaca aaacgcacat actctcaaca ctacgtttgc   1080
aactaactaa ttttggtccc aacatacgtt tggatgataa aagaatcaag tacctagatt   1140
ccttagtaaa agcttttggc aaaaaaaagc tcatctatt                          1179
```

<210> SEQ ID NO 115
<211> LENGTH: 772
<212> TYPE: DNA
<213> ORGANISM: Homo sapiens

<400> SEQUENCE: 115

```
gcaaaactgc tgacaaagct ggagacggaa ctacaacagc tactgttctt gctgaagcta     60
tctatacaga aggattacgc aatgtaacag ctggagcaaa tccaatggac ctcaaacgag    120
gtattgataa agctgttaag gttgttgttg atcaaatcag aaaaatcagc aaacctgttc    180
agcatcataa agaaattgct caagttgcaa caatttctgc taataatgat gcagaaatcg    240
ggaatctgat tgctgaagca atggagaaag ttggtaaaaa cggctctatc actgttgaag    300
aagcaaaagg atttgaaacc gttttggatg ttgttgaagg aatgaatttc aatagaggtt    360
acctctctag ctacttcgca acaaatccag aaactcaaga atgtgtatta gaagacgctt    420
tggttctaat ctacgataag aaaatttctg ggatcaaaga tttccttcct gttttacaac    480
aagttgctga atccggccgt cctcttctta ttatagcaga agacattgaa ggcgaagctt    540
tagctacttt ggtcgtgaac agaattcgtg gaggattccg ggtttgcgca gttaaagctc    600
caggctttgg agatagaaga aaagctatgt tggaagacat cgctatctta actggcggtc    660
aactcattag cgaagagttg ggcatgaaat tagaaaacgc taacttagct atgttaggta    720
aagctaaaaa agttatcgtt tctaaggaag acacgaccat cgtcgaagga at           772
```

<210> SEQ ID NO 116
<211> LENGTH: 487
<212> TYPE: DNA
<213> ORGANISM: Homo sapiens

<400> SEQUENCE: 116

```
gcagctcctg caaagccaca agctcctgtc gcacaaacac ggcattttaa aaagagccat     60
cagattttct ctcctaattt tacgcagtct tcccaacagg tgaataaacc tgaggaaaga    120
agacgtcctt tggagtctcg atacttacaa ggcgcggcta agcaggcagc tgctgcaaag    180
gaaaaaaagg ctcttgaaca ggaagtatcc aaacaagaag aagaagcttc taaactctgg    240
gaagagaaac agagttatgc tcgtcgtgct gtgaatgcca tcaatttcag tgtaagaaag    300
caaatagaag agcaacagaa aaccatttcc aatccaggaa atgaccagac tcttcctggg    360
```

```
aagaaagatc cacatacatc cggagaacct gttatccaaa cggtacaaga ctgttctcag    420
gatcaagaag aagagaaaaa agttctagag cgattaaaca aacgttctct gacgtgtcag    480
gatctta                                                              487

<210> SEQ ID NO 117
<211> LENGTH: 1014
<212> TYPE: DNA
<213> ORGANISM: Homo sapiens

<400> SEQUENCE: 117
ctcgtgccga atcttctaac aagagaacaa gctcctttct ttcttttcta acaaggttc     60 agcgctttct attaaaagaa accctattca gaccctatgc agcacatagt tttataaaaa   120 attttttctat taacagagga aaaataacct attgataaac agagcggtac aaggagatgc   180
aaataaagct gctttaggat ccttacctag attctagaaa atggttgcat gaatttgaac   240
aaacaaacta attaaaaatt aaaactgaaa aaaatagttt aaaacaacaa ctagaggata   300 tttttttcatg gcgctaaaag atacggcaaa aaaatgact gacttgttgg aaagtatcca   360 acaaatttg cttaaagcag aaaaggaaa taaagccgca gcacaaagag ttcgtacaga     420
atctatcaaa ttagaaaga tcgcgaaggt atatcgtaaa gagtccatta agcagaaaa     480 aatgggctta atgaaaaaaa gcaaagccgc tgctaaaaaa gctaaagctg ctgctaagaa   540
gcctgttcgc gctacaaaaa cagtggctaa aaaagcttgt acaaaaagaa cttgtgctac   600
taaagcaaag gtcaaaccaa caaaaaaagc cgctcctaaa acaaagttaa aaacagcgaa   660
aaaaactcgc tcaacaaaaa aataatattt tagcgctttc tcttttttat agagggcact   720
tttatcaaca gggccctctt tcctcttctc attgatccct tctctttttt ttgttatcct   780
ttccgttctc gcaaaggcaa gtccttgcaa ataaaagtac aacctcacac ctcctttgga   840
ggaaaaacct ttcactttct ttaggattca agttgctctc ctgctatcgt aactgtaaac   900
attttggcgt ctgtggaggc tgttcatctc ctcaaatgga atatgcatcc tcttttaaaaa   960 caaaagagct tgcgctccat aatttatttg cacctcttat cccatcccaa aata          1014

<210> SEQ ID NO 118
<211> LENGTH: 287
<212> TYPE: DNA
<213> ORGANISM: Homo sapiens

<400> SEQUENCE: 118
atgcaaataa agctgcttta ggatccttac ctagattcta gaaaatggtt gcatgaattt     60
gaacaaacaa actaattaaa aattaaaact gaaaaaaata gtttaaaaca acaactagag    120
gatatttttt catggcgcta aaagatacgg caaaaaaat gactgacttg ttggaaagta    180
tccaacaaaa tttgcttaaa gcagaaaaag gaaataaagc cgcagcacaa agagttcgta    240
cagaatctat caaattagaa aagatcgcga aggtatatcg taaagag                  287

<210> SEQ ID NO 119
<211> LENGTH: 1002
<212> TYPE: DNA
<213> ORGANISM: Homo sapiens

<400> SEQUENCE: 119
catatgcatc accatcacca tcacatgagt attcgaccta ctaatgggag tggaaatgga     60
tacccgtcta ttaatccttc taacgataat caatacggtc ttgtgcaatc gacctctggg    120
```

```
cctaattacg gaggccatac ggtatcttct cgaggaggat ttcaaggat atgcgtacga      180
atagccgatt tattccgtaa ctgtttctct cgtaatagag gcactactac tacgccatct    240
cgaactgtta tcactcaggc agatatttat catccgacta tttctggaca aggagctcaa    300
cctattgtct ctacaggaga taagaaatta gatagcgcaa ttattcaagc agatttgcgt    360
gcgcagaata aacagacttt ggctacacat attcaaagta agctaggttc tatggaggga    420
caatctcctc aagattataa agctggtgcg tatagtgcgc taagattgat gctgtttact    480
ccaggcgaaa ctactgtgag tagcgagcgg gaacgtcaag cgtgcgttac gggtcgggat    540
ctctgggaac aggctgcagg agatcttgct accaatggga atacagatgg gcttatgtta    600
atggctaacc tatctgtggg agggaagcat gtgcctgcgg ggcatttaag agaatacatg    660
gatactgtaa agggtacgtt tactgatgag aacgaggcta cagatcctac ggtagatgcc    720
attttagatt tagcagcaaa aatcgatgcg acggaattct ctagtcctgg ttcagggcaa    780
gtcattctta attatatagg aaattatgga caagtcgttt tagaaaacga ggagatgaac    840
cttcttgttt tagaagatca aaatgggcaa gatcctcaac gtgttcaaga taactcaaaa    900
gagttacaaa aactgttaga aaatgctcga aaacagatc ctgagttata tttccaaaca    960
ctaactgtca taacttcttc tgttttctta gactaaggat cc                      1002

<210> SEQ ID NO 120
<211> LENGTH: 1218
<212> TYPE: DNA
<213> ORGANISM: Homo sapiens

<400> SEQUENCE: 120
atgcatcacc atcaccatca cgtgagtagc ataagcccta gggggggaa ttctgggcca      60
gagggatttt ctagtgcatc tcgaggcgat gagattgatg atgtaccaga tagtgaagag    120
ggagagctag aagagcgcgt ttcggatcat gcagagtcta tcattaccga gagctcggaa    180
acgctgtttc gtactacttc ttcatcaggg gtcagtgaag atcttcagca acacgttagc    240
ttggaggaat ctccacgaca acgaggtttc cttggacgga tccgtgatgc agtagcttct    300
atttggaagc gtcgtgttgc acgaaggaat gaaaactatg atgtgaaaaa agcagaagag    360
cagcaaggga ttgtgcaata tctgcaggat tcgaaaatgc tgctttaac gcgtgcctat    420
cgccatctcc gtgctttcaa ttctgcatgc ttacgtacga ttcgtgagtt tttcgctacc    480
atttttcgtg ctttaaggga tgcgtattat cgacattgta cacgttctgg gatcaacttt    540
tgtggagctg ataaagactc tttagaagtt cttgttgcgg tgggtttgct tttgcgtatg    600
gctaccttac gctcttttga acatgtcggt gggaattacg aagatcgatt agtaaataat    660
gatgctccgg tgacaggtgc ggggagaact cttgttgatg atgctgtaga cgatattgaa    720
tcgattttaa atacgagaac caactggcct caacatgtca tgatagggtt ttctcgtggt    780
ctcgttcaat tatgtgcgac tccttataat gcgacttctc aagaatgttt caagtcgatt    840
gttcgtttag aaaagaaga cccttcttca gattattctc aagctttatt attagcaggg    900
ataatagatc gcttggcgga gaaagcccct atggctgcaa agtatgtttt ggatgcattg    960
cgtgttcgaa cttcggagct cataggagaa ctcattattc tcgatttgct tcctcctgta   1020
tggaaggttg gccgcggagg cgtattccct cctgtgaatg agcagctcgt tgtgcaaatt   1080
gttaatgcaa acgtagaacg attgcattcc actttcgctc atgagccaca agcttatttg   1140
cgtatgatcg aaggtttggt aaccaatttc ttttcttac ctagcgagga agatccttct   1200
tcggttggga atatctaa                                                 1218
```

<210> SEQ ID NO 121
<211> LENGTH: 726
<212> TYPE: DNA
<213> ORGANISM: Homo sapiens

<400> SEQUENCE: 121

```
catatgcatc accatcacca tcacacaaag catggaaaac gcattcgtgg tatccaagag      60
acttacgatt tagctaagtc gtattctttg ggtgaagcga tagatatttt aaaacagtgt     120
cctactgtgc gtttcgatca aacggttgat gtgtctgtta aattagggat cgatccaaga    180
aagagtgatc agcaaattcg tggttcggtt tctttacctc acggtacagg taaagttttg    240
cgaattttag ttttttgctgc tggagataag gctgcagagg ctattgaagc aggagcggac   300
tttgttggta gcgacgactt ggtagaaaaa atcaaaggtg gatgggttga cttcgatgtt    360
gcggttgcca ctcccgatat gatgagagag gtcggaaagc taggaaaagt tttaggtcca    420
agaaacctta tgcctacgcc taaagccgga actgtaacaa cagatgtggt taaaactatt    480
gcggaactgc gaaaaggtaa aattgaattt aaagctgatc gagctggtgt atgcaacgtc    540
ggagttgcga agctttcttt cgatagtgcg caaatcaaag aaaatgttga agcgttgtgt    600
gcagccttag ttaaagctaa gcccgcaact gctaaaggac aatatttagt taatttcact    660
atttcctcga ccatggggcc aggggttacc gtggatacta gggagttgat tgcgttataa    720
gaattc                                                               726
```

<210> SEQ ID NO 122
<211> LENGTH: 330
<212> TYPE: PRT
<213> ORGANISM: Homo sapiens

<400> SEQUENCE: 122

```
Met His His His His His Met Ser Ile Arg Pro Thr Asn Gly Ser
            5                  10                  15
Gly Asn Gly Tyr Pro Ser Ile Asn Pro Ser Asn Asp Asn Gln Tyr Gly
        20                  25                  30
Leu Val Gln Ser Thr Ser Gly Pro Asn Tyr Gly Gly His Thr Val Ser
    35                  40                  45
Ser Arg Gly Gly Phe Gln Gly Ile Cys Val Arg Ile Ala Asp Leu Phe
50                  55                  60
Arg Asn Cys Phe Ser Arg Asn Arg Gly Thr Thr Thr Pro Ser Arg
65                  70                  75                  80
Thr Val Ile Thr Gln Ala Asp Ile Tyr His Pro Thr Ile Ser Gly Gln
                85                  90                  95
Gly Ala Gln Pro Ile Val Ser Thr Gly Asp Lys Lys Leu Asp Ser Ala
            100                 105                 110
Ile Ile Gln Ala Asp Leu Arg Ala Gln Asn Lys Gln Thr Leu Ala Thr
        115                 120                 125
His Ile Gln Ser Lys Leu Gly Ser Met Glu Gly Gln Ser Pro Gln Asp
    130                 135                 140
Tyr Lys Ala Gly Ala Tyr Ser Ala Leu Arg Leu Met Leu Phe Thr Pro
145                 150                 155                 160
Gly Glu Thr Thr Val Ser Ser Glu Arg Glu Arg Gln Ala Cys Val Thr
                165                 170                 175
Gly Arg Asp Leu Trp Glu Gln Ala Ala Gly Asp Leu Ala Thr Asn Gly
            180                 185                 190
```

```
Asn Thr Asp Gly Leu Met Leu Met Ala Asn Leu Ser Val Gly Gly Lys
            195                 200                 205

His Val Pro Ala Gly His Leu Arg Glu Tyr Met Asp Thr Val Lys Gly
        210                 215                 220

Thr Phe Thr Asp Glu Asn Glu Ala Thr Asp Pro Thr Val Asp Ala Ile
225                 230                 235                 240

Leu Asp Leu Ala Ala Lys Ile Asp Ala Thr Glu Phe Ser Ser Pro Gly
                245                 250                 255

Ser Gly Gln Val Ile Leu Asn Tyr Ile Gly Asn Tyr Gly Gln Val Val
            260                 265                 270

Leu Glu Asn Glu Glu Met Asn Leu Val Leu Glu Asp Gln Asn Gly
            275                 280                 285

Gln Asp Pro Gln Arg Val Gln Asp Asn Ser Lys Glu Leu Gln Lys Leu
        290                 295                 300

Leu Glu Asn Ala Arg Lys Thr Asp Pro Glu Leu Tyr Phe Gln Thr Leu
305                 310                 315                 320

Thr Val Ile Thr Ser Ser Val Phe Leu Asp
                325                 330

<210> SEQ ID NO 123
<211> LENGTH: 405
<212> TYPE: PRT
<213> ORGANISM: Homo sapiens

<400> SEQUENCE: 123

Met His His His His His Val Ser Ser Ile Ser Pro Ile Gly Gly
                5                  10                  15

Asn Ser Gly Pro Glu Gly Phe Ser Ser Ala Ser Arg Gly Asp Glu Ile
            20                  25                  30

Asp Asp Val Pro Asp Ser Glu Glu Gly Glu Leu Glu Glu Arg Val Ser
        35                  40                  45

Asp His Ala Glu Ser Ile Ile Thr Glu Ser Ser Glu Thr Leu Phe Arg
    50                  55                  60

Thr Thr Ser Ser Ser Gly Val Ser Glu Asp Leu Gln Gln His Val Ser
65                  70                  75                  80

Leu Glu Glu Ser Pro Arg Gln Arg Gly Phe Leu Gly Arg Ile Arg Asp
                85                  90                  95

Ala Val Ala Ser Ile Trp Lys Arg Arg Val Ala Arg Arg Asn Glu Asn
            100                 105                 110

Tyr Asp Val Lys Lys Ala Glu Glu Gln Gln Gly Ile Val Gln Tyr Leu
        115                 120                 125

Gln Asp Ser Lys Met Pro Ala Leu Thr Arg Ala Tyr Arg His Leu Arg
    130                 135                 140

Ala Phe Asn Ser Ala Cys Leu Arg Thr Ile Arg Glu Phe Phe Ala Thr
145                 150                 155                 160

Ile Phe Arg Ala Leu Arg Asp Ala Tyr Tyr Arg His Cys Thr Arg Ser
                165                 170                 175

Gly Ile Asn Phe Cys Gly Ala Asp Lys Asp Ser Leu Glu Val Leu Val
            180                 185                 190

Ala Val Gly Leu Leu Leu Arg Met Ala Thr Leu Arg Ser Phe Glu His
        195                 200                 205

Val Gly Gly Asn Tyr Glu Asp Arg Leu Val Asn Asn Asp Ala Pro Val
    210                 215                 220

Thr Gly Ala Gly Arg Thr Leu Val Asp Asp Ala Val Asp Asp Ile Glu
225                 230                 235                 240
```

-continued

```
Ser Ile Leu Asn Thr Arg Thr Asn Trp Pro Gln His Val Met Ile Gly
            245                 250                 255
Phe Ser Arg Gly Leu Val Gln Leu Cys Ala Thr Pro Tyr Asn Ala Thr
        260                 265                 270
Ser Gln Glu Cys Phe Lys Ser Ile Val Arg Leu Lys Glu Asp Pro
    275                 280                 285
Ser Ser Asp Tyr Ser Gln Ala Leu Leu Leu Ala Gly Ile Ile Asp Arg
290                 295                 300
Leu Ala Glu Lys Ala Pro Met Ala Ala Lys Tyr Val Leu Asp Ala Leu
305                 310                 315                 320
Arg Val Arg Thr Ser Glu Leu Ile Gly Glu Leu Ile Ile Leu Asp Leu
                325                 330                 335
Leu Pro Pro Val Trp Lys Val Gly Arg Gly Val Phe Pro Pro Val
            340                 345                 350
Asn Glu Gln Leu Val Val Gln Ile Val Asn Ala Asn Val Glu Arg Leu
                355                 360                 365
His Ser Thr Phe Ala His Glu Pro Gln Ala Tyr Leu Arg Met Ile Glu
    370                 375                 380
Gly Leu Val Thr Asn Phe Phe Leu Pro Ser Glu Asp Pro Ser
385                 390                 395                 400
Ser Val Gly Asn Ile
            405

<210> SEQ ID NO 124
<211> LENGTH: 238
<212> TYPE: PRT
<213> ORGANISM: Homo sapiens

<400> SEQUENCE: 124

Met His His His His His Thr Lys His Gly Lys Arg Ile Arg Gly
                5                   10                  15
Ile Gln Glu Thr Tyr Asp Leu Ala Lys Ser Tyr Ser Leu Gly Glu Ala
            20                  25                  30
Ile Asp Ile Leu Lys Gln Cys Pro Thr Val Arg Phe Asp Gln Thr Val
        35                  40                  45
Asp Val Ser Val Lys Leu Gly Ile Asp Pro Arg Lys Ser Asp Gln Gln
    50                  55                  60
Ile Arg Gly Ser Val Ser Leu Pro His Gly Thr Gly Lys Val Leu Arg
65                  70                  75                  80
Ile Leu Val Phe Ala Ala Gly Asp Lys Ala Ala Glu Ala Ile Glu Ala
                85                  90                  95
Gly Ala Asp Phe Val Gly Ser Asp Leu Val Glu Lys Ile Lys Gly
            100                 105                 110
Gly Trp Val Asp Phe Asp Val Ala Val Ala Thr Pro Asp Met Met Arg
        115                 120                 125
Glu Val Gly Lys Leu Gly Lys Val Leu Gly Pro Arg Asn Leu Met Pro
    130                 135                 140
Thr Pro Lys Ala Gly Thr Val Thr Thr Asp Val Val Lys Thr Ile Ala
145                 150                 155                 160
Glu Leu Arg Lys Gly Lys Ile Glu Phe Lys Ala Asp Arg Ala Gly Val
                165                 170                 175
Cys Asn Val Gly Val Ala Lys Leu Ser Phe Asp Ser Ala Gln Ile Lys
            180                 185                 190
Glu Asn Val Glu Ala Leu Cys Ala Ala Leu Val Lys Ala Lys Pro Ala
```

```
                195                 200                     205
         Thr Ala Lys Gly Gln Tyr Leu Val Asn Phe Thr Ile Ser Ser Thr Met
            210                 215                 220

Gly Pro Gly Val Thr Val Asp Thr Arg Glu Leu Ile Ala Leu
         225                 230                 235
```

<210> SEQ ID NO 125
<211> LENGTH: 713
<212> TYPE: DNA
<213> ORGANISM: Chlamydia trachomatis

<400> SEQUENCE: 125

| | | | | | | |
|---|---|---|---|---|---|---|
| ataacaatcc | ctcccaatca | tcgttgaacg | tacaaggagg | agccatctat | gccaaaacct | 60 |
| ctttgtctat | tggatcttcc | gatgctggaa | cctcctatat | tttctcgggg | aacagtgtct | 120 |
| ccactgggaa | atctcaaaca | cagggcaaa | tagcgggagg | agcgatctac | tcccctactg | 180 |
| ttacattgaa | ttgtcctgcg | acattctcta | acaatacagc | ctctatagct | acaccgaaga | 240 |
| cttcttctga | agatggatcc | tcaggaaatt | ctattaaaga | taccattgga | ggagccattg | 300 |
| cagggacagc | cattaccta | tctggagtct | ctcgattttc | agggaatacg | gctgatttag | 360 |
| gagctgcaat | aggaactcta | gctaatgcaa | atacacccag | tgcaactagc | ggatctcaaa | 420 |
| atagcattac | agaaaaaatt | actttagaaa | acggttcttt | tatttttgaa | agaaaccaag | 480 |
| ctaataaacg | tggagcgatt | tactctccta | gcgtttccat | taagggaat | aatattacct | 540 |
| tcaatcaaaa | tacatccact | catgatggaa | gcgctatcta | ctttacaaaa | gatgctacga | 600 |
| ttgagtcttt | aggatctgtt | cttttacag | gaaataacgt | tacagctaca | caagctagtt | 660 |
| ctgcaacatc | tggacaaaat | acaaatactg | ccaactatgg | ggcagccatc | ttt | 713 |

<210> SEQ ID NO 126
<211> LENGTH: 780
<212> TYPE: DNA
<213> ORGANISM: Chlamydia trachomatis

<400> SEQUENCE: 126

| | | | | | | |
|---|---|---|---|---|---|---|
| ccttctcctt | actcaggagt | tttaaaagaa | aacgcaccgt | ttttacgttt | cctcacacaa | 60 |
| ttaactaaca | agcatactca | ttctggattt | cattgcctcc | taaaattctt | agtcaaatcc | 120 |
| gaaagaagcc | gacactcgag | cgctcttctc | ctaaaaatct | tgttttttct | ctgcttccga | 180 |
| gttataacgc | ggctgtctca | taacccacac | taacatgatg | aaacctctac | gtttcggtta | 240 |
| tttcttttgc | acaatctatt | ttactttgtt | acaggcagcg | tttgctaaag | aaccgaattc | 300 |
| ttgtcccgac | tgccagaata | attggaaaga | agtcacccac | acggatcaac | tccctgaaaa | 360 |
| catcattcat | gctgatgatg | cttgttatca | ctctggttat | gtacaggctc | tcattgatat | 420 |
| gcatttctta | gatagctgct | gccaggtcat | cgttgaaaac | caaactgctt | acttatttc | 480 |
| tcttcctaca | gatgatgtta | cgcgcaacgc | cattatcaac | ctaattaaag | accttccatt | 540 |
| cattcactcc | gtagaaatct | gccaagcatc | ctatcaaacc | tgtcatcatc | aaggccctca | 600 |
| tggaaagact | tctcttccag | aacaacgttc | tttctgtaca | aaggtctgtg | aaaagaagc | 660 |
| tatttggtta | ccacagaata | ccatcctatt | ctcgcctctt | gtagcagata | ctatccaagc | 720 |
| aactaatagt | gcaggtatcc | gttttaacga | cgaagtcgta | ggaaaacgtg | ttggctctgc | 780 |

<210> SEQ ID NO 127
<211> LENGTH: 433
<212> TYPE: DNA
<213> ORGANISM: Chlamydia trachomatis

<400> SEQUENCE: 127

```
ctttaaagat tcgtcgtcct tttggtacta cgagagaagt tcgtgtgaaa tggcgttatg      60
ttcctgaagg tgtaggagat ttggctacca tagctccttc tatcagggct ccacagttac     120
agaaatcgat gagaagcttt tccctaaga aagatgatgc gtttcatcgg tctagttcgc      180
tattctactc tccaatggtt ccgcattttt gggcagagct tcgcaatcat tatgcaacga     240
gtggtttgaa aagcgggtac aatattggga gtaccgatgg gtttctccct gtcattgggc     300
ctgttatatg ggagtcggag ggtctttttcc gcgcttatat tcttcggtg actgatgggg     360
atggtaagag ccataaagta ggatttctaa gaattcctac atatagttgg caggacatgg     420
aagattttga tcc                                                         433
```

<210> SEQ ID NO 128
<211> LENGTH: 803
<212> TYPE: DNA
<213> ORGANISM: Chlamydia trachomatis

<400> SEQUENCE: 128

```
atctattaat taatagcaag cttgaaacta aaaacctaat ttatttaaag ctcaaaataa      60
aaagagttt taaatgggga aattctggtt tttatttgta taacactgaa aactgcgtct     120
ttgctgataa tatcaaagtt gggcaaatga cagagccgct caaggaccag caataatcc      180
ttgggacaac atcaacacct gtcgcagcca aaatgacagc ttctgatgga atatctttaa     240
cagtctccaa taattcatca accatgctt ctattacaat tggtttggat gcggaaaaag      300
cttaccagct tattctagaa aagttgggag atcaaattct tgatggaatt gctgatacta     360
ttgttgatag tacagtccaa gatattttag acaaaatcaa aacagaccct tctctaggtt     420
tgttgaaagc ttttaacaac tttccaatca ctaataaaat tcaatgcaac gggttattca     480
ctcccagtaa cattgaaact ttattaggag gaactgaaat aggaaaattc acagtcacac     540
ccaaaagctc tgggagcatg ttcttagtct cagcagatat tattgcatca agaatggaag     600
gcggcgttgt tctagctttg gtacgagaag gtgattctaa gccctgcgcg attagttatg     660
gatactcatc aggcattcct aatttatgta gtctaagaac cagtattact aatacaggat     720
tgactccgac aacgtattca ttcgtgtag gcggtttaga aagcggtgtg gtatgggtta     780
atgcccttcc taatctcgtg ccg                                              803
```

<210> SEQ ID NO 129
<211> LENGTH: 842
<212> TYPE: DNA
<213> ORGANISM: Chlamydia trachomatis

<400> SEQUENCE: 129

```
tgggaatgtc gaagaatacg attacgttct cgtatctata ggacgccgtt tgaatacaga      60
aaatattggc ttggataaag ctggtgttat ttgtgatgaa cgcggagtca tccctaccga     120
tgccacaatg cgcacaaacg tacctaacat ttatgctatt ggagatatca caggaaaatg     180
gcaacttgcc catgtagctt ctcatcaagg aatcattgca gcacggaata tagctggcca     240
taaagaggaa atcgattact ctgccgtccc ttctgtgatc tttaccttcc ctgaagtcgc     300
ttcagtaggc ctctccccaa cagcagctca acaacaaaaa atccccgtca agtaacaaa      360
attcccattt cgagctattg gaaaagcggt cgcaatgggc gaggccgatg gatttgcagc     420
cattatcagc catgagacta ctcagcagat cctaggagct tatgtgattg gccctcatgc     480
```

```
ctcatcactg atttccgaaa ttaccctagc agttcgtaat gaactgactc ttccttgtat      540
ttacgaaact atccacgcac atccaacctt agcagaagtt tgggctgaaa gtgcgttgtt      600
agctgctgat accccattac atatgccccc tgctaaaaaa tgaccgattc agaatctcct      660
actcctaaaa aatctatacc cgccagattc cctaagtggc tacgccagaa actccctta      720 gggcgggtat ttgctcaaac tgataatact atcaaaaata aagggcttcc tacagtctgt      780
gaggaagcct cttgtccgaa tcgcacccat tgttggtcta gacatacagc tacctatcta      840
gc                                                                    842

<210> SEQ ID NO 130
<211> LENGTH: 813
<212> TYPE: DNA
<213> ORGANISM: Chlamydia trachomatis

<400> SEQUENCE: 130
aaaatacttt gagctgcaca agctcccccc tgttctagag aagaacatga tgcaaattcc       60
aatccaccct taatcttttc aaagataaga tcttctgtag aatataaagc cgctccagac      120
aaagaagctt tcacgtcagt taatgtgatt ccagccttac tactatcccc aacaaaagca      180
atacctaaaa aagattctcc gtcacgagga gaatcaaggt tgctgctcgt aaaactacaa      240 attaacccctt gggaagagac ttgatccgtg tggtccacac cttggaaaac tacgggattg      300
gttactgaga acaaagtact ttgctctacc ttaccgggaa gagtatccgc atctttctct      360
tggaaagaac ttggatctcc tacaattaac ctatactgtc cttcagcctg actatcttta      420
gacccaacga atagatctcg aatttggtct aacaataaaa ccgcttgagg gcctacatat      480
accagctcat ttacagactg tcctccagca tgaagatcta cgcaactagc taacccgcta      540
acagaggcaa ggatagctgc tactacagac aaagaaaact tagaacaggt gctttttata      600
tctttctcgg aactcatttc aaacctgcga aatagcactt ttttgacaaa ctagcgtacc      660
gaaacaatcg gtccaacaac gcgttctgcc tatgatttca caaagacaaa cgacccata       720 gacaagctcc agagacgaca ttagagcttt agaccgtgga atgtacaatg ctgactgctt      780
tttgagaaag atttttttata agaacaggc cct                                  813

<210> SEQ ID NO 131
<211> LENGTH: 1947
<212> TYPE: DNA
<213> ORGANISM: Chlamydia trachomatis

<400> SEQUENCE: 131
tcttttgcct atagagcaat ctcttatcat tgggtctgat ccaccagact atttcttcta       60
gatagagatt ctactacccc atccatggca ttcaacctct catcagtaaa cactttatta      120
gagttgttta tctgcccatc atcgatgata tcttctgaag tctttaatac cttcttacat      180
aagatccatc tcttccggaga acagtgtcct tctatggata aaattcctac gcagatattc      240
acgcatccca aaatagcagg aataccagta tagatggcat ttacaaacga agctgccgaa      300
actaggaata tcaaagcagt aatcactaaa gtagtcccta tcaccactaa tcccaccttta      360 aatgcagtgg aagatagaag attcgatata cgctctttca gtgttaatgg tgcagaacta      420
gtggaaatat cctgtgccga attggaagat ccagctcctt gaacaacggg tacagtgctc      480
atattttaca ttccttttttt ggttgtgagc agggagtcta cacaaacact tattttttc      540 aaaaacccgt ctagaatatg ctctgagacc gaaaatgaac tctttatttt tcatatagat      600
aacaaaaaaa agccgcccag gaatccctgg acggcaccta cacatcgata aaatcaaaga      660
```

```
ttaatagatg tgtgtattct ctgtatcaga aactggaaca gtcaatgtat cggaagaaag      720
aatcgcttcc ccacgagcat ctccagctga tactgctttc aatgttacag aaaactctac      780 agtttctttta gaacctaatc taggtaacga atcgaatact actgtattgc ctgtaatcgt      840
tcctttagtt ggtccagaga aggatacagg ttgcagttct ttagagaatt taagcattaa      900
agaaacattt gtatcttctg cagaacctct gttggtgaca caaatacggt aaacagtatt      960
ttctcctaca caaacagggt cacaagtatc tactacgcac atatgagtag cagcaactcc     1020
tttccagtaa gttgtcgctt ctgcgcaaga agtacaagta ccacagtcag agcagctctt     1080
cacaacaaca ttatttgtga attgtccagg agtttgtgct cttactagaa ctttatactg     1140
tagagactct ccaggattca gttctttcac agtccaaact actttattac aagaaatttg     1200
agctcctgca gcttcaagaa ctgtgactcc gggagaaaga gtgtcttcaa cgacgacatc     1260
tcgcaacaca agatcccag gattggaaac ggagatcaca tattctacag cttacaaac      1320 ataagaccaa tctgctcctg caatacttac ttgtacgcaa ggctcattga tcacagttgt     1380
tacgcttgct gtattttat gtcctccaca gtaagaaacc gttgctatat tggtagcacg     1440
accacgttta agcggacaaa actctacagt aattgttctg tgctctccag gttgcatatc     1500
tccaagagta aacgtcagta cacgctgtcc agaagagtga gcgtaaccat ctggaacagg     1560
attttcaaca acaacgttac gagctattgc tgttccttgg ttcactacat taattttgta     1620
aactactggg caacgcaaac aagcattctc tgggccttct tgtttaacac agatagcagg     1680
ttgtccacat tttgtaaccg aacggatctc tggacaagcg catactgttg cagctgtaaa     1740
gcagcaacct tctttaagag gttttaccca tacagtaatt ttactctttt cgccttgtcc     1800
taagcggtca attttccaaa ctagcttacc atcagcagta ggagttgtcg ctggatcact     1860
gcgtacgaac tctgcttcac atggtaattg ctgagtaatg ataacatcaa cacaatccct     1920
tttacctgta gcagtaattt caatagg                                         1947

<210> SEQ ID NO 132
<211> LENGTH: 1278
<212> TYPE: DNA
<213> ORGANISM: Chlamydia trachomatis

<400> SEQUENCE: 132
gataacaaaa aaaagccgcc caggaatccc tggacggcac ctacacatcg ataaaatcaa       60
agattaatag atgtgtgtat tctctgtatc agaaactgga acagtcaatg tatcggaaga      120
aagaatcgct tccccacgag catctccagc tgatactgct ttcaatgtta cagaaaactc      180
tacagtttct ttagaaccta atctaggtaa cgaatcgaat actactgtat tgcctgtaat      240 cgttcctttta gttggtccag agaaggatac aggttgcagt tctttagaga atttaagcat      300
taaagaaaca tttgtatctt ctgcagaacc tctgttggtg acacaaatac ggtaaacagt      360
attttctcct acacaaacag ggtcacaagt atctactacg cacatatgag tagcagcaac      420 tccttttccag taagttgtcg cttctgcgca agaagtacaa gtaccacagt cagagcagct      480
cttcacaaca acattatttg tgaattgtcc aggagtttgt gctcttacta aactttata       540 ctgtagagac tctccaggat tcagttcttt cacagtccaa actactttat tacaagaaat      600
ttgagctcct gcagcttcaa gaactgtgac tccgggagaa agagtgtctt caacgacgac      660
atctcgcaac acaagatctc caggattgga aacggagatc acatattcta caggcttaca      720
aacataagac caatctgctc ctgcaatact tacttgtacg caaggctcat tgatcacagt      780
```

```
tgttacgctt gctgtatttt tatgtcctcc acagtaagaa accgttgcta tattggtagc     840
acgaccacgt ttaagcggac aaaactctac agtaattgtt ctgtgctctc caggttgcat     900
atctccaaga gtaaacgtca gtacacgctg tccagaagag tgagcgtaac catctggaac     960
aggattttca acaacaacgt tacgagctat tgctgttcct tggttcacta cattaatttt    1020
gtaaactact gggcaacgca acaagcatt ctctgggcct tcttgtttaa cacagatagc    1080
aggttgtcca cattttgtaa ccgaacggat ctctggacaa gcgcatactg ttgcagctgt    1140
aaagcagcaa ccttctttaa gaggttttac ccatacagta attttactct tttcgccttg    1200
tcctaagcgg tcaattttcc aaactagctt accatcagca gtaggagttg tcgctggatc    1260
actgcgtacg aactctgc                                                   1278
```

<210> SEQ ID NO 133
<211> LENGTH: 916
<212> TYPE: DNA
<213> ORGANISM: Chlamydia trachomatis

<400> SEQUENCE: 133

```
atggcgacaa tttaacgatt accggacaaa accatacatt atcatttaca gattctcaag      60
ggccagttct tcaaaattat gccttcattt cagcaggaga gacacttact ctgaaagatt     120
tttcgagttt gatgttctcg aaaaatgttt cttgcggaga aaagggaatg atctcaggga     180
aaaccgtgag tatttccgga gcaggcgaag tgatttttg ggataactct gtgggtatt      240 ctcctttgtc tattgtgcca gcatcgactc caactcctcc agcaccagca ccagctcctg     300
ctgcttcaag ctctttatct ccaacagtta gtgatgctcg gaaagggtct attttttctg     360
tagagactag tttggagatc tcaggcgtca aaaaagggt catgttcgat aataatgccg     420
ggaattttgg aacagttttt cgaggtaata gtaataataa tgctggtagt ggggtagtg     480 ggtctgctac aacaccaagt tttacagtta aaaactgtaa agggaaagtt tctttcacag     540
ataacgtagc ctcctgtgga ggcggagtag tctacaaagg aactgtgctt ttcaaagaca     600
atgaaggagg catattcttc cgagggaaca cagcatacga tgatttaggg attcttgctg     660
ctactagtcg ggatcagaat acggagacag gaggcggtgg aggagttatt tgctctccag     720
atgattctgt aaagtttgaa ggcaataaag gttctattgt ttttgattac aactttgcaa     780
aaggcagagg cggaagcatc ctaacgaaag aattctctct tgtagcagat gattcggttg     840
tctttagtaa caatacagca gaaaaaggcg gtggagctat ttatgctcct acgtatcgat     900
ataagcacga atggag                                                      916
```

<210> SEQ ID NO 134
<211> LENGTH: 751
<212> TYPE: DNA
<213> ORGANISM: Chlamydia trachomatis
<220> FEATURE:
<221> NAME/KEY: misc_feature
<222> LOCATION: 741
<223> OTHER INFORMATION: n = A,T,C or G

<400> SEQUENCE: 134

```
agcctctggc gaaggagagc cataaaaagt gcctaccagc ggagaaacaa taaatctcc       60 ctgagcaggc acctcacttt cttcttctc gatactctct ttaacaatag gattcccaag     120
gttttgatct gaggataagt tttgaaatcc agcaaacagt ctgttatcat aaaagactgg     180
ctcctgaata cttgggactg tatccctttc taactctaac tccaaacctt cacgcttgat     240
aacaatgcgc ttcacgtgcc gaattcggca cgaggctctt tcttacgagg atctcgagtc     300
```

```
aagaagcctt gagccttcaa ttcttgcttc atgtcttctt tctcttgcag aacagctcta    360
gctaaaccca atcgagtagc aataacctga ccttgaaccc ctcctccact tactcggata    420
atcaaatcga aactgttgac atcaccgagc attctgagcg gagctaagat ggttgctctt    480
tgaacttcaa gagggaaata ttgctctaaa gtctttccat ttacgtcaat ttttccattc    540
ccagaacgaa gacgaacgca cacctgcttt cttctgcctg ttgcaacaga ctcttgtatc    600
atattctttg tcacaaatta ccccaaatta cgcgtctaaa acaattggtt tgatagcttc    660
atactgtgcg taagaactac cttcaaaac tcttaaagat ttcatttgac gtcttccaag     720
ttttgtttta ggcaacattc nttaacagca t                                   751

<210> SEQ ID NO 135
<211> LENGTH: 410
<212> TYPE: DNA
<213> ORGANISM: Chlamydia trachomatis

<400> SEQUENCE: 135
ataatccaga ctcttcctca tctggagata gcgctggaga ctctgaagaa ctgactgaga     60
cagaagctgg ttctacaaca gaaactccta ctttaatagg aggaggtgct atctatggag    120
aaactgttaa gattgagaac ttctctggcc aaggaatatt ttctggaaac aaagctatcg    180
ataacaccac agaaggctcc tcttccaaat ctgacgtcct cggaggtgcg gtctatgcta    240
aaacattgtt taatctcgat agcgggagct ctagacgaac tgtcaccttc tccgggaata    300
ctgtctcttc tcaatctaca acaggtcagg ttgctggagg agctatctac tctcctactg    360
taaccattgc tactcctgta gtattttcta aaaactctgc aacaaacaat               410

<210> SEQ ID NO 136
<211> LENGTH: 2719
<212> TYPE: DNA
<213> ORGANISM: Chlamydia trachomatis

<400> SEQUENCE: 136
ctcgtgccga aaagctttct gctctaccaa agagattcgt ttttttaaatt cttcattctc    60 tctaagagat ttagtttctt tcgcagaaca attgatagat actccgtacg tttggggtgg   120
ccggtgcatt cataaacagc ttcctcgtaa tggtgtagat tgttcggggt atattcaact   180
actttaccaa gtcacaggaa gaaatatccc tcgcaatgct agagatcaat acagagactg   240
ttctccagta aaagatttct cgtctctacc tataggagga cttatcttcc tcaagaaagc   300
aagcacggga caaatcaacc atgttatgat gaaaatctcg gagcatgaat tcattcatgc   360
tgcggaaaaa atagggaaag tagaaaaagt aatcctagga aatagggctt tctttaaagg   420
gaatctattc tgctcattag gtgaaccgcc tatagaagct gttttggcg ttcctaaaaa    480 tagaaaagcc ttcttttgaa agaaggcttt tctgaaacgc actccaatat atggacaagc   540
aatagcttat cgtttggaga attggaaact cttacgagct ttcttacgac cgtatttttt   600
acgctctttc ttacgaggat ctcgagtcaa gaagccttga gccttcaatt cttgcttcat   660
gtcttctttc tcttgcagaa cagctctagc taaacccaat cgagtagcaa taacctgacc   720 ttgaaccccct cctccactta ctcggataat caaatcgaaa ctgttgacat caccgagcat   780
tctgagcgga gctaagatgg ttgctctttg aacttcaaga gggaaatatt gctctaaagt   840
ctttccattt acgtcaattt ttccattccc agaacgaaga cgaacgctag aaacagcctg   900 cttttcttctg cctgttgcaa cagactcttg tatcatattt tttgtcacaa attaccccaa   960
```

```
attacgcgtc taaaacaatt ggtttgatag cttcatactg tgcgtaagaa ctacctttca    1020
aaactcttaa agatttcatt tgacgtcttc caagttttgt tttaggcaac attcctttaa    1080
cagcatgctc gataacataa gcaggctttc gcgcaatcat gttttcaaaa ggaacttctc    1140
gcatcccaga aataaagcct gtgtaatagt gatacacttt ctgagttcct tttgcgccag    1200
tcaaacgcac tttctcagca ttgatcacaa tgacaccatc tcccatcgct acgtgaggag    1260
taaaagtcac cttatgctta cctctcagga tcttcgcaac ttctgaagat aatctcccta    1320
aggtcttccc ttcagcatta actacatacc aggctttgtt tcgatcgtcc gaagccttag    1380
ctagggtcgt tttcgtatct tttcttttt ccataactta aatcacctta tcagagggaa    1440
tgattataat tttgatgatt attttttcca acaaaaagc agctgtattt gccttctaaa     1500
gaatttagaa aagaaaaaat ttcaaaaaga tctcttttct ttttgccttc aaaaacagcc    1560
ttacacttct atacttcttt cgaaaaaata ttttagggaa gttcttgaat catgatttac    1620
ataataaaaa aaatagttag ctgccatcag ctaaatttaa aaaggtgcta ccagacgcta    1680
aaagctggtc cacgtaatta atatcataat cagaagaag aaacttcgga ttatccaaca    1740
tgaactgatg aaaaggaatt gtagaatgca ccccaccaat atggaactct tttaaagctc    1800
ttttcataat ggctatcgct tcctctcgat tctttccttt tgtgattacc ttagcaatca    1860
tggaatcata ataaggaggt atcgcataac cactgtagca agccccgtct actcgcacag    1920
caggacctgc aggagggaga taataatcta atctaccagg ggaaggagta aagttattaa    1980
ttggatcctc tgcattgatt cggcattgaa tcacgtgccc tttaaactct atattctttt    2040
gcttccaagg cagttttct cccttagcga cactaatctg agcctttaac aaatcgatcc     2100
ctgtcacttc ttccgtaata gtatgttcca cttggatacg cgtattcatc tccatgaaat    2160
aaaaacgctt ctccttatct aacagaaatt ctactgttcc aacagagaaa tacccggcac    2220
tccgagctaa atccactgct acttttccaa ctttagctcg catttctgga gttaaaatag    2280
gacttggagt ctcttctatt aatttttgcc gacgcctttg tactgacaat ctcgttctcc    2340
aagatacacg taatttccgt gcttatctcc aattacttga acttctaaat gtcttggatt    2400
ttcaataaat ttttcaatat acacgtcagg attattaaat cccgcttctg cttcagcccg    2460
agcggcagta aaagccctat agaattcgtc tttttctcta acaatccgta ttcctcgtcc    2520
accgcctcca gcaacagctt tgatgacgat ggggaatccg atcttttctg caattctaat    2580
cccttccacc tcatccttca ctacaccttc agatccaggg attacagggc acttaatctt    2640
tttagccaac tgcttagctg cgactttatc tcccatagtc gctatcgact cagcactagg    2700
accgataaat ctcgtgccg                                                  2719
```

<210> SEQ ID NO 137
<211> LENGTH: 2354
<212> TYPE: DNA
<213> ORGANISM: Chlamydia trachomatis

<400> SEQUENCE: 137

```
gtgcaagatg ggacgagttt gaagtttaat actagcacat aacttccctt ctggaggttt      60
aggagagagc ccttttatta gggctctctt tttttgtgtg tgaggaaagc tagcgtctaa     120
ctaaatgtct ctaagtaagg atgtttttag gggaaatagc gattttcagt gttgagaagc     180
ttagttacaa gacaataaac aaggctaaga aaaacctttc ttagccttgt ttctcaacga     240
atcgcctata gaagactaat cttccagcgt tgccctatgg ctcagcttca actggccttt     300
ttcgttaatg ctaaggagtt taacagcaag cttgtctcct tctttgacaa agccagagat     360
```

-continued

```
attgtctact ttttgtttag acaattcaga aatatgacag agcccttctt ttcctgggag      420
gacttctacg aatactccaa atgttgcgat agatgtaaca cggccattat aaactttacc      480
gacttcaact tctccagtta atccttcgat aagttcttta gctttgttaa tcgattcttg      540
ggtgcttgca gctatgttaa tgacgccgtc atcattgatg tcaacttgcg caccagaacg      600
ctcgataatt tgacggattt gttttcctcc gggaccaatg accgttgcga ttttgaggt       660 attgatctgc atagtttcaa tgcgcggagc atatttagaa acagttccct taggggaggc      720
cagaacctgt gtcataagat taaggatatg actacgccct tgtttagctt gcgctagagc      780
ttgctccata atcttatgag tgattccctc tatcttgata tccatttgga aagctgtaat      840
acctttagct gttccggcta cttaaagtc catatctcct agatgatctt ctataccgga       900
aatatcagac aagatgatgg cttgatctcg atctaagatt aagcccatag caatacctgc      960
cacgggagct ttgataggaa ctccagcatc catgagtgca agacagcctc cacatacgga     1020
tgccatggag gaagatccat tagactcagt aatattagat tctaggcgaa tgatataagg     1080
gaatcgcgat gtctcaggaa gaacatgact taaagctttc tcagctaatt tcccatgtcc     1140
aatttcacgt cttcctgggg aaccaattct gccaacttct cctacggaga aaggagggaa     1200
gaaatactgt agatagaagc gagcggctcc atctccattc agatcttcga atcgctgtgc     1260
catattttcg cctccaagcg tacatacggc catgctttgc gtctctccgc gagtaaataa     1320
gcaacttccg tgtgttcttg aagaaaaagg agtctctatg gaaatggggc gaatctctgt     1380
ggtggttcgt ccatctacac gaataccaag atcttggata gagctcgca tttgattgga      1440 ttttgctgtc ttaaatgcag ccttaacgtt caacaaagaa aaatcactgt tttcttcttg     1500
aaccaagtta gcaataacgg attcctctaa ttcttcgag gcttgctcta gagcttcttt      1560
atctctaaaa gacaatgctt ttcgaatttt ttctctaata aaatctgaaa ctacattttg     1620
tacgtcttct ggcatatcaa gaacggcaga gaaattcttt tgtttgccga tagctttctg     1680
ccatgcttca atagcatcgc atattttagc tatataggtt tgcccaaaaa caatagcttc     1740
tagaacttgc tcttctgtta aaagtcgca atgtccttca atcattaaaa ctgcagaagc      1800
tgttcctgcc atgacgagat ccagcctgga ggcacttaac tcatctctgg ttgggttaat     1860
gacccacttt cctccgacga gcccaacgcg tacacccgca acgatacaat tttgaggaac    1920
ctctgagata gctaaagcgg cagaagctcc gcaaatagct agaggatcag gtaaagtttt    1980
cccgtcgtaa gaccaaacgt aggacaagac ttgaatatct tgcatgagtc tattaggaaa    2040
cgacggacgc aaagagcgat ccattagccg agaaacaaga atttctctct cggaaggccg    2100
tccttcacgt tttagaaatc ctccagaggt tcttcctgcg gaggaaaact tctcttgata    2160
gtctactctg aaaggcagaa aatcgacagc ctctgacaag gaggctgcac acgctgaaga    2220
aaaaacccaa gtctcgttca ttttgacgag aacagcccca ctggcctggc gagctatttt    2280
ccctgtctcg aaaattaatg ttttattttt gtctaacgca acagaaaaag tctcaaaagc    2340
catggagttg tcct                                                      2354
```

<210> SEQ ID NO 138
<211> LENGTH: 898
<212> TYPE: DNA
<213> ORGANISM: Chlamydia trachomatis

<400> SEQUENCE: 138

```
tcatcttgtc tgatatttcc ggtatagaag atcatctagg agatatggac tttaaagtag       60
```

-continued

```
ccggaacagc taaaggtatt acagctttcc aaatggatat caagatagag ggaatcactc    120
ataagattat ggagcaagct ctagcgcaag ctaaacaagg gcgtagtcat atccttaatc    180
ttatgacaca ggttctggcc tcccctaagg gaactgtttc taaatatgct ccgcgcattg    240
aaactatgca gatcaatacc tcaaaaatcg caacggtcat tggtcccgga ggaaaacaaa    300
tccgtcaaat tatcgagcgt tctggtgcgc aagttgacat caatgatgac ggcgtcatta    360
acatagctgc aagcacccaa gaatcgatta caaaagctaa agaacttatc gaaggattaa    420
ctggagaagt tgaagtcggt aaagtttata atggccgtgt tacatctatc gcaacatttg    480
gagtattcgt agaagtcctc ccaggaaaag aagggctctg tcatatttct gaattgtcta    540
aacaaaaagt agacaatatc tctggctttg tcaagaagg agacaagctt gctgttaaac    600
tccttagcat taacgaaaaa ggccagttga agctgagcca tagggcaacg ctggaagatt    660
agtcttctat aggcgattcg ttgagaaaca aggctaagaa aggtttttct tagccttgtt    720
tattgtcttg taactaagct tctcaacact gaaaatcgct atttccccta aaacatcct    780
tacttagaga catttagtta gacgctagct ttcctcacac acaaaaaaag agagccctaa    840
taaagggct ctctcctaaa cctccagaag ggaagttatg tgctagtatt aaacttca      898
```

<210> SEQ ID NO 139
<211> LENGTH: 660
<212> TYPE: PRT
<213> ORGANISM: Chlamydia trachomatis

<400> SEQUENCE: 139

```
Met His His His His His His Met Glu Ser Gly Pro Glu Ser Val Ser
                5                   10                  15
Ser Asn Gln Ser Ser Met Asn Pro Ile Ile Asn Gly Gln Ile Ala Ser
            20                  25                  30
Asn Ser Glu Thr Lys Glu Ser Thr Lys Ala Ser Glu Ala Ser Pro Ser
        35                  40                  45
Ala Ser Ser Ser Val Ser Ser Trp Ser Phe Leu Ser Ser Ala Lys Asn
    50                  55                  60
Ala Leu Ile Ser Leu Arg Asp Ala Ile Leu Asn Lys Asn Ser Ser Pro
65                  70                  75                  80
Thr Asp Ser Leu Ser Gln Leu Glu Ala Ser Thr Ser Thr Ser Thr Val
                85                  90                  95
Thr Arg Val Ala Ala Lys Asp Tyr Asp Glu Ala Lys Ser Asn Phe Asp
            100                 105                 110
Thr Ala Lys Ser Gly Leu Glu Asn Ala Lys Thr Leu Ala Glu Tyr Glu
        115                 120                 125
Thr Lys Met Ala Asp Leu Met Ala Ala Leu Gln Asp Met Glu Arg Leu
    130                 135                 140
Ala Asn Ser Asp Pro Ser Asn Asn His Thr Glu Glu Val Asn Asn Ile
145                 150                 155                 160
Lys Lys Ala Leu Glu Ala Gln Lys Asp Thr Ile Asp Lys Leu Asn Lys
                165                 170                 175
Leu Val Thr Leu Gln Asn Gln Asn Lys Ser Leu Thr Glu Val Leu Lys
            180                 185                 190
Thr Thr Asp Ser Ala Asp Gln Ile Pro Ala Ile Asn Ser Gln Leu Glu
        195                 200                 205
Ile Asn Lys Asn Ser Ala Asp Gln Ile Ile Lys Asp Leu Glu Arg Gln
    210                 215                 220
Asn Ile Ser Tyr Glu Ala Val Leu Thr Asn Ala Gly Glu Val Ile Lys
```

-continued

```
        225                 230                 235                 240
Ala Ser Ser Glu Ala Gly Ile Lys Leu Gly Gln Ala Leu Gln Ser Ile
                245                 250                 255
Val Asp Ala Gly Asp Gln Ser Gln Ala Ala Val Leu Gln Ala Gln Gln
                260                 265                 270
Asn Asn Ser Pro Asp Asn Ile Ala Ala Thr Lys Glu Leu Ile Asp Ala
                275                 280                 285
Ala Glu Thr Lys Val Asn Glu Leu Lys Gln Glu His Thr Gly Leu Thr
                290                 295                 300
Asp Ser Pro Leu Val Lys Lys Ala Glu Glu Gln Ile Ser Gln Ala Gln
305                 310                 315                 320
Lys Asp Ile Gln Glu Ile Lys Pro Ser Gly Ser Asp Ile Pro Ile Val
                325                 330                 335
Gly Pro Ser Gly Ser Ala Ala Ser Ala Gly Ser Ala Ala Gly Ala Leu
                340                 345                 350
Lys Ser Ser Asn Asn Ser Gly Arg Ile Ser Leu Leu Leu Asp Asp Val
                355                 360                 365
Asp Asn Glu Met Ala Ala Ile Ala Leu Gln Gly Phe Arg Ser Met Ile
                370                 375                 380
Glu Gln Phe Asn Val Asn Asn Pro Ala Thr Ala Lys Glu Leu Gln Ala
385                 390                 395                 400
Met Glu Ala Gln Leu Thr Ala Met Ser Asp Gln Leu Val Gly Ala Asp
                405                 410                 415
Gly Glu Leu Pro Ala Glu Ile Gln Ala Ile Lys Asp Ala Leu Ala Gln
                420                 425                 430
Ala Leu Lys Gln Pro Ser Ala Asp Gly Leu Ala Thr Ala Met Gly Gln
                435                 440                 445
Val Ala Phe Ala Ala Lys Val Gly Gly Gly Ser Ala Gly Thr Ala
                450                 455                 460
Gly Thr Val Gln Met Asn Val Lys Gln Leu Tyr Lys Thr Ala Phe Ser
465                 470                 475                 480
Ser Thr Ser Ser Ser Tyr Ala Ala Ala Leu Ser Asp Gly Tyr Ser
                485                 490                 495
Ala Tyr Lys Thr Leu Asn Ser Leu Tyr Ser Glu Ser Arg Ser Gly Val
                500                 505                 510
Gln Ser Ala Ile Ser Gln Thr Ala Asn Pro Ala Leu Ser Arg Ser Val
                515                 520                 525
Ser Arg Ser Gly Ile Glu Ser Gln Gly Arg Ser Ala Asp Ala Ser Gln
                530                 535                 540
Arg Ala Ala Glu Thr Ile Val Arg Asp Ser Gln Thr Leu Gly Asp Val
545                 550                 555                 560
Tyr Ser Arg Leu Gln Val Leu Asp Ser Leu Met Ser Thr Ile Val Ser
                565                 570                 575
Asn Pro Gln Ala Asn Gln Glu Ile Met Gln Lys Leu Thr Ala Ser
                580                 585                 590
Ile Ser Lys Ala Pro Gln Phe Gly Tyr Pro Ala Val Gln Asn Ser Ala
                595                 600                 605
Asp Ser Leu Gln Lys Phe Ala Ala Gln Leu Glu Arg Glu Phe Val Asp
                610                 615                 620
Gly Glu Arg Ser Leu Ala Glu Ser Gln Glu Asn Ala Phe Arg Lys Gln
625                 630                 635                 640
Pro Ala Phe Ile Gln Gln Val Leu Val Asn Ile Ala Ser Leu Phe Ser
                645                 650                 655
```

Gly Tyr Leu Ser
        660

<210> SEQ ID NO 140
<211> LENGTH: 598
<212> TYPE: PRT
<213> ORGANISM: Chlamydia trachomatis

<400> SEQUENCE: 140

Met His His His His His Met Ser Ile Arg Gly Val Gly Gly Asn
                 5                  10                  15

Gly Asn Ser Arg Ile Pro Ser His Asn Gly Asp Gly Ser Asn Arg Arg
             20                  25                  30

Ser Gln Asn Thr Lys Gly Asn Asn Lys Val Glu Asp Arg Val Cys Ser
         35                  40                  45

Leu Tyr Ser Ser Arg Ser Asn Glu Asn Arg Glu Ser Pro Tyr Ala Val
     50                  55                  60

Val Asp Val Ser Ser Met Ile Glu Ser Thr Pro Thr Ser Gly Glu Thr
 65                  70                  75                  80

Thr Arg Ala Ser Arg Gly Val Leu Ser Arg Phe Gln Arg Gly Leu Val
                 85                  90                  95

Arg Ile Ala Asp Lys Val Arg Arg Ala Val Gln Cys Ala Trp Ser Ser
            100                 105                 110

Val Ser Thr Ser Arg Ser Ser Ala Thr Arg Ala Ala Glu Ser Gly Ser
        115                 120                 125

Ser Ser Arg Thr Ala Arg Gly Ala Ser Ser Gly Tyr Arg Glu Tyr Ser
    130                 135                 140

Pro Ser Ala Ala Arg Gly Leu Arg Leu Met Phe Thr Asp Phe Trp Arg
145                 150                 155                 160

Thr Arg Val Leu Arg Gln Thr Ser Pro Met Ala Gly Val Phe Gly Asn
                165                 170                 175

Leu Asp Val Asn Glu Ala Arg Leu Met Ala Ala Tyr Thr Ser Glu Cys
            180                 185                 190

Ala Asp His Leu Glu Ala Lys Glu Leu Ala Gly Pro Asp Gly Val Ala
        195                 200                 205

Ala Ala Arg Glu Ile Ala Lys Arg Trp Glu Lys Arg Val Arg Asp Leu
    210                 215                 220

Gln Asp Lys Gly Ala Ala Arg Lys Leu Leu Asn Asp Pro Leu Gly Arg
225                 230                 235                 240

Arg Thr Pro Asn Tyr Gln Ser Lys Asn Pro Gly Glu Tyr Thr Val Gly
                245                 250                 255

Asn Ser Met Phe Tyr Asp Gly Pro Gln Val Ala Asn Leu Gln Asn Val
            260                 265                 270

Asp Thr Gly Phe Trp Leu Asp Met Ser Asn Leu Ser Asp Val Val Leu
        275                 280                 285

Ser Arg Glu Ile Gln Thr Gly Leu Arg Ala Arg Ala Thr Leu Glu Glu
    290                 295                 300

Ser Met Pro Met Leu Glu Asn Leu Glu Glu Arg Phe Arg Arg Leu Gln
305                 310                 315                 320

Glu Thr Cys Asp Ala Ala Arg Thr Glu Ile Glu Ser Gly Trp Thr
                325                 330                 335

Arg Glu Ser Ala Ser Arg Met Glu Gly Asp Glu Ala Gln Gly Pro Ser
            340                 345                 350

Arg Val Gln Gln Ala Phe Gln Ser Phe Val Asn Glu Cys Asn Ser Ile

-continued

```
            355               360               365
Glu Phe Ser Phe Gly Ser Phe Gly Glu His Val Arg Val Leu Cys Ala
    370               375               380
Arg Val Ser Arg Gly Leu Ala Ala Gly Glu Ala Ile Arg Arg Cys
385               390               395               400
Phe Ser Cys Cys Lys Gly Ser Thr His Arg Tyr Ala Pro Arg Asp Asp
                405               410               415
Leu Ser Pro Glu Gly Ala Ser Leu Ala Glu Thr Leu Ala Arg Phe Ala
            420               425               430
Asp Asp Met Gly Ile Glu Arg Gly Ala Asp Gly Thr Tyr Asp Ile Pro
        435               440               445
Leu Val Asp Asp Trp Arg Arg Gly Val Pro Ser Ile Glu Gly Glu Gly
    450               455               460
Ser Asp Ser Ile Tyr Glu Ile Met Met Pro Ile Tyr Glu Val Met Asn
465               470               475               480
Met Asp Leu Glu Thr Arg Arg Ser Phe Ala Val Gln Gln Gly His Tyr
                485               490               495
Gln Asp Pro Arg Ala Ser Asp Tyr Asp Leu Pro Arg Ala Ser Asp Tyr
            500               505               510
Asp Leu Pro Arg Ser Pro Tyr Pro Thr Pro Pro Leu Pro Pro Arg Tyr
        515               520               525
Gln Leu Gln Asn Met Asp Val Glu Ala Gly Phe Arg Glu Ala Val Tyr
    530               535               540
Ala Ser Phe Val Ala Gly Met Tyr Asn Tyr Val Val Thr Gln Pro Gln
545               550               555               560
Glu Arg Ile Pro Asn Ser Gln Gln Val Glu Gly Ile Leu Arg Asp Met
                565               570               575
Leu Thr Asn Gly Ser Gln Thr Phe Arg Asp Leu Met Lys Arg Trp Asn
            580               585               590
Arg Glu Val Asp Arg Glu
        595

<210> SEQ ID NO 141
<211> LENGTH: 788
<212> TYPE: DNA
<213> ORGANISM: Chlamydia trachomatis

<400> SEQUENCE: 141
gctttacgta gccatttgca ttaatgctcc gtctcaggaa cgtattcata ctcggatagc      60
gcgtcatcct ctaaaaagga aggaaatgac cgtgcttcct acacatgccg aaggcggtaa     120
ggaagcaatt acccattgcc aagttctagc tacgaatgga cgattaagtg tggttgctct     180
atcccagaa acaggcagaa cccaccagct tcgtgtacat atgaagcacc tgggcacacc      240
gattctcgga gatcccgttt acgggatccc ctctataaat tttcgttatg gtcttgacaa     300
acaacaattg catgcctata gcttggtttt tgctcatccg gagagtgcgg agcgagtgaa     360
gctagtgaca aagcttccag acgatatgac ttccttaata gaaaggaat ttagagaagg      420
tgtctctata ctggatggtt cgtgtgattg gtttaaaatc actaggtagt tttgtttttt     480
aagtaagaag tataaatag attatagata ctattttat ttttctttca caccttcaga      540
aaaaagcttg tgtaggattt gcttcgcatg aaagagtttt tagcgtacat tgtaaaaaat     600
cttgttgata agccgagga agtgcatctg aaagaggtgc agggaaccaa tacgattatc      660
tacgaattga ctgttgctaa gggagatatc ggtaaaatta tcggtaaaga aggacgcact     720
```

```
attaaggcta tccgtacttt attggtttcc gtagcaagtc gagataatgt gaaagtcagc    780
ctagaaat                                                             788
```

<210> SEQ ID NO 142
<211> LENGTH: 788
<212> TYPE: DNA
<213> ORGANISM: Chlamydia trachomatis

<400> SEQUENCE: 142

```
gctttacgta gccatttgca ttaatgctcc gtctcaggaa cgtattcata ctcggatagc     60
gcgtcatcct ctaaaaagga aggaaatgac cgtgctttct acacatgccg aaggcggtaa    120
ggaagcaatt acccattgcc aagttctagc tacgaatgga cgattaagtg tggttgctct    180
atacccagaa acaggcagaa cccaccagct tcgtgtacat atgaagcacc tgggcacacc    240
gattctcgga gatcccgttt acgggatccc ctctataaat tttcgttatg gtcttgacaa    300
acaacaattg catgcctata gcttggtttt tgctcatccg gagagtgcgg agcgagtgaa    360
gctagtgaca aagcttccag acgatatgac ttccttaata gaaaaggaat ttagagaagg    420
tgtctctata ctggatggtt cgtgtgattg gtttaaaatc actaggtagt tttgtttttt    480
aagtaagaag tataaaatag attatagata ctattttat ttttctttca ccttcaga     540 aaaaagcttg tgtaggattt gcttcgcatg aaagagtttt tagcgtacat tgtaaaaaat    600
cttgttgata agccagagga agtgcatctg aaagaggtgc agggaaccaa tacgattatc    660
tacgaattga ctgttgctaa gggagatatc ggtaaaatta tcggtaaaga aggacgcact    720
attaaggcta tccgtacttt attggtttcc gtagcaagtc gagataatgt gaaagtcagc    780
ctagaaat                                                             788
```

<210> SEQ ID NO 143
<211> LENGTH: 1754
<212> TYPE: DNA
<213> ORGANISM: Chlamydia trachomatis

<400> SEQUENCE: 143

```
atataatgaa ttaaacaacg cacaccaaat cctgttgcat atttggggta aggcaactct     60 tcttttcat ggtaagcagt accggcaatg tccaaatgtg cccatgctac tgaattgtct    120
tcgaggaaac gttgtaaaaa tagcgctgca gtaatcgatc ctgcacgatt gctgccgata    180 ttttcatat ctgcaatatc tgaatgaagt gcctggtcat atttctctac caaaggcatt    240
ctccatagag cttccccggt ctctgatgaa gcttctgcta gatctcttgc caacacgtcg    300
ttatttgcaa aaaatccagc cacagattct cctaaagaaa caaccatagc acccgtcaag    360
gtagcaaagt caatgatgcg ggtaggatta caatatttca aagcatagga gatggcatct    420
gctaaaatca aacgcccttc cgcatcagtg ctgccaattt ctacagaaag gccggtcatt    480
ccaacatata catctcccat cttataggca gccgatccaa tcgcattctc tgtagctgga    540
atgatcccgg tcacattgat cggaagctcc aaggaagcta aagcagaaaa aattcctaga    600
acggtagccc ctccagccat gtcttccttc atggtaatca ttgccttccc aggtttcaaa    660
tctagtcctc cggaatcgaa tgttacccct ttaccaatga gtacggttct atctttagat    720
ttaggtttac cttggtaatc cagaacaata accgaggct caacagcagc gcccttggca    780
acagcagcca acaatcccat ttttctttt aatatcgcct tcctatctag aattttttaca    840 tccagactcg cgaactcccc tgctagacct tttgctaccg cagcaagttt ttctggagtg    900
acttcatctg cattggtatt cactaaatct ctagttaaat atacccttc aaataggctc    960
```

```
tcttcttttc taaagatctt gtccctacc ttagagacaa tacccattac agttactttc    1020
tctaggaaag gcaaagacgt atccactttg tgataggttg ggtaattata gttcagagat    1080 agcaccctg ctgccaagtt cgttaaaaac tcttctaagg agaagcgcaa ctgtgaaatt     1140
gttgggagta aaatatttac aatcttacac ttagctttc ttaaaacagt agtagcctga     1200
gcgtaggctt ctaaaacggt tgttccggat acttcttcgc tcttccctag accaagaaga    1260
acaatttttt gttcttttgt gtgatcattt ccaaaaagaa aagccgtttc ccctttcttc    1320
cctgaaaaat tggataatgc gttttgatag acaagcttgt agtcctcatc aacaaccgca    1380
gcttcttgag ctttagaatt cttcatccaa aaggaagaa caagagcatc cgctttcgat     1440
cgtttatccc aactcgcttg agaatagagt aataccacaa taacctcttt gttgaatcga    1500
ttgagtcaat aattaaacac cagtagaacg cgttttgctc atttccgtct caagctggcg    1560
gcctgaccca ttctctgcag tagaaaaggc cagaacaagc aaaacaacat ggttttcatc    1620
tctacattat tccgagatga aaaaaggac tataggaaag agtagtcttt ttagcaaata     1680
agctctgtta ctccatagac aagaagattc aagagcttct taagatatgg gattgaatca    1740
aatgaataga atag                                                     1754

<210> SEQ ID NO 144
<211> LENGTH: 3037
<212> TYPE: DNA
<213> ORGANISM: Chlamydia trachomatis

<400> SEQUENCE: 144
agtgcggatc atgattctgg ggagctgttt taaaaataga tactaaaaag cttcctaagt      60
gttcagcaaa aaatgaagcc aaagaaaacg ttaagaacat ggagacaatg aacgtaatcg     120
cagaaggaaa atcttgagat ttggctacct gccccttttt tctagcatcc cgaagacgct     180
tgggggtcgc cttttctgtt ttttcgccca tagatggcca gttgcttaag cgctataagg     240
aatacttcgc aagttaccgt atataaatgt ttttctcaag aaagaaggtg gcagatgctc     300
atcccattta taaacaaga gtaagggggtt ctttagagaa cggaatatt tttttaaaga     360 gcgttttca tgaagcacta atcttgcttt ttctttagaa tttctttttc cttaataata      420 aaaggctgt gttagcctta agaaaaagct gtacaacttc ttaggtaatg aaaatgggac      480
aaacagagtg tggaatagta ggtcttccta atgtagggaa atcaggatta tttaatgcgt     540
tgacaggcgc acaagttgcc tcctgtaatt atccttctg cacaatagat cctaatgtcg      600
gtattgtgcc tgttatcgat ccaaggttag agaccttagc acgtatcagt cagagccaaa    660
agattatcta tgcagatatg aagtttgtag acatcgcagg attagtaaaa ggagcagcta     720
gcggtgctgg cttagggaat cgtttttat cacatattcg agagactcac gctattgcgc     780
atgttgttcg ttgcttcgac aatgatgata taacccatgt atctgggaaa attgatcctg    840
aagaagatat agctgtgatt aatctagagc tcgtattagc agacttttct tctgccacta    900
gcgtgcgaga gaaacttgga aaacaggcta aagggaaaaa agatattggg cagttgctac    960
ctctattaga tcgcgtagtt gatcatttag aatcaggaaa tcctgttcga accctctcgc    1020
tttctttaga ggaaaagtt ttattgaaac cctatccttt cctcacagga aagcctatgc     1080
tctatattgc gaatattgat gaagactctt taacggatct ggataacccc tatgtccaga    1140
aagtacggga gatcgctaaa agagaagagg cgaatgtagt tcctatctgt gtaaaattag    1200
aggaagaaat tctatcgctc cctctagagg aacgacaaga tttttacat agcttaggtc     1260
```

-continued

| | |
|---|---|
| tacaagagtc tggattgaat cgtttagtag cttcagcata ccacactctt gggttaattt | 1320 |
| cttatttcac tacaggacca caagagactc gagcttggac aatttctaaa ggggctacag | 1380 |
| cggcagagc tgcaggggaa attcattcgg atattcaaag aggatttatt cgcgctgaag | 1440 |
| ttgtaactat ggaggatatt gttgcttacg atggaagagc tggagcgcga aagccggga | 1500 |
| aactacgtgc tgaaggtagg gactatattg ttcaggatgg ggatattatg ctcttttgc | 1560 |
| ataattaaag gagcattcat ctattttat tgagacgggt ttggcggata tcttcttgaa | 1620 |
| tggcaaggac aagctcgtct ttagaagaaa agagcttttc ttccctgaga aattgctcag | 1680 |
| gaatcacagt aatactctta tcgtagagat cttctgaaaa atcaaggata tgtgcctcta | 1740 |
| ggcatagttg gtgtctttgc attgtgggcg ccatacctaa attcataaca cctgcatagc | 1800 |
| tgaacccttc aataacgata gtacaagtat ataccccctaa aggaagtaga aatgggtaa | 1860 |
| ggggaagatt gattgttgca tatccaaag atgccccgat tcctcgtcca tgagcaacct | 1920 |
| ttcctgtata agaaaaggt ctcccaagaa acttttctgc agagcacaaa tctttctttc | 1980 |
| taagaaattg tcgaatttt ctgctagata caatagtacc ttcaatctgt aggggaggga | 2040 |
| cttcttctag atatcccct aaagaggcag caaaaggcct taacgtttgt gctgttccta | 2100 |
| aaccacccctt cccaagtcta gaatcgtaac ccaagacaat tcttgatgga cgtagagtct | 2160 |
| tgtaaataga ctggataaat ggctctgcct cttgattagc tatttcctgg ttaaaaggga | 2220 |
| gaacggctag ataatcaatg ccgcagccag ccagaagctg aacacgctcc tcaagagagg | 2280 |
| taatagtttc tggaggagag ttagacaaag tatgctcagg atgctggctg aacgtaatta | 2340 |
| ctccagattt gctaggaaac ttcgttaaaa aagaaagcaa agcttggtgt cctaaatgac | 2400 |
| acccatcgaa aaaacctata gtaacagatt ctacaggatt agaggacggg agcaggctgt | 2460 |
| agaataagtc catttgcatc acgtaaataa ggagatacat cgaacccggg ttcgtctaaa | 2520 |
| agattcccat caatacactg atcgatagag aagcttccac tacgtaaccg tcggagttct | 2580 |
| tctaaataag ctccgcatcc caacatattg cctaactcat gagcgatact gcggatgtat | 2640 |
| gttcctttgc tgcattgaac tacaaaatgt agacagaggt attcgtattt aaccaaacga | 2700 |
| agatttaccg ttactgtggc aaaacgtcgt tctatagata acccctgcct agcatattcg | 2760 |
| tataatttt ttccttgtac tttctttgca gagaacatag gagggacttg ttgaatttcc | 2820 |
| ccttgaaaat agcttgtgca agtcaaaact tcgtccatag ttggaacttt tttagatcgc | 2880 |
| ccaacaattt tcccatcgca atcgtaagta tccgtcgtgg ttcctaaatg cgctaccgct | 2940 |
| gcatactctt tgtcttcaaa cagcatgatg tccgatagtc gggtgaattt tctccctatt | 3000 |
| agcataacca taacgcctgt agcaaaagga tctaaag | 3037 |

<210> SEQ ID NO 145
<211> LENGTH: 1353
<212> TYPE: DNA
<213> ORGANISM: Chlamydia trachomatis

<400> SEQUENCE: 145

| | |
|---|---|
| atcactatgg tccgttgtat tggaagcacc gtaaaaagcg agaggaattc gttccccaag | 60 |
| aagaataatc tctgatttag tctttttcat atgtgcccat cagctctgcc gtagctatga | 120 |
| tatgtccgtc catagcttct aacagctgtt ctttggtcac tccttcttca tcggaaagca | 180 |
| caacatcgag cgcataagca taaagtaat agcgatgctt cgcatctgga gggcaaggag | 240 |
| ggcagtatcc tatttctcca gcagtattta acccttggac agcaaaaatt tgtgctcctt | 300 |
| ctgcaagatt agagactgca ggcgaaaggt tatacactat ccagtgtatc cacaacccat | 360 |

-continued

```
cctctcgaac actaggagga acatctggat cttcaacaat aagaacaaga cttttagcct    420
ctctagggac atcagaaaaa gacagcggtg gggagatccc aacgccctga cacgaatact    480
ttttaggaat cggacggccg taagaaaaag cttgtgaggt gagttgcata attgaggtct    540
cctgtattta gggccatgct ctgtaaagcg tggccctatt cttgtactac tgtcgtagtg    600
gatcagactg ggcttgcgct tctttacgga aagggctac ctcataccga gtggcaatta     660
cttctctgaa caaggcgatc aaactgatgg aattaaaaat aaccatcccg caaaaaccta    720
gatcggatag cgcccagata aactgcattc ctaagacacc acccatgggg attatcgcga    780
tataaatagc cttcaacaat aggttagcgc gcttccctgg gatcatatat tctaaacttt    840
tttctgcgca agcaaaccat gacagagctg tagtataccc aaacaagatc atggatataa    900
gaacaacact tccgcccaac atgcctaacg aagatttgaa agcattcata accatcaaaa    960 ccccccaactc tccagaatca taggctcctg tcacaagaag caccatcatc gtaatagagc   1020
atacgaccgc aacgataacg ggaggtaaga gagtgactaa tccgtctgtc acaggattcg   1080
tgcttttaga attagattgc agaatagaaa ccattccgct tccaccgtct gtagccataa   1140
tagcacgatt taatcctgta gagattacct gtcctaatgt atagccccca accccggcta   1200
tcccagcctt gacacctaaa gcagaagaga aaacgagctg caaagcagga agaattttat   1260
cacaatgcat agccaaaact ataacggaga aaggaaata gaatcctgct acgaaaggaa    1320
tcgctttagc agagaagcgg agaactcgag tat                                1353
```

<210> SEQ ID NO 146
<211> LENGTH: 1627
<212> TYPE: DNA
<213> ORGANISM: Chlamydia trachomatis

<400> SEQUENCE: 146

```
ccgtttagta agccgcggtt ttaaggtagc cattgctgag caggccgata atactgaagg     60
gagcaaaggc ctcgttcctc ggacaatcaa ccgattgata acccctggag cactcttatc    120
ctcttctttg ctcccagaaa aagcaaataa ctatgtcctt gcaatcaatc aagtagggtc    180
tctctatggt ctctcctgtt tagacttgtc gataggaact ttccttgttg ctgaatacga    240
taataccaag gaccttattg aggcgatctg tcggctggct cctacagagt tattgagcca    300
cgcaaaattt tatcaaaaaa atgaagctgt tattaaacaa ctccaacagc atttacgtat    360
cacactatcc gaatacgttt cttgggcttt cgagtatcag tctgcaacaa agaaattata    420
cacgtgtttt caagtttcct ctttagatgg ttttggattg caaggactag tccctgctat    480
taatgcggcc ggagcattac tgtcttatat tcaggacaca cttcttcttc ctatttcccc    540
tcgtgccgaa ttcggcacga gctctgattt agtcttttc atatgtgccc atcagctctg    600
ccgtagctat gatatgtccg tccatagctt ctaacagctg ttctttggtc actccttctt    660
catcggaaag cacaacatcg agcgcataag cataaaagta atagcgatgc ttcgcatctg    720
gagggcaagg agggcagtat cctatttctc cagcagtatt taacccttgg acagcaaaaa    780
tttgtgctcc ttctgcaaga ttagagactg caggcgaaag gttatacact atccagtgta    840
tccacaaccc atcctctcga acactaggag gaacatctgg atcttcaaca ataagaacaa    900 gactttagc ctctctaggg acatcagaaa aagacagcgg tggggagatc caacgccct     960 gacacgaata cttttaggga atcggacggc cgtaagaaaa agcttgtgag gtgagttgca   1020
taattgaggt ctcctgtatt tagggccatg ctctgtaaag cgtggcccta ttcttgtact   1080
```

-continued

```
actgtcgtag tggatcagac tgggcttgcg cttctttacg gagaagggct acctcatacc   1140
gagtggcaat tacttctctg aacaaggcga tcaaactgat ggaattaaaa ataaccatcc   1200
cgcaaaaacc tagatcggat agcgcccaga taaactgcat tcctaagaca ccacccatgg   1260
ggattatcgc gatataaata gccttcaaca ataggttagc gcgcttccct gggatcatat   1320
attctaaact ttttctgcg caagcaaacc atgacagagc tgtagtatac ccaaacaaga    1380
tcatggatat aagaacaaca cttccgccca acatgcctaa cgaagatttg aaagcattca   1440
taaccatcaa aaccccaac tctccagaat cataggctcc tgtcacaaga agcaccatca    1500
tcgtaataga gcatacgacc gcaacgataa cgggaggtaa gagagtgact aatccgtctg   1560
tcacaggatt cgtgctttta gaattagatt gcagaataga aaccattccg cttccaccgt   1620
ctgtagc                                                             1627
```

<210> SEQ ID NO 147
<211> LENGTH: 1262
<212> TYPE: DNA
<213> ORGANISM: Chlamydia trachomatis

<400> SEQUENCE: 147

```
gtaaaagctc tttttaaagg acggctattc attgctgaga tggtattaat tttcccgtga     60
atatcacggg atacgtaggt ggcgtaatca tgatttccta ggcaagcaaa acagcctaag   120
ggcgcatgca gagaacatag gaaatgtttt aatctttcag gagtttctac tttagcgcga   180
cagacaaagt ctcctgtaaa tacaagaata tctggagaaa gagaagagat cttacgagat   240
acttttttta gaaaggcatc aggcgtcgag tggtttaggt gtaaatccga aatctgtata   300
atgcgaagcc catgaagatg agcaaatttt ttaggcagat tccaatttaa acgcgttact   360
ctcaataggt taggctctaa gtgattggcc caaacccatg tcaaaacagg tgctgctaag   420
atagttgtta aagatacagt aatacccaca gaaacgaaca aaaagaatga actagttcct   480
catcttaaag acgaggaaca cgtgagtcaa tttctatttt atttaatgat gtgttgagaa   540
accatttttg tcatttggaa catatcgata ggttttcag ttccaaaaac tttagccaat    600
ttatcatcgg gattgatatt acgtttgttt gtaggatctt gaaggctatt cttcttaatg   660
taatcccaca ttttcttaat gatctctgtg cgaggcatag gtcctgcacc aacgatggca   720
gctaaatcag cggatacgtt cacaggctgc atgaaagcag agttcttatt ttgactcatg   780
gatgactcct agtaaagaa gatgataaga aagtttagg gctcttcctt cgcaactctt     840
ttatgcctta actaggttta tcgtcaaaat aaaaaacata gccaagtctt cagcaagaag   900
agaggtaaaa gcgaattaga aaacgattta ttcctcggac tattacgcaa gaaattgatc   960
cctaagagaa gatcatgtta ccatgagcgt gttttagctg tcaccgccac cgtaatagtg  1020
gaaataactg gcaaggaaaa tagctctttg aaaaagaaga gtttgaagtt ggatattttg  1080
cgaaaggtta gcaagattat gcatgagaat tttgacaaac gattggaact tttgcttgaa  1140
ggtttggctt taactcggag gtctctttga cccggaagga aagaaaatg agttaaagga    1200 attggaacag caggcggtgc aagatggttt tgggacgat gttgctcgtg cagctcgtgc    1260
cg                                                                 1262
```

<210> SEQ ID NO 148
<211> LENGTH: 1596
<212> TYPE: DNA
<213> ORGANISM: Chlamydia trachomatis

<400> SEQUENCE: 148

-continued

```
acccttgct tcattagca ggagattctg cggagctgag agaatatttg gatcagcaaa      60
cagctccttt tttgttacga gtcgttgata atgagagagg gaaattgtta cctatagagc   120
aagagttact aaaaacaccg ttttagcta aatgggtatg caaacagttt ttcctgaacg   180
aaagactagt tgcttcaaaa agtttttac aaacggttta tgatcatctt atgacaggct    240
ctacagcaag attacggctt cgtaatcgaa cagttttggt aaaagctagg ggagtaatca   300
tagaaagtat atattgatag tgttttggg gcttccctag tgggttcagc agattgctga    360
aagaaaaaca cttcttgttt tttatctcta aattagagg tttataaaca aaataataaa    420
atattttgat atattgaata attatctgcc tatttgatta gcattgtagt gagttttatg   480
gctaaagata aaaaacaaa tccagaatcc aaaaaagtt ttcctactgc tttttctt      540
ctcttgttcg gagtgatttt tggcgtagtc acagttcaaa acttttctc tgctaaaaag   600
gcttcggtag gcttcagtca tcaactcgaa catcttgtta acctgaaatt actcattcca   660
gaagagagtc gcaagactgc cttgaacgat aatttagtgt catttagtgg tcgtttccgc  720
gaggtggtcc ctgctgaagg tcaggttcgg tatcaatatc ttgatcttat tgaacgtaag   780
catcagatcg actttgagct ggaagaggcg agtaagtctt taacggtttt atcaaaagaa   840
gtgcgtaatg cgatcacttg gttttcagct atttctggaa tgcctatccc cgaagcaggc   900
tatactattt ctcctcgaac ggatgttggg ctctctgttt tagaaccttt agtggtttac   960
ggccctgtag atgctcaaat tgtgaacctt gctgcgctag aaaatcgggt gcgctctttg  1020
cctaaatcta cagaaagtct tagagttttt ggttcggatc tctatgcatt aattgggaaa  1080
tatctttctc cagctcttgg tatcgggtct gaatccttaa aaaagaaat caaagatttg   1140
catcagcaag tagaaaactc cttaactcag gttatagaag gggatcaggc tgttgctttg   1200
tataaaactg tgcttgagac gttgcataga atttccttag cactagtttc tcctgaagaa   1260
gggactcgtt tccatcaatt acgctctgta cgtctatatc gtgaagattt caaccgatgt   1320
gtcaaattat taggggagag tgatgagact caggtgcagc tcgataagtt cagaggcgaa   1380
ttagtccaag ctgtttggta tttcaataac caagaactct cttctcgagc tttggagaaa   1440
caagatcctg aagtgtttag tcgttggttt gaaggcgcta acaggaatgg gcagcattc    1500
tcttcaaata aatctttatc atttagagct ccagatcaac cgcgtaattt agttttagag  1560
aagactttca gaagtgaaga gccaacgcct cattac                             1596
```

<210> SEQ ID NO 149
<211> LENGTH: 2624
<212> TYPE: DNA
<213> ORGANISM: Chlamydia trachomatis

<400> SEQUENCE: 149

```
tccgaattct aatacagaag gaagttcagc tagcactaac cttaaaggat ctcaagggga    60
tactgctgat acagggactg gtgatgttaa caatgagtct caagacacat cggatactgg   120
aaacgctgaa tctggagaac aactacaaga ttctacacaa tctaatgaag aaaatgccct   180
tcccaatagt aatattgatc aatctaacga aaacacagac gaatcatctg atagccacac   240
tgaggaaata actgacgaga gtgtctcatc gtcctctgaa agtggatcat ctactcctca   300
agatggagga gcagcttctt cagggctcc ctcaggagat caatctatct ctgcaaacgc    360
ttgtttagct aaaagctatg ctgcgagtac tgatagctcc cccgtatcta attcttcagg   420
tttagaagag cctgtcactt cttcttcaga ttcagacgtt actgcatctt ctgataatcc   480
```

-continued

```
agactcttcc tcatctggag atagcgctgg agactctgaa gaactgactg agacagaagc    540
tggttctaca acagaaactc ctactttaat aggaggaggt gctatctatg gagaaactgt    600
taagattgag aacttctctg gccaaggaat attttctgga aacaaagcta tcgataacac    660
cacagaaggc tcctcttcca aatctgacgt cctcggaggt gcggtctatg ctaaaacatt    720
gtttaatctc gatagcggga gctctagacg aactgtcacc ttctccggga atactgtctc    780
ttctcaatct acaacaggtc aggttgctgg aggagctatc tactctccta ctgtaaccat    840
tgctactcct gtagtatttt ctaaaaactc tgcaacaaac aatgctaata acgctacaga    900
tactcagaga aaagacacct tcggaggagc tatcggagct acttctgctg tttctctatc    960
aggaggggct catttcttag aaaacgttgc tgacctcgga tctgctattg ggttggtgcc    1020
aggcacacaa aatacagaaa cagtgaaatt agagtctggc tcctactact ttgaaaaaaa    1080
taaagcttta aaacgagcta ctatttacgc acctgtcgtt tccattaaag cctatactgc    1140
gacatttaac caaacagat ctctagaaga aggaagcgcg atttacttta caaaagaagc    1200
atctattgag tctttaggct ctgttctctt cacaggaaac ttagtaaccc aacgctaag    1260 cacaactata gaaggcacac cagccacaac ctcaggagat gtaacaaaat atggtgctgc    1320
tatctttgga caaatagcaa gctcaaacgg atctcagacg ataaccttc ccctgaaact    1380 cattgcttca ggaggaaata tttgtttccg aaacaatgaa taccgtccta cttcttctga    1440
taccggaacc tctactttct gtagtattgc gggagatgtt aaattaacca tgcaagctgc    1500
aaaagggaaa acgatcagtt tctttgatgc aatccggacc tctactaaga aaacaggtac    1560
acaggcaact gcctacgata ctctcgatat taataaatct gaggattcag aaactgtaaa    1620
ctctgcgttt acaggaacga ttctgttctc ctctgaatta catgaaaata atcctatat    1680 tccacaaaac gtagttctac acagtggatc tcttgtattg aagccaaata ccgagcttca    1740
tgtcatttct tttgagcaga agaaggctc ttctctcgtt atgacacctg gatctgttct    1800
ttcgaaccag actgttgctg atggagcttt ggtcataaat aacatgacca ttgatttatc    1860
cagcgtagag aaaaatggta ttgctgaagg aaatatcttt actcctccag aattgagaat    1920
cgtagacact actacaagtg gaagcggtgg aaccccatct acagatagtg aaagtaacca    1980
gaatagtgat gataccgagg agcaaaaacaa taatgacgcc tcgaatcaag gagaaagcgc    2040
gaatggatcg tcttctcctg cagtagctgt tgcacacaca tctcgtacaa gaaactttgc    2100
cgctgcagct acagccacac ctacgacaac accaacggct acaactacaa caagcaacca    2160
agtaatccta ggaggagaaa ttaaactcat cgatcctaat gggaccttct tccagaaccc    2220
tgcattaaga tccgaccaac aaatctcctt gttagtgctc cctacagact catcaaaaat    2280
gcaagctcag aaaatagtac tgacgggtac tcgtgccgaa ttcggcacga gacacagccc    2340
gatacccagt actccacgcc gcattggagt agtatggcta tctgtaatga ttacgcctag    2400
ctctttcact cgaaaataat ttcttaacca ttctccgatg cgattacacg atcccaaaat    2460
atctttagga tataaaacaa aaggctggtc cgtattcgat tcatcaatcc ctgcagaagg    2520
aatcaaaata ccttctttttt tcgttagata tatcccgctt ttctcacaaa acaaataagc    2580
atccgcttct ttttttatca gctctgcaat tcgatatcaa gctt              2624
```

<210> SEQ ID NO 150
<211> LENGTH: 2052
<212> TYPE: DNA
<213> ORGANISM: Chlamydia trachomatis

<400> SEQUENCE: 150

-continued

```
ctttcgaaag ggattaggga aaacatctca ggaactcaaa gcgattcttg atgctgtgta      60
ttttcctaca ccagaagctg cgcgactgct ggtggatgtt cagggacatt tatcagaaga     120
attttcttat gaagattttg ccattgccaa attttttggt gagagagagg aagtgaagaa     180
aattatggat agatttattc aatctccaga gtttcttca caggtaacca tgaattacat      240
gcgttggcct tttgatttca atacgcagt gcttttactt actttaaaag atgtttcaaa      300
aggttttgct gtagatcaag ttgttcagac cttctataaa gagaataagc cttttattat     360
ggcttctggg gatgatgcta acgatatcga cctgctatct cgaggagatt ttaaaattgt     420
tatacagacg gctccagagg agatgcatgg attagcggac ttttttggctc ccccggcgaa    480 ggatcttggt attctctccg cctgggaagc tggtgagctg cgttacaaac agctagttaa     540
tccttaggaa acatttctgg acctatgccc atcacattgg ctccgtgatc cacatagaga     600
gtttctcccg taattgcgct agctagggga gagactaaga aggctgctgc tgcgcctact     660
tgttcagctt ccattggaga aggtagtgga gcccagtctt ggtagtaatc caccattctc    720
tcaataaatc caatagcttt tcctgcacg ctagctaatg gccctgccga gatagtattc     780
actcggactc cccaacgtcg gccggcttcc caagccagta cttttgtatc actttctaaa   840
gcagcttttg ctgcgttcat tcctccgcca taccctggaa cagcacgcat ggaagcaaga    900
taagttagag agatggtgct agctcctgca ttcataattg ggccaaaatg agagagaagg    960
ctgataaagg agtagctgga tgtacttaag gcggcaagat agcctttacg agaggtatca   1020
agtaatggtt tagcaatttc cggactgttt gctaaagagt gaacaagaat atcaatgtgt   1080
ccaaaatctt ttttcacctg ttctacaact tcggatacag tgtacccaga aagatctttg   1140
taacgtttat tttccaaaat ttcctgagga atatcttctg gggtgtcgaa actggcatcc   1200
atgggataga ttttagcgaa agttagcaat tctccattgg agagttcacg agatgcattg   1260
aattttccta actcccaaga ttgagagaaa attttataga taggaaccca ggtccccaca   1320
agtatggttg cgcctgcttc tgctaacatt ttggcaatgc cccagccata cccgttatca   1380
tcgcctatgc cggctatgaa agcaattttt cctgttaaat caattttcaa catgagctaa   1440
ccccattttg tcttcttgag agaggagagt agcagattct ttattattga gaaacgggcc   1500
tcataataca taaggagtag attcactggc tggatccagg tttctagagt aaagagtttc   1560
cttgtcaaat gtttaatagt tttaatcttt aaagtgtgaa aaacaggttt tatatgtaga   1620
atttcctgtt aaaaataaaa aatccttaaa agaatccggg agttaaaggt atgtcatttg   1680
gtattggtag tgcttgttca tctttatgga gccgtttgtg tggttcatca ggcagtgagg   1740
gtaacagcga agaaggagtg acgtcttcag gttcagacgc cgcctcaggt tctggtgctg   1800
cttctgctgt atgccagcaa cctacgagca gcgcttctac agaagggaat ggtcctagtg   1860
tacagatacc aatggtaggg acgtactcag ctaatgtgca aagccttgtg aatcagggtc   1920
atggcggacg cggtttcgtg aatagatgct accaaaaata ttctgctagt ggagtaagtc   1980
ttacatctat atccattgga gggggagact ctgtggatgg cccgcttcct tcggtagtaa   2040
ttacccaaca gc                                                         2052
```

<210> SEQ ID NO 151
<211> LENGTH: 732
<212> TYPE: DNA
<213> ORGANISM: Chlamydia trachomatis

<400> SEQUENCE: 151

-continued

| | |
|---|---|
| tcgcatgaaa gagttttag cgtacattgt aaaaaatctt gttgataagc cagaggaagt | 60 |
| gcatctgaaa gaggtgcagg gaaccaatac gattatctac gaattgactg ttgctaaggg | 120 |
| agatatcggt aaaattatcg gtaaagaagg acgcactatt aaggctatcc gtactttatt | 180 |
| ggtttccgta gcaagtcgag ataatgtgaa agtcagccta gaattatgg aagagcggta | 240 |
| aacgtatacg tttacagctt tttgagtcat tgttagagaa agtcttagcg cgcgtatttt | 300 |
| ctaacaccgt ttttcttctc gagaagactg tagtctttt ggcccgagag tttaaggatc | 360 |
| tcaagggccg agtcacgttt tagaagttct cttcttgatc gagcgcagcg agttcttttg | 420 |
| ctttcttatg agcggagact ctctcggtag gtaggtcatc aaattttgca atttttgtct | 480 |
| ttcgatgccc gagttgtctg taggtttcga gcagcttctt aatgtagaga actgtgtatt | 540 |
| ttttcagttg gctcagatct ttctgtacgc tactgcgttt cttttctaag catgccaact | 600 |
| ccttctcata ggaattttca tcaaaacaga ggatttttt gatagttaga gctgctagtt | 660 |
| gagcggttgc ttgcttatca ggagccggga gcgtgtcaag aaatggagtc agagcttcca | 720 |
| aaacagcgtt gt | 732 |

<210> SEQ ID NO 152
<211> LENGTH: 1326
<212> TYPE: DNA
<213> ORGANISM: Chlamydia trachomatis

<400> SEQUENCE: 152

| | |
|---|---|
| atatgctcag gatcacaagg ccatgctaca tctttctctc caggagctaa gggcttccct | 60 |
| acactatgta aacacttata gaaagtccca ttagaaccca acatcgctaa aacagaagct | 120 |
| cccatacgcg tcatgatctt catagaacat acaacataag gagagtctgt aatctcaaca | 180 |
| ccaatcaaag aaaatggaga gttcaaaggc cccatacaaa aaggcacaat gtagagtgtg | 240 |
| cgacctcgca tacaccctcg gaataatgca tgcagtctg cacgcatctc ttgaggatct | 300 |
| ctccagttat ttgttggacc agcttcttct tgagtcttgg tacaaataaa agtaaattgt | 360 |
| tcagcacgag cgacatcact aggagaagaa cgaacgagga agcagttagg atgcagctca | 420 |
| ggatttagag gggtcatcac cccagcatcc tgcatctgct ggcaaagctg ttggtattcg | 480 |
| gcttctgaac catcgcataa ccttacgtcg tcaggtgaca ccaaagcaat tacttcttct | 540 |
| atccaagatt ttaatcctga atgggttatc ttagatatcc aatcgccggt catactaaac | 600 |
| tctcttttcg tttcttcaat tgatccagat gttccaaagc tttccctgta cctaaacaga | 660 |
| ccgctaaaag tggatgcggc gctgtaataa cagagagccc ggtgttttta ctcaatgctt | 720 |
| tatctaaccc tttaatcaga gctcctcctc cagctagcac catcccacgc tctactaaat | 780 |
| ctgcagagag ttctggagga cacttctcta gagtcaaccg tacacattct ataatttgct | 840 |
| gaataggttc tgctaagcac tcccggattt ctacggaatt gattctttc gtgataggca | 900 |
| gcccagctac ctgatcgcgt ccgcgtactt ccatctccaa ttcctgatca cctaacggat | 960 |
| aagcagaacc tatagtaatc ttgatctcct ctgctgtccg cggaccgatc attaaattgt | 1020 |
| atgtgcggcg catataatta ataatacact catcgaactc atcccctgct atacgcaaag | 1080 |
| aacgcgactc tacaattcct ccaagagaaa taatagctat ttctgttgtc cctcccccaa | 1140 |
| tgtcaataat catacttgct gcaggttcat gtacagggag atcgacgcca atggctgctg | 1200 |
| ccataggctc ttcaatcaga attgcttcct gtgctcccgc atgcaaagca gagtcttcaa | 1260 |
| cagcgcgttt ttcaaccttg gtagatcaaa tagaatccta ctttgtaatc aagcctgcaa | 1320 |
| atgtat | 1326 |

<210> SEQ ID NO 153
<211> LENGTH: 3141
<212> TYPE: DNA
<213> ORGANISM: Chlamydia trachomatis

<400> SEQUENCE: 153

```
ccgaattctt gattattccc ataccacaaa gatcgccatt tcttagtaac cgctgtgcgg      60
aaccctactg gacatccttt tgacccata ccttactcct actgccctct ctcgccaaca     120
atcacagtta gatgactcgt gcgcttcaaa atcggggctc ttcccccacg actcttagac    180
ttcattcttt tgaacattgg gccggcatca acccgaactt ctagaacgca aagattttca    240
cattttatat tttcattgga ctctgcattt gcaatagcgc tatccaacac ttttttaagg    300
catcttccag ccttcatctg agaaaagctg agttgctgtt gagcttcaac aacactacgg    360
tttctcatca atcctgcagc taaacgagcc tttcttggct gaacccgtat gtatcgggct    420
gtcgctttaa acataacctg tctccttatg acttacccct ttttaacggg atggctctta    480
aacattcttg ttggagagaa ctctcccaac ttgtgtccaa ccatagtttc tgacacaaag    540
accgtcaaaa atttacggcc attatgaacc tcaaaagtgt gcccaatcat ttcagggta    600
atcatagaac gacgagacca cgttttgatt ggagttttct tctccaaagc gttcatatct    660
cggaccttt tgagaaggtg atgatcaaca aaaggacctt ttcttagcga tctactcata    720
atccctattt ccttctatcc ttaactatcc acttattact cttacgctta tcacgagttt    780
tcaatccttt cgtgacttta ccccaagggg tctgggaaat gtatccgtta tgacgccctt    840
caccacctcc gtgtgggtga tcaacagggt tcatagctgt tcctgaact gttggccgaa    900
ttcctttcca tcgacgacgc ccagctttac cgtctacaca cagattgtga tctgcattgg    960
agacctctcc gacagtagct cggcacattt cattcaacat acgaaattcg ccagaaggca   1020
tcttcaaagc gacgtatcca gctgttttag cgatgatctg ggctgaaagt cctgcagaac   1080
ggactaattt accccggag ccaggtctca tctccacgtt atgaacagaa agtcccagag    1140
ggatgctctt aagagtcatg cagcatccag ttttgaaagg acttccttct ccagaaatca   1200
cacgatcgcc tcgcttaatt cctttaggag ctagaatata acgcttttct ccatctacat   1260
aattcaatag agcaatataa gcagaacggt ttggatcata ctccacagaa gcaaccttcg   1320
cttcaatacc gtctttatta cgtttgaagt cgatcactct ataatgacgt cttactcctc   1380
ctccacgatg gcagcaggaa atatgtccta aattatctcg tcctccagag ctcttttga    1440
aaaaagaaag cttttattt ggacgaacac ttcttctaga actagatccc tttaactctc    1500
cttgagtagt aagctcatca aaagaaggca gaattaactg tctcgtcccg ggagttactg   1560
gcttaaactt tttaaacatg ttattcttct cttccttctt tactaaccaa tagagtgacc   1620
atcaacaaaa gtcacaatag ccttcttaaa ccctgcggtt cttcctttc ttcggcctcg    1680
gaatattctt gtaggttgag gtttaacaca catggtgttt acttttttaa ccttcacacc   1740
tttagcagaa taaattgctt ctatggcttc agcaatcatg gcttcgtgg cgtcccagc     1800
aacaataaat gtgtacttag gatctttgca gaaactgcct ttcttttac cttctccgtc    1860
tccgagactc aagccttcca acatctttgc cttctcggtc acataatgtc ttttgacaac   1920
atcataagga tctttcatat cctagcttcc ccttaatct tttgttgtag agacaagact    1980
ctcgacaagc aattctaaag ccttttctga accacaata tttctagcag cggcaatatc    2040
gtatccgctg atattctctc cgtaagtaaa tcctcttaca gcagacaaat tacgcacact   2100
```

```
cagtctcaaa ttctcattgc ttccaacatg agctaagccg tcaacgaaca atacccacg    2160 gcattctacg ttgcattctt ttaagaatct taaagcttct tttgtcttag gagcatccaa    2220
gctgctaata aacacagagt tctctgcaac aatcagcttg cctgtttgaa tttttttgagc   2280 caaaagcaac tgaatagccg ctcttctctc tttttttgttg atacgaatat gctgatcaaa   2340
ttttggctta ggaccgaaaa caatccctcc tcctcggaat tgaggagctg ccaagcaacc    2400
ttgacgggca ttccccgtgc cttttttgtct aaaaggcttt ttagtggaat ggctaacttc   2460
cgatcgtcct cttgtgcaag cgctccactg acgtttgttg gcctgaatgg ccactagata    2520 atctttact gactgctctt tcccttcagt aaagaaggca tcaggcaatt caaacttccc     2580
cgactctttt ccagaaaaat caaattttga taatagaacc attaggacct ctaccctct    2640 actccgcaag aacgcttcac aacaacaacg gatcctttaa aaccaggaat tgctccctta   2700
acgagcatta cctttctatc caagtcaact tttacgacct ctaaattctt gaccgtaacc   2760
cgatcacatc ccatgtgact tggacgttta cttccgggga acatcggcc aggagtagat    2820 cgcatcccag tagatcctgc atgacgatga atccagaac cgtggctttt tggtcctcct    2880
cggaaaccaa attttttcat caccccttgg aagcctttac ccttagaaat tccacagatg   2940
tcaacgttag atactccgtc gaaaatttct aacccaaatt catcgcctaa agaaacagac    3000
tgaacagcct cttctgaaac gacaacttct tttaaaacac gacaagcacg tcctccggac   3060
ttcttaaaat gtccgagtag tgctttggag aaacgctttt caatggtttt ttctggagct   3120
tggactacat cagctcccat t                                              3141

<210> SEQ ID NO 154
<211> LENGTH: 2275
<212> TYPE: DNA
<213> ORGANISM: Chlamydia trachomatis

<400> SEQUENCE: 154 tttttttaagg aatctaatag ataattccca gtgtctaacc gtatgtctaa agctcgtgat     60
cccggtctag ggccttggat ttctttatca ttaggagaca ccttaataat atcactagct   120
tcatatttcg atgcgcggtg ggagggatag tatagctctc cttccgcagc atcgagctgc   180
ttacacccct taaggtaata gtacatcagg gctggagtat acatgtttga aaaaagaagc   240
ttggtagctc ttttctgatg gacctcatta aaatgaggca atacatggct cgttttttagt   300 tctttggaaa ggatcaattg ggaagaagcg gctttttttaa ttactggcag gagcttccac   360
cctagattaa aagcgtcatg gatattggaa tttactcccg acaggtaaga aaaggataga   420
ttattagcaa tgctcccccaa gaaaatataa cggtcatgac aaaaaggata ctgtagaaga   480
gatgaggaaa tggagagagg atcctctgct agcgcaaggc cataggtata cagaagtttc    540
cagagtctgc attccaaatt cgccgaagtc aacaaacgtt gctcccttac tcaatccagc   600
aaactgacct ttctgctgct tgcgaaattt tgttcgttta ggcattaaca taataattca   660 cacacccctta taacctatct gcactacgca gcacctgcat gattagccgc aggaacggcc   720
ttcttttcac caagattaat ccaaactttt atgccgataa ttccataagt agtctctgca    780
gacgctgtag cataatcaat atctgctctg agcgtatgaa gaggcacacg accgttctta    840
taccattccg accgagcaat ctcagctcca gctaaacgac cagaaacctg aacttttact    900
cccaaagcac ctgcatccat tacagattgc aaagcctttt tcattgctct tctgaaagaa    960
accgtctttt ctatctgttt ggcaataccg tctgcgacga gctgagcgtt aagctctggg   1020
cgtttaactt ctgcaatctc aacccaaaca tctttgcctg ttagcttttt cagctcggct   1080
```

```
ttcagagact ctacttcagc cccttcttc ccgattacta atccaggtct agcagtatgg      1140
atagtaactt caattttacc gctcatacgt ttaacaacga atcccgcagc accttgacaa      1200
gaaggtttct tcttcaaaaa ttctctaatt ttcacatctt caatgagaaa ttttccgaat      1260
tcttgattat tcccatacca caaagatcgc catttcttag taaccgctgt gcggaaccct      1320 actgacatc cttttgacc cataccttac tcctactgcc ctctcgcc aacaatcaca      1380 gttagatgac tcgtgcgctt caaaatcggg gctcttcccc cacgactctt agacttcatt      1440
cttttgaaca ttgggccggc atcaacccga acttctagaa cgcaaagatt ttcacatttt      1500
atattttcat tggactctgc atttgcaata gcgctatcca acacttttt aaggcatctt      1560 ccagccttca tctgagaaaa gctgagttgc tgttgagctt caacaacact acggtttctc      1620
atcaatcctg cagctaaacg agcctttctt ggctgaaccc gtatgtatcg ggctgtcgct      1680
ttaaacataa cctgtctcct tatgacttac ccttttttaa cgggatggct cttaaacatt      1740
cttgttggag agaactctcc caacttgtgt ccaaccatag tttctgacac aaagaccgtc      1800
aaaaatttac ggccattatg aacctcaaaa gtgtgcccaa tcatttcagg gtaatcata      1860 gaacgacgag accacgtttt gattggagtt ttcttctcca aagcgttcat atctcggacc      1920
tttttgagaa ggtgatgatc aacaaaagga ccttttctta gcgatctact cataatccct      1980
atttccttct atccttaact atccacttat tactcttacg cttatcacga gttttcaatc      2040
ctttcgtgac tttaccccaa ggggtctggg aaatgtatcc gttatgacgc ccttcaccac      2100
ctccgtgtgg gtgatcaaca gggttcatag ctgttcctcg aactgttggc cgaattcctt      2160
tccatcgacg acgccagct ttaccgtcta cacacagatt gtgatctgca ttggagacct      2220
ctccgacagt agctcggcac atttcattca acatacgaaa ttcgccagaa ggcat          2275
```

<210> SEQ ID NO 155
<211> LENGTH: 1909
<212> TYPE: DNA
<213> ORGANISM: Chlamydia trachomatis

<400> SEQUENCE: 155

```
ataccgtctg cgacgagctg agcgttaagc tctgggcgtt taacttctgc aatctcaacc        60
caaacatctt tgcctgttag ctttttcagc tcggctttca gagactctac ttcagcccct       120
ttcttcccga ttactaatcc aggtctagca gtatggatag taacttcaat tttaccgctc       180
atacgtttaa caacgaatcc cgcagcacct tgacaagaag gtttcttctt caaaattct       240 ctaattttca catcttcaat gagaaattt ccgaattctt gattattccc ataccacaaa       300
gatcgccatt tcttagtaac cgctgtgcgg aaccctactg acatcctttt tgacccata       360 ccttactcct actgccctct ctcgccaaca atcacagtta gatgactcgt gcgcttcaaa       420 atcgggctc ttcccccacg actcttagac ttcattcttt tgaacattgg gccggcatca       480
acccgaactt ctagaacgca aagattttca catttatat tttcattgga ctctgcattt       540
gcaatagcgc tatccaacac ttttttaagg catcttccag ccttcatctg agaaaagctg       600
agttgctgtt gagcttcaac aacactacgg tttctcatca atcctgcagc taaacgagcc       660
tttcttggct gaacccgtat gtatcgggct gtcgctttaa acataacctg tctccttatg       720
acttaccctt ttttaacggg atggctctta aacattcttg ttggagagaa ctctcccaac       780
ttgtgtccaa ccatagtttc tgacacaaag accgtcaaaa atttacggcc attatgaacc       840
tcaaaagtgt gcccaatcat ttcaggggta atcatagaac gacgagacca cgttttgatt       900
```

```
ggagttttct tctccaaagc gttcatatct cggaccttttt tgagaaggtg atgatcaaca    960
aaaggacctt ttcttagcga tctactcata atccctattt ccttctatcc ttaactatcc   1020
acttattact cttacgctta tcaccgagtt ttcaatcctt tcgtgacttt accccaaggg   1080
gtctgggaaa tgtatccgtt atgacgccct tcaccacctc cgtgtgggtg atcaacaggg   1140
ttcatagctg ttcctcgaac tgttggccga attcctttcc atcgacgacg cccagcttta   1200
ccgtctacac acagattgtg atctgcattg gagacctctc cgacagtagc tcggcacatt   1260
tcattcaaca tacgaaattc gccagaaggc atcttcaaag tgacgtatcc agctgtttta   1320
gcgatgatct gggctgaaag tcctgcagaa cggactaatt taccccccgga gccaggtctc   1380 atctccacgt tatgaacaga aagtcccaga gggatgctct taagagtcat gcagcatcca   1440
gttttgaaag gacttccttc tccagaaatc acacgatcgc ctcgcttaat cctttagga    1500 gctagaatat aacgcttttc tccatctaca taattcaata gagcaatata agcagaacgg   1560
tttggatcat actccacaga agcaaccttc gcttcaatac cgtctttatt acgtttgaag   1620
tcgatcactc tataatgacg tcttactcct cctccacgat ggcagcagga aatatgtcct   1680
aaattatctc gtcctccaga gctcttttttg aaaaagaaa gctttttatt tggacgaaca   1740
cttcttctag aactagatcc ctttaactct ccttgagtag taagctcatc aaaagaaggc   1800
agaattaact gtctcgtccc gggagttact ggcttaaact ttttaaacat gttattcttc   1860
tcttccttct ttactaacca atagagtgac catcaacaaa agtcacaat              1909
```

<210> SEQ ID NO 156
<211> LENGTH: 1157
<212> TYPE: DNA
<213> ORGANISM: Chlamydia trachomatis

<400> SEQUENCE: 156

```
ttttgttcgt ttaggcatta acataataat tcacacaccc ttataaccta tctgcactac     60
gcagcacctg catgattagc cgcaggaacg gccttctttt caccaagatt aatccaaact    120
tttatgccga taattccata agtagtctct gcagacgctg tagcataatc aatatctgct    180
ctgagcgtat gaagaggcac acgaccgttc ttataccatt ccgaccgagc aatctcagct    240
ccagctaaac gaccagaaac ctgaactttt actcccaaag cacctgcatc cattacagat    300
tgcaaagcct ttttcattgc tcttctgaaa gaaacccgtc tttctatctg tttggcaata    360
ccgtctgcga cgagctgagc gttaagctct gggcgtttaa cttctgcaat ctcaacccaa    420
acatctttgc ctgttagctt tttcagctcg gctttcagag actctacttc agccccttttc   480 ttcccgatta ctaatccagg tctagcagta tggatagtaa cttcaatttt accgctcata    540
cgtttaacaa cgaatcccgc agcaccttga caagaaggtt tcttcttcaa aaattctcta    600 atttttcacat cttcaatgag aaattttccg aattcttgat tattcccata ccacaaagat    660
cgccatttct tagtaaccgc tgtgcggaac cctactggac atccttttttg acccatacct    720 tactcctact gccctctctc gccaacaatc acagttagat gactcgtgcg cttcaaaatc    780 gggctcttc ccccacgact cttagacttc attcttttga acattgggcc ggcatcaacc    840
cgaacttcta gaacgcaaag attttcacat tttatatttt cattggactc tgcatttgca    900
atagcgctat ccaacacttt tttaaggcat cttccagcct tcatctgaga aaagctgagt    960
tgctgttgag cttcaacaac actacggttt ctcatcaatc ctgcagctaa acgagccttt   1020
cttggctgaa cccgtatgta tcgggctgtc gcttaaaca taacctgtct ccttatgact    1080
tacccttttt taacgggatg gctcttaaac attcttgttg gagagaactc tcccaacttg   1140
```

-continued

```
tgtccaacca tagtttc                                              1157

<210> SEQ ID NO 157
<211> LENGTH: 3957
<212> TYPE: DNA
<213> ORGANISM: Chlamydia trachomatis

<400> SEQUENCE: 157
ttttatggct aaagataaaa aaacaaatcc agaatccaaa aaaagttttc ctactgcttt     60
tttctttctc ttgttcggag tgattttttgg cgtagtcaca gttcaaaact ttttctctgc    120
taaaaaggct tcggtaggct tcagtcatca actcgaacat cttgttaacc tgaaattact    180
cattccagaa gagagtcgca agactgcctt gaacgataat ttagtgtcat ttagtggtcg    240
tttccgcgag gtggtccctg ctgaaggtca ggttcggtat caatatcttg atcttattga    300
acgtaagcat cagatcgact tgagctgga agaggcgagt aagtctttaa cggttttatc    360
aaaagaagtg cgtaatgcga tcacttggtt ttcagctatt tctggaatgc ctatccccga    420
agcaggctat actatttctc ctcgaacgga tgttgggctc tctgttttag aacctttagt    480
ggtttacggc cctgtagatg ctcaaattgt gaaccttgct gcgctagaaa atcgggtgcg    540
ctctttgcct aaatctacag aaagtcttag agttttttggt tcggatctct atgcattaat    600
tgggaaatat ctttctccag ctcttggtat cgggtctgaa tccttaaaaa aagaaatcaa    660
agatttgcat cagcaagtag aaaactcctt aactcaggtt atagaagggg atcaggctgt    720
tgctttgtat aaaactgtgc ttgagacgtt gcatagaatt tccttagcac tagtttctcc    780
tgaagaaggg actcgtttcc atcaattacg ctctgtacgt ctatatcgtg aagatttcaa    840
ccgatgtgtc aaattattag gggagagtga tgagactcag gtgcagctcg ataagttcag    900
aggcgaatta gtccaagctg tttggtattt caataaccaa gaactctctt ctcgagcttt    960
ggagaaacaa gatcctgaag tgtttagtcg ttggtttgaa ggcgctaaac aggaatgggc   1020
agcattctct tcaaataaat ctttatcatt tagagctcca gatcaaccgc gtaatttagt   1080
tttagagaag actttcagaa gtgaagagcc aacgcctcat tactctggtt atttattcac   1140
ttttatgcca attatttttgg ttctgctgtt tatctacttt atcttttctc gtcaggtcaa   1200
agggatgaac ggttctgcta tgtcgttcgg aaaatctcct gcgcgcttgt tagcaaaagg   1260
acaaaacaaa gtaacttttg cggatgtagc agggatagag gaagccaaag aagaactcgt   1320
tgagatcgta gatttcttga agaagcctac taaatttact agtttaggag ggcgtatccc   1380
taaaggaatt cttctcatag gagctccagg gacagggaaa acattgatag ctaaggctgt   1440
cgctggtgag gctgatcgac ctttcttctc catagccggt tctgatttcg ttgaaatgtt   1500
tgttggggtt ggagcaagta gaatccgaga tatgttcgag caggcgaagc gtaatgctcc   1560
ttgcattatc ttcattgatg aaatcgacgc agttggaaga catcgtggtg ctggtattgg   1620
aggtggtcat gacgagagag agcagactct aaaccagctg ttagtagaaa tggatggttt   1680
tggtactaac gaaggagtca tccttatggc tgctaccaac cggccggatg ttttggacaa   1740
ggctttgttg cgtccaggac gttttgatcg tcgtgttgtt gtgaatcttc ctgatataaa   1800
aggtcgtttt gaaattctcg ctgtccacgc caaacgcatt aagctagatc ctactgtaga   1860
tcttatggcg gttgcgcgta gcactccagg agcttcagga gctgatttgg aaaatcttct   1920
taacgaagca gcattattgg ctgctagaaa agatcgtgca gcggtgacag cagttgaagt   1980
tgcagaagct cgagacaagg ttctgtatgg taaagaacgg cgtagtttag agatggatgc   2040
```

-continued

```
tcaagagaaa aaaacaacgg cataccacga gtcagggcat gctattgtag ggctttgtgt    2100
tgagcattcg gatcctgtag ataaggtgac gattattcca agaggcttat ctttaggagc    2160
cacgcatttc cttccagaaa aaataaatt aagctactgg aagaaagagc tttatgatca     2220
gttagcggtt cttatgggag ctcgtgccga attcggcacg aggcatgccg ctctagcctg    2280
tttagatgcc tctgaaacaa cttttccatt aaaaacatct agagacttga ttttaaacaa    2340
agattcgctg tggtcaagag aaatagcctt tatcaaggtt ccgataaat ccagaatctc     2400 taaagaaaca agaaagttaa tcccagacgc ataattttt ctagttagat aagataaagt     2460
agataaccaa atttccgacg cgtccccaaa agcaaaaaca atctactttt atggaaagcc    2520
atcgagccca ttttcttaac caaagctatt caaaatcgga gctctaagat tttaagaaat    2580
tttttaacaa aagtccatta tgaccaagtc taccaccaag agttgcaaag tctaccacca    2640
agagttgcaa agtctaccac caagagttgc aaagtctacc accaagagtt gcaaatctct    2700
ctcgtgaaat caaatcccta aatatatata tataatagat atatatatat gagctgacgg    2760
aggatcagct cttttgctta aaagttcaa aaagctgttg tagaagattt tcgttatagg     2820
aggacaaaga aactccggaa cacatgatgc gaagtatctc tattaagaaa tcagataatt    2880
ggcgattctt ctctgaatca gacttatcta tcgtttctct aacgtctttg tttctagatg    2940
aaggaagaaa ttgatccaac acccttatcg ccgatgagtt cgacattcca catactttcc    3000
ctatcacatc gaccttggtt tttaaatcgc cttttctagc ggccaaaata tatgcggatt    3060
tataggggat cgattgaaac tcttttttgta gagtttggtt ggggaggttt ataaaaagct    3120
cgtaatatgc aagagcattg taagcagaag acttagttct aaaaactaac tctatccaag    3180
atgaaaaagt tgtgaggaga agtgatcctt actcaggatt tttctagcat tatagatttt    3240
ttctcctaaa agaagtacgt gttgcttctg tatggatttt atctgaccag taagcagttt    3300
taccgctagg atgtcttctt gataaaattc ttcatccgaa tagttttggg actctgataa    3360
aaataatcga tccaaactct gactttcctc agaattcaaa gttgctgaga atagttcaat    3420
ggagggaagc gtcttcttaa aatctagaga agcggcagtt tgatttttt taaaaaagac    3480 atccgcttct ttttttagtt tgttcacgtt gtcctctgag agtaatctcg ttcatattcg    3540
atatgcaaaa tatttgctat ttcatgcgtt aacttcagaa tatcttctgc ggccctagaa    3600
tttggataga cattagctac agaatcttct ttaagaagag aacggctgag agaaatatct    3660
cgacgaattt ttgttgaaaa aagcttgttt ttgtaaatag actcgataat gtctatatac    3720
atttggttag tcgagttacg atcatcccaa aaagacaaag ctattccaag aatgtgttct    3780
tcttcaggtt ttccgaccga acttaagaat tcacgtatct tttgtaaccc tagaatagaa    3840
aaaggttctg gagttaaaca agcaattaat ttgtctcctg caacaaaagc ttctttcgtt    3900
aaccctccta ggctaggtgg agtgtctatt atgcagatgt cataaaaagg agcgcag      3957
```

<210> SEQ ID NO 158
<211> LENGTH: 1626
<212> TYPE: DNA
<213> ORGANISM: Chlamydia

<400> SEQUENCE: 158

```
caggatccct taggtgaaac cgccctcctc actaaaaatc ctaatcatgt cgtctgtaca     60
ttttttgagg actgtaccat ggagagcctc tttcctgctc tttgtgctca tgcatcacaa    120
gatgatcctt tgtatgtact tggaaattcc tactgttggt tcgtatctaa actccatatc    180
acggacccca agaggctct ttttaaagaa aaaggagatc tttccattca aaattttcgc     240
```

-continued

```
ttcctttcct tcacagattg ctcttccaag gaaagctctc cttctattat tcatcaaaag    300
aatggtcagt tatccttgcg caataatggt agcatgagtt tctgtcgaaa tcatgctgaa    360
ggctctggag gagccatctc tgcggatgcc ttttctctac aacacaacta tcttttcaca    420
gcttttgaag agaattcttc taaaggaaat ggcggagcca ttcaggctca aaccttctct    480
ttatctagaa atgtgtcgcc tatttctttc gcccgtaatc gtgcggattt aaatggcggc    540
gctatttgct gtagtaatct tatttgttca gggaatgtaa accctctctt tttcactgga    600
aactccgcca cgaatggagg cgctatttgt tgtatcagcg atctaaacac tcagaaaaaa    660
ggctctctct ctcttgcttg taaccaagaa acgctatttg caagcaattc tgctaaagaa    720
aaaggcgggg ctatttatgc caagcacatg gtattgcgtt ataacggtcc tgtttccttc    780
attaacaaca gcgctaaaat aggtggagct atcgccatcc agtccggagg gagtctctct    840
atccttgcag gtgaaggatc tgttctgttc cagaataact cccaacgcac tccgaccaa     900
ggtctagtaa gaaacgccat ctacttagag aaagatgcga ttctttcttc cttagaagct    960
cgcaacggag atattctttt ctttgatcct attgtacaag aaagtagcag caaagaatcg   1020
cctcttccct cctctttgca agccagcgtg acttctccca ccccagccac cgcatctcct   1080
ttagttattc agacaagtgc aaaccgttca gtgattttct cgagcgaacg tctttctgaa   1140
gaagaaaaaa ctcctgataa cctcacttcc caactacagc agcctatcga actgaaatcc   1200
ggacgcttag ttttaaaaga tcgcgctgtc ctttccgcgc cttctctctc tcaggatcct   1260
caagctctcc tcattatgga agcgggaact tctttaaaaa cttcctctga tttgaagtta   1320
gctacgctaa gtattcccct tcattcctta gatactgaaa aaagcgtaac tatccacgcc   1380
cctaacctt ctatccaaaa gatcttcctc tctaattctg gagatgagaa tttttatgaa    1440
aatgtagagc ttctcagtaa agagcaaaac aatattcctc tccttactct ctctaaagag   1500
caatctcatt tacatcttcc tgatgggaac ctctcttctc actttggata tcaaggagat   1560
tggactttt cttggaaaga ttctgatgaa gggcattctc tgattgctaa ttggacgcct    1620
aaaaac                                                              1626
```

<210> SEQ ID NO 159
<211> LENGTH: 1992
<212> TYPE: DNA
<213> ORGANISM: Chlamydia

<400> SEQUENCE: 159

```
agctctcctc aagtgttaac acctaatgta accactcctt ttaaggggga cgatgtttac     60
ttgaatggag actgcgcttt tgtcaatgtc tatgcagggg cagagaacgg ctcaattatc    120
tcagctaatg gcgacaattt aacgattacc ggacaaaacc atacattatc atttacagat    180
tctcaagggc cagttcttca aaattatgcc ttcatttcag caggagagac acttactctg    240
aaagattttt cgagtttgat gttctcgaaa aatgtttctt gcggagaaaa gggaatgatc    300
tcagggaaaa ccgtgagtat ttccggagca ggcgaagtga tttttttggga taactctgtg    360
gggtattctc ctttgtctat tgtgccagca tcgactccaa ctcctccagc accagcacca    420
gctcctgctg cttcaagctc tttatctcca acagttagtg atgctcggaa agggtctatt    480
ttttctgtag agactagttt ggagatctca ggcgtcaaaa aagggggtcat gttcgataat    540
aatgccggga ttttggaac agtttttcga ggtaatagta ataataatgc tggtagtggg    600
ggtagtgggt ctgctacaac accaagtttt acagttaaaa actgtaaagg gaaagtttct    660
```

-continued

| | |
|---|---|
| ttcacagata acgtagcctc ctgtggaggc ggagtagtct acaaaggaac tgtgcttttc | 720 |
| aaagacaatg aaggaggcat attcttccga gggaacacag catacgatga tttagggatt | 780 |
| cttgctgcta ctagtcggga tcagaatacg gagacaggag gcggtggagg agttatttgc | 840 |
| tctccagatg attctgtaaa gtttgaaggc aataaaggtt ctattgtttt tgattacaac | 900 |
| tttgcaaaag gcagaggcgg aagcatccta acgaaagaat tctctcttgt agcagatgat | 960 |
| tcggttgtct ttagtaacaa tacagcagaa aaaggcggtg gagctattta tgctcctact | 1020 |
| atcgatataa gcacgaatgg aggatcgatt ctatttgaaa gaaaccgagc tgcagaagga | 1080 |
| ggcgccatct gcgtgagtga agcaagctct ggttcaactg gaaatcttac tttaagcgct | 1140 |
| tctgatgggg atattgtttt ttctgggaat atgacgagtg atcgtcctgg agagcgcagc | 1200 |
| gcagcaagaa tcttaagtga tggaacgact gtttctttaa atgcttccgg actatcgaag | 1260 |
| ctgatctttt atgatcctgt agtacaaaat aattcagcag cgggtgcatc gacaccatca | 1320 |
| ccatcttctt cttctatgcc tggtgctgtc acgattaatc agtccggtaa tggatctgtg | 1380 |
| attttaccg ccgagtcatt gactccttca gaaaaacttc aagttcttaa ctctacttct | 1440 |
| aacttcccag gagctctgac tgtgtcagga ggggagttgg ttgtgacgga aggagctacc | 1500 |
| ttaactactg ggaccattac agccacctct ggacgagtga ctttaggatc cggagcttcg | 1560 |
| ttgtctgccg ttgcaggtgc tgcaaataat aattatactt gtacagtatc taagttgggg | 1620 |
| attgatttag aatccttttt aactcctaac tataagacgg ccatactggg tgcggatgga | 1680 |
| acagttactg ttaacagcgg ctctactttta gacctagtga tggagagtga ggcagaggta | 1740 |
| tatgataatc cgcttttgt gggatcgctg acaattcctt ttgttactct atcttctagt | 1800 |
| agtgctagta acggagttac aaaaaattct gtcactatta atgatgcaga cgctgcgcac | 1860 |
| tatgggtatc aaggctcttg gtctgcagat tggacgaaac cgcctctggc tcctgatgct | 1920 |
| aaggggatgg tacctcctaa taccaataac actctgtatc tgacatggag acctgcttcg | 1980 |
| aattacggtg aa | 1992 |

<210> SEQ ID NO 160
<211> LENGTH: 2010
<212> TYPE: DNA
<213> ORGANISM: Chlamydia

<400> SEQUENCE: 160

| | |
|---|---|
| gcagaaatca tgattcctca aggaatttac gatggggaga cgttaactgt atcatttccc | 60 |
| tatactgtta taggagatcc gagtgggact actgtttttt ctgcaggaga gttaacgtta | 120 |
| aaaaatcttg acaattctat tgcagctttg cctttaagtt gttttgggaa cttattaggg | 180 |
| agttttactg ttttagggag aggacactcg ttgactttcg agaacatacg gacttctaca | 240 |
| aatggagctg cactaagtga cagcgctaat agcgggttat ttactattga gggtttttaaa | 300 |
| gaattatctt tttccaattg caactcatta cttgccgtac tgcctgctgc aacgactaat | 360 |
| aatggtagcc agactccgac gacaacatct acaccgtcta atggtactat ttattctaaa | 420 |
| acagatcttt tgttactcaa taatgagaag ttctcattct atagtaattt agtctctgga | 480 |
| gatgggggag ctatagatgc taagagctta acggttcaag gaattagcaa gctttgtgtc | 540 |
| ttccaagaaa atactgctca agctgatggg ggagcttgtc aagtagtcac cagtttctct | 600 |
| gctatggcta acgaggctcc tattgccttt atagcgaatg ttgcaggagt aagaggggga | 660 |
| gggattgctg ctgttcagga tgggcagcag ggagtgtcat catctactc aacagaagat | 720 |
| ccagtagtaa gttttccag aaatactgcg gtagagtttg atgggaacgt agcccgagta | 780 |

-continued

```
ggaggaggga tttactccta cgggaacgtt gctttcctga ataatggaaa aaccttgttt      840
ctcaacaatg ttgcttctcc tgtttacatt gctgctgagc aaccaacaaa tggacaggct      900
tctaatacga gtgataatta cggagatgga ggagctatct tctgtaagaa tggtgcgcaa      960
gcagcaggat ccaataactc tggatcagtt tcctttgatg agagggagt agttttcttt     1020 agtagcaatg tagctgctgg gaaaggggga gctatttatg ccaaaaagct ctcggttgct     1080
aactgtggcc ctgtacaatt cttagggaat atcgctaatg atggtggagc gatttattta     1140
ggagaatctg gagagctcag tttatctgct gattatggag atattatttt cgatgggaat     1200 cttaaagaa cagccaaaga gaatgctgcc gatgttaatg gcgtaactgt gtcctcacaa     1260
gccatttcga tgggatcggg agggaaaata acgacattaa gagctaaagc agggcatcag     1320
attctcttta atgatcccat cgagatggca aacggaaata accagccagc gcagtcttcc     1380
gaacctctaa aaattaacga tggtgaagga tacacagggg atattgtttt tgctaatgga     1440
aacagtactt tgtaccaaaa tgttacgata gagcaaggaa ggattgttct tcgtgaaaag     1500
gcaaaattat cagtgaattc tctaagtcag acaggtggga gtctgtatat ggaagctggg     1560
agtacattgg attttgtaac tccacaacca ccacaacagc ctcctgccgc taatcagttg     1620
atcacgcttt ccaatctgca tttgtctctt tcttctttgt tagcaaacaa tgcagttacg     1680
aatcctccta ccaatcctcc agcgcaagat tctcatcctg caatcattgg tagcacaact     1740
gctggttctg ttacaattag tgggcctatc ttttttgagg attggatga tacagcttat     1800 gataggtatg attggctagg ttctaatcaa aaaatcgatg tcctgaaatt acagttaggg     1860
actcagccct cagctaatgc cccatcagat ttgactctag ggaatgagat gcctaagtat     1920
ggctatcaag gaagctggaa gcttgcgtgg gatcctaata cagcaaataa tggtccttat     1980
actctgaaag ctacatggac taaaactggg                                      2010
```

<210> SEQ ID NO 161
<211> LENGTH: 2106
<212> TYPE: DNA
<213> ORGANISM: Chlamydia

<400> SEQUENCE: 161

```
aatgaaacgg atacgctaca gttccggcga tttacttttt cggatagaga gattcagttc       60
gtcctagatc ccgcctcttt aattaccgcc caaaacatcg ttttatctaa tttacagtca      120 aacgaaccg gagcctgtac catttcaggc aatacgcaaa ctcaaatctt ttctaattcc      180
gttaacacca ccgcagattc tggtggagcc tttgatatgg ttactacctc attcacggcc      240
tctgataatg ctaatctact cttctgcaac aactactgca cacataataa aggcggagga      300
gctattcgtt ccggaggacc tattcgattc ttaaataatc aagacgtgct tttttataat      360
aacatatcgg caggggctaa atatgttgga acaggagatc acaacgaaaa aaatagggc      420 ggtgcgcttt atgcaactac tatcactttg acagggaatc gaactcttgc ctttattaac      480
aatatgtctg gagactgcgg tggagccatc tctgctgaca ctcaaatatc aataactgat      540
accgttaaag gaattttatt tgaaaacaat cacacgctca atcatatacc gtacacgcaa      600
gctgaaaata tggcacgagg aggagcaatc tgtagtagaa gagacttgtg ctcaatcagc      660
aataattctg gtcccatagt ttttaactat aaccaaggcg ggaaaggtgg agctattagc      720
gctacccgat gtgttattga caataacaaa gaaagaatca tcttttcaaa caatagttcc      780
ctgggatgga gccaatcttc ttctgcaagt aacggaggag ccattcaaac gacacaagga      840
```

```
tttactttac gaaataataa aggctctatc tacttcgaca gcaacactgc tacacacgcc      900
gggggagcca ttaactgtgg ttacattgac atccgagata acggaccgt  ctattttcta     960 aataactctg ctgcctgggg agcggccttt aatttatcga aaccacgttc agcgacaaat    1020
tatatccata cagggacagg cgatattgtt tttaataata acgttgtctt tactcttgac    1080
ggtaatttat tagggaaacg gaaactttt  catattaata ataatgagat aacaccatat    1140
acattgtctc tcggcgctaa aaaagatact cgtatctatt tttatgatct tttccaatgg    1200
gagcgtgtta aagaaaatac tagcaataac ccaccatctc ctaccagtag aaacaccatt    1260
accgttaacc cggaaacaga gttttctgga gctgttgtgt tctcctacaa tcaaatgtct    1320
agtgacatac gaactctgat gggtaaagaa cacaattaca ttaaagaagc cccaactact    1380
ttaaaattcg gaacgctagc catagaagat gatgcagaat tagaaatctt caatatcccg    1440
tttacccaaa atccgactag ccttcttgct ttaggaagcg gcgctacgct gactgttgga    1500
aagcacggta agctcaatat tacaaatctt ggtgttattt tacccattat tctcaaagag    1560
gggaagagtc cgccttgtat tcgcgtcaac ccacaagata tgacccaaaa tactggtacc    1620
ggccaaactc catcaagcac aagtagtata agcactccaa tgattatctt taatgggcgc    1680
ctctcaattg tagacgaaaa ttatgaatca gtctacgaca gtatggacct ctccagaggg    1740
aaagcagaac aactaattct atccatagaa accactaatg atgggcaatt agactccaat    1800
tggcaaagtt ctctgaatac ttctctactc tctcctccac actatggcta tcaaggtcta    1860
tggactccta attggataac aacaacctat accatcacgc ttaataataa ttcttcagct    1920
ccaacatctg ctacctccat cgctgagcag aaaaaaacta gtgaaacttt tactcctagt    1980
aacacaacta cagctagtat ccctaatatt aaagcttccg caggatcagg ctctggatcg    2040
gcttccaatt caggagaagt tacgattacc aaacataccc ttgttgtaaa ctgggcacca    2100
gtcggc                                                              2106

<210> SEQ ID NO 162
<211> LENGTH: 1896
<212> TYPE: DNA
<213> ORGANISM: Chlamydia

<400> SEQUENCE: 162
agagaggttc cttctagaat ctttcttatg cccaactcag ttccagatcc tacgaaagag      60
tcgctatcaa ataaaattag tttgacagga gacactcaca atctcactaa ctgctatctc     120
gataacctac gctacatact ggctattcta caaaaaactc ccaatgaagg agctgctgtc     180
acaataacag attacctaag cttttttgat acacaaaaag aaggtattta ttttgcaaaa     240
aatctcaccc ctgaaagtgg tggtgcgatt ggttatgcga gtcccaattc tcctaccgtg     300
gagattcgtg atacaatagg tcctgtaatc tttgaaaata atacttgttg cagactattt     360
acatggagaa atccttatgc tgctgataaa ataagagaag gcggagccat tcatgctcaa     420
aatctttaca taaatcataa tcatgatgtg gtcggattta tgaagaactt ttcttatgtc     480
caaggaggag ccattagtac cgctaatacc tttgttgtga gcgagaatca gtcttgtttt     540
ctctttatgg acaacatctg tattcaaact aatacagcag aaaaggtgg  cgctatctat     600 gctgaacga  gcaattcttt tgagagtaat aactgcgatc tcttcttcat caataacgcc     660
tgttgtgcag gaggagcgat cttctcccct atctgttctc taacaggaaa tcgtggtaac     720
atcgttttct ataacaatcg ctgctttaaa aatgtagaaa cagcttcttc agaagcttct     780
gatggaggag caattaaagt aactactcgc ctagatgtta caggcaatcg tggtaggatc     840
```

-continued

```
tttttttagtg acaatatcac aaaaaattat ggcggagcta tttacgctcc tgtagttacc        900
ctagtggata atggccctac ctactttata aacaatatcg ccaataataa ggggggcgct        960
atctatatag acgaaccag taactccaaa atttctgccg accgccatgc tattattttt       1020
aatgaaaata ttgtgactaa tgtaactaat gcaaatggta ccagtacgtc agctaatcct       1080
cctagaagaa atgcaataac agtagcaagc tcctctggtg aaattctatt aggagcaggg       1140
agtagccaaa atttaatttt ttatgatcct attgaagtta gcaatgcagg ggtctctgtg       1200
tccttcaata aggaagctga tcaaacaggc tctgtagtat tttcaggagc tactgttaat       1260
tctgcagatt ttcatcaacg caatttacaa acaaaaacac ctgcacccct tactctcagt       1320
aatggttttc tatgtatcga agatcatgct cagcttacag tgaatcgatt cacacaaact       1380
gggggtgttg tttctcttgg gaatggagca gttctgagtt gctataaaaa tggtacagga       1440
gattctgcta gcaatgcctc tataacactg aagcatattg gattgaatct ttcttccatt       1500
ctgaaaagtg gtgctgagat tcctttattg tgggtagagc ctacaaataa cagcaataac       1560
tatacagcag atactgcagc taccttttca ttaagtgatg taaaactctc actcattgat       1620
gactacggga actctcctta tgaatccaca gatctgaccc atgctctgtc atcacagcct       1680
atgctatcta tttctgaagc tagcgataac cagctacaat cagaaaatat agattttcg        1740
ggactaaatg tccctcatta tggatggcaa ggactttgga cttggggctg ggcaaaaact       1800
caagatccag aaccagcatc ttcagcaaca atcactgatc cacaaaaagc caatagattt       1860
catagaacct tactactaac atggcttcct gccggg                                 1896
```

<210> SEQ ID NO 163
<211> LENGTH: 3519
<212> TYPE: DNA
<213> ORGANISM: Chlamydia

<400> SEQUENCE: 163

```
agttgcgtag atcttcatgc tggaggacag tctgtaaatg agctggtata tgtaggccct         60
caagcggttt tattgttaga ccaaattcga gatctattcg ttgggtctaa agatagtcag        120
gctgaaggac agtataggtt aattgtagga gatccaagtt ctttccaaga gaaagatgcg        180
gatactcttc ccgggaaggt agagcaaagt actttgttct cagtaaccaa tcccgtggtt        240
ttccaaggtg tggaccaaca ggatcaagtc tcttcccaag ggttaatttg tagttttacg        300
agcagcaacc ttgattctcc tcgtgacgga gaatcttttt taggtattgc ttttgttggg        360
gatagtagta aggctggaat cacattaact gacgtgaaag cttctttgtc tggagcggct        420
ttatattcta cagaagatct tatctttgaa aagattaagg gtggattgga atttgcatca        480
tgttcttctc tagaacaggg gggagcttgt gcagctcaaa gtattttgat tcatgattgt        540
caaggattgc aggttaaaca ctgtactaca gccgtgaatg ctgagggggtc tagtgcgaat       600
gatcatcttg gatttggagg aggcgctttc tttgttacgg gttctctttc tggagagaaa        660
agtctctata tgcctgcagg agatatggta gttgcgaatt gtgatgggc tatatctttt        720
gaaggaaaca gcgcgaactt tgctaatgga ggagcgattg ctgcctctgg aaagtgctt         780
tttgtcgcta atgataaaaa gacttctttt atagagaacc gagctttgtc tggaggagcg        840
attgcagcct cttctgatat tgcctttcaa aactgcgcag aactagtttt caaaggcaat        900
tgtgcaattg aacagagga taaaggttct ttaggtggag gggctatatc ttctctaggc        960
accgttcttt tgcaagggaa tcacgggata acttgtgata agaatgagtc tgcttcgcaa       1020
```

-continued

```
ggaggcgcca tttttggcaa aaattgtcag atttctgaca acgaggggcc agtggttttc    1080
agagatagta cagcttgctt aggaggaggc gctattgcag ctcaagaaat tgtttctatt    1140
cagaacaatc aggctgggat ttccttcgag ggaggtaagg ctagtttcgg aggaggtatt    1200
gcgtgtggat ctttttcttc cgcaggtggt gcttctgttt tagggaccat tgatatttcg    1260
aagaatttag gcgcgatttc gttctctcgt actttatgta cgacctcaga tttaggacaa    1320
atggagtacc agggaggagg agctctattt ggtgaaaata tttctctttc tgagaatgct    1380
ggtgtgctca cctttaaaga caacattgtg aagacttttg cttcgaatgg gaaaattctg    1440
ggaggaggag cgattttagc tactggtaag gtggaaatta ctaataattc cgaaggaatt    1500
tcttttacag gaaatgcgag agctccacaa gctcttccaa ctcaagagga gtttcctta     1560
ttcagcaaaa aagaagggcg accactctct tcaggatatt ctgggggagg agcgatttta    1620
ggaagagaag tagctattct ccacaacgct gcagtagtat ttgagcaaaa tcgtttgcag    1680
tgcagcgaag aagaagcgac attattaggt tgttgtggag gaggcgctgt tcatgggatg    1740
gatagcactt cgattgttgg caactcttca gtaagatttg gtaataatta cgcaatggga    1800
caaggagtct caggaggagc tcttttatct aaaacagtgc agttagctgg gaatggaagc    1860
gtcgattttt ctcgaaatat tgctagtttg ggaggaggag ctcttcaagc ttctgaagga    1920
aattgtgagc tagttgataa cggctatgtg ctattcagag ataatcgagg gagggtttat    1980
gggggtgcta tttcttgctt acgtggagat gtagtcattt ctggaaacaa gggtagagtt    2040
gaatttaaag acaacatagc aacacgtctt tatgtggaag aaactgtaga aaaggttgaa    2100
gaggtagagc cagctcctga gcaaaaagac aataatgagc tttctttctt agggagagca    2160
gaacagagtt ttattactgc agctaatcaa gctcttttcg catctgaaga tggggattta    2220
tcacctgagt catccatttc ttctgaagaa cttgcgaaaa aagagagtg tgctggagga    2280
gctattttg caaaacgggt tcgtattgta gataaccaag aggccgttgt attctcgaat    2340
aacttctctg atatttatgg cggcgccatt tttacaggtt ctcttcgaga agaggataag    2400
ttagatgggc aaatccctga agtcttgatc tcaggcaatg caggggatgt tgttttttcc    2460
ggaaattcct cgaagcgtga tgagcatctt cctcatacag gtgggggagc catttgtact    2520
caaaatttga cgatttctca gaatacaggg aatgttctgt tttataacaa cgtggcctgt    2580
tcggaggag ctgttcgtat agaggatcat ggtaatgttc ttttagaagc ttttggagga    2640
gatattgttt ttaaaggaaa ttcttcttc agagcacaag gatccgatgc tatctatttt    2700
gcaggtaaag aatcgcatat tacagccctg aatgctacgg aaggacatgc tattgttttc    2760
cacgacgcat tagttttga aaatctagaa gaaaggaaat ctgctgaagt attgttaatc    2820
aatagtcgag aaaatccagg ttacactgga tctattcgat ttttagaagc agaaagtaaa    2880
gttcctcaat gtattcatgt acaacaagga agccttgagt tgctaaatgg agccacatta    2940
tgtagttatg gttttaaaca agatgctgga gctaagttgg tattggctgc tggagctaaa    3000
ctgaagattt tagattcagg aactcctgta caacaagggc atgctatcag taaacctgaa    3060
gcagaaatcg agtcatcttc tgaaccagag ggtgcacatt ctctttggat tgcgaagaat    3120
gctcaaacaa cagttcctat ggttgatatc catactattt ctgtagattt agcctccttc    3180
tcttctagtc aacaggaggg gacagtagaa gctcctcagg ttattgttcc tggaggaagt    3240
tatgttcgat ctggagagct taatttggag ttagttaaca caacaggtac tggttatgaa    3300
aatcatgctt tattgaagaa tgaggctaaa gttccattga tgtctttcgt tgcttctggt    3360
gatgaagctt cagccgaaat cagtaacttg tcggtttctg atttacagat tcatgtagta    3420
```

-continued

| | |
|---|---|
| actccagaga ttgaagaaga cacatacggc catatgggag attggtctga ggctaaaatt | 3480 |
| caagatggaa ctcttgtcat tagttggaat cctactgga | 3519 |

<210> SEQ ID NO 164
<211> LENGTH: 4257
<212> TYPE: DNA
<213> ORGANISM: Chlamydia

<400> SEQUENCE: 164

| | |
|---|---|
| agctcgatcc aagatcaaat aaagaatacc gactgcaatg ttagcaaatt aggatattca | 60 |
| acttctcaag catttactga tatgatgcta gcagacaaca cagagtatcg agctgctgat | 120 |
| agtgtttcat tctatgactt ttcgacatct tccagattac ctagaaaaca tcttagtagt | 180 |
| agtagtgaag cttctccaac gacagaagga gtgtcttcat cttcatctgg agaaactgat | 240 |
| gagaaaacag aagaagaact agacaatggc ggaatcattt atgctagaga gaaactaact | 300 |
| atctcagaat ctcaggactc tctctctaat caaagcatag aactccatga caatagtatt | 360 |
| ttcttcggag aaggtgaagt tatctttgat cacagagttg ccctcaaaaa cggaggagct | 420 |
| atttatggag agaaagaggt agtctttgaa aacataaaat ctctactagt agaagtaaat | 480 |
| atcgcggtcg agaaggggg tagcgtctat gcaaagaac gagtatcttt agaaaatgtt | 540 |
| accgaagcaa ccttctcctc caatggtggg gaacaaggtg gtggtggaat ctattcagaa | 600 |
| caggatatgt taatcagtga ttgcaacaat gtacatttcc aagggaatgc tgcaggagca | 660 |
| acagcagtaa aacaatgtct ggatgaagaa atgatcgtat tgctcgcaga atgcgttgat | 720 |
| agcttatccg aagatacact ggatagcact ccagaaacgg aacagactga gtcaaatgga | 780 |
| aatcaagacg gttcgtctga aacagaagat acacaagtat cagaatcacc agaatcaact | 840 |
| cctagccccg acgatgtttt aggtaaaggt ggtggtatct atacagaaaa atctttgacc | 900 |
| atcactggaa ttacagggac tatagatttt gtcagtaaca tagctaccga ttctggagca | 960 |
| ggtgtattca ctaaagaaaa cttgtcttgc accaacacga atagcctaca gttttgaaa | 1020 |
| aactcggcag gtcaacatgg aggaggagcc tacgttactc aaaccatgtc tgttactaat | 1080 |
| acaactagtg aaagtataac tactccccct ctcataggag aagtgatttt ctctgaaaat | 1140 |
| acagctaaag ggcacggtgg tggtatctgc actaacaaac tttctttatc taatttaaaa | 1200 |
| acggtgactc tcactaaaaa actctgcaaag gagtctggag gagctatttt tacagatctg | 1260 |
| gcgtctatac caataacaga taccccagaa tcttctaccc cctcttcctc ctcgcctgca | 1320 |
| agcactcctg aagtagttgc ttctgctaaa ataaatcgat tcttgcctc tacggcaaaa | 1380 |
| ccggcagccc cttctctaac agaggctgag tctgatcaaa cggatcaaac agaaacttct | 1440 |
| gatactaata gcgatataga cgtgtcgatt gagaacattt tgaatgtcgc tatcaatcaa | 1500 |
| aacacttctg cgaaaaaagg aggggctatt tacgggaaaa agctaaaact ttcccgtatt | 1560 |
| aacaatcttg aactttcagg gaattcatcc caggatgtag gaggaggtct ctgtttaact | 1620 |
| gaaagcgtag aatttgatgc aattggatcg ctcttatccc actataactc tgctgctaaa | 1680 |
| gaaggtgggg ctattcattc taaaacggtt actctatcta acctcaagtc taccttcact | 1740 |
| tttgcagata acactgttaa agcaatagta gaaagcactc ctgaagctcc agaagagatt | 1800 |
| cctccagtag aaggagaaga gtctacagca acagaagatc caaattctaa tacagaagga | 1860 |
| agttcggcta acactaacct tgaaggatct caagggata ctgctgatac agggactggt | 1920 |
| gatgttaaca atgagtctca agacacatca gatactggaa acgctgaatc tgaagaacaa | 1980 |
| ctacaagatt ctacacaatc taatgaagaa aatacccttc ccaatagtaa tattgatcaa | 2040 |

-continued

```
tctaacgaaa acacagacga atcatctgat agccacactg aggaaataac tgacgagagt       2100
gtctcatcgt cctctgaaag tggatcatct actcctcaag atggaggagc agcttcttca       2160
ggggctccct caggagatca atctatctct gcaaacgctt gtttagctaa aagctatgct       2220
gcgagtactg atagctcccc cgtatctaat tcttcaggtt cagaagagcc tgtcacttct       2280
tcttcagatt cagacgttac tgcatcttct gataatccag actcttcctc atctggagat       2340
agcgctggag actctgaaga accgactgag ccagaagctg gttctacaac agaaactctt       2400
actttaatag gaggaggtgc tatctatgga gaaactgtta agattgagaa cttctctggc       2460
caaggaatat tttctggaaa caaagctatc gataacacca cagaaggctc ctcttccaaa       2520
tctgacgtcc tcggaggtgc ggtctatgct aaaacattgt ttaatctcga tagcgggagc       2580
tctagacgaa ctgtcacctt ctccgggaat actgtctctt ctcaatctac aacaggtcag       2640
gttgctggag gagctatcta ctctcctact gtaaccattg ctactcctgt agtatttttct      2700 aaaaactctg caacaaacaa tgctaataac actacagata ctcagagaaa agacaccttt       2760
ggaggagcta tcggagctac ttctgctgtt tctctatcag gagggctca tttcttagaa        2820 aacgttgctg acctcggatc tgctattggg ttggtgccag gcacacaaaa tacagaaaca       2880
gtgaaattag agtctggctc ctactacttt gaaaaaaata aagctttaaa acgagctact       2940
atttacgcac ctgtcgtttc cattaaagcc tatactgcga catttaacca aaacagatct       3000
ctagaagaag gaagcgcgat ttactttaca aaagaagcat ctattgagtc tttaggctct       3060
gttctcttca caggaaactt agtaacccta acgctaagca aactacagaa aggcacacca       3120
gccacaacct caggagatgt aacaaaatat ggtgctgcta tctttggaca aatagcaagc       3180
tcaaacggat ctcagacgga taaccttccc ctgaaactca ttgcttcagg aggaaatatt       3240
tgtttccgaa acaatgaata ccgtcctact tcttctgata ccggaaccctc tactttctgt      3300 agtattgcgg gagatgttaa attaaccatg caagctgcaa aagggaaaac gatcagtttc       3360
tttgatgcaa tccggacctc tactaagaaa acaggtacac aggcaactgc ctacgatact       3420
ctcgatatta ataaatctga ggattcagaa actgtaaact ctgcgtttac aggaacgatt       3480
ctgttctcct ctgaattaca tgaaaataaa tcctatattc cacaaaacgt agttctacac       3540
agtggatctc ttgtattgaa gccaaatacc gagcttcatg ttatttcttt tgagcagaaa       3600
gaaggctctt ctctcgttat gacacctgga tctgttcttt cgaaccagac tgttgctgat       3660 ggagcttttgg tcataaataa catgaccatt gatttatcca gcgtagagaa aaatggtatt       3720
gctgaaggaa atatctttac tcctccagaa ttgagaatca tagacactac tacaggtgga       3780
agcggtggaa ccccatctac agatagtgaa agtaaccaga atagtgatga taccgaggag       3840
caaaataata atgacgcctc gaatcaagga gaaagcgcga atggatcgtc ttctcctgca       3900
gtagctgctg cacacacatc tcgtacaaga aactttgccg ctgcagctac agccacacct       3960
acgacaacac caacggctac aactacaaca agcaaccaag taatcctagg aggagaaatt       4020
aaactcatcg atcctaatgg gaccttcttc cagaaccctg cattaagatc cgaccaacaa       4080
atctccttgt tagtgctccc tacagactca tcaaaaatgc aagctcagaa aatagtactg       4140
acgggtgata ttgctcctca gaaaggatat acaggaacac tcactctgga tcctgatcaa       4200
ctacaaaatg gaacgatctc agtgctctgg aaatttgact cttatagaca atgggct        4257
```

```
<210> SEQ ID NO 165
<211> LENGTH: 4191
<212> TYPE: DNA
```

<213> ORGANISM: Chlamydia

<400> SEQUENCE: 165

```
gaacctaaag aattaaattt ctctcgcgta ggaacttctt cctctaccac ttttactgaa      60
acagttggag aagctggggc agaatatatc gtctctggta acgcatcttt cacaaaattt     120
accaacattc ctactaccga tacaacaact cccacgaact caaactcctc tagctctaac     180
ggagagactg cttccgtttc tgaggatagt gactctacaa caacgactcc tgatcctaaa     240
ggtggcggcg ccttttataa cgcgcactcc ggagttttat cctttatgac acgatcagga     300
acagaaggtt ccttaactct gtctgagata aaataactgt gtgaaggcgg tgctatcttc     360
tctcaaggag agctgctatt tacagatctg acaggtctaa ccatccaaaa taacttatcc     420
cagctatccg gaggagcgat ttttggagaa tctacaatct ccctatcagg gattactaaa     480
gcgactttct cctccaactc tgcagaagtt cctgctcctg ttaagaaacc tacagaacct     540
aaagctcaaa cagcaagcga aacgtcgggt tctagtagtt ctagcggaaa tgattcggtg     600
tcttcccca gttccagtag agctgaaccc gcagcagcta atcttcaaag tcactttatt     660
tgtgctacag ctactcctgc tgctcaaacc gatacagaaa catcaactcc ctctcataag     720
ccaggatctg ggggagctat ctatgctaaa ggcgacctta ctatcgcaga ctctcaagag     780
gtactattct caataaataa agctactaaa gatggaggag cgatctttgc tgagaaagat     840
gtttctttcg agaatattac atcattaaaa gtacaaacta acggtgctga agaaaaggga     900
ggagctatct atgctaaagg tgacctctca attcaatctt ctaaacagag tcttttttaat     960
tctaactaca gtaaacaagg tggtggggct ctatatgttg aaggagatat aaacttccaa    1020
gatcttgaag aaattcgcat taagtacaat aaagctggaa cgttcgaaac aaaaaaaatc    1080
actttaccaa aagctcaagc atctgcagga aatgcagatg cttgggcctc ttcctctcct    1140
caatctggtt ctggagcaac tacagtctcc aactcaggag actctagctc tggctcagac    1200
tcggatacct cagaaacagt tccagccaca gctaaaggcg gtgggcttta tactgataag    1260
aatctttcga ttactaacat cacaggaatt atcgaaattg caaataacaa agcgacagat    1320
gttggaggtg gtgcttacgt aaaaggaacc cttacttgtg aaaactctca ccgtctacaa    1380
tttttgaaaa actcttccga taaacaaggt ggaggaatct acggagaaga caacatcacc    1440
ctatctaatt tgacagggaa gactctattc caagagaata ctgccaaaga gagggcggt    1500
ggactcttca taaaaggtac agataaagct cttacaatga caggactgga tagtttctgt    1560
ttaattaata acacatcaga aaaacatggt ggtggagcct tgttaccaa agaaatctct    1620
cagacttaca cctctgatgt ggaaacaatt ccaggaatca cgcctgtaca tggtgaaaca    1680
gtcattactg gcaataaatc tacaggaggt aatggtggag cgtgtgtac aaaacgtctt    1740
gccttatcta accttcaaag catttctata tccgggaatt ctgcagctga aatggtggt    1800
ggagcccaca catgcccaga tagcttccca acggcggata ctgcagaaca gcccgcagca    1860
gcttctgccg cgacgtctac tcccgagtct gccccagtgg tctcaactgc tctaagcaca    1920
ccttcatctt ctaccgtctc ttcattaacc ttactagcag cctcttcaca agcctctcct    1980
gcaacctcta ataaggaaac tcaagatcct aatgctgata cagacttatt gatcgattat    2040
gtagttgata cgactatcag caaaaacact gctaagaaag cggtggaat ctatgctaaa    2100
aaagccaaga tgtcccgcat agaccaactg aatatctctg agaactccgc tacagagata    2160
ggtggaggta tctgctgtaa agaatcttta gaactagatg ccctagtctc cttatctgta    2220
acagagaacc ttgttgggaa agaaggtgga ggcttacatg ctaaaactgt aaatatttct    2280
```

```
aatctgaaat caggcttctc tttctcgaac aacaaagcaa actcctcatc cacaggagtc    2340
gcaacaacag cttcagcacc tgctgcagct gctgcttccc tacaagcagc cgcagcagcc    2400
gtaccatcat ctccagcaac accaacttat tcaggtgtag taggaggagc tatctatgga    2460
gaaaaggtta cattctctca atgtagcggg acttgtcagt tctctgggaa ccaagctatc    2520
gataacaatc cctcccaatc atcgttgaac gtacaaggag gagccatcta tgccaaaacc    2580
tctttgtcta ttggatcttc cgatgctgga acctcctata ttttctcggg gaacagtgtc    2640
tccactggga aatctcaaac aacagggcaa atagcgggag gagcgatcta ctcccctact    2700
gttacattga attgtcctgc gacattctct aacaatacag cctctatggc tacaccaaag    2760
acttcttctg aagatggatc ctcaggaaat tctattaaag ataccattgg aggagccatt    2820
gcagggacag ccattaccct atctggagtc tctcgatttt cagggaatac ggctgattta    2880
ggagctgcaa taggaactct agctaatgca aatacaccca gtgcaactag cggatctcaa    2940
aatagcatta cagaaaaaat tactttagaa aacggttctt ttattttga agaaaccaa    3000 gctaataaac gtggagcgat ttactctcct agcgtttcca ttaaagggaa taatattacc    3060
ttcaatcaaa atacatccac tcatgatgga agtgctatct actttacaaa agatgctacg    3120
attgagtctt taggatctgt tcttttttaca ggaaataacg ttacagctac acaagctagt    3180
tctgcaacat ctggacaaaa tacaaatact gccaactatg gggcagccat ctttggagat    3240
ccaggaacca ctcaatcgtc tcaaacagat gccattttaa cccttcttgc ttcttctgga    3300
aacattactt ttagcaacaa cagtttacag aataaccaag tgatactccc gctagcaag    3360 ttttgtagta ttgcaggata cgtcaaactc tctctacaag ccgctaaagg gaagactatt    3420 agcttttttcg attgtgtgca cacctctacc aaaaaaatag gttcaacaca aaacgttta    3480 gaaactttag atattaataa agaagagaac agtaatccat atacaggaac tattgtgttc    3540
tcttctgaat tacatgaaaa caaatcttac atcccacaga atgcaatcct tcacaacgga    3600
actttagttc ttaaagagaa aacagaactc cacgtagtct cttttgagca gaaagaaggg    3660
tctaaattaa ttatgaaacc cggagctgtg ttatctaacc aaaacatagc taacggagct    3720
ctagttatca atgggttaac gattgatctt tccagtatgg ggactcctca agcagggaa    3780 atcttctctc ctccagaatt acgtatcgtt gccacgacct ctagtgcatc cggaggaagc    3840
ggggtcagca gtagtatacc aacaaatcct aaaaggattt ctgcagcagc gccttcaggt    3900
tctgccgcaa ctactccaac tatgagcgag aacaaagttt tcctaacagg agaccttact    3960
ttaatagatc ctaatggaaa ctttttaccaa acccctatgt taggaagcga tctagatgta    4020
ccactaatta agcttccgac taacacaagt gacgtccaag tctatgattt aactttatct    4080
ggggatcttt tccctcagaa agggtacatg ggaacctgga cattagattc taatcccacaa    4140 acagggaaac ttcaagccag atggacattc gatacctatc gtcgctgggt a              4191
```

<210> SEQ ID NO 166
<211> LENGTH: 1830
<212> TYPE: DNA
<213> ORGANISM: Chlamydia

<400> SEQUENCE: 166

```
gaaatggaat tagctatttc tggacataaa caaggtaaag atcgagatac ctttaccatg      60
atctcttcct gtcctgaagg cactaattac atcatcaatc gcaaactcat actcagtgat    120
ttctcgttac taaataaagt ttcatcaggg ggagcctttc ggaatctagc agggaaaatt    180
```

-continued

```
tccttcttag gaaaaaattc ttctgcgtcc attcatttta aacacattaa tatcaatggt    240
tttggagccg gagtctttc tgaatcctct attgaattta ctgatttacg aaaacttgtt    300
gcttttggat ctgaaagcac aggaggaatt tttactgcga agaggacat ctcttttaaa    360 aacaaccacc acattgcctt ccgcaataat atcaccaaag ggaatggtgg cgttatccag    420
ctccaaggag atatgaaagg aagcgtatcc tttgtagatc aacgtggagc tatcatcttt    480
accaataacc aagctgtaac ttcttcatca atgaaacata gtggtcgtgg aggagcaatt    540
agcggtgact tcgcaggatc cagaattctt tttcttaata accaacaaat tactttcgaa    600
ggcaatagcc ctgtgcatgg aagtgctatc tacaataaga atggccttgt cgagttctta    660
ggaaatgcag gacctcttgc cttaaagag aacacaacaa tagctaacgg gggagctata    720
tacacaagta atttcaaagc gaatcaacaa acatccccca ttctattctc tcaaaatcat    780
gcgaataaga aggcggagc gatttacgcg caatatgtga acttagaaca gaatcaagat    840
actattcgct ttgaaaaaaa taccgctaaa gaaggcggtg gagccatcac ctcttctcaa    900
tgctcaatta ctgctcataa taccatcatt ttttccgata atgctgccgg agatcttgga    960
ggaggagcaa ttcttctaga agggaaaaaa ccttctctaa ccttgattgc tcatagtggt    1020
aatattgcat ttagcggcaa taccatgctt catatcacca aaaagcttc cctagatcga    1080 cacaattcta tcttaatcaa agaagctccc tataaaatcc aacttgcagc gaacaaaaac    1140
cattctattc atttctttga tcctgtcatg gcattgtcag catcatcttc ccctatacaa    1200
atcaatgctc ctgagtatga aactcccttc ttctcaccta agggtatgat cgttttctcg    1260
ggtgcgaatc ttttagatga tgctagggaa gatgttgcaa atagaacatc gatttttaac    1320
caacccgttc atctatataa tggcacccta tctatcgaaa atggagccca tctgattgtc    1380
caaagcttca acagaccgg aggacgtatc agtttatctc caggatcctc cttggctcta    1440
tacacgatga actcgttctt ccatggcaac atatccagca agaacccct agaaattaat    1500 ggtttaagct ttggagtaga tatctctcct tctaatcttc aagcagagat ccgtgccggc    1560
aacgctcctt tacgattatc cggatcccca tctatccatg atcctgaagg attattctac    1620
gaaaatcgcg atactgcagc atcaccatac caaatggaaa tcttgctcac ctctgataaa    1680
attgtagata tctccaaatt tactactgat tctctagtta cgaacaaaca atcaggattc    1740
caaggagcct ggcattttag ctggcagcca aatactataa acaatactaa acaaaaaata    1800
ttaagagctt cttggctccc aacaggagaa                                    1830
```

<210> SEQ ID NO 167
<211> LENGTH: 542
<212> TYPE: PRT
<213> ORGANISM: Chlamydia

<400> SEQUENCE: 167

```
Gln Asp Pro Leu Gly Glu Thr Ala Leu Leu Thr Lys Asn Pro Asn His
              5                  10                  15

Val Val Cys Thr Phe Phe Glu Asp Cys Thr Met Glu Ser Leu Phe Pro
         20                  25                  30

Ala Leu Cys Ala His Ala Ser Gln Asp Asp Pro Leu Tyr Val Leu Gly
     35                  40                  45

Asn Ser Tyr Cys Trp Phe Val Ser Lys Leu His Ile Thr Asp Pro Lys
 50                  55                  60

Glu Ala Leu Phe Lys Glu Lys Gly Asp Leu Ser Ile Gln Asn Phe Arg
65                  70                  75                  80
```

```
Phe Leu Ser Phe Thr Asp Cys Ser Ser Lys Glu Ser Pro Ser Ile
                85                  90                  95
Ile His Gln Lys Asn Gly Gln Leu Ser Leu Arg Asn Asn Gly Ser Met
            100                 105                 110
Ser Phe Cys Arg Asn His Ala Glu Gly Ser Gly Gly Ala Ile Ser Ala
            115                 120                 125
Asp Ala Phe Ser Leu Gln His Asn Tyr Leu Phe Thr Ala Phe Glu Glu
    130                 135                 140
Asn Ser Ser Lys Gly Asn Gly Ala Ile Gln Ala Gln Thr Phe Ser
145                 150                 155                 160
Leu Ser Arg Asn Val Ser Pro Ile Ser Phe Ala Arg Asn Arg Ala Asp
                165                 170                 175
Leu Asn Gly Gly Ala Ile Cys Cys Ser Asn Leu Ile Cys Ser Gly Asn
            180                 185                 190
Val Asn Pro Leu Phe Phe Thr Gly Asn Ser Ala Thr Asn Gly Gly Ala
        195                 200                 205
Ile Cys Cys Ile Ser Asp Leu Asn Thr Ser Glu Lys Gly Ser Leu Ser
    210                 215                 220
Leu Ala Cys Asn Gln Glu Thr Leu Phe Ala Ser Asn Ser Ala Lys Glu
225                 230                 235                 240
Lys Gly Gly Ala Ile Tyr Ala Lys His Met Val Leu Arg Tyr Asn Gly
                245                 250                 255
Pro Val Ser Phe Ile Asn Asn Ser Ala Lys Ile Gly Gly Ala Ile Ala
            260                 265                 270
Ile Gln Ser Gly Gly Ser Leu Ser Ile Leu Ala Gly Glu Gly Ser Val
    275                 280                 285
Leu Phe Gln Asn Asn Ser Gln Arg Thr Ser Asp Gln Gly Leu Val Arg
    290                 295                 300
Asn Ala Ile Tyr Leu Glu Lys Asp Ala Ile Leu Ser Ser Leu Glu Ala
305                 310                 315                 320
Arg Asn Gly Asp Ile Leu Phe Phe Asp Pro Ile Val Gln Glu Ser Ser
                325                 330                 335
Ser Lys Glu Ser Pro Leu Pro Ser Ser Leu Gln Ala Ser Val Thr Ser
            340                 345                 350
Pro Thr Pro Ala Thr Ala Ser Pro Leu Val Ile Gln Thr Ser Ala Asn
        355                 360                 365
Arg Ser Val Ile Phe Ser Ser Glu Arg Leu Ser Glu Glu Lys Thr
370                 375                 380
Pro Asp Asn Leu Thr Ser Gln Leu Gln Gln Pro Ile Glu Leu Lys Ser
385                 390                 395                 400
Gly Arg Leu Val Leu Lys Asp Arg Ala Val Leu Ser Ala Pro Ser Leu
                405                 410                 415
Ser Gln Asp Pro Gln Ala Leu Leu Ile Met Glu Ala Gly Thr Ser Leu
            420                 425                 430
Lys Thr Ser Ser Asp Leu Lys Leu Ala Thr Leu Ser Ile Pro Leu His
        435                 440                 445
Ser Leu Asp Thr Glu Lys Ser Val Thr Ile His Ala Pro Asn Leu Ser
    450                 455                 460
Ile Gln Lys Ile Phe Leu Ser Asn Ser Gly Asp Glu Asn Phe Tyr Glu
465                 470                 475                 480
Asn Val Glu Leu Leu Ser Lys Glu Gln Asn Asn Ile Pro Leu Leu Thr
                485                 490                 495
Leu Ser Lys Glu Gln Ser His Leu His Leu Pro Asp Gly Asn Leu Ser
```

```
                  500                 505                 510
Ser His Phe Gly Tyr Gln Gly Asp Trp Thr Phe Ser Trp Lys Asp Ser
            515                 520                 525

Asp Glu Gly His Ser Leu Ile Ala Asn Trp Thr Pro Lys Asn
        530                 535                 540

<210> SEQ ID NO 168
<211> LENGTH: 664
<212> TYPE: PRT
<213> ORGANISM: Chlamydia

<400> SEQUENCE: 168

Ser Ser Pro Gln Val Leu Thr Pro Asn Val Thr Thr Pro Phe Lys Gly
                  5                  10                  15

Asp Asp Val Tyr Leu Asn Gly Asp Cys Ala Phe Val Asn Val Tyr Ala
             20                  25                  30

Gly Ala Glu Asn Gly Ser Ile Ile Ser Ala Asn Gly Asp Asn Leu Thr
         35                  40                  45

Ile Thr Gly Gln Asn His Thr Leu Ser Phe Thr Asp Ser Gln Gly Pro
     50                  55                  60

Val Leu Gln Asn Tyr Ala Phe Ile Ser Ala Gly Glu Thr Leu Thr Leu
 65                  70                  75                  80

Lys Asp Phe Ser Ser Leu Met Phe Ser Lys Asn Val Ser Cys Gly Glu
                 85                  90                  95

Lys Gly Met Ile Ser Gly Lys Thr Val Ser Ile Ser Gly Ala Gly Glu
            100                 105                 110

Val Ile Phe Trp Asp Asn Ser Val Gly Tyr Ser Pro Leu Ser Ile Val
        115                 120                 125

Pro Ala Ser Thr Pro Thr Pro Pro Ala Pro Ala Pro Ala Pro Ala Ala
    130                 135                 140

Ser Ser Ser Leu Ser Pro Thr Val Ser Asp Ala Arg Lys Gly Ser Ile
145                 150                 155                 160

Phe Ser Val Glu Thr Ser Leu Glu Ile Ser Gly Val Lys Lys Gly Val
                165                 170                 175

Met Phe Asp Asn Asn Ala Gly Asn Phe Gly Thr Val Phe Arg Gly Asn
            180                 185                 190

Ser Asn Asn Asn Ala Gly Ser Gly Gly Ser Gly Ser Ala Thr Thr Pro
        195                 200                 205

Ser Phe Thr Val Lys Asn Cys Lys Gly Lys Val Ser Phe Thr Asp Asn
    210                 215                 220

Val Ala Ser Cys Gly Gly Val Val Tyr Lys Gly Thr Val Leu Phe
225                 230                 235                 240

Lys Asp Asn Glu Gly Gly Ile Phe Phe Arg Gly Asn Thr Ala Tyr Asp
                245                 250                 255

Asp Leu Gly Ile Leu Ala Ala Thr Ser Arg Asp Gln Asn Thr Glu Thr
            260                 265                 270

Gly Gly Gly Gly Gly Val Ile Cys Ser Pro Asp Asp Ser Val Lys Phe
        275                 280                 285

Glu Gly Asn Lys Gly Ser Ile Val Phe Asp Tyr Asn Phe Ala Lys Gly
    290                 295                 300

Arg Gly Gly Ser Ile Leu Thr Lys Glu Phe Leu Val Ala Asp Asp
305                 310                 315                 320

Ser Val Val Phe Ser Asn Asn Thr Ala Glu Lys Gly Gly Ala Ile
                325                 330                 335
```

```
Tyr Ala Pro Thr Ile Asp Ile Ser Thr Asn Gly Gly Ser Ile Leu Phe
            340                 345                 350

Glu Arg Asn Arg Ala Ala Glu Gly Gly Ala Ile Cys Val Ser Glu Ala
        355                 360                 365

Ser Ser Gly Ser Thr Gly Asn Leu Thr Leu Ser Ala Ser Asp Gly Asp
    370                 375                 380

Ile Val Phe Ser Gly Asn Met Thr Ser Asp Arg Pro Gly Glu Arg Ser
385                 390                 395                 400

Ala Ala Arg Ile Leu Ser Asp Gly Thr Thr Val Ser Leu Asn Ala Ser
            405                 410                 415

Gly Leu Ser Lys Leu Ile Phe Tyr Asp Pro Val Val Gln Asn Asn Ser
        420                 425                 430

Ala Ala Gly Ala Ser Thr Pro Ser Pro Ser Ser Ser Ser Met Pro Gly
    435                 440                 445

Ala Val Thr Ile Asn Gln Ser Gly Asn Gly Ser Val Ile Phe Thr Ala
450                 455                 460

Glu Ser Leu Thr Pro Ser Glu Lys Leu Gln Val Leu Asn Ser Thr Ser
465                 470                 475                 480

Asn Phe Pro Gly Ala Leu Thr Val Ser Gly Gly Glu Leu Val Val Thr
                485                 490                 495

Glu Gly Ala Thr Leu Thr Thr Gly Thr Ile Thr Ala Thr Ser Gly Arg
            500                 505                 510

Val Thr Leu Gly Ser Gly Ala Ser Leu Ser Ala Val Ala Gly Ala Ala
        515                 520                 525

Asn Asn Asn Tyr Thr Cys Thr Val Ser Lys Leu Gly Ile Asp Leu Glu
    530                 535                 540

Ser Phe Leu Thr Pro Asn Tyr Lys Thr Ala Ile Leu Gly Ala Asp Gly
545                 550                 555                 560

Thr Val Thr Val Asn Ser Gly Ser Thr Leu Asp Leu Val Met Glu Ser
            565                 570                 575

Glu Ala Glu Val Tyr Asp Asn Pro Leu Phe Val Gly Ser Leu Thr Ile
        580                 585                 590

Pro Phe Val Thr Leu Ser Ser Ser Ala Ser Asn Gly Val Thr Lys
    595                 600                 605

Asn Ser Val Thr Ile Asn Asp Ala Asp Ala Ala His Tyr Gly Tyr Gln
610                 615                 620

Gly Ser Trp Ser Ala Asp Trp Thr Lys Pro Leu Ala Pro Asp Ala
625                 630                 635                 640

Lys Gly Met Val Pro Pro Asn Thr Asn Asn Thr Leu Tyr Leu Thr Trp
                645                 650                 655

Arg Pro Ala Ser Asn Tyr Gly Glu
            660

<210> SEQ ID NO 169
<211> LENGTH: 670
<212> TYPE: PRT
<213> ORGANISM: Chlamydia

<400> SEQUENCE: 169

Ala Glu Ile Met Ile Pro Gln Gly Ile Tyr Asp Gly Glu Thr Leu Thr
                5                  10                  15

Val Ser Phe Pro Tyr Thr Val Ile Gly Asp Pro Ser Gly Thr Thr Val
            20                  25                  30

Phe Ser Ala Gly Glu Leu Thr Leu Lys Asn Leu Asp Asn Ser Ile Ala
        35                  40                  45
```

```
Ala Leu Pro Leu Ser Cys Phe Gly Asn Leu Leu Gly Ser Phe Thr Val
 50                  55                  60

Leu Gly Arg Gly His Ser Leu Thr Phe Glu Asn Ile Arg Thr Ser Thr
 65                  70                  75                  80

Asn Gly Ala Ala Leu Ser Asp Ser Ala Asn Ser Gly Leu Phe Thr Ile
                 85                  90                  95

Glu Gly Phe Lys Glu Leu Ser Phe Ser Asn Cys Asn Ser Leu Leu Ala
                100                 105                 110

Val Leu Pro Ala Ala Thr Thr Asn Asn Gly Ser Gln Thr Pro Thr Thr
                115                 120                 125

Thr Ser Thr Pro Ser Asn Gly Thr Ile Tyr Ser Lys Thr Asp Leu Leu
        130                 135                 140

Leu Leu Asn Asn Glu Lys Phe Ser Phe Tyr Ser Asn Leu Val Ser Gly
145                 150                 155                 160

Asp Gly Gly Ala Ile Asp Ala Lys Ser Leu Thr Val Gln Gly Ile Ser
                165                 170                 175

Lys Leu Cys Val Phe Gln Glu Asn Thr Ala Gln Ala Asp Gly Gly Ala
                180                 185                 190

Cys Gln Val Val Thr Ser Phe Ser Ala Met Ala Asn Glu Ala Pro Ile
        195                 200                 205

Ala Phe Ile Ala Asn Val Ala Gly Val Arg Gly Gly Ile Ala Ala
        210                 215                 220

Val Gln Asp Gly Gln Gln Gly Val Ser Ser Thr Ser Thr Glu Asp
225                 230                 235                 240

Pro Val Val Ser Phe Ser Arg Asn Thr Ala Val Glu Phe Asp Gly Asn
                245                 250                 255

Val Ala Arg Val Gly Gly Ile Tyr Ser Tyr Gly Asn Val Ala Phe
                260                 265                 270

Leu Asn Asn Gly Lys Thr Leu Phe Leu Asn Asn Val Ala Ser Pro Val
        275                 280                 285

Tyr Ile Ala Ala Glu Gln Pro Thr Asn Gly Gln Ala Ser Asn Thr Ser
290                 295                 300

Asp Asn Tyr Gly Asp Gly Gly Ala Ile Phe Cys Lys Asn Gly Ala Gln
305                 310                 315                 320

Ala Ala Gly Ser Asn Asn Ser Gly Ser Val Ser Phe Asp Gly Glu Gly
                325                 330                 335

Val Val Phe Phe Ser Ser Asn Val Ala Ala Gly Lys Gly Gly Ala Ile
                340                 345                 350

Tyr Ala Lys Lys Leu Ser Val Ala Asn Cys Gly Pro Val Gln Phe Leu
        355                 360                 365

Gly Asn Ile Ala Asn Asp Gly Gly Ala Ile Tyr Leu Gly Glu Ser Gly
        370                 375                 380

Glu Leu Ser Leu Ser Ala Asp Tyr Gly Asp Ile Ile Phe Asp Gly Asn
385                 390                 395                 400

Leu Lys Arg Thr Ala Lys Glu Asn Ala Ala Asp Val Asn Gly Val Thr
                405                 410                 415

Val Ser Ser Gln Ala Ile Ser Met Gly Ser Gly Lys Ile Thr Thr
                420                 425                 430

Leu Arg Ala Lys Ala Gly His Gln Ile Leu Phe Asn Asp Pro Ile Glu
        435                 440                 445

Met Ala Asn Gly Asn Asn Gln Pro Ala Gln Ser Glu Pro Leu Lys
450                 455                 460
```

-continued

```
Ile Asn Asp Gly Glu Gly Tyr Thr Gly Asp Ile Val Phe Ala Asn Gly
465                 470                 475                 480

Asn Ser Thr Leu Tyr Gln Asn Val Thr Ile Glu Gln Gly Arg Ile Val
                485                 490                 495

Leu Arg Glu Lys Ala Lys Leu Ser Val Asn Ser Leu Ser Gln Thr Gly
            500                 505                 510

Gly Ser Leu Tyr Met Glu Ala Gly Ser Thr Leu Asp Phe Val Thr Pro
        515                 520                 525

Gln Pro Pro Gln Gln Pro Ala Ala Asn Gln Leu Ile Thr Leu Ser
    530                 535                 540

Asn Leu His Leu Ser Leu Ser Ser Leu Leu Ala Asn Asn Ala Val Thr
545                 550                 555                 560

Asn Pro Pro Thr Asn Pro Pro Ala Gln Asp Ser His Pro Ala Ile Ile
                565                 570                 575

Gly Ser Thr Thr Ala Gly Ser Val Thr Ile Ser Gly Pro Ile Phe Phe
                580                 585                 590

Glu Asp Leu Asp Asp Thr Ala Tyr Asp Arg Tyr Asp Trp Leu Gly Ser
            595                 600                 605

Asn Gln Lys Ile Asp Val Leu Lys Leu Gln Leu Gly Thr Gln Pro Ser
        610                 615                 620

Ala Asn Ala Pro Ser Asp Leu Thr Leu Gly Asn Glu Met Pro Lys Tyr
625                 630                 635                 640

Gly Tyr Gln Gly Ser Trp Lys Leu Ala Trp Asp Pro Asn Thr Ala Asn
                645                 650                 655

Asn Gly Pro Tyr Thr Leu Lys Ala Thr Trp Thr Lys Thr Gly
                660                 665                 670

<210> SEQ ID NO 170
<211> LENGTH: 702
<212> TYPE: PRT
<213> ORGANISM: Chlamydia

<400> SEQUENCE: 170

Asn Glu Thr Asp Thr Leu Gln Phe Arg Arg Phe Thr Phe Ser Asp Arg
                5                   10                  15

Glu Ile Gln Phe Val Leu Asp Pro Ala Ser Leu Ile Thr Ala Gln Asn
            20                  25                  30

Ile Val Leu Ser Asn Leu Gln Ser Asn Gly Thr Gly Ala Cys Thr Ile
        35                  40                  45

Ser Gly Asn Thr Gln Thr Gln Ile Phe Ser Asn Ser Val Asn Thr Thr
    50                  55                  60

Ala Asp Ser Gly Gly Ala Phe Asp Met Val Thr Thr Ser Phe Thr Ala
65                  70                  75                  80

Ser Asp Asn Ala Asn Leu Leu Phe Cys Asn Asn Tyr Cys Thr His Asn
                85                  90                  95

Lys Gly Gly Gly Ala Ile Arg Ser Gly Pro Ile Arg Phe Leu Asn
            100                 105                 110

Asn Gln Asp Val Leu Phe Tyr Asn Asn Ile Ser Ala Gly Ala Lys Tyr
        115                 120                 125

Val Gly Thr Gly Asp His Asn Glu Lys Asn Arg Gly Gly Ala Leu Tyr
    130                 135                 140

Ala Thr Thr Ile Thr Leu Thr Gly Asn Arg Thr Leu Ala Phe Ile Asn
145                 150                 155                 160

Asn Met Ser Gly Asp Cys Gly Gly Ala Ile Ser Ala Asp Thr Gln Ile
                165                 170                 175
```

```
Ser Ile Thr Asp Thr Val Lys Gly Ile Leu Phe Glu Asn Asn His Thr
            180                 185                 190

Leu Asn His Ile Pro Tyr Thr Gln Ala Glu Asn Met Ala Arg Gly Gly
        195                 200                 205

Ala Ile Cys Ser Arg Arg Asp Leu Cys Ser Ile Ser Asn Asn Ser Gly
        210                 215                 220

Pro Ile Val Phe Asn Tyr Asn Gln Gly Lys Gly Gly Ala Ile Ser
225                 230                 235                 240

Ala Thr Arg Cys Val Ile Asp Asn Asn Lys Glu Arg Ile Ile Phe Ser
                245                 250                 255

Asn Asn Ser Ser Leu Gly Trp Ser Gln Ser Ser Ala Ser Asn Gly
            260                 265                 270

Gly Ala Ile Gln Thr Thr Gln Gly Phe Thr Leu Arg Asn Asn Lys Gly
            275                 280                 285

Ser Ile Tyr Phe Asp Ser Asn Thr Ala Thr His Ala Gly Gly Ala Ile
            290                 295                 300

Asn Cys Gly Tyr Ile Asp Ile Arg Asp Asn Gly Pro Val Tyr Phe Leu
305                 310                 315                 320

Asn Asn Ser Ala Ala Trp Gly Ala Ala Phe Asn Leu Ser Lys Pro Arg
                325                 330                 335

Ser Ala Thr Asn Tyr Ile His Thr Gly Thr Gly Asp Ile Val Phe Asn
            340                 345                 350

Asn Asn Val Val Phe Thr Leu Asp Gly Asn Leu Leu Gly Lys Arg Lys
            355                 360                 365

Leu Phe His Ile Asn Asn Asn Glu Ile Thr Pro Tyr Thr Leu Ser Leu
        370                 375                 380

Gly Ala Lys Lys Asp Thr Arg Ile Tyr Phe Tyr Asp Leu Phe Gln Trp
385                 390                 395                 400

Glu Arg Val Lys Glu Asn Thr Ser Asn Asn Pro Pro Ser Pro Thr Ser
                405                 410                 415

Arg Asn Thr Ile Thr Val Asn Pro Glu Thr Glu Phe Ser Gly Ala Val
            420                 425                 430

Val Phe Ser Tyr Asn Gln Met Ser Ser Asp Ile Arg Thr Leu Met Gly
            435                 440                 445

Lys Glu His Asn Tyr Ile Lys Glu Ala Pro Thr Thr Leu Lys Phe Gly
        450                 455                 460

Thr Leu Ala Ile Glu Asp Asp Ala Glu Leu Glu Ile Phe Asn Ile Pro
465                 470                 475                 480

Phe Thr Gln Asn Pro Thr Ser Leu Leu Ala Leu Gly Ser Gly Ala Thr
                485                 490                 495

Leu Thr Val Gly Lys His Gly Lys Leu Asn Ile Thr Asn Leu Gly Val
            500                 505                 510

Ile Leu Pro Ile Ile Leu Lys Glu Gly Lys Ser Pro Pro Cys Ile Arg
            515                 520                 525

Val Asn Pro Gln Asp Met Thr Gln Asn Thr Gly Thr Gly Gln Thr Pro
530                 535                 540

Ser Ser Thr Ser Ser Ile Ser Thr Pro Met Ile Ile Phe Asn Gly Arg
545                 550                 555                 560

Leu Ser Ile Val Asp Glu Asn Tyr Glu Ser Val Tyr Asp Ser Met Asp
                565                 570                 575

Leu Ser Arg Gly Lys Ala Glu Gln Leu Ile Leu Ser Ile Glu Thr Thr
            580                 585                 590
```

```
Asn Asp Gly Gln Leu Asp Ser Asn Trp Gln Ser Ser Leu Asn Thr Ser
            595                 600                 605

Leu Leu Ser Pro Pro His Tyr Gly Tyr Gln Gly Leu Trp Thr Pro Asn
        610                 615                 620

Trp Ile Thr Thr Thr Tyr Thr Ile Thr Leu Asn Asn Asn Ser Ser Ala
625                 630                 635                 640

Pro Thr Ser Ala Thr Ser Ile Ala Glu Gln Lys Lys Thr Ser Glu Thr
                645                 650                 655

Phe Thr Pro Ser Asn Thr Thr Ala Ser Ile Pro Asn Ile Lys Ala
            660                 665                 670

Ser Ala Gly Ser Gly Ser Gly Ser Ala Ser Asn Ser Gly Glu Val Thr
            675                 680                 685

Ile Thr Lys His Thr Leu Val Val Asn Trp Ala Pro Val Gly
            690                 695                 700

<210> SEQ ID NO 171
<211> LENGTH: 632
<212> TYPE: PRT
<213> ORGANISM: Chlamydia

<400> SEQUENCE: 171

Arg Glu Val Pro Ser Arg Ile Phe Leu Met Pro Asn Ser Val Pro Asp
                5                   10                  15

Pro Thr Lys Glu Ser Leu Ser Asn Lys Ile Ser Leu Thr Gly Asp Thr
            20                  25                  30

His Asn Leu Thr Asn Cys Tyr Leu Asp Asn Leu Arg Tyr Ile Leu Ala
        35                  40                  45

Ile Leu Gln Lys Thr Pro Asn Glu Gly Ala Ala Val Thr Ile Thr Asp
    50                  55                  60

Tyr Leu Ser Phe Phe Asp Thr Gln Lys Glu Gly Ile Tyr Phe Ala Lys
65                  70                  75                  80

Asn Leu Thr Pro Glu Ser Gly Gly Ala Ile Gly Tyr Ala Ser Pro Asn
                85                  90                  95

Ser Pro Thr Val Glu Ile Arg Asp Thr Ile Gly Pro Val Ile Phe Glu
            100                 105                 110

Asn Asn Thr Cys Cys Arg Leu Phe Thr Trp Arg Asn Pro Tyr Ala Ala
        115                 120                 125

Asp Lys Ile Arg Glu Gly Gly Ala Ile His Ala Gln Asn Leu Tyr Ile
    130                 135                 140

Asn His Asn His Asp Val Val Gly Phe Met Lys Asn Phe Ser Tyr Val
145                 150                 155                 160

Gln Gly Gly Ala Ile Ser Thr Ala Asn Thr Phe Val Val Ser Glu Asn
                165                 170                 175

Gln Ser Cys Phe Leu Phe Met Asp Asn Ile Cys Ile Gln Thr Asn Thr
            180                 185                 190

Ala Gly Lys Gly Gly Ala Ile Tyr Ala Gly Thr Ser Asn Ser Phe Glu
        195                 200                 205

Ser Asn Asn Cys Asp Leu Phe Phe Ile Asn Asn Ala Cys Cys Ala Gly
    210                 215                 220

Gly Ala Ile Phe Ser Pro Ile Cys Ser Leu Thr Gly Asn Arg Gly Asn
225                 230                 235                 240

Ile Val Phe Tyr Asn Asn Arg Cys Phe Lys Asn Val Glu Thr Ala Ser
                245                 250                 255

Ser Glu Ala Ser Asp Gly Gly Ala Ile Lys Val Thr Thr Arg Leu Asp
            260                 265                 270
```

-continued

```
Val Thr Gly Asn Arg Gly Arg Ile Phe Phe Ser Asp Asn Ile Thr Lys
            275                 280                 285
Asn Tyr Gly Ala Ile Tyr Ala Pro Val Val Thr Leu Val Asp Asn
        290                 295                 300
Gly Pro Thr Tyr Phe Ile Asn Asn Ile Ala Asn Asn Lys Gly Gly Ala
305                 310                 315                 320
Ile Tyr Ile Asp Gly Thr Ser Asn Ser Lys Ile Ser Ala Asp Arg His
                325                 330                 335
Ala Ile Ile Phe Asn Glu Asn Ile Val Thr Asn Val Thr Asn Ala Asn
                340                 345                 350
Gly Thr Ser Thr Ser Ala Asn Pro Pro Arg Arg Asn Ala Ile Thr Val
                355                 360                 365
Ala Ser Ser Gly Glu Ile Leu Leu Gly Ala Gly Ser Ser Gln Asn
        370                 375                 380
Leu Ile Phe Tyr Asp Pro Ile Glu Val Ser Asn Ala Gly Val Ser Val
385                 390                 395                 400
Ser Phe Asn Lys Glu Ala Asp Gln Thr Gly Ser Val Val Phe Ser Gly
                405                 410                 415
Ala Thr Val Asn Ser Ala Asp Phe His Gln Arg Asn Leu Gln Thr Lys
                420                 425                 430
Thr Pro Ala Pro Leu Thr Leu Ser Asn Gly Phe Leu Cys Ile Glu Asp
                435                 440                 445
His Ala Gln Leu Thr Val Asn Arg Phe Thr Gln Thr Gly Gly Val Val
        450                 455                 460
Ser Leu Gly Asn Gly Ala Val Leu Ser Cys Tyr Lys Asn Gly Thr Gly
465                 470                 475                 480
Asp Ser Ala Ser Asn Ala Ser Ile Thr Leu Lys His Ile Gly Leu Asn
                485                 490                 495
Leu Ser Ser Ile Leu Lys Ser Gly Ala Glu Ile Pro Leu Leu Trp Val
                500                 505                 510
Glu Pro Thr Asn Asn Ser Asn Asn Tyr Thr Ala Asp Thr Ala Ala Thr
                515                 520                 525
Phe Ser Leu Ser Asp Val Lys Leu Ser Leu Ile Asp Asp Tyr Gly Asn
        530                 535                 540
Ser Pro Tyr Glu Ser Thr Asp Leu Thr His Ala Leu Ser Ser Gln Pro
545                 550                 555                 560
Met Leu Ser Ile Ser Glu Ala Ser Asp Asn Gln Leu Gln Ser Glu Asn
                565                 570                 575
Ile Asp Phe Ser Gly Leu Asn Val Pro His Tyr Gly Trp Gln Gly Leu
        580                 585                 590
Trp Thr Trp Gly Trp Ala Lys Thr Gln Asp Pro Glu Pro Ala Ser Ser
        595                 600                 605
Ala Thr Ile Thr Asp Pro Gln Lys Ala Asn Arg Phe His Arg Thr Leu
        610                 615                 620
Leu Leu Thr Trp Leu Pro Ala Gly
625                 630
```

<210> SEQ ID NO 172
<211> LENGTH: 1173
<212> TYPE: PRT
<213> ORGANISM: Chlamydia

<400> SEQUENCE: 172

Ser Cys Val Asp Leu His Ala Gly Gly Gln Ser Val Asn Glu Leu Val

-continued

```
                 5                  10                 15
Tyr Val Gly Pro Gln Ala Val Leu Leu Asp Gln Ile Arg Asp Leu
             20                 25                 30

Phe Val Gly Ser Lys Asp Ser Gln Ala Glu Gly Gln Tyr Arg Leu Ile
             35                 40                 45

Val Gly Asp Pro Ser Ser Phe Gln Glu Lys Asp Ala Asp Thr Leu Pro
             50                 55                 60

Gly Lys Val Glu Gln Ser Thr Leu Phe Ser Val Thr Asn Pro Val Val
 65                 70                 75                 80

Phe Gln Gly Val Asp Gln Gln Asp Gln Val Ser Ser Gln Gly Leu Ile
                 85                 90                 95

Cys Ser Phe Thr Ser Ser Asn Leu Asp Ser Pro Arg Asp Gly Glu Ser
                100                105                110

Phe Leu Gly Ile Ala Phe Val Gly Asp Ser Ser Lys Ala Gly Ile Thr
                115                120                125

Leu Thr Asp Val Lys Ala Ser Leu Ser Gly Ala Ala Leu Tyr Ser Thr
                130                135                140

Glu Asp Leu Ile Phe Glu Lys Ile Lys Gly Gly Leu Glu Phe Ala Ser
145                150                155                160

Cys Ser Ser Leu Glu Gln Gly Ala Cys Ala Ala Gln Ser Ile Leu
                165                170                175

Ile His Asp Cys Gln Gly Leu Gln Val Lys His Cys Thr Thr Ala Val
                180                185                190

Asn Ala Glu Gly Ser Ser Ala Asn Asp His Leu Gly Phe Gly Gly Gly
                195                200                205

Ala Phe Phe Val Thr Gly Ser Leu Ser Gly Glu Lys Ser Leu Tyr Met
210                215                220

Pro Ala Gly Asp Met Val Val Ala Asn Cys Asp Gly Ala Ile Ser Phe
225                230                235                240

Glu Gly Asn Ser Ala Asn Phe Ala Asn Gly Ala Ile Ala Ala Ser
                245                250                255

Gly Lys Val Leu Phe Val Ala Asn Asp Lys Lys Thr Ser Phe Ile Glu
                260                265                270

Asn Arg Ala Leu Ser Gly Gly Ala Ile Ala Ala Ser Ser Asp Ile Ala
                275                280                285

Phe Gln Asn Cys Ala Glu Leu Val Phe Lys Gly Asn Cys Ala Ile Gly
                290                295                300

Thr Glu Asp Lys Gly Ser Leu Gly Gly Gly Ala Ile Ser Ser Leu Gly
305                310                315                320

Thr Val Leu Leu Gln Gly Asn His Gly Ile Thr Cys Asp Lys Asn Glu
                325                330                335

Ser Ala Ser Gln Gly Gly Ala Ile Phe Gly Lys Asn Cys Gln Ile Ser
                340                345                350

Asp Asn Glu Gly Pro Val Val Phe Arg Asp Ser Thr Ala Cys Leu Gly
                355                360                365

Gly Gly Ala Ile Ala Ala Gln Glu Ile Val Ser Ile Gln Asn Asn Gln
                370                375                380

Ala Gly Ile Ser Phe Glu Gly Lys Ala Ser Phe Gly Gly Ile
385                390                395                400

Ala Cys Gly Ser Phe Ser Ser Ala Gly Gly Ala Ser Val Leu Gly Thr
                405                410                415

Ile Asp Ile Ser Lys Asn Leu Gly Ala Ile Ser Phe Ser Arg Thr Leu
                420                425                430
```

```
Cys Thr Thr Ser Asp Leu Gly Gln Met Glu Tyr Gln Gly Gly Gly Ala
        435                 440                 445

Leu Phe Gly Glu Asn Ile Ser Leu Ser Glu Asn Ala Gly Val Leu Thr
    450                 455                 460

Phe Lys Asp Asn Ile Val Lys Thr Phe Ala Ser Asn Gly Lys Ile Leu
465                 470                 475                 480

Gly Gly Gly Ala Ile Leu Ala Thr Gly Lys Val Glu Ile Thr Asn Asn
                485                 490                 495

Ser Glu Gly Ile Ser Phe Thr Gly Asn Ala Arg Ala Pro Gln Ala Leu
            500                 505                 510

Pro Thr Gln Glu Glu Phe Pro Leu Phe Ser Lys Lys Glu Gly Arg Pro
        515                 520                 525

Leu Ser Ser Gly Tyr Ser Gly Gly Ala Ile Leu Gly Arg Glu Val
    530                 535                 540

Ala Ile Leu His Asn Ala Ala Val Val Phe Glu Gln Asn Arg Leu Gln
545                 550                 555                 560

Cys Ser Glu Glu Glu Ala Thr Leu Leu Gly Cys Cys Gly Gly Gly Ala
                565                 570                 575

Val His Gly Met Asp Ser Thr Ser Ile Val Gly Asn Ser Ser Val Arg
            580                 585                 590

Phe Gly Asn Asn Tyr Ala Met Gly Gln Gly Val Ser Gly Gly Ala Leu
        595                 600                 605

Leu Ser Lys Thr Val Gln Leu Ala Gly Asn Gly Ser Val Asp Phe Ser
    610                 615                 620

Arg Asn Ile Ala Ser Leu Gly Gly Ala Leu Gln Ala Ser Glu Gly
625                 630                 635                 640

Asn Cys Glu Leu Val Asp Asn Gly Tyr Val Leu Phe Arg Asp Asn Arg
                645                 650                 655

Gly Arg Val Tyr Gly Gly Ala Ile Ser Cys Leu Arg Gly Asp Val Val
            660                 665                 670

Ile Ser Gly Asn Lys Gly Arg Val Glu Phe Lys Asp Asn Ile Ala Thr
        675                 680                 685

Arg Leu Tyr Val Glu Glu Thr Val Glu Lys Val Glu Glu Val Glu Pro
    690                 695                 700

Ala Pro Glu Gln Lys Asp Asn Asn Glu Leu Ser Phe Leu Gly Arg Ala
705                 710                 715                 720

Glu Gln Ser Phe Ile Thr Ala Ala Asn Gln Ala Leu Phe Ala Ser Glu
                725                 730                 735

Asp Gly Asp Leu Ser Pro Glu Ser Ser Ile Ser Ser Glu Glu Leu Ala
            740                 745                 750

Lys Arg Arg Glu Cys Ala Gly Ala Ile Phe Ala Lys Arg Val Arg
        755                 760                 765

Ile Val Asp Asn Gln Glu Ala Val Phe Ser Asn Asn Phe Ser Asp
    770                 775                 780

Ile Tyr Gly Gly Ala Ile Phe Thr Gly Ser Leu Arg Glu Glu Asp Lys
785                 790                 795                 800

Leu Asp Gly Gln Ile Pro Glu Val Leu Ile Ser Gly Asn Ala Gly Asp
                805                 810                 815

Val Val Phe Ser Gly Asn Ser Ser Lys Arg Asp Glu His Leu Pro His
            820                 825                 830

Thr Gly Gly Gly Ala Ile Cys Thr Gln Asn Leu Thr Ile Ser Gln Asn
        835                 840                 845
```

```
Thr Gly Asn Val Leu Phe Tyr Asn Asn Val Ala Cys Ser Gly Gly Ala
    850                 855                 860

Val Arg Ile Glu Asp His Gly Asn Val Leu Leu Glu Ala Phe Gly Gly
865                 870                 875                 880

Asp Ile Val Phe Lys Gly Asn Ser Ser Phe Arg Ala Gln Gly Ser Asp
                885                 890                 895

Ala Ile Tyr Phe Ala Gly Lys Glu Ser His Ile Thr Ala Leu Asn Ala
    900                 905                 910

Thr Glu Gly His Ala Ile Val Phe His Asp Ala Leu Val Phe Glu Asn
    915                 920                 925

Leu Glu Glu Arg Lys Ser Ala Glu Val Leu Leu Ile Asn Ser Arg Glu
    930                 935                 940

Asn Pro Gly Tyr Thr Gly Ser Ile Arg Phe Leu Glu Ala Glu Ser Lys
945                 950                 955                 960

Val Pro Gln Cys Ile His Val Gln Gln Gly Ser Leu Glu Leu Asn
                965                 970                 975

Gly Ala Thr Leu Cys Ser Tyr Gly Phe Lys Gln Asp Ala Gly Ala Lys
                980                 985                 990

Leu Val Leu Ala Ala Gly Ala Lys Leu Lys Ile Leu Asp Ser Gly Thr
    995                 1000                1005

Pro Val Gln Gln Gly His Ala Ile Ser Lys Pro Glu Ala Glu Ile Glu
    1010                1015                1020

Ser Ser Ser Glu Pro Glu Gly Ala His Ser Leu Trp Ile Ala Lys Asn
1025                1030                1035                1040

Ala Gln Thr Thr Val Pro Met Val Asp Ile His Thr Ile Ser Val Asp
                1045                1050                1055

Leu Ala Ser Phe Ser Ser Gln Gln Glu Gly Thr Val Glu Ala Pro
    1060                1065                1070

Gln Val Ile Val Pro Gly Gly Ser Tyr Val Arg Ser Gly Glu Leu Asn
    1075                1080                1085

Leu Glu Leu Val Asn Thr Thr Gly Thr Gly Tyr Glu Asn His Ala Leu
    1090                1095                1100

Leu Lys Asn Glu Ala Lys Val Pro Leu Met Ser Phe Val Ala Ser Gly
1105                1110                1115                1120

Asp Glu Ala Ser Ala Glu Ile Ser Asn Leu Ser Val Ser Asp Leu Gln
                1125                1130                1135

Ile His Val Val Thr Pro Glu Ile Glu Glu Asp Thr Tyr Gly His Met
                1140                1145                1150

Gly Asp Trp Ser Glu Ala Lys Ile Gln Asp Gly Thr Leu Val Ile Ser
    1155                1160                1165

Trp Asn Pro Thr Gly
    1170

<210> SEQ ID NO 173
<211> LENGTH: 1419
<212> TYPE: PRT
<213> ORGANISM: Chlamydia

<400> SEQUENCE: 173

Ser Ser Ile Gln Asp Gln Ile Lys Asn Thr Asp Cys Asn Val Ser Lys
                5                   10                  15

Leu Gly Tyr Ser Thr Ser Gln Ala Phe Thr Asp Met Met Leu Ala Asp
            20                  25                  30

Asn Thr Glu Tyr Arg Ala Ala Asp Ser Val Ser Phe Tyr Asp Phe Ser
        35                  40                  45
```

```
Thr Ser Ser Arg Leu Pro Arg Lys His Leu Ser Ser Ser Glu Ala
     50                  55                  60

Ser Pro Thr Thr Glu Gly Val Ser Ser Ser Ser Gly Glu Thr Asp
 65                  70                  75                  80

Glu Lys Thr Glu Glu Leu Asp Asn Gly Gly Ile Ile Tyr Ala Arg
                 85                  90                  95

Glu Lys Leu Thr Ile Ser Glu Ser Gln Asp Ser Leu Ser Asn Gln Ser
             100                 105                 110

Ile Glu Leu His Asp Asn Ser Ile Phe Phe Gly Glu Gly Glu Val Ile
         115                 120                 125

Phe Asp His Arg Val Ala Leu Lys Asn Gly Gly Ala Ile Tyr Gly Glu
     130                 135                 140

Lys Glu Val Val Phe Glu Asn Ile Lys Ser Leu Leu Val Glu Val Asn
145                 150                 155                 160

Ile Ala Val Glu Lys Gly Gly Ser Val Tyr Ala Lys Glu Arg Val Ser
                 165                 170                 175

Leu Glu Asn Val Thr Glu Ala Thr Phe Ser Ser Asn Gly Gly Glu Gln
             180                 185                 190

Gly Gly Gly Gly Ile Tyr Ser Glu Gln Asp Met Leu Ile Ser Asp Cys
         195                 200                 205

Asn Asn Val His Phe Gln Gly Asn Ala Ala Gly Ala Thr Ala Val Lys
     210                 215                 220

Gln Cys Leu Asp Glu Glu Met Ile Val Leu Leu Ala Glu Cys Val Asp
225                 230                 235                 240

Ser Leu Ser Glu Asp Thr Leu Asp Ser Thr Pro Glu Thr Glu Gln Thr
                 245                 250                 255

Glu Ser Asn Gly Asn Gln Asp Gly Ser Ser Glu Thr Glu Asp Thr Gln
             260                 265                 270

Val Ser Glu Ser Pro Glu Ser Thr Pro Ser Pro Asp Asp Val Leu Gly
         275                 280                 285

Lys Gly Gly Gly Ile Tyr Thr Glu Lys Ser Leu Thr Ile Thr Gly Ile
     290                 295                 300

Thr Gly Thr Ile Asp Phe Val Ser Asn Ile Ala Thr Asp Ser Gly Ala
305                 310                 315                 320

Gly Val Phe Thr Lys Glu Asn Leu Ser Cys Thr Asn Thr Asn Ser Leu
                 325                 330                 335

Gln Phe Leu Lys Asn Ser Ala Gly Gln His Gly Gly Gly Ala Tyr Val
             340                 345                 350

Thr Gln Thr Met Ser Val Thr Asn Thr Thr Ser Glu Ser Ile Thr Thr
         355                 360                 365

Pro Pro Leu Ile Gly Glu Val Ile Phe Ser Glu Asn Thr Ala Lys Gly
     370                 375                 380

His Gly Gly Gly Ile Cys Thr Asn Lys Leu Ser Leu Ser Asn Leu Lys
385                 390                 395                 400

Thr Val Thr Leu Thr Lys Asn Ser Ala Lys Glu Ser Gly Gly Ala Ile
                 405                 410                 415

Phe Thr Asp Leu Ala Ser Ile Pro Ile Thr Asp Thr Pro Glu Ser Ser
             420                 425                 430

Thr Pro Ser Ser Ser Ser Pro Ala Ser Thr Pro Glu Val Val Ala Ser
         435                 440                 445

Ala Lys Ile Asn Arg Phe Phe Ala Ser Thr Ala Lys Pro Ala Ala Pro
     450                 455                 460
```

-continued

```
Ser Leu Thr Glu Ala Glu Ser Asp Gln Thr Asp Gln Thr Glu Thr Ser
465                 470                 475                 480

Asp Thr Asn Ser Asp Ile Asp Val Ser Ile Glu Asn Ile Leu Asn Val
            485                 490                 495

Ala Ile Asn Gln Asn Thr Ser Ala Lys Lys Gly Gly Ala Ile Tyr Gly
        500                 505                 510

Lys Lys Ala Lys Leu Ser Arg Ile Asn Asn Leu Glu Leu Ser Gly Asn
    515                 520                 525

Ser Ser Gln Asp Val Gly Gly Leu Cys Leu Thr Glu Ser Val Glu
    530                 535                 540

Phe Asp Ala Ile Gly Ser Leu Leu Ser His Tyr Asn Ser Ala Ala Lys
545                 550                 555                 560

Glu Gly Gly Ala Ile His Ser Lys Thr Val Thr Leu Ser Asn Leu Lys
                565                 570                 575

Ser Thr Phe Thr Phe Ala Asp Asn Thr Val Lys Ala Ile Val Glu Ser
            580                 585                 590

Thr Pro Glu Ala Pro Glu Glu Ile Pro Pro Val Glu Gly Glu Glu Ser
        595                 600                 605

Thr Ala Thr Glu Asp Pro Asn Ser Asn Thr Glu Gly Ser Ser Ala Asn
    610                 615                 620

Thr Asn Leu Glu Gly Ser Gln Gly Asp Thr Ala Asp Thr Gly Thr Gly
625                 630                 635                 640

Asp Val Asn Asn Glu Ser Gln Asp Thr Ser Asp Thr Gly Asn Ala Glu
                645                 650                 655

Ser Glu Glu Gln Leu Gln Asp Ser Thr Gln Ser Asn Glu Glu Asn Thr
            660                 665                 670

Leu Pro Asn Ser Asn Ile Asp Gln Ser Asn Glu Asn Thr Asp Glu Ser
        675                 680                 685

Ser Asp Ser His Thr Glu Glu Ile Thr Asp Glu Ser Val Ser Ser Ser
    690                 695                 700

Ser Glu Ser Gly Ser Ser Thr Pro Gln Asp Gly Gly Ala Ala Ser Ser
705                 710                 715                 720

Gly Ala Pro Ser Gly Asp Gln Ser Ile Ser Ala Asn Ala Cys Leu Ala
                725                 730                 735

Lys Ser Tyr Ala Ala Ser Thr Asp Ser Ser Pro Val Ser Asn Ser Ser
            740                 745                 750

Gly Ser Glu Glu Pro Val Thr Ser Ser Asp Ser Asp Val Thr Ala
        755                 760                 765

Ser Ser Asp Asn Pro Asp Ser Ser Ser Gly Asp Ser Ala Gly Asp
    770                 775                 780

Ser Glu Glu Pro Thr Glu Pro Glu Ala Gly Ser Thr Thr Glu Thr Leu
785                 790                 795                 800

Thr Leu Ile Gly Gly Ala Ile Tyr Gly Glu Thr Val Lys Ile Glu
                805                 810                 815

Asn Phe Ser Gly Gln Gly Ile Phe Ser Gly Asn Lys Ala Ile Asp Asn
            820                 825                 830

Thr Thr Glu Gly Ser Ser Lys Ser Asp Val Leu Gly Gly Ala Val
        835                 840                 845

Tyr Ala Lys Thr Leu Phe Asn Leu Asp Ser Gly Ser Ser Arg Arg Thr
    850                 855                 860

Val Thr Phe Ser Gly Asn Thr Val Ser Ser Gln Ser Thr Thr Gly Gln
865                 870                 875                 880

Val Ala Gly Gly Ala Ile Tyr Ser Pro Thr Val Thr Ile Ala Thr Pro
```

-continued

```
                885                 890                 895
Val Val Phe Ser Lys Asn Ser Ala Thr Asn Asn Ala Asn Asn Thr Thr
            900                 905                 910
Asp Thr Gln Arg Lys Asp Thr Phe Gly Gly Ala Ile Gly Ala Thr Ser
            915                 920                 925
Ala Val Ser Leu Ser Gly Gly Ala His Phe Leu Glu Asn Val Ala Asp
            930                 935                 940
Leu Gly Ser Ala Ile Gly Leu Val Pro Gly Thr Gln Asn Thr Glu Thr
945                 950                 955                 960
Val Lys Leu Glu Ser Gly Ser Tyr Tyr Phe Glu Lys Asn Lys Ala Leu
            965                 970                 975
Lys Arg Ala Thr Ile Tyr Ala Pro Val Val Ser Ile Lys Ala Tyr Thr
            980                 985                 990
Ala Thr Phe Asn Gln Asn Arg Ser Leu Glu Glu Gly Ser Ala Ile Tyr
            995                 1000                1005
Phe Thr Lys Glu Ala Ser Ile Glu Ser Leu Gly Ser Val Leu Phe Thr
            1010                1015                1020
Gly Asn Leu Val Thr Leu Thr Leu Ser Thr Thr Thr Glu Gly Thr Pro
1025                1030                1035                1040
Ala Thr Thr Ser Gly Asp Val Thr Lys Tyr Gly Ala Ala Ile Phe Gly
            1045                1050                1055
Gln Ile Ala Ser Ser Asn Gly Ser Gln Thr Asp Asn Leu Pro Leu Lys
            1060                1065                1070
Leu Ile Ala Ser Gly Gly Asn Ile Cys Phe Arg Asn Asn Glu Tyr Arg
            1075                1080                1085
Pro Thr Ser Ser Asp Thr Gly Thr Ser Thr Phe Cys Ser Ile Ala Gly
            1090                1095                1100
Asp Val Lys Leu Thr Met Gln Ala Ala Lys Gly Lys Thr Ile Ser Phe
1105                1110                1115                1120
Phe Asp Ala Ile Arg Thr Ser Thr Lys Lys Thr Gly Thr Gln Ala Thr
            1125                1130                1135
Ala Tyr Asp Thr Leu Asp Ile Asn Lys Ser Glu Asp Ser Glu Thr Val
            1140                1145                1150
Asn Ser Ala Phe Thr Gly Thr Ile Leu Phe Ser Ser Glu Leu His Glu
            1155                1160                1165
Asn Lys Ser Tyr Ile Pro Gln Asn Val Val Leu His Ser Gly Ser Leu
            1170                1175                1180
Val Leu Lys Pro Asn Thr Glu Leu His Val Ile Ser Phe Glu Gln Lys
1185                1190                1195                1200
Glu Gly Ser Ser Leu Val Met Thr Pro Gly Ser Val Leu Ser Asn Gln
            1205                1210                1215
Thr Val Ala Asp Gly Ala Leu Val Ile Asn Asn Met Thr Ile Asp Leu
            1220                1225                1230
Ser Ser Val Glu Lys Asn Gly Ile Ala Glu Gly Asn Ile Phe Thr Pro
            1235                1240                1245
Pro Glu Leu Arg Ile Ile Asp Thr Thr Thr Gly Gly Ser Gly Gly Thr
            1250                1255                1260
Pro Ser Thr Asp Ser Glu Ser Asn Gln Asn Ser Asp Asp Thr Glu Glu
1265                1270                1275                1280
Gln Asn Asn Asn Asp Ala Ser Asn Gln Gly Glu Ser Ala Asn Gly Ser
            1285                1290                1295
Ser Ser Pro Ala Val Ala Ala Ala His Thr Ser Arg Thr Arg Asn Phe
            1300                1305                1310
```

-continued

```
Ala Ala Ala Ala Thr Ala Thr Pro Thr Thr Pro Thr Ala Thr Thr
        1315                1320                1325

Thr Thr Ser Asn Gln Val Ile Leu Gly Gly Glu Ile Lys Leu Ile Asp
    1330                1335                1340

Pro Asn Gly Thr Phe Phe Gln Asn Pro Ala Leu Arg Ser Asp Gln Gln
1345                1350                1355                1360

Ile Ser Leu Leu Val Leu Pro Thr Asp Ser Ser Lys Met Gln Ala Gln
                1365                1370                1375

Lys Ile Val Leu Thr Gly Asp Ile Ala Pro Gln Lys Gly Tyr Thr Gly
            1380                1385                1390

Thr Leu Thr Leu Asp Pro Asp Gln Leu Gln Asn Gly Thr Ile Ser Val
        1395                1400                1405

Leu Trp Lys Phe Asp Ser Tyr Arg Gln Trp Ala
    1410                1415

<210> SEQ ID NO 174
<211> LENGTH: 1397
<212> TYPE: PRT
<213> ORGANISM: Chlamydia

<400> SEQUENCE: 174

Glu Pro Lys Glu Leu Asn Phe Ser Arg Val Gly Thr Ser Ser Ser Thr
                5                  10                  15

Thr Phe Thr Glu Thr Val Gly Glu Ala Gly Ala Glu Tyr Ile Val Ser
            20                  25                  30

Gly Asn Ala Ser Phe Thr Lys Phe Thr Asn Ile Pro Thr Thr Asp Thr
        35                  40                  45

Thr Thr Pro Thr Asn Ser Asn Ser Ser Ser Asn Gly Glu Thr Ala
    50                  55                  60

Ser Val Ser Glu Asp Ser Asp Ser Thr Thr Thr Pro Asp Pro Lys
65                  70                  75                  80

Gly Gly Gly Ala Phe Tyr Asn Ala His Ser Gly Val Leu Ser Phe Met
                85                  90                  95

Thr Arg Ser Gly Thr Glu Gly Ser Leu Thr Leu Ser Glu Ile Lys Ile
            100                 105                 110

Thr Gly Glu Gly Ala Ile Phe Ser Gln Gly Glu Leu Leu Phe Thr
        115                 120                 125

Asp Leu Thr Gly Leu Thr Ile Gln Asn Asn Leu Ser Gln Leu Ser Gly
    130                 135                 140

Gly Ala Ile Phe Gly Glu Ser Thr Ile Ser Leu Ser Gly Ile Thr Lys
145                 150                 155                 160

Ala Thr Phe Ser Ser Asn Ser Ala Glu Val Pro Ala Pro Val Lys Lys
                165                 170                 175

Pro Thr Glu Pro Lys Ala Gln Thr Ala Ser Glu Thr Ser Gly Ser Ser
            180                 185                 190

Ser Ser Ser Gly Asn Asp Ser Val Ser Ser Pro Ser Ser Arg Ala
    195                 200                 205

Glu Pro Ala Ala Ala Asn Leu Gln Ser His Phe Ile Cys Ala Thr Ala
    210                 215                 220

Thr Pro Ala Ala Gln Thr Asp Thr Glu Thr Ser Thr Pro Ser His Lys
225                 230                 235                 240

Pro Gly Ser Gly Gly Ala Ile Tyr Ala Lys Gly Asp Leu Thr Ile Ala
                245                 250                 255

Asp Ser Gln Glu Val Leu Phe Ser Ile Asn Lys Ala Thr Lys Asp Gly
```

-continued

```
                260                 265                 270
Gly Ala Ile Phe Ala Glu Lys Asp Val Ser Phe Glu Asn Ile Thr Ser
            275                 280                 285
Leu Lys Val Gln Thr Asn Gly Ala Glu Lys Gly Gly Ala Ile Tyr
290                 295                 300
Ala Lys Gly Asp Leu Ser Ile Gln Ser Ser Lys Gln Ser Leu Phe Asn
305                 310                 315                 320
Ser Asn Tyr Ser Lys Gln Gly Gly Ala Leu Tyr Val Glu Gly Asp
            325                 330                 335
Ile Asn Phe Gln Asp Leu Glu Glu Ile Arg Ile Lys Tyr Asn Lys Ala
            340                 345                 350
Gly Thr Phe Glu Thr Lys Lys Ile Thr Leu Pro Lys Ala Gln Ala Ser
            355                 360                 365
Ala Gly Asn Ala Asp Ala Trp Ala Ser Ser Ser Pro Gln Ser Gly Ser
            370                 375                 380
Gly Ala Thr Thr Val Ser Asn Ser Gly Asp Ser Ser Gly Ser Asp
385                 390                 395                 400
Ser Asp Thr Ser Glu Thr Val Pro Ala Thr Ala Lys Gly Gly Leu
            405                 410                 415
Tyr Thr Asp Lys Asn Leu Ser Ile Thr Asn Ile Thr Gly Ile Ile Glu
            420                 425                 430
Ile Ala Asn Asn Lys Ala Thr Asp Val Gly Gly Ala Tyr Val Lys
            435                 440                 445
Gly Thr Leu Thr Cys Glu Asn Ser His Arg Leu Gln Phe Leu Lys Asn
            450                 455                 460
Ser Ser Asp Lys Gln Gly Gly Ile Tyr Gly Glu Asp Asn Ile Thr
465                 470                 475                 480
Leu Ser Asn Leu Thr Gly Lys Thr Leu Phe Gln Glu Asn Thr Ala Lys
            485                 490                 495
Glu Glu Gly Gly Gly Leu Phe Ile Lys Gly Thr Asp Lys Ala Leu Thr
            500                 505                 510
Met Thr Gly Leu Asp Ser Phe Cys Leu Ile Asn Asn Thr Ser Glu Lys
            515                 520                 525
His Gly Gly Gly Ala Phe Val Thr Lys Glu Ile Ser Gln Thr Tyr Thr
            530                 535                 540
Ser Asp Val Glu Thr Ile Pro Gly Ile Thr Pro Val His Gly Glu Thr
545                 550                 555                 560
Val Ile Thr Gly Asn Lys Ser Thr Gly Gly Asn Gly Gly Val Cys
            565                 570                 575
Thr Lys Arg Leu Ala Leu Ser Asn Leu Gln Ser Ile Ser Ile Ser Gly
            580                 585                 590
Asn Ser Ala Ala Glu Asn Gly Gly Ala His Thr Cys Pro Asp Ser
            595                 600                 605
Phe Pro Thr Ala Asp Thr Ala Glu Gln Pro Ala Ala Ser Ala Ala
            610                 615                 620
Thr Ser Thr Pro Glu Ser Ala Pro Val Val Ser Thr Ala Leu Ser Thr
625                 630                 635                 640
Pro Ser Ser Ser Thr Val Ser Ser Leu Thr Leu Leu Ala Ala Ser Ser
            645                 650                 655
Gln Ala Ser Pro Ala Thr Ser Asn Lys Glu Thr Gln Asp Pro Asn Ala
            660                 665                 670
Asp Thr Asp Leu Leu Ile Asp Tyr Val Val Asp Thr Thr Ile Ser Lys
            675                 680                 685
```

```
Asn Thr Ala Lys Lys Gly Gly Ile Tyr Ala Lys Lys Ala Lys Met
    690             695             700

Ser Arg Ile Asp Gln Leu Asn Ile Ser Glu Asn Ser Ala Thr Glu Ile
705             710             715             720

Gly Gly Gly Ile Cys Cys Lys Glu Ser Leu Glu Leu Asp Ala Leu Val
                725             730             735

Ser Leu Ser Val Thr Glu Asn Leu Val Gly Lys Glu Gly Gly Leu
            740             745             750

His Ala Lys Thr Val Asn Ile Ser Asn Leu Lys Ser Gly Phe Ser Phe
        755             760             765

Ser Asn Asn Lys Ala Asn Ser Ser Ser Thr Gly Val Ala Thr Thr Ala
    770             775             780

Ser Ala Pro Ala Ala Ala Ala Ser Leu Gln Ala Ala Ala Ala Ala
785             790             795             800

Val Pro Ser Ser Pro Ala Thr Pro Thr Tyr Ser Gly Val Val Gly Gly
            805             810             815

Ala Ile Tyr Gly Glu Lys Val Thr Phe Ser Gln Cys Ser Gly Thr Cys
        820             825             830

Gln Phe Ser Gly Asn Gln Ala Ile Asp Asn Asn Pro Ser Gln Ser Ser
    835             840             845

Leu Asn Val Gln Gly Gly Ala Ile Tyr Ala Lys Thr Ser Leu Ser Ile
    850             855             860

Gly Ser Ser Asp Ala Gly Thr Ser Tyr Ile Phe Ser Gly Asn Ser Val
865             870             875             880

Ser Thr Gly Lys Ser Gln Thr Thr Gly Gln Ile Ala Gly Ala Ile
            885             890             895

Tyr Ser Pro Thr Val Thr Leu Asn Cys Pro Ala Thr Phe Ser Asn Asn
        900             905             910

Thr Ala Ser Met Ala Thr Pro Lys Thr Ser Ser Glu Asp Gly Ser Ser
        915             920             925

Gly Asn Ser Ile Lys Asp Thr Ile Gly Gly Ala Ile Ala Gly Thr Ala
    930             935             940

Ile Thr Leu Ser Gly Val Ser Arg Phe Ser Gly Asn Thr Ala Asp Leu
945             950             955             960

Gly Ala Ala Ile Gly Thr Leu Ala Asn Ala Asn Thr Pro Ser Ala Thr
            965             970             975

Ser Gly Ser Gln Asn Ser Ile Thr Glu Lys Ile Thr Leu Glu Asn Gly
            980             985             990

Ser Phe Ile Phe Glu Arg Asn Gln Ala Asn Lys Arg Gly Ala Ile Tyr
    995             1000            1005

Ser Pro Ser Val Ser Ile Lys Gly Asn Asn Ile Thr Phe Asn Gln Asn
    1010            1015            1020

Thr Ser Thr His Asp Gly Ser Ala Ile Tyr Phe Thr Lys Asp Ala Thr
1025            1030            1035            1040

Ile Glu Ser Leu Gly Ser Val Leu Phe Thr Gly Asn Asn Val Thr Ala
            1045            1050            1055

Thr Gln Ala Ser Ser Ala Thr Ser Gly Gln Asn Thr Asn Thr Ala Asn
            1060            1065            1070

Tyr Gly Ala Ala Ile Phe Gly Asp Pro Gly Thr Thr Gln Ser Ser Gln
            1075            1080            1085

Thr Asp Ala Ile Leu Thr Leu Leu Ala Ser Ser Gly Asn Ile Thr Phe
            1090            1095            1100
```

-continued

```
Ser Asn Asn Ser Leu Gln Asn Asn Gln Gly Asp Thr Pro Ala Ser Lys
1105                1110                1115                1120

Phe Cys Ser Ile Ala Gly Tyr Val Lys Leu Ser Leu Gln Ala Ala Lys
            1125                1130                1135

Gly Lys Thr Ile Ser Phe Phe Asp Cys Val His Thr Ser Thr Lys Lys
        1140                1145                1150

Ile Gly Ser Thr Gln Asn Val Tyr Glu Thr Leu Asp Ile Asn Lys Glu
    1155                1160                1165

Glu Asn Ser Asn Pro Tyr Thr Gly Thr Ile Val Phe Ser Ser Glu Leu
1170                1175                1180

His Glu Asn Lys Ser Tyr Ile Pro Gln Asn Ala Ile Leu His Asn Gly
1185                1190                1195                1200

Thr Leu Val Leu Lys Glu Lys Thr Glu Leu His Val Val Ser Phe Glu
                1205                1210                1215

Gln Lys Glu Gly Ser Lys Leu Ile Met Lys Pro Gly Ala Val Leu Ser
                1220                1225                1230

Asn Gln Asn Ile Ala Asn Gly Ala Leu Val Ile Asn Gly Leu Thr Ile
            1235                1240                1245

Asp Leu Ser Ser Met Gly Thr Pro Gln Ala Gly Glu Ile Phe Ser Pro
    1250                1255                1260

Pro Glu Leu Arg Ile Val Ala Thr Thr Ser Ser Ala Ser Gly Gly Ser
1265                1270                1275                1280

Gly Val Ser Ser Ile Pro Thr Asn Pro Lys Arg Ile Ser Ala Ala
            1285                1290                1295

Ala Pro Ser Gly Ser Ala Ala Thr Thr Pro Thr Met Ser Glu Asn Lys
        1300                1305                1310

Val Phe Leu Thr Gly Asp Leu Thr Leu Ile Asp Pro Asn Gly Asn Phe
    1315                1320                1325

Tyr Gln Asn Pro Met Leu Gly Ser Asp Leu Asp Val Pro Leu Ile Lys
1330                1335                1340

Leu Pro Thr Asn Thr Ser Asp Val Gln Val Tyr Asp Leu Thr Leu Ser
1345                1350                1355                1360

Gly Asp Leu Phe Pro Gln Lys Gly Tyr Met Gly Thr Trp Thr Leu Asp
                1365                1370                1375

Ser Asn Pro Gln Thr Gly Lys Leu Gln Ala Arg Trp Thr Phe Asp Thr
            1380                1385                1390

Tyr Arg Arg Trp Val
        1395

<210> SEQ ID NO 175
<211> LENGTH: 610
<212> TYPE: PRT
<213> ORGANISM: Chlamydia

<400> SEQUENCE: 175

Glu Met Glu Leu Ala Ile Ser Gly His Lys Gln Gly Lys Asp Arg Asp
                5                  10                  15

Thr Phe Thr Met Ile Ser Ser Cys Pro Glu Gly Thr Asn Tyr Ile Ile
            20                  25                  30

Asn Arg Lys Leu Ile Leu Ser Asp Phe Ser Leu Leu Asn Lys Val Ser
        35                  40                  45

Ser Gly Gly Ala Phe Arg Asn Leu Ala Gly Lys Ile Ser Phe Leu Gly
    50                  55                  60

Lys Asn Ser Ser Ala Ser Ile His Phe Lys His Ile Asn Ile Asn Gly
65                  70                  75                  80
```

```
Phe Gly Ala Gly Val Phe Ser Glu Ser Ile Glu Phe Thr Asp Leu
                85                  90                  95
Arg Lys Leu Val Ala Phe Gly Ser Glu Ser Thr Gly Ile Phe Thr
                100                 105                 110
Ala Lys Glu Asp Ile Ser Phe Lys Asn Asn His His Ile Ala Phe Arg
                115                 120                 125
Asn Asn Ile Thr Lys Gly Asn Gly Val Ile Gln Leu Gln Gly Asp
                130                 135                 140
Met Lys Gly Ser Val Ser Phe Val Asp Gln Arg Gly Ala Ile Ile Phe
145                 150                 155                 160
Thr Asn Asn Gln Ala Val Thr Ser Ser Met Lys His Ser Gly Arg
                165                 170                 175
Gly Gly Ala Ile Ser Gly Asp Phe Ala Gly Ser Arg Ile Leu Phe Leu
                180                 185                 190
Asn Asn Gln Gln Ile Thr Phe Glu Gly Asn Ser Ala Val His Gly Gly
                195                 200                 205
Ala Ile Tyr Asn Lys Asn Gly Leu Val Glu Phe Leu Gly Asn Ala Gly
                210                 215                 220
Pro Leu Ala Phe Lys Glu Asn Thr Thr Ile Ala Asn Gly Gly Ala Ile
225                 230                 235                 240
Tyr Thr Ser Asn Phe Lys Ala Asn Gln Gln Thr Ser Pro Ile Leu Phe
                245                 250                 255
Ser Gln Asn His Ala Asn Lys Lys Gly Gly Ala Ile Tyr Ala Gln Tyr
                260                 265                 270
Val Asn Leu Glu Gln Asn Gln Asp Thr Ile Arg Phe Glu Lys Asn Thr
                275                 280                 285
Ala Lys Glu Gly Gly Gly Ala Ile Thr Ser Ser Gln Cys Ser Ile Thr
                290                 295                 300
Ala His Asn Thr Ile Ile Phe Ser Asp Asn Ala Ala Gly Asp Leu Gly
305                 310                 315                 320
Gly Gly Ala Ile Leu Leu Glu Gly Lys Lys Pro Ser Leu Thr Leu Ile
                325                 330                 335
Ala His Ser Gly Asn Ile Ala Phe Ser Gly Asn Thr Met Leu His Ile
                340                 345                 350
Thr Lys Lys Ala Ser Leu Asp Arg His Asn Ser Ile Leu Ile Lys Glu
                355                 360                 365
Ala Pro Tyr Lys Ile Gln Leu Ala Ala Asn Lys Asn His Ser Ile His
                370                 375                 380
Phe Phe Asp Pro Val Met Ala Leu Ser Ala Ser Ser Pro Ile Gln
385                 390                 395                 400
Ile Asn Ala Pro Glu Tyr Glu Thr Pro Phe Ser Pro Lys Gly Met
                405                 410                 415
Ile Val Phe Ser Gly Ala Asn Leu Leu Asp Asp Ala Arg Glu Asp Val
                420                 425                 430
Ala Asn Arg Thr Ser Ile Phe Asn Gln Pro Val His Leu Tyr Asn Gly
                435                 440                 445
Thr Leu Ser Ile Glu Asn Gly Ala His Leu Ile Val Gln Ser Phe Lys
                450                 455                 460
Gln Thr Gly Gly Arg Ile Ser Leu Ser Pro Gly Ser Ser Leu Ala Leu
465                 470                 475                 480
Tyr Thr Met Asn Ser Phe Phe His Gly Asn Ile Ser Ser Lys Glu Pro
                485                 490                 495
```

-continued

```
Leu Glu Ile Asn Gly Leu Ser Phe Gly Val Asp Ile Ser Pro Ser Asn
            500                 505                 510

Leu Gln Ala Glu Ile Arg Ala Gly Asn Ala Pro Leu Arg Leu Ser Gly
        515                 520                 525

Ser Pro Ser Ile His Asp Pro Glu Gly Leu Phe Tyr Glu Asn Arg Asp
    530                 535                 540

Thr Ala Ala Ser Pro Tyr Gln Met Glu Ile Leu Leu Thr Ser Asp Lys
545                 550                 555                 560

Ile Val Asp Ile Ser Lys Phe Thr Thr Asp Ser Leu Val Thr Asn Lys
                565                 570                 575

Gln Ser Gly Phe Gln Gly Ala Trp His Phe Ser Trp Gln Pro Asn Thr
            580                 585                 590

Ile Asn Asn Thr Lys Gln Lys Ile Leu Arg Ala Ser Trp Leu Pro Thr
            595                 600                 605

Gly Glu
    610
```